(12) United States Patent
Tucker

(10) Patent No.: US 7,879,602 B2
(45) Date of Patent: Feb. 1, 2011

(54) CHIMERIC ADENOVIRAL VECTORS

(75) Inventor: Sean N. Tucker, San Francisco, CA (US)

(73) Assignee: Vaxart, Inc., San Francisco, CA (US)

(*) Notice: Subject to any disclaimer, the term of this patent is extended or adjusted under 35 U.S.C. 154(b) by 128 days.

(21) Appl. No.: 11/712,794

(22) Filed: Feb. 28, 2007

(65) Prior Publication Data

US 2007/0269410 A1 Nov. 22, 2007

Related U.S. Application Data

(60) Provisional application No. 60/778,026, filed on Feb. 28, 2006, provisional application No. 60/802,992, filed on May 22, 2006, provisional application No. 60/801,645, filed on May 19, 2006, provisional application No. 60/821,492, filed on Aug. 4, 2006, provisional application No. 60/846,658, filed on Sep. 22, 2006, provisional application No. 60/848,195, filed on Sep. 28, 2006.

(51) Int. Cl.
| | |
|---|---|
| *C12N 15/861* | (2006.01) |
| *C12N 15/00* | (2006.01) |
| *A61K 48/00* | (2006.01) |

(52) U.S. Cl. ............... 435/320.1; 514/44 R; 424/199.1
(58) Field of Classification Search ............ 435/320.1; 514/44 R; 424/199.1
See application file for complete search history.

(56) References Cited

U.S. PATENT DOCUMENTS

| 6,511,845 B1 * | 1/2003 | Davis et al. ............. 435/320.1 |
| 2002/0182223 A1 | 12/2002 | LaCount et al. |
| 2005/0239728 A1 * | 10/2005 | Pachuk et al. ............. 514/44 |
| 2007/0219149 A1 | 9/2007 | Hasegawa et al. |

FOREIGN PATENT DOCUMENTS

| WO | WO 2004/011624 | * | 2/2004 |
| WO | WO 2005/014038 A1 | | 2/2005 |

OTHER PUBLICATIONS

Ichinohe et al. (2005) J. Virol. vol. 79, No. 5, 2910-2919.*
Bell et al. (2006) PNAS, vol. 103(23), 8792-8797.*
Alexopoulou, L., et al., "Recognition of double-stranded RNA and activation of NF-κB by Toll-like receptor 3," *Nature*, vol. 413, pp. 732-738 (Oct. 18, 2001).
Ichinohe, T., et al., "Synthetic double-stranded RNA poly(I:C) Combined with mucosal vaccine protects against influenza virus infection," *Journal of Virology*, vol. 79(5), pp. 2910-2919 (Mar. 2005).

* cited by examiner

*Primary Examiner*—Anne Marie S Wehbe
(74) *Attorney, Agent, or Firm*—Townsend and Townsend and Crew LLP

(57) ABSTRACT

The present invention provides chimeric adenoviral vectors and methods for using the vectors to elicit an immune response to an antigen of interest.

14 Claims, 10 Drawing Sheets

SEQUENCE LISTING

<160> NUMBER OF SEQ ID NOS: 17

<210> SEQ ID NO 1
<211> LENGTH: 11025
<212> TYPE: DNA
<213> ORGANISM: Artificial Sequence
<220> FEATURE:
<223> OTHER INFORMATION: chimeric adenoviral vector DS1

<400> SEQUENCE: 1

```
taacatcatc aataatatac cttattttgg attgaagcca atatgataat gagggggtgg      60
agtttgtgac gtggcgcggg gcgtgggaac ggggcgggtg acgtagtagt gtggcggaag     120
tgtgatgttg caagtgtggc ggaacacatg taagcgacgg atgtggcaaa agtgacgttt     180
ttggtgtgcg ccggtgtaca caggaagtga caattttcgc gcggttttag gcggatgttg     240
tagtaaattt gggcgtaacc gagtaagatt tggccatttt cgcgggaaaa ctgaataaga     300
ggaagtgaaa tctgaataat tttgtgttac tcatagcgcg taatactggt accgcggccg     360
cctcgagtct agagatctgg cgaaaggggg atgtgctgca aggcgattaa gttgggtaac     420
gccagggttt tcccagtcac gacgttgtaa aacgacggcc agtgaattgt aatacgactc     480
actatagggc gaattgggta ctggccacag agcttggccc attgcatacg ttgtatccat     540
atcataatat gtacatttat attggctcat gtccaacatt accgccatgt tgacattgat     600
tattgactag ttattaatag taatcaatta cggggtcatt agttcatagc ccatatatgg     660
agttccgcgt tacataactt acggtaaatg gcccgcctgg ctgaccgccc aacgaccccc     720
gcccattgac gtcaataatg acgtatgttc ccatagtaac gccaataggg actttccatt     780
gacgtcaatg ggtggagtat ttacggtaaa ctgcccactt ggcagtacat caagtgtatc     840
atatgccaag tacgccccct attgacgtca atgacggtaa atggcccgcc tggcattatg     900
cccagtacat gaccttatgg actttcctac ttggcagta catctacgta ttagtcatcg     960
ctattaccat ggtgatgcgg ttttggcagt acatcaatgg gcgtggatag cggtttgact    1020
cacggggatt tccaagtctc cacccccattg acgtcaatgg gagtttgttt tggcaccaaa    1080
atcaacggga ctttccaaaa tgtcgtaaca actccgcccc attgacgcaa atgggcggta    1140
ggcgtgtacg gtgggaggtc tatataagca gagctcgttt agtgaaccgt cagatcgcct    1200
ggagacgcca tccacgctgt tttgacctcc atagaagaca ccgggaccga tccagcctga    1260
ctctagccta gctctgaagt tggtggtgag gccctgggca ggttggtatc aaggttacaa    1320
gacaggttta aggagaccaa tagaaactgg gcatgtggag acagagaaga ctcttgggtt    1380
tctgataggc actgactctc tctgcctatt ggtctatttt cccacccctta ggctgctggt    1440
ctgagcctag gagatctctc gaggtcgacg gtatagcttc tagagatccc tcgacctcga    1500
gatccattgt gctctaaagg agatacccgg ccagacaccc tcacctgcgg tgcccagctg    1560
cccaggctga ggcaagagaa ggccagaaac catgcccatg ggtctctgc aaccgctggc    1620
caccttgtac ctgctgggga tgctggtcgc ttccgtgcta gctgtggaga agctgtgggt    1680
gactgtatac tatggggtgc ctgtgtggaa ggaggccacc accaccctgt tctgtgcctc    1740
tgatgccaag gcctatgaca ctgaggtcca aatgtctgg gccacccatg cctgtgtgcc    1800
cactgacccc aaccctcagg aggtggtgct ggagaatgtg actgagcact tcaacatgtg    1860
gaagaacaac atggtggagc agatgcagga ggacatcatc agcctgtggg accagagcct    1920
gaagccctgt gtgaagctga cccccctgtg tgtgaccctg aactgcaagg atgtgaatgc    1980
```

-continued

```
caccaacacc accaatgact ctgagggcac tatggagagg ggtgagatca agaactgcag    2040
cttcaacatc accaccagca tcagggatga ggtgcagaag gagtatgccc tgttctacaa    2100
gctggatgtg gtgcccattg acaacaacaa caccagctac aggctgatca gctgtgacac    2160
ctctgtgatc acccaggcct gccccaagat cagctttgag cccatcccca tccactactg    2220
tgcccctgct ggctttgcca tcctgaagtg caatgacaag accttcaatg caaaggccc     2280 ttgcaagaat gtgagcactg tgcagtgcac tcatggcatc aggcctgtgg tgagcaccca    2340
gctgctgctg aatggcagcc tggctgagga ggaggtggtg atcaggtctg acaacttcac    2400
caacaatgcc aagaccatca ttgtgcagct gaaggagtct gtggagatca actgcaccag    2460
gcccaacaac aacaccagga gagcattca cattggccct gcagggcct tctacaccac      2520 tggggagatc attggggaca tcaggcaggc ccactgcaac atcagcaggg ccaagtggaa    2580
tgacaccctg aagcagattg tgatcaagct gagggagcag tttgagaaca agaccattgt    2640
gttcaatcac agctctggtg gtgatcctga gattgtgatg cacagcttca actgtggtgg    2700
tgagttcttc tactgcaaca gcacccagct gttcaacagc acctggaaca caaacactga    2760
gggcagcaac aacactgagg gcaacaccat caccctgcct tgcaggatca gcagatcat    2820 caacatgtgg caggaggtgg gcaaggccat gtatgctcct cccatcaggg gccagatcag    2880
gtgcagcagc aacatcactg gcctgctgct gaccagggat ggtggcatca atgagaatgg    2940
cactgagatt ttcaggcctg gtggtgggga catgagggac aactggaggt ctgagctgta    3000
caagtacaag gtggtgaaga ttgagcccct tggtgtggct cccaccaagg ctaagcgcag    3060
ggtggtgcag agggagaagc gcgctgtggg ctgaggatcc cgagggtgag tgctcctgcc    3120
tggacgcatc ccggctatgc agccccagtc cagggcagca aggcaggccc cgtctgcctc    3180
ttcacccgga gcctctgccc gccccactca tgctcaggga gagggtcttc tggcttttc    3240 ccaggctctg ggcaggcaca ggctaggtgc ccctaaccca ggccctgcac acaaaggggc    3300
aggtgctggg ctcagacctg ccaagagcca tatccgggag gaccctgccc ctgacctaag   3360
cccaccccaa aggccaaact ctccactccc tcagctcgga caccttctct cctcccagat    3420
tccagtaact cccaatcttc tctctgcaga gcccaaatct tgtgacaaaa ctcacacatg    3480
cccaccgtgc ccaggtaagc cagcccaggc ctcgccctcc agctcaaggc gggacaggtg    3540
ccctagagta gcctgcatcc agggacaggc cccagccggg tgctgacacg tccacctcca    3600
tctcttcctc agcacctgaa ctcctggggg gaccgtcagt cttcctcttc cccccaaaac    3660
ccaaggacac cctcatgatc tcccggaccc ctgaggtcac atgcgtggtg gtggacgtga    3720
gccacgaaga ccctgaggtc aagttcaact ggtacgtgga cggcgtggag gtgcataatg    3780
ccaagacaaa gccgcgggag gagcagtaca acagcacgta ccgggtggtc agcgtcctca    3840
ccgtcctgca ccaggactgg ctgaatggca aggagtacaa gtgcaaggtc tccaacaaag    3900
ccctcccagc ccccatcgag aaaaccatct ccaaagccaa aggtgggacc cgtggggtgc    3960
gagggccaca tggacagagg ccggctcggc ccaccctctg ccctgagagt gaccgctgta    4020
ccaacctctg tcctacaggg cagccccgag aaccacaggt gtacaccctg cccccatccc    4080
gggatgagct gaccaagaac caggtcagcc tgacctgcct ggtcaaaggc ttctatccca    4140
gcgacatcgc cgtggagtgg gagagcaatg ggcagccgga gaacaactac aagaccacgc    4200
ctcccgtgct ggactccgac ggctccttct cctctacag caagctcacc gtggacaaga    4260
gcaggtggca gcaggggaac gtcttctcat gctccgtgat gcatgaggct ctgcacaacc    4320
```

```
actacacgca gaagagcctc tccctgtctc cgggtaaatg agtgcgacgg ccgcaggtaa    4380
gccagcccag gcctcgccct ccagctcaag gcgggacagg tgcccagag tagcctgcat    4440 ccagggacag gccccagccg ggtgctgaca cgtccacctc catctcttcc tcaggtctgc    4500
ccgggtggca tccctgtgac ccctccccag tgcctctcct ggccctggaa gttgccactc    4560
cagtgcccac cagccttgtc ctaataaaat taagttgcat cattttgtct gactaggtgt    4620
ccttctataa tattatgggg tggaggggg tggtatggag caaggggccc aagttaactt    4680
gtttattgca gcttataatg gttacaaata aagcaatagc atcacaaatt tcacaaataa    4740 agcattttt tcactgcatt ctagttgtgg tttgtccaaa ctcatcaatg tatcttatca    4800
tgtctggatc tgggcgtggt taagggtggg aaagaatata aaggtgggg gtcttatgta    4860 gttttgtatc tgttttgcag cagccgccgc cgccatgagc accaactcgt ttgatggaag    4920
cattgtgagc tcatatttga caacgcgcat gccccatgg gccggggtgc gtcagaatgt    4980
gatgggctcc agcattgatg gtcgcccgt cctgcccgca aactctacta ccttgaccta    5040
cgagaccgtg tctggaacgc cgttggagac tgcagcctcc gccgccgctt cagccgctgc    5100
agccaccgcc cgcgggattg tgactgactt tgctttcctg agcccgcttg caagcagtgc    5160
agcttcccgt tcatccgccc gcgatgacaa gttgacggct cttttggcac aattggattc    5220 tttgaccccgg gaacttaatg tcgtttctca gcagctgttg gatctgcgcc agcaggtttc    5280
tgccctgaag gcttcctccc ctcccaatgc ggtttaaaac ataaataaaa aaccagactc    5340
tgtttggatt tggatcaagc aagtgtcttg ctgtcttat ttaggggttt tgcgcgcgcg    5400
gtaggcccgg gaccagcggt ctcggtcgtt gagggtcctg tgtatttttt ccaggacgtg    5460
gtaaaggtga ctctggatgt tcagatacat gggcataagc ccgtctctgg ggtggaggta    5520
gcaccactgc agagcttcat gctgcggggt ggtgttgtag atgatccagt cgtagcagga    5580
gcgctgggcg tggtgcctaa aaatgtcttt cagtagcaag ctgattgcca ggggcaggcc    5640
cttggtgtaa gtgtttacaa agcggttaag ctgggatggg tgcatacgtg gggatatgag    5700
atgcatcttg gactgtattt ttaggttggc tatgttccca gccatatccc tccggggatt    5760
catgttgtgc agaaccacca gcacagtgta tccggtgcac ttgggaaatt tgtcatgtag    5820
cttagaagga aatgcgtgga agaacttgga gacgcccttg tgacctccaa gattttccat    5880
gcattcgtcc ataatgatgg caatgggccc acgggcggcg gcctgggcga agatatttct    5940
gggatcacta acgtcatagt tgtgttccag gatgagatcg tcataggcca tttttacaaa    6000
gcgcgggcgg agggtgccag actgcggtat aatggttcca tccggcccag gggcgtagtt    6060
accctcacag atttgcattt cccacgcttt gagttcagat ggggggatca tgtctacctg    6120
cggggcgatg aagaaaacgg tttccggggt aggggagatc agctgggaag aaagcaggtt    6180
cctgagcagc tgcgacttac cgcagccggt gggcccgtaa atcacaccta ttaccgggtg    6240
caactggtag ttaagagagc tgcagctgcc gtcatccctg agcagggggg ccacttcgtt    6300
aagcatgtcc ctgactcgca tgttttccct gaccaaatcc gccagaaggc gctcgccgcc    6360
cagcgatagc agttccttgca aggaagcaaa gttttttcaac ggtttgagac cgtccgccgt    6420
aggcatgctt ttgagcgttt gaccaagcag ttccaggcgg tcccacagct cggtcacctg    6480
ctctacggca tctcgatcca gcatatctcc tcgtttcgcg ggttggggcg ctttcgctg    6540 tacggcagta gtcggtgctc gtccagacgg gccagggtca tgtcttcca cgggcgcagg    6600 gtcctcgtca gcgtagtctg ggtcacggtg aaggggtgcg ctccgggctg cgcgctggcc    6660
agggtgcgct tgaggctggt cctgctggtg ctgaagcgct gccggtcttc gccctgcgcg    6720
```

```
tcggccaggt agcatttgac catggtgtca tagtccagcc cctccgcggc gtggcccttg   6780
gcgcgcagct tgcccttgga ggaggcgccg cacgagggc agtgcagact tttgagggcg   6840
tagagcttgg gcgcgagaaa taccgattcc ggggagtagg catccgcgcc gcaggccccg   6900
cagacggtct cgcattccac gagccaggtg agctctggcc gttcggggtc aaaaaccagg   6960
tttcccccat gctttttgat gcgtttctta cctctggttt ccatgagccg gtgtccacgc   7020
tcggtgacga aaggctgtc cgtgtccccg tatacagact tgagagggag tttaaacgaa    7080
ttcaatagct tgttgcatgg gcggcgatat aaaatgcaag gtgctgctca aaaaatcagg   7140
caaagcctcg cgcaaaaaag aaagcacatc gtagtcatgc tcatgcagat aaaggcaggt   7200
aagctccgga accaccacag aaaaagacac cattttctc tcaaacatgt ctgcgggttt     7260
ctgcataaac acaaataaa ataacaaaaa acatttaaa cattagaagc ctgtcttaca     7320
acaggaaaaa caaccttat aagcataaga cggactacgg ccatgccggc gtgaccgtaa    7380
aaaaactggt caccgtgatt aaaaagcacc accgacagct cctcggtcat gtccggagtc   7440
ataatgtaag actcggtaaa cacatcaggt tgattcatcg gtcagtgcta aaaagcgacc   7500
gaaatagccc gggggaatac atacccgcag gcgtagagac aacattacag cccccatagg   7560
aggtataaca aaattaatag gagagaaaaa cacataaaca cctgaaaaac cctcctgcct   7620
aggcaaaata gcaccctccc gctccagaac aacatacagc gcttcacagc ggcagcctaa   7680
cagtcagcct taccagtaaa aagaaaacc tattaaaaaa acaccactcg acacggcacc    7740
agctcaatca gtcacagtgt aaaaagggc caagtgcaga gcgagtatat ataggactaa    7800
aaaatgacgt aacggttaaa gtccacaaaa aacacccaga aaaccgcacg cgaacctacg   7860
cccagaaacg aaagccaaaa aacccacaac ttcctcaaat cgtcacttcc gttttcccac   7920
gttacgtaac ttcccatttt aagaaaacta caattcccaa cacatacaag ttactccgcc   7980
ctaaaaccta cgtcacccgc cccgttccca cgccccgcgc cacgtcacaa actccacccc   8040
ctcattatca tattggcttc aatccaaaat aaggtatatt attgatgatg ttaattaaca   8100
tgcatggatc catatgcggt gtgaaatacc gcacagatgc gtaaggagaa ataccgcat    8160
caggcgctct tccgcttcct cgctcactga ctcgctgcgc tcggtcgttc ggctgcggcg   8220
agcggtatca gctcactcaa aggcggtaat acgttatcc acagaatcag gggataacgc    8280
aggaaagaac atgtgagcaa aaggccagca aaaggccagg aaccgtaaaa aggccgcgtt   8340
gctggcgttt ttccataggc tccgcccccc tgacgagcat cacaaaaatc gacgctcaag   8400
tcagaggtgg cgaaacccga caggactata agataccag gcgtttcccc ctggaagctc    8460
cctcgtgcgc tctcctgttc cgaccctgcc gcttaccgga tacctgtccg cctttctccc   8520
ttcgggaagc gtggcgcttt ctcatagctc acgctgtagg tatctcagtt cggtgtaggt   8580
cgttcgctcc aagctgggct gtgtgcacga acccccgtt cagcccgacc gctgcgcctt    8640
atccggtaac tatcgtcttg agtccaaccc ggtaagacac gacttatcgc cactggcagc   8700
agccactggt aacaggatta gcagagcgag gtatgtaggc ggtgctacag agttcttgaa   8760
gtggtggcct aactacggct acactagaag gacagtattt ggtatctgcg ctctgctgaa   8820
gccagttacc ttcggaaaaa gagttggtag ctcttgatcc ggcaaacaaa ccaccgctgg   8880
tagcggtggt ttttttgttt gcaagcagca gattacgcgc agaaaaaaag gatctcaaga   8940
agatcctttg atcttttcta cggggtctga cgctcagtgg aacgaaaact cacgttaagg   9000
gattttggtc atgagattat caaaaaggat cttcacctag atccttttaa attaaaaatg   9060
```

-continued

```
aagtttttaaa tcaatctaaa gtatatatga gtaaacttgg tctgacagtt accaatgctt      9120
aatcagtgag gcacctatct cagcgatctg tctatttcgt tcatccatag ttgcctgact      9180
ccccgtcgtg tagataacta cgatacggga gggcttacca tctggcccca gtgctgcaat      9240
gataccgcga gacccacgct caccggctcc agatttatca gcaataaacc agccagccgg      9300
aagggccgag cgcagaagtg gtcctgcaac tttatccgcc tccatccagt ctattaattg      9360
ttgccgggaa gctagagtaa gtagttcgcc agttaatagt ttgcgcaacg ttgttgccat      9420
tgctgcagcc atgagattat caaaaaggat cttcacctag atccttttca cgtagaaagc      9480
cagtccgcag aaacggtgct gacccccgat gaatgtcagc tactgggcta tctggacaag      9540
ggaaaacgca agcgcaaaga gaaagcaggt agcttgcagt gggcttacat ggcgatagct      9600
agactgggcg gttttatgga cagcaagcga accggaattg ccagctgggg cgccctctgg      9660
taaggttggg aagccctgca agtaaactg gatggctttc tcgccgccaa ggatctgatg      9720
gcgcagggga tcaagctctg atcaagagac aggatgagga tcgtttcgca tgattgaaca      9780
agatggattg cacgcaggtt ctccggccgc ttgggtggag aggctattcg gctatgactg      9840
ggcacaacag acaatcggct gctctgatgc cgccgtgttc cggctgtcag cgcaggggcg      9900
cccggttctt tttgtcaaga ccgacctgtc cggtgccctg aatgaactgc aagacgaggc      9960
agcgcggcta tcgtggctgg ccacgacggg cgttccttgc gcagctgtgc tcgacgttgt     10020
cactgaagcg ggaagggact ggctgctatt gggcgaagtg ccggggcagg atctcctgtc     10080
atctcacctt gctcctgccg agaaagtatc catcatggct gatgcaatgc ggcggctgca     10140
tacgcttgat ccggctacct gcccattcga ccaccaagcg aaacatcgca tcgagcgagc     10200
acgtactcgg atggaagccg gtcttgtcga tcaggatgat ctggacgaag agcatcaggg     10260
gctcgcgcca gccgaactgt tcgccaggct caaggcgagc atgcccgacg gcgaggatct     10320
cgtcgtgacc catggcgatg cctgcttgcc gaatatcatg gtggaaaatg gccgcttttc     10380
tggattcatc gactgtggcc ggctgggtgt ggcggaccgc tatcaggaca tagcgttggc     10440
tacccgtgat attgctgaag agcttggcgg cgaatgggct gaccgcttcc tcgtgcttta     10500
cggtatcgcc gctcccgatt cgcagcgcat cgccttctat cgccttcttg acgagttctt     10560
ctgaattttg ttaaaatttt tgttaaatca gctcattttt taaccaatag gccgaaatcg     10620
gcaacatccc ttataaatca aaagaataga ccgcgatagg gttgagtgtt gttccagttt     10680
ggaacaagag tccactatta agaacgtgg actccaacgt caaagggcga aaaccgtct     10740
atcagggcga tggcccacta cgtgaaccat cacccaaatc aagttttttg cggtcgaggt     10800
gccgtaaagc tctaaatcgg aaccctaaag ggagccccg atttagagct tgacggggaa     10860
agccggcgaa cgtggcgaga aaggaaggga agaaagcgaa aggagcgggc gctagggcgc     10920
tggcaagtgt agcggtcacg ctgcgcgtaa ccaccacacc cgccgcgctta atgcgccgct     10980
acagggcgcg tccattcgcc attcaggatc gaattaattc ttaat                     11025
```

<210> SEQ ID NO 2
<211> LENGTH: 11933
<212> TYPE: DNA
<213> ORGANISM: Artificial Sequence
<220> FEATURE:
<223> OTHER INFORMATION: chimeric adenoviral vector DS2

<400> SEQUENCE: 2

```
taacatcatc aataatatac cttatttttgg attgaagcca atatgataat gagggggtgg       60
agtttgtgac gtggcgcggg gcgtgggaac ggggcgggtg acgtagtagt gtggcggaag      120
```

```
tgtgatgttg caagtgtggc ggaacacatg taagcgacgg atgtggcaaa agtgacgttt    180
ttggtgtgcg ccggtgtaca caggaagtga caattttcgc gcggttttag gcggatgttg    240
tagtaaattt gggcgtaacc gagtaagatt tggccatttt cgcgggaaaa ctgaataaga    300
ggaagtgaaa tctgaataat tttgtgttac tcatagcgcg taatactgct agagatctgg    360
cgaaagggga tgtgctgca aggcgattaa gttgggtaac gccagggttt cccagtcac     420
gacgttgtaa aacgacggcc agtgaattgt aatacgactc actatagggc gaattgggta    480
ctggccacag agcttggccc attgcatacg ttgtatccat atcataatat gtacatttat    540
attggctcat gtccaacatt accgccatgt tgacattgat tattgactag ttattaatag    600
taatcaatta cggggtcatt agttcatagc ccatatatgg agttccgcgt tacataactt    660
acggtaaatg gcccgcctgg ctgaccgccc aacgaccccc gcccattgac gtcaataatg    720
acgtatgttc ccatagtaac gccaataggg actttccatt gacgtcaatg ggtggagtat    780
ttacggtaaa ctgcccactt ggcagtacat caagtgtatc atatgccaag tacgccccct    840
attgacgtca atgacggtaa atggcccgcc tggcattatg cccagtacat gaccttatgg    900
gactttccta cttggcagta catctacgta ttagtcatcg ctattaccat ggtgatgcgg    960
ttttggcagt acatcaatgg gcgtggatag cggtttgact cacggggatt tccaagtctc   1020
caccccattg acgtcaatgg gagtttgttt tggcaccaaa atcaacggga ctttccaaaa   1080
tgtcgtaaca actccgcccc attgacgcaa atgggcggta ggcgtgtacg gtgggaggtc   1140
tatataagca gagctcgttt agtgaaccgt cagatcgcct ggagacgcca tccacgctgt   1200
tttgacctcc atagaagaca ccgggaccga tccagcctga ctctagccta gctctgaagt   1260
tggtggtgag gccctgggca ggttggtatc aaggttacaa acaggttta aggagaccaa   1320
tagaaactgg gcatgtggag acagagaaga ctcttgggtt tctgataggc actgactctc   1380
tctgcctatt ggtctatttt cccacccctta ggctgctggt ctgagcctag agatctctc   1440
gaggtcgacg gtatcgatgg gtacagcttc tagagatccc tcgacctcga gatccattgt   1500
gctctaaagg agatacccgg ccagacaccc tcacctgcgg tgcccagctg cccaggctga   1560
ggcaagagaa ggccagaaac catgcccatg ggtctctgc aaccgctggc caccttgtac   1620
ctgctgggga tgctggtcgc ttccgtgcta gctgtggaga gctgtgggt gactgtatac   1680
tatggggtgc ctgtgtggaa ggaggccacc accaccctgt tctgtgcctc tgatgccaag   1740
gcctatgaca ctgaggtcca caatgtctgg gccacccatg cctgtgtgcc cactgacccc   1800
aaccctcagg aggtggtgct ggagaatgtg actgagcact tcaacatgtg aagaacaac    1860
atggtggagc agatgcagga ggacatcatc agcctgtggg accagagcct gaagccctgt    1920
gtgaagctga ccccctgtg tgtgaccctg aactgcaagg atgtgaatgc caccaacacc    1980
accaatgact ctgagggcac tatggagagg ggtgagatca agaactgcag cttcaacatc    2040
accaccagca tcagggatga ggtgcagaag gagtatgccc tgttctacaa gctggatgtg    2100
gtgcccattg acaacaacaa caccagctac aggctgatca gctgtgacac ctctgtgatc    2160
acccaggcct gccccaagat cagctttgag cccatcccca tccactactg tgcccctgct    2220
ggctttgcca tcctgaagtg caatgacaag accttcaatg gcaaaggccc ttgcaagaat    2280
gtgagcactg tgcagtgcac tcatggcatc aggcctgtgg tgagcaccca gctgctgctg    2340
aatggcagcc tggctgagga ggaggtggtg atcaggtctg acaacttcac caacaatgcc    2400
aagaccatca ttgtgcagct gaaggagtct gtggagatca actgcaccag gcccaacaac    2460
```

```
aacaccagga agagcattca cattggccct ggcagggcct tctacaccac tggggagatc    2520
attggggaca tcaggcaggc ccactgcaac atcagcaggg ccaagtggaa tgacaccctg    2580
aagcagattg tgatcaagct gagggagcag tttgagaaca agaccattgt gttcaatcac    2640
agctctggtg gtgatcctga gattgtgatg cacagcttca actgtggtgg tgagttcttc    2700
tactgcaaca gcacccagct gttcaacagc acctggaaca caacactga gggcagcaac     2760 aacactgagg gcaacaccat caccctgcct tgcaggatca agcagatcat caacatgtgg    2820
caggaggtgg gcaaggccat gtatgctcct cccatcaggg ccagatcag gtgcagcagc     2880 aacatcactg gcctgctgct gaccagggat ggtggcatca atgagaatgg cactgagatt    2940
ttcaggcctg gtggtgggga catgagggac aactggaggt ctgagctgta caagtacaag    3000
gtggtgaaga ttgagcccct tggtgtggct cccaccaagg ctaagcgcag gtggtgcag     3060 agggagaagc gcgctgtggg ctgaggatcc cgagggtgag tgctcctgcc tggacgcatc    3120
ccggctatgc agcccagtc cagggcagca aggcaggccc cgtctgcctc ttcacccgga     3180
gcctctgccc gccccactca tgctcaggga gagggtcttc tggcttttc ccaggctctg     3240 ggcaggcaca ggctaggtgc ccctaaccca ggccctgcac acaaaggggc aggtgctggg    3300
ctcagacctg ccaagagcca tatccgggag gaccctgccc ctgacctaag cccacccaa    3360 aggccaaact ctccactccc tcagctcgga caccttctct cctcccagat tccagtaact    3420
cccaatcttc tctctgcaga gcccaaatct tgtgacaaaa ctcacacatg cccaccgtgc    3480
ccaggtaagc cagcccaggc ctcgcccctcc agctcaaggc gggacaggtg ccctagagta    3540
gcctgcatcc agggacaggc cccagccggg tgctgacacg tccacctcca tctcttcctc    3600
agcacctgaa ctcctggggg gaccgtcagt cttcctcttc cccccaaaac caaggacac     3660 cctcatgatc tcccggaccc ctgaggtcac atgcgtggtg gtggacgtga gccacgaaga    3720
ccctgaggtc aagttcaact ggtacgtgga cggcgtggag gtgcataatg ccaagacaaa    3780
gccgcgggag gagcagtaca acagcacgta ccgggtggtc agcgtcctca ccgtcctgca    3840
ccaggactgg ctgaatggca aggagtacaa gtgcaaggtc tccaacaaag ccctcccagc    3900
ccccatcgag aaaaccatct ccaaagccaa aggtgggacc cgtggggtgc gagggccaca    3960
tggacagagg ccggctcggc ccaccctctg ccctgagagt gaccgctgta ccaacctctg    4020
tcctacaggg cagccccgag aaccacaggt gtacaccctg cccccatccc gggatgagct    4080
gaccaagaac caggtcagcc tgacctgcct ggtcaaaggc ttctatccca gcgacatcgc    4140
cgtggagtgg gagagcaatg ggcagccgga gaacaactac aagaccacgc ctcccgtgct    4200
ggactccgac ggctccttct tcctctacag caagctcacc gtggacaaga gcaggtggca    4260
gcaggggaac gtcttctcat gctccgtgat gcatgaggct ctgcacaacc actacacgca    4320
gaagagcctc tccctgtctc cgggtaaatg agtgcgacgg ccgcaggtaa gccagcccag    4380
gcctcgccct ccagctcaag gcgggacagg tgccctagat agcctgcat ccaggacag     4440 gccccagccg ggtgctgaca cgtccacctc catctcttcc tcaggtctgc ccgggtggca    4500
tccctgtgac ccctccccag tgcctctcct ggccctggaa gttgccactc cagtgcccac    4560
cagccttgtc ctaataaaat taagttgcat cattttgtct gactaggtgt ccttctataa    4620
tattatgggg tggagggggg tggtatggag caaggggccc aagttaactt gtttattgca    4680
gcttataatg gttacaaata aagcaatagc atcacaaatt tcacaaataa agcatttttt    4740
tcactgcatt ctagttgtgg tttgtccaaa ctcatcaatg tatcttatca tgtctggatc    4800
tgggcgtggt taagggtggg aaagaatata taaggtgggg gtcttatgta gttttgtatc    4860
```

```
tgttttgcag cagccgccgc cgccatgagc accaactcgt tgatggaag cattgtgagc    4920 tcatcggcgg ccgccctatt ctatagtgtc acctaaatgc tagagctcgc tgatcagcct    4980
cgactgtgcc ttctagttgc cagccatctg ttgtttgccc ctcccccgtg ccttccttga    5040
ccctggaagg tgccactccc actgtccttt cctaataaaa tgaggaaatt gcatcgcatt    5100
gtctgagtag gtgtcattct attctggggg gtggggtggg gcaggacagc aaggggagg     5160 attgggaaga caatagcagg catgctgggg atgcggtggg ctctatggct tctgaggcgg    5220
aaagaaccta tggcttctga ggcggaaaga accaaccacc gcggtggcgg ccgccacaca    5280
aaaaaccaac acacagatgt aatgaaaata aagatatttt atttctagag aaacgatatg    5340
ggctgaatac ggatccgtat tcagcccata tcgtttcctg caggaattcg ccctttagat    5400
atcatcgatg tctcggcggt ggtggcgcgt cgcgccgctg ggttttatag ggcgccgccg    5460
cggccgctcg agccataaaa ggcaactttc ggaacggcgc acgctgattg ccccgcgcc     5520 gctcactcac cggcttcgcc gcacagtgca gcattttttt accccctctc ccctcctttt    5580
gcgaaaaaaa aaagagcga gagcgagatt gaggaagagg aggagggaga gttttggcgt    5640
tggccgcctt ggggtgctgg gcgtcgacga tatctaaggg cgaattcgat atcaagctag    5700
cttgtcgact cgaagatctg ggcgtggtta agggtgggaa agaatatata aggtgggggt    5760
cttatgtagt tttgtatctg ttttgcagca gccgccgccg ccatgagcac caactcgttt    5820
gatggaagca ttgtgagctc atatttgaca acgcgcatgc cccatgggc cggggtgcgt     5880 cagaatgtga tgggctccag cattgatggt cgccccgtcc tgcccgcaaa ctctactacc    5940
ttgacctacg agaccgtgtc tggaacgccg ttggagactg cagcctccgc cgccgcttca    6000
gccgctgcag ccaccgcccg cgggattgtg actgactttg ctttcctgag cccgcttgca    6060
agcagtgcag cttcccgttc atccgcccgc gatgacaagt tgacggctct tttggcacaa    6120
ttggattctt tgacccggga acttaatgtc gtttctcagc agctgttgga tctgcgccag    6180
caggtttctg ccctgaaggc ttcctcccct cccaatgcgg tttaaaacat aaataaaaaa    6240
ccagactctg tttggatttg gatcaagcaa gtgtcttgct gtctttattt aggggttttg    6300
cgcgcgcggt aggcccggga ccagcggtct cggtcgttga gggtcctgtg tatttttttcc   6360 aggacgtggt aaaggtgact ctggatgttc agatacatgg gcataagccc gtctctgggg    6420
tggaggtagc accactgcag agcttcatgc tgcggggtgg tgttgtagat gatccagtcg    6480
tagcaggagc gctgggcgtg gtgcctaaaa atgtctttca gtagcaagct gattgccagg    6540
ggcaggccct tggtgtaagt gtttacaaag cggttaagct gggatgggtg catacgtggg    6600
gatatgagat gcatcttgga ctgtattttt aggttggcta tgttcccagc catatccctc    6660
cggggattca tgttgtgcag aaccaccagc acagtgtatc cggtgcactt gggaaatttg    6720
tcatgtagct tagaaggaaa tgcgtggaag aacttggaga cgcccttgtg acctccaaga    6780
ttttccatgc attcgtccat aatgatggca atgggcccac gggcggcggc ctgggcgaag    6840
atatttctgg gatcactaac gtcatagttg ttgtccagga tgagatcgtc ataggccatt    6900
tttacaaagc gcgggcggag ggtgccagac tgcggtataa tggttccatc cggcccaggg    6960
gcgtagttac cctcacagat ttgcatttcc cacgctttga gttcagatgg ggggatcatg    7020
tctacctgcg gggcgatgaa gaaaacggtt tccggggtag gggagatcag ctgggaagaa    7080
agcaggttcc tgagcagctg cgacttaccg cagccggtgg gccgtaaat cacacctatt     7140 accgggtgca actggtagtt aagagagctg cagctgccgt catccctgag cagggggcc     7200
```

```
acttcgttaa gcatgtccct gactcgcatg ttttccctga ccaaatccgc cagaaggcgc    7260
tcgccgccca gcgatagcag ttcttgcaag gaagcaaagt ttttcaacgg tttgagaccg    7320
tccgccgtag gcatgctttt gagcgtttga ccaagcagtt ccaggcggtc ccacagctcg    7380
gtcacctgct ctacggcatc tcgatccagc atatctcctc gtttcgcggg ttggggcggc    7440
tttcgctgta cggcagtagt cggtgctcgt ccagacgggc cagggtcatg tctttccacg    7500
ggcgcagggt cctcgtcagc gtagtctggg tcacggtgaa ggggtgcgct ccgggctgcg    7560
cgctggccag ggtgcgcttg aggctggtcc tgctggtgct gaagcgctgc cggtcttcgc    7620
cctgcgcgtc ggccaggtag catttgacca tggtgtcata gtccagcccc tccgcggcgt    7680
ggcccttggc gcgcagcttg cccttggagg aggcgccgca cgaggggcag tgcagacttt    7740
tgagggcgta gagcttgggc gcgagaaata ccgattccgg ggagtaggca tccgcgccgc    7800
aggccccgca gacggtctcg cattccacga gccaggtgag ctctggccgt tcggggtcaa    7860
aaaccaggtt tccccatgc tttttgatgc gtttcttacc tctggtttcc atgagccggt    7920
gtccacgctc ggtgacgaaa aggctgtccg tgtccccgta tacagacttg agagggagtt    7980
taaacgaatt caatagcttg ttgcatgggc ggcgatataa aatgcaaggt gctgctcaaa    8040
aaatcaggca aagcctcgcg caaaaaagaa agcacatcgt agtcatgctc atgcagataa    8100
aggcaggtaa gctccggaac caccacagaa aaagacacca ttttctctc aaacatgtct    8160 gcgggtttct gcataaacac aaaataaaat aacaaaaaaa catttaaaca ttagaagcct    8220
gtcttcaaac aggaaaaaca acccttataa gcataagacg gactacgcc atgccggcgt    8280 gaccgtaaaa aaactggtca ccgtgattaa aaagcaccac cgacagctcc tcggtcatgt    8340
ccggagtcat aatgtaagac tcggtaaaca catcaggttg attcatcggt cagtgctaaa    8400
aagcgaccga aatagcccgg gggaatacat acccgcaggc gtagagacaa cattacagcc    8460
cccataggag gtataacaaa attaatagga gagaaaaaca cataaacacc tgaaaaaccc    8520
tcctgcctag gcaaaatagc accctcccgc tccagaacaa catacagcgc ttcacagcgg    8580
cagcctaaca gtcagcctta ccagtaaaaa agaaaaccta ttaaaaaaac accactcgac    8640
acggcaccag ctcaatcagt cacagtgtaa aaaagggcca agtgcagagc gagtatatat    8700
aggactaaaa aatgacgtaa cggttaaagt ccacaaaaaa cacccagaaa accgcacgcg    8760
aacctacgcc cagaaacgaa agccaaaaaa cccacaactt cctcaaatcg tcacttccgt    8820
tttcccacgt tacgtaactt cccatttta gaaaactaca attcccaaca catacaagtt    8880
actccgccct aaaacctacg tcacccgccc cgttcccacg ccccgcgcca cgtcacaaac    8940
tccaccccct cattatcata ttggcttcaa tccaaaataa ggtatattat tgatgatgtt    9000
aattaacatg catggatcca tatgcggtgt gaaataccgc acagatgcgt aaggagaaaa    9060
taccgcatca ggcgctcttc cgcttcctcg ctcactgact cgctgcgctc ggtcgttcgg    9120
ctgcggcgag cggtatcagc tcactcaaag gcggtaatac ggttatccac agaatcaggg    9180
gataacgcag gaaagaacat gtgagcaaaa ggccagcaaa aggccaggaa ccgtaaaaag    9240
gccgcgttgc tggcgttttt ccataggctc cgcccccctg acgagcatca caaaaatcga    9300
cgctcaagtc agaggtggcg aaacccgaca ggactataaa gataccaggc gtttccccct    9360
ggaagctccc tcgtgcgctc tcctgttccg accctgccgc ttaccggata cctgtccgcc    9420
tttctccctt cgggaagcgt ggcgctttct catagctcac gctgtaggta tctcagttcg    9480
gtgtaggtcg ttcgctccaa gctgggctgt gtgcacgaac cccccgttca gcccgaccgc    9540
tgcgccttat ccggtaacta tcgtcttgag tccaacccgg taagacacga cttatcgcca    9600
```

```
ctggcagcag ccactggtaa caggattagc agagcgaggt atgtaggcgg tgctacagag    9660
ttcttgaagt ggtggcctaa ctacggctac actagaagga cagtatttgg tatctgcgct    9720
ctgctgaagc cagttacctt cggaaaaaga gttggtagct cttgatccgg caaacaaacc    9780
accgctggta gcggtggttt ttttgtttgc aagcagcaga ttacgcgcag aaaaaaagga    9840
tctcaagaag atcctttgat cttttctacg gggtctgacg ctcagtggaa cgaaaactca    9900
cgttaaggga ttttggtcat gagattatca aaaaggatct tcacctagat ccttttaaat    9960
taaaaatgaa gttttaaatc aatctaaagt atatatgagt aaacttggtc tgacagttac   10020
caatgcttaa tcagtgaggc acctatctca gcgatctgtc tatttcgttc atccatagtt   10080
gcctgactcc ccgtcgtgta gataactacg atacgggagg gcttaccatc tggccccagt   10140
gctgcaatga taccgcgaga cccacgctca ccggctccag atttatcagc aataaaccag   10200
ccagccggaa gggccgagcg cagaagtggt cctgcaactt tatccgcctc catccagtct   10260
attaattgtt gccgggaagc tagagtaagt agttcgccag ttaatagttt gcgcaacgtt   10320
gttgccattg ctgcagccat gagattatca aaaaggatct tcacctagat ccttttcacg   10380
tagaaagcca gtccgcagaa acggtgctga ccccggatga atgtcagcta ctgggctatc   10440
tggacaaggg aaaacgcaag cgcaaagaga agcaggtag cttgcagtgg gcttacatgg   10500
cgatagctag actgggcggt tttatggaca gcaagcgaac cggaattgcc agctggggcg   10560
ccctctggta aggttgggaa gccctgcaaa gtaaactgga tggctttctc gccgccaagg   10620
atctgatggc gcagggatc aagctctgat caagagacag gatgaggatc gtttcgcatg   10680
attgaacaag atggattgca cgcaggttct ccggccgctt gggtggagag gctattcggc   10740
tatgactggg cacaacagac aatcggctgc tctgatgccg ccgtgttccg gctgtcagcg   10800
caggggcgcc cggttctttt tgtcaagacc gacctgtccg gtgccctgaa tgaactgcaa   10860
gacgaggcag cgcggctatc gtggctggcc acgacgggcg ttccttgcgc agctgtgctc   10920
gacgttgtca ctgaagcggg aagggactgg ctgctattgg gcgaagtgcc ggggcaggat   10980
ctcctgtcat ctcaccttgc tcctgccgag aaagtatcca tcatggctga tgcaatgcgg   11040
cggctgcata cgcttgatcc ggctacctgc ccattcgacc accaagcgaa acatcgcatc   11100
gagcgagcac gtactcggat ggaagccggt cttgtcgatc aggatgatct ggacgaagag   11160 catcagggc tcgcgccagc cgaactgttc gccaggctca aggcgagcat gcccgacggc   11220
gaggatctcg tcgtgaccca tggcgatgcc tgcttgccga atatcatggt ggaaaatggc   11280
cgcttttctg gattcatcga ctgtggccgg ctgggtgtgg cggaccgcta tcaggacata   11340
gcgttggcta cccgtgatat tgctgaagag cttggcggcg aatgggctga ccgcttcctc   11400
gtgctttacg gtatcgccgc tcccgattcg cagcgcatcg ccttctatcg ccttcttgac   11460
gagttcttct gaattttgtt aaatttttg ttaaatcagc tcattttta accaataggc   11520 cgaaatcggc aacatccctt ataaatcaaa agaatagacc gcgatagggt tgagtgttgt   11580
tccagtttgg aacaagagtc cactattaaa gaacgtggac tccaacgtca agggcgaaa   11640 aaccgtctat cagggcgatg gcccactacg tgaaccatca cccaaatcaa gttttttgcg   11700
gtcgaggtgc cgtaaagctc taaatcggaa ccctaaaggg agcccccgat ttagagcttg   11760
acggggaaag ccggcgaacg tggcgagaaa ggaagggaag aaagcgaaag gagcgggcgc   11820
tagggcgctg gcaagtgtag cggtcacgct gcgcgtaacc accacacccg cgcgcttaat   11880
gcgccgctac agggcgcgtc cattcgccat tcaggatcga attaattctt aat   11933
```

<210> SEQ ID NO 3
<211> LENGTH: 46
<212> TYPE: DNA
<213> ORGANISM: Artificial Sequence
<220> FEATURE:
<223> OTHER INFORMATION: toll-like receptor 3 (TLR-3) agonist

<400> SEQUENCE: 3

```
gaaacgatat gggctgaata cttaagtatt cagcccatat cgtttc        46
```

<210> SEQ ID NO 4
<211> LENGTH: 1190
<212> TYPE: DNA
<213> ORGANISM: Artificial Sequence
<220> FEATURE:
<223> OTHER INFORMATION: toll-like receptor 3 (TLR-3) agonist

<400> SEQUENCE: 4

```
cgggcccccc ctcgaggtcg acggtatcga taagcttgat atcgaattcg cccttagata      60
tcgtcgacgc ccagcacccc aaggcggcca acgccaaaac tctccctcct cctcttcctc     120
aatctcgctc tcgctctttt tttttttcgc aaaaggaggg gagaggggt aaaaaaatgc      180
tgcactgtgc ggcgaagccg gtgagtgagc ggcgcggggc caatcagcgt gcgccgttcc     240
gaaagttgcc ttttatggct cgagcggccg cggcggcgcc ctataaaacc cagcggcgcg     300
acgcgccacc accgccgaga catcgatgat atctaaaggg cgaattcctg cagcccgggg     360
gatccactag tctagatgca tgctcgagcg gccgccagtg tgatggatat ctgcagaatt     420
cgcccttcag ctgcggatcc attcgccatt caggctgcgc aactgttggg aagggcgatc     480
ggtgcgggcc tcttcgctat tacgccagct ggcgaaaggg gatgtgctg caaggcgatt      540
aagttgggta acgccagggt tttcccagtc acgacgttgt aaaacgacgg ccagtgaatt     600
gtaatacgac tcactatagg gcgaattggg taccgggccc cccctcgagg tcgacggtat     660
cgataagctt gatatcgaat tcctgcagcc cggggggatcc actagtttct agaaataaaa    720
tatctttatt ttcattacat ctgtgtgttg gttttttgtg tggcggccgc caccgcggtg     780
gagctatcga attcaagctt gtcgactcga agatcctaga ctagtggatc ccccgggctg     840
caggaattcg cccttagat atcatcgatg tctcggcgt ggtggcgcgt cgcgccgctg       900
ggttttatag ggcgccgccg cggccgctcg agccataaaa ggcaactttc ggaacggcgc     960
acgctgattg gccccgcgcc gctcactcac cggcttcgcc gcacagtgca gcatttttt     1020
acccctctc ccctcctttt gcgaaaaaaa aaagagcga gagcgagatt gaggaagagg      1080
aggagggaga gttttggcgt tggccgcctt ggggtgctgg gcgtcgacga tatctaaggg    1140
cgaattcgat atcaagctta tcgataccgt cgacctcgag ggggggcccg               1190
```

<210> SEQ ID NO 5
<211> LENGTH: 1757
<212> TYPE: DNA
<213> ORGANISM: Artificial Sequence
<220> FEATURE:
<223> OTHER INFORMATION: toll-like receptor 3 (TLR-3) agonist

<400> SEQUENCE: 5

```
cgggcccccc ctcgaggtcg acggtatcga taagcttgat atcgaattcg cccttagata      60
tcgtcgacgc ccagcacccc aaggcggcca acgccaaaac tctccctcct cctcttcctc     120
aatctcgctc tcgctctttt tttttttcgc aaaaggaggg gagaggggt aaaaaaatgc      180
tgcactgtgc ggcgaagccg gtgagtgagc ggcgcggggc caatcagcgt gcgccgttcc     240
```

```
gaaagttgcc ttttatggct cgagcggccg cggcggcgcc ctataaaacc cagcggcgcg    300
acgcgccacc accgccgaga catcgatgat atctaaaggg cgaattcctg cagcccgggg    360
gatccactag tctagatgca tgctcgagcg gccgccagtg tgatggatat ctgcagaatt    420
cgcccttcag ctgcggatcc attcgccatt caggctgcgc aactgttggg aagggcgatc    480
ggtgcgggcc tcttcgctat tacgccagct ggcgaaaggg ggatgtgctg caaggcgatt    540
aagttgggta acgccagggt tttcccagtc acgacgttgt aaaacgacgg ccagtgaatt    600
gtaatacgac tcactatagg gcgaattggg taccgggccc ccctcgaggt cgacggtat    660 cgataagctt gatatcgaat cctgcagcc cggggatcc actagtttct agaaataaaa    720
tatctttatt ttcattacat ctgtgtgttg gttttttgtg tggcggccgc caccgcggtg    780
gagctatcga attcaagctt gtcgactcga agatcgtaca caggaagtga caattttcgc    840
gcggttttag gcggatgttg tagtaaattt gggcgtaacc gagtaagatt tggccatttt    900
cgcgggaaaa ctgaataaga ggaagtgaaa tctgaataat tttgtgttac tcatagcgcg    960
taatactggt accgggcccc ccctcgaggt cgacggtatc gataagcttg atatcgaatt    1020
cgcccttaga tatcgtcgac gcccagcacc ccaaggcggc caacgccaaa actctccctc    1080
ctcctcttcc tcaatctcgc tctcgctctt ttttttttc gcaaaaggag gggaggggg    1140 gtaaaaaat gctgcactgt gcggcgaagc cggtgagtga gcggcgcggg gccaatcagc    1200
gtgcgccgtt ccgaaagttg cctttatgg ctcgagcggc cgcggcgcg ccctataaaa    1260 cccagcggcg cgacgcgcca ccaccgccga gacatcgatg atatctaaag gcgaattcc    1320 tgcagcccgg gggatccact agtctagaac tagtggatcc cccgggctgc aggaattcga    1380
tatcaagctt atcgataccg tcgacctcga ggggggccc ggtacccaat cgccctata    1440 gtgagtcgta ttacaattca ctggccgtcg ttttacaacg tcgtgactgg gaaaaccctg    1500
gcgttaccca acttaatcgc cttgcagcac atccccccttt cgccagctgg cgtaatagcg    1560
aagaggcccg caccgatcgc ccttcccaac agttgcgcag cctgaatggc gaatggatcc    1620
gcagctgaag gcgaattct gcagatatcc atcacactgg cggccgctcg agcatgcatc    1680
tagaaataaa atatctttat tttcattaca tctgtgtgtt ggttttttgt gtggcggccg    1740
ccaccgcggt ggagcta                                                  1757

<210> SEQ ID NO 6
<211> LENGTH: 10153
<212> TYPE: DNA
<213> ORGANISM: Artificial Sequence
<220> FEATURE:
<223> OTHER INFORMATION: chimeric adenoviral vector encoding influenza
      hemagglutinin (HA) and TLR-3 agonist luc in same
      orientation

<400> SEQUENCE: 6
taacatcatc aataatatac cttattttgg attgaagcca atatgataat gagggggtgg     60
agtttgtgac gtggcgcggg gcgtgggaac ggggcgggtg acgtagtagt gtggcggaag    120
tgtgatgttg caagtgtggc ggaacacatg taagcgacgg atgtggcaaa agtgacgttt    180
ttggtgtgcg ccggtgtaca caggaagtga caattttcgc gcggttttag gcggatgttg    240
tagtaaattt gggcgtaacc gagtaagatt tggccatttt cgcgggaaaa ctgaataaga    300
ggaagtgaaa tctgaataat tttgtgttac tcatagcgcg taatactgct agagatctgg    360
cgaaaggggg atgtgctgca aggcgattaa gttgggtaac gccagggttt tcccagtcac    420
```

```
gacgttgtaa aacgacggcc agtgaattgt aatacgactc actatagggc gaattgggta    480
ctggccacag agcttggccc attgcatacg ttgtatccat atcataatat gtacatttat    540
attggctcat gtccaacatt accgccatgt tgacattgat tattgactag ttattaatag    600
taatcaatta cggggtcatt agttcatagc ccatatatgg agttccgcgt tacataactt    660
acggtaaatg gcccgcctgg ctgaccgccc aacgaccccc gcccattgac gtcaataatg    720
acgtatgttc ccatagtaac gccaataggg actttccatt gacgtcaatg ggtggagtat    780
ttacggtaaa ctgcccactt ggcagtacat caagtgtatc atatgccaag tacgccccct    840
attgacgtca atgacggtaa atggcccgcc tggcattatg cccagtacat gaccttatgg    900
gactttccta cttggcagta catctacgta ttagtcatcg ctattaccat ggtgatgcgg    960
ttttggcagt acatcaatgg gcgtggatag cggtttgact cacggggatt tccaagtctc   1020 cacccccattg acgtcaatgg gagtttgttt tggcaccaaa atcaacggga ctttccaaaa   1080
tgtcgtaaca actccgcccc attgacgcaa atgggcggta ggcgtgtacg gtgggaggtc   1140
tatataagca gagctcgttt agtgaaccgt cagatcgcct ggagacgcca tccacgctgt   1200
tttgacctcc atagaagaca ccgggaccga tccagcctga ctctagccta gctctgaagt   1260
tggtggtgag gccctgggca ggttggtatc aaggttacaa gacaggttta aggagaccaa   1320
tagaaactgg gcatgtggag acagagaaga ctcttgggtt tctgataggc actgactctc   1380
tctgcctatt ggtctatttt cccacccttag gctgctggt ctgagcctag agatctctc   1440 gaggtcgacg gtatcgatgc caccatggag aaaatcgtcc tgttgctcgc tattgtgtct   1500
ctagtgaaga gcgatcaaat ttgtatcggc taccatgcca ataactcaac agagcaggtc   1560
gatactatca tggagaaaaa cgtaacagtt actcatgccc aagacatctt ggaaaagacc   1620
cacaacggca aactttgcga cctggatgga gtgaagcccc tgatcctccg ggactgttca   1680
gtcgctggtt ggctgctcgg gaaccctatg tgtgatgagt ttatcaacgt gcctgaatgg   1740
tcttacattg tggagaaggc taaccctacc aatgacctct gctatcctgg gtcatttaac   1800
gattacgagg aactgaaaca cctgttgtct agaattaacc actttgaaaa gatacagatt   1860
atacccaagt ctagttggag tgatcacgaa gcctcctcag gcgttagctc agcgtgtccc   1920
tatctgggct ctccatcctt ctttagaaat gtggtctggt taatcaaaaa gaacagtacc   1980
tacccaacca tcaaaaagtc ttataacaat accaatcagg aggacctgct cgtgttgtgg   2040
ggtatccatc acccgaacga cgccgctgaa cagactaggc tgtatcagaa ccccactaca   2100
tacatcagta ttggcacgag tactctgaac cagcgattag tgccaaagat tgcaacacgg   2160
agcaaagtaa atgggcaatc tggcaggatg gagttttct ggacaatctt aaaacccaac   2220
gatgcgataa atttcgagtc caatggcaat ttcatcgccc ctgaatacgc ctataagatc   2280
gtgaaaaagg gggactctgc aattatgaag tccgaattag agtatggcaa ttgcaacacg   2340
aagtgccaga caccaatggg agccattaat agctcaatgc ccttccataa tattcatcca   2400
ttgaccattg gggagtgccc aaagtacgtg aagtccaacc gcctggtcct cgcaaccggt   2460
ctaagaaata gcccgcagag agaatcgcgg aggaagaaac gtggcctgtt tggcgcgatt   2520
gccggattca tcgagggagg ctggcagggt atggtcgatg gttggtacgg ataccaccat   2580
agcaacgaac aggggtccgg ctatgcagca gataaggaga gcactcagaa agctattgac   2640
ggagttacaa acaaggttaa tagtattata gataaaatga acacgcaatt cgaggccgtt   2700
gggagggagt ttaacaatct ggaacgccgg atcgaaaatc tgaataagaa aatggaagac   2760
ggcttccttg acgtgtggac ttataatgca gagctgcttg tactcatgga gaacgagagg   2820
```

```
accctggatt tccacgatag caacgtgaag aacctttacg acaaggtgag acttcagctc    2880
cgagacaacg ccaaggagct ggggaatgga tgcttcgagt tttaccacaa atgtgacaat    2940
gagtgcatgg aaagtatacg caacgggacc tacaattacc ctcagtatag cgaagaggct    3000
cggctcaaac gcgaagagat aagcggggtg aaattggaat caatcggaac atatcaaatc    3060
ctgtccatct attccaccgt cgcctcttcg ctggccctcg ctatcatgat ggctggtctg    3120
tccctatgga tgtgttccaa tggaagcctt cagtgccgta tttgtatatg agcggccgcc    3180
ctattctata gtgtcaccta aatgctagag ctcgctgatc agcctcgact gtgccttcta    3240
gttgccagcc atctgttgtt tgcccctccc ccgtgccttc cttgaccctg aaggtgcca     3300
ctcccactgt cctttcctaa taaaatgagg aaattgcatc gcattgtctg agtaggtgtc    3360
attctattct gggggtggg gtgggcagg acagcaaggg ggaggattgg gaagacaata      3420
gcaggcatgc tggggatgcg gtgggctcta tggcttctga ggcggaaaga accaaccacc    3480
gcggtggcgg ccgccacaca aaaaaccaac acacagatgt aatgaaaata aagatatttt    3540
atttctagag aaacgatatg ggctgaatac ggatccgtat tcagcccata tcgtttcctg    3600
caggaattcg ccctttagat atcatcgatg tctcggcggt ggtggcgcgt cgcgccgctg    3660
ggttttatag ggcgccgccg cggccgctcg agccataaaa ggcaactttc ggaacgcgc    3720
acgctgattg gccccgcgcc gctcactcac cggcttcgcc gcacagtgca gcatttttt    3780
accccctctc ccctcctttt gcgaaaaaaa aaaagagcga gagcgagatt gaggaagagg    3840
aggagggaga gttttggcgt tggccgcctt ggggtgctgg gcgtcgacga tatctaaggg    3900
cgaattcgat atcaagctag cttgtcgact cgaagatctg ggcgtggtta agggtgggaa    3960
agaatatata aggtgggggt cttatgtagt tttgtatctg ttttgcagca gccgccgccg    4020
ccatgagcac caactcgttt gatggaagca ttgtgagctc atatttgaca acgcgcatgc    4080
ccccatgggc cggggtgcgt cagaatgtga tgggctccag cattgatggt cgccccgtcc    4140
tgcccgcaaa ctctactacc ttgacctacg agaccgtgtc tggaacgccg ttggagactg    4200
cagcctccgc cgccgcttca gccgctgcag ccaccgcccg cgggattgtg actgactttg    4260
cttttcctgag cccgcttgca agcagtgcag cttcccgttc atccgcccgc gatgacaagt    4320
tgacggctct tttggcacaa ttggattctt tgacccggga acttaatgtc gtttctcagc    4380
agctgttgga tctgcgccag caggtttctg ccctgaaggc ttcctcccct cccaatgcgg    4440
tttaaaacat aaataaaaaa ccagactctg tttggatttg gatcaagcaa gtgtcttgct    4500
gtctttattt aggggttttg cgcgcgcggt aggcccggga ccagcggtct cggtcgttga    4560
gggtcctgtg tatttttttcc aggacgtggt aaaggtgact ctggatgttc agatacatgg    4620
gcataagccc gtctctgggg tggaggtagc accactgcag agcttcatgc tgcgggtgg    4680
tgttgtagat gatccagtcg tagcaggagc gctgggcgtg gtgcctaaaa atgtctttca    4740
gtagcaagct gattgccagg ggcaggccct tggtgtaagt gtttacaaag cggttaagct    4800
gggatgggtg catacgtggg gatatgagat gcatcttgga ctgtatttt aggttggcta    4860
tgttcccagc catatccctc cggggattca tgttgtgcag aaccaccagc acagtgtatc    4920
cggtgcactt gggaaatttg tcatgtagct tagaaggaaa tgcgtggaag aacttggaga    4980
cgcccttgtg acctccaaga ttttccatgc attcgtccat aatgatggca atgggcccac    5040
gggcggcggc ctgggcgaag atatttctgg gatcactaac gtcatagttg tgttccagga    5100
tgagatcgtc ataggccatt tttacaaagc gcgggcggag ggtgccagac tgcggtataa    5160
```

```
tggttccatc cggcccaggg gcgtagttac cctcacagat ttgcatttcc cacgctttga    5220
gttcagatgg ggggatcatg tctacctgcg ggcgatgaa gaaaacggtt tccggggtag    5280
gggagatcag ctgggaagaa agcaggttcc tgagcagctg cgacttaccg cagccggtgg    5340
gcccgtaaat cacacctatt accgggtgca actggtagtt aagagagctg cagctgccgt    5400
catccctgag caggggggcc acttcgttaa gcatgtccct gactcgcatg ttttccctga    5460
ccaaatccgc cagaaggcgc tcgccgccca gcgatagcag ttcttgcaag gaagcaaagt    5520
ttttcaacgg tttgagaccg tccgccgtag gcatgctttt gagcgtttga ccaagcagtt    5580
ccaggcggtc ccacagctcg gtcacctgct ctacggcatc tcgatccagc atatctcctc    5640
gtttcgcggg ttggggcggc tttcgctgta cggcagtagt cggtgctcgt ccagacgggc    5700
cagggtcatg tctttccacg ggcgcagggt cctcgtcagc gtagtctggg tcacggtgaa    5760
ggggtgcgct ccgggctgcg cgctggccag ggtgcgcttg aggctggtcc tgctggtgct    5820
gaagcgctgc cggtcttcgc cctgcgcgtc ggccaggtag catttgacca tggtgtcata    5880
gtccagcccc tccgcggcgt ggcccttggc gcgcagcttg cccttggagg aggcgccgca    5940
cgaggggcag tgcagacttt tgagggcgta gagcttgggc gcgagaaata ccgattccgg    6000
ggagtaggca tccgcgccgc aggccccgca gacggtctcg cattccacga gccaggtgag    6060
ctctggccgt tcggggtcaa aaccaggtt tcccccatgc tttttgatgc gtttcttacc    6120
tctggttttc atgagccggt gtccacgctc ggtgacgaaa aggctgtccg tgtcccgta    6180 tacagacttg agagggagtt taacgaatt caatagcttg ttgcatgggc ggcgatataa    6240
aatgcaaggt gctgctcaaa aaatcaggca aagcctcgcg caaaaagaa agcacatcgt    6300 agtcatgctc atgcagataa aggcaggtaa gctccggaac caccacagaa aaagacacca    6360
tttttctctc aaacatgtct gcgggtttct gcataaacac aaaataaat aacaaaaaaa    6420 catttaaaca ttagaagcct gtcttacaac aggaaaaaca acccttataa gcataagacg    6480
gactacggcc atgccggcgt gaccgtaaaa aaactggtca ccgtgattaa aaagcaccac    6540
cgacagctcc tcggtcatgt ccggagtcat aatgtaagac tcggtaaaca catcaggttg    6600
attcatcggt cagtgctaaa aagcgaccga aatagcccgg gggaatacat acccgcaggc    6660
gtagagacaa cattcagcc cccataggag gtataacaaa attaatagga gagaaaaca    6720 cataaacacc tgaaaaaccc tcctgcctag gcaaaatagc accctcccgc tccagaacaa    6780
catacagcgc ttcacagcgg cagcctaaca gtcagcctta ccagtaaaaa agaaaaccta    6840
ttaaaaaaac accactcgac acggcaccag ctcaatcagt cacagtgtaa aaaagggcca    6900
agtgcagagc gagtatatat aggactaaaa aatgacgtaa cggttaaagt ccacaaaaaa    6960
cacccagaaa accgcacgcg aacctacgcc cagaaacgaa agccaaaaaa cccacaactt    7020
cctcaaatcg tcacttccgt tttcccacgt tacgtaactt cccattttaa gaaaactaca    7080
attcccaaca catacaagtt actccgccct aaaacctacg tcacccgccc cgttcccacg    7140
ccccgcgcca cgtcacaaac tccacccccct cattatcata ttggcttcaa tccaaaataa    7200
ggtatattat tgatgatgtt aattaacatg catggatcca tatgcggtgt gaaataccgc    7260
acagatgcgt aaggagaaaa taccgcatca ggcgctcttc cgcttcctcg ctcactgact    7320
cgctgcgctc ggtcgttcgg ctgcggcgag cggtatcagc tcactcaaag gcggtaatac    7380
ggttatccac agaatcaggg gataacgcag gaaagaacat gtgagcaaaa ggccagcaaa    7440
aggccaggaa ccgtaaaaag gccgcgttgc tggcgttttt ccataggctc cgcccccctg    7500
acgagcatca caaaaatcga cgctcaagtc agaggtggcg aaacccgaca ggactataaa    7560
```

```
gataccaggc gtttcccct ggaagctccc tcgtgcgctc tcctgttccg accctgccgc    7620
ttaccggata cctgtccgcc tttctccctt cgggaagcgt ggcgctttct catagctcac    7680
gctgtaggta tctcagttcg gtgtaggtcg ttcgctccaa gctgggctgt gtgcacgaac    7740
cccccgttca gcccgaccgc tgcgccttat ccggtaacta tcgtcttgag tccaacccgg    7800
taagacacga cttatcgcca ctggcagcag ccactggtaa caggattagc agagcgaggt    7860
atgtaggcgg tgctacagag ttcttgaagt ggtggcctaa ctacggctac actagaagga    7920
cagtatttgg tatctgcgct ctgctgaagc cagttacctt cggaaaaaga gttggtagct    7980
cttgatccgg caaacaaacc accgctggta gcggtggttt ttttgtttgc aagcagcaga    8040
ttacgcgcag aaaaaaagga tctcaagaag atcctttgat cttttctacg ggtctgacg     8100
ctcagtggaa cgaaaactca cgttaaggga ttttggtcat gagattatca aaaaggatct    8160
tcacctagat ccttttaaat taaaaatgaa gttttaaatc aatctaaagt atatatgagt    8220
aaacttggtc tgacagttac caatgcttaa tcagtgaggc acctatctca gcgatctgtc    8280
tatttcgttc atccatagtt gcctgactcc ccgtcgtgta gataactacg atacgggagg    8340
gcttaccatc tggccccagt gctgcaatga taccgcgaga cccacgctca ccggctccag    8400
atttatcagc aataaaccag ccagccggaa gggccgagcg cagaagtggt cctgcaactt    8460
tatccgcctc catccagtct attaattgtt gccgggaagc tagagtaagt agttcgccag    8520
ttaatagttt gcgcaacgtt gttgccattg ctgcagccat gagattatca aaaaggatct    8580
tcacctagat ccttttcacg tagaaagcca gtccgcagaa acggtgctga ccccggatga    8640
atgtcagcta ctgggctatc tggacaaggg aaaacgcaag cgcaaagaga aagcaggtag    8700
cttgcagtgg gcttacatgg cgatagctag actgggcggt tttatggaca gcaagcgaac    8760
cggaattgcc agctggggcg ccctctggta aggttgggaa gccctgcaaa gtaaactgga    8820
tggctttctc gccgccaagg atctgatggc gcagggatc aagctctgat caagagacag    8880
gatgaggatc gtttcgcatg attgaacaag atggattgca cgcaggttct ccggccgctt    8940
gggtggagag ctattcggc tatgactggg cacaacagac aatcggctgc tctgatgccg    9000
ccgtgttccg gctgtcagcg caggggcgcc cggttctttt tgtcaagacc gacctgtccg    9060
gtgccctgaa tgaactgcaa gacgaggcag cgcggctatc gtggctggcc acgacgggcg    9120
ttccttgcgc agctgtgctc gacgttgtca ctgaagcggg aagggactgg ctgctattgg    9180
gcgaagtgcc ggggcaggat ctcctgtcat ctcaccttgc tcctgccgag aaagtatcca    9240
tcatggctga tgcaatgcgg cggctgcata cgcttgatcc ggctacctgc ccattcgacc    9300
accaagcgaa acatcgcatc gagcgagcac gtactcggat ggaagccggt cttgtcgatc    9360
aggatgatct ggacgaagag catcaggggc tcgcgccagc cgaactgttc gccaggctca    9420
aggcgagcat gcccgacggc gaggatctcg tcgtgaccca tggcgatgcc tgcttgccga    9480
atatcatggt ggaaaatggc cgcttttctg gattcatcga ctgtggccgg ctgggtgtgg    9540
cggaccgcta tcaggacata gcgttggcta cccgtgatat tgctgaagag cttggcggcg    9600
aatgggctga ccgcttcctc gtgctttacg gtatcgccgc tcccgattcg cagcgcatcg    9660
ccttctatcg ccttcttgac gagttcttct gaatttgtt aaaattttg ttaaatcagc     9720
tcattttta accaataggc cgaaatcggc aacatccctt ataaatcaaa agaatagacc    9780
gcgatagggt tgagtgttgt tccagtttgg aacaagagtc cactattaaa gaacgtggac    9840
tccaacgtca aagggcgaaa aaccgtctat cagggcgatg gcccactacg tgaaccatca    9900
```

```
cccaaatcaa gttttttgcg gtcgaggtgc cgtaaagctc taaatcggaa ccctaaaggg      9960
agcccccgat ttagagcttg acggggaaag ccggcgaacg tggcgagaaa ggaagggaag     10020
aaagcgaaag gagcgggcgc tagggcgctg gcaagtgtag cggtcacgct gcgcgtaacc     10080
accacacccg cgcgcttaat gcgccgctac agggcgcgtc cattcgccat tcaggatcga     10140
attaattctt aat                                                        10153

<210> SEQ ID NO 7
<211> LENGTH: 10153
<212> TYPE: DNA
<213> ORGANISM: Artificial Sequence
<220> FEATURE:
<223> OTHER INFORMATION: chimeric adenoviral vector encoding influenza
      hemagglutinin (HA) and TLR-3 agonist luc in
      opposite orientation (DS2b-for)

<400> SEQUENCE: 7
taacatcatc aataatatac cttatttttgg attgaagcca atatgataat gagggggtgg      60
agtttgtgac gtggcgcggg gcgtgggaac ggggcgggtg acgtagtagt gtggcggaag     120
tgtgatgttg caagtgtggc ggaacacatg taagcgacgg atgtggcaaa agtgacgttt     180
ttggtgtgcg ccggtgtaca caggaagtga caattttcgc gcggttttag gcggatgttg     240
tagtaaattt gggcgtaacc gagtaagatt tggccatttt cgcggaaaa ctgaataaga      300 ggaagtgaaa tctgaataat tttgtgttac tcatagcgcg taatactgct agagatctgg      360
cgaaaggggg atgtgctgca aggcgattaa gttgggtaac gccagggttt cccagtcac      420 gacgttgtaa aacgacggcc agtgaattgt aatacgactc actatagggc gaattgggta     480
ctggccacag agcttggccc attgcatacg ttgtatccat atcataatat gtacatttat     540
attggctcat gtccaacatt accgccatgt tgacattgat tattgactag ttattaatag     600
taatcaatta cggggtcatt agttcatagc ccatatatgg agttccgcgt tacataactt     660
acggtaaatg gcccgcctgg ctgaccgccc aacgaccccc gcccattgac gtcaataatg     720
acgtatgttc ccatagtaac gccaataggg actttccatt gacgtcaatg ggtggagtat     780
ttacggtaaa ctgcccactt ggcagtacat caagtgtatc atatgccaag tacgccccct     840
attgacgtca atgacggtaa atggcccgcc tggcattatg cccagtacat gaccttatgg     900
gactttccta cttggcagta catctacgta ttagtcatcg ctattaccat ggtgatgcgg     960
ttttggcagt acatcaatgg gcgtggatag cggtttgact cacggggatt tccaagtctc     1020 cacccccattg acgtcaatgg gagtttgttt tggcaccaaa atcaacggga ctttccaaaa    1080
tgtcgtaaca actccgcccc attgacgcaa atgggcggta ggcgtgtacg gtgggaggtc    1140
tatataagca gagctcgttt agtgaaccgt cagatcgcct ggagacgcca tccacgctgt    1200
tttgacctcc atagaagaca ccgggaccga tccagcctga ctctagccta gctctgaagt    1260
tggtggtgag gccctgggca ggttggtatc aaggttacaa gacaggttta aggagaccaa    1320
tagaaactgg gcatgtggag acagagaaga ctcttgggtt tctgataggc actgactctc    1380
tctgcctatt ggtctatttt cccacccctta ggctgctggt ctgagcctag agatctctc    1440 gaggtcgacg gtatcgatgc caccatggag aaaatcgtcc tgttgctcgc tattgtgtct    1500
ctagtgaaga gcgatcaaat ttgtatcggc taccatgcca ataactcaac agagcaggtc    1560
gatactatca tggagaaaaa cgtaacagtt actcatgccc aagacatctt ggaaaagacc    1620
cacaacggca aactttgcga cctggatgga gtgaagcccc tgatcctccg ggactgttca    1680
gtcgctggtt ggctgctcgg gaaccctatg tgtgatgagt ttatcaacgt gcctgaatgg    1740
```

```
tcttacattg tggagaaggc taaccctacc aatgacctct gctatcctgg gtcatttaac    1800
gattacgagg aactgaaaca cctgttgtct agaattaacc actttgaaaa gatacagatt    1860
atacccaagt ctagttggag tgatcacgaa gcctcctcag gcgttagctc agcgtgtccc    1920
tatctgggct ctccatcctt ctttagaaat gtggtctggt taatcaaaaa gaacagtacc    1980
tacccaacca tcaaaaagtc ttataacaat accaatcagg aggacctgct cgtgttgtgg    2040
ggtatccatc acccgaacga cgccgctgaa cagactaggc tgtatcagaa ccccactaca    2100
tacatcagta ttggcacgag tactctgaac cagcgattag tgccaaagat tgcaacacgg    2160
agcaaagtaa atgggcaatc tggcaggatg gagttttttct ggacaatctt aaaacccaac    2220
gatgcgataa atttcgagtc caatggcaat ttcatcgccc ctgaatacgc ctataagatc    2280
gtgaaaaagg gggactctgc aattatgaag tccgaattag agtatggcaa ttgcaacacg    2340
aagtgccaga caccaatggg agccattaat agctcaatgc ccttccataa tattcatcca    2400
ttgaccattg gggagtgccc aaagtacgtg aagtccaacc gcctggtcct cgcaaccggt    2460
ctaagaaata gcccgcagag agaatcgcgg aggaagaaac gtggcctgtt tggcgcgatt    2520
gccggattca tcgagggagg ctggcagggt atggtcgatg gttggtacgg ataccaccat    2580
agcaacgaac aggggtccgg ctatgcagca gataaggaga gcactcagaa agctattgac    2640
ggagttacaa acaaggttaa tagtattata gataaaatga acacgcaatt cgaggccgtt    2700
gggagggagt ttaacaatct ggaacgccgg atcgaaaatc tgaataagaa aatggaagac    2760
ggcttccttg acgtgtggac ttataatgca gagctgcttg tactcatgga gaacgagagg    2820
accctggatt ccacgatag caacgtgaag aacctttacg acaaggtgag acttcagctc    2880
cgagacaacg ccaaggagct ggggaatgga tgcttcgagt tttaccacaa atgtgacaat    2940
gagtgcatgg aaagtatacg caacgggacc tacaattacc ctcagtatag cgaagaggct    3000
cggctcaaac gcgaagagat aagcggggtg aaattggaat caatcggaac atatcaaatc    3060
ctgtccatct attccaccgt cgcctcttcg ctggccctcg ctatcatgat ggctggtctg    3120
tccctatgga tgtgttccaa tggaagcctt cagtgccgta tttgtatatg agcggccgcc    3180
ctattctata gtgtcaccta aatgctagag ctcgctgatc agcctcgact gtgccttcta    3240
gttgccagcc atctgttgtt tgcccctccc ccgtgccttc cttgaccctg gaaggtgcca    3300
ctcccactgt cctttcctaa taaaatgagg aaattgcatc gcattgtctg agtaggtgtc    3360
attctattct ggggggtggg gtggggcagg acagcaaggg ggaggattgg gaagacaata    3420
gcaggcatgc tggggatgcg gtgggctcta tggcttctga ggcggaaaga accaaccacc    3480
gcggtggcgg ccgccacaca aaaaccaac acacagatgt aatgaaaata agatatttt    3540
atttctagag aaacgatatg gctgaatac ggatccgtat tcagcccata tcgtttcctg    3600
caggaattcg ccctttagat atcatcgatg tctcggcgt ggtggcgcgt cgcgccgctg    3660
ggttttatag ggcgccgccg cggccgctcg agccataaaa ggcaactttc ggaacggcgc    3720
acgctgattg gccccgcgcc gctcactcac cggcttcgcc gcacagtgca gcatttttt    3780
accccctctc ccctcctttt gcgaaaaaaa aaagagcga gagcgagatt gaggaagagg    3840
aggagggaga gttttggcgt tggccgcctt ggggtgctgg gcgtcgacga tatctaaggg    3900
cgaattcgat atcaagctag cttgtcgact cgaagatctg ggcgtggtta agggtgggaa    3960
agaatatata aggtggggt cttatgtagt tttgtatctg ttttgcagca gccgccgccg    4020
ccatgagcac caactcgttt gatggaagca ttgtgagctc atatttgaca acgcgcatgc    4080
```

```
ccccatgggc cggggtgcgt cagaatgtga tgggctccag cattgatggt cgccccgtcc    4140
tgcccgcaaa ctctactacc ttgacctacg agaccgtgtc tggaacgccg ttggagactg    4200
cagcctccgc cgccgcttca gccgctgcag ccaccgcccg cgggattgtg actgactttg    4260
ctttcctgag cccgcttgca agcagtgcag cttcccgttc atccgcccgc gatgacaagt    4320
tgacggctct tttggcacaa ttggattctt tgacccggga acttaatgtc gtttctcagc    4380
agctgttgga tctgcgccag caggtttctg ccctgaaggc ttcctcccct cccaatgcgg    4440
tttaaaacat aaataaaaaa ccagactctg tttggatttg gatcaagcaa gtgtcttgct    4500
gtctttattt aggggttttg cgcgcgcggt aggcccggga ccagcggtct cggtcgttga    4560
gggtcctgtg tattttttcc aggacgtggt aaaggtgact ctggatgttc agatacatgg    4620
gcataagccc gtctctgggg tggaggtagc accactgcag agcttcatgc tgcgggggtgg   4680
tgttgtagat gatccagtcg tagcaggagc gctgggcgtg gtgcctaaaa atgtctttca    4740
gtagcaagct gattgccagg ggcaggccct tggtgtaagt gtttacaaag cggttaagct    4800
gggatgggtg catacgtggg gatatgagat gcatcttgga ctgtatttt aggttggcta    4860
tgttcccagc catatccctc cggggattca tgttgtgcag aaccaccagc acagtgtatc    4920
cggtgcactt gggaaatttg tcatgtagct tagaaggaaa tgcgtggaag aacttggaga    4980
cgccttgtg acctccaaga ttttccatgc attcgtccat aatgatgca atgggcccac      5040
gggcggcggc ctgggcgaag atatttctgg gatcactaac gtcatagttg tgttccagga    5100
tgagatcgtc ataggccatt tttacaaagc gcgggcggag ggtgccagac tgcggtataa    5160
tggttccatc cggcccaggg gcgtagttac cctcacagat ttgcatttcc cacgctttga    5220
gttcagatgg ggggatcatg tctacctgcg gggcgatgaa gaaaacggtt tccggggtag    5280
gggagatcag ctgggaagaa agcaggttcc tgagcagctg cgacttaccg cagccggtgg    5340
gcccgtaaat cacacctatt accgggtgca actggtagtt aagagagctg cagctgccgt    5400
catccctgag caggggggcc acttcgttaa gcatgtccct gactcgcatg ttttccctga    5460
ccaaatccgc cagaaggcgc tcgccgccca gcgatagcag ttcttgcaag gaagcaaagt    5520
ttttcaacgg tttgagaccg tccgccgtag gcatgctttt gagcgtttga ccaagcagtt    5580
ccaggcggtc ccacagctcg gtcacctgct ctacggcatc tcgatccagc atatctcctc    5640
gtttcgcggg ttggggcggc tttcgctgta cggcagtagt cggtgctcgt ccagacgggc    5700
cagggtcatg tctttccacg ggcgcagggt cctcgtcagc gtagtctggg tcacggtgaa    5760
ggggtgcgct ccgggctgcg cgctggccag ggtgcgcttg aggctggtcc tgctggtgct    5820
gaagcgctgc cggtcttcgc cctgcgcgtc ggccaggtag catttgacca tggtgtcata    5880
gtccagcccc tccgcggcgt ggcccttggc gcgcagcttg ccttggagg aggcgccgca     5940
cgaggggcag tgcagacttt tgagggcgta gagcttgggc gcgagaaata ccgattccgg    6000
ggagtaggca tccgcgccgc aggccccgca gacggtctcg cattccacga gccaggtgag    6060
ctctggccgt tcggggtcaa aaaccaggtt tcccccatgc tttttgatgc gtttcttacc    6120
tctggtttcc atgagccggt gtccacgctc ggtgacgaaa aggctgtccg tgtcccgta     6180
tacagacttg agagggagtt taaacgaatt caatagcttg ttgcatgggc ggcgatataa    6240
aatgcaaggt gctgctcaaa aaatcaggca aagcctcgcg caaaaagaa agcacatcgt     6300
agtcatgctc atgcagataa aggcaggtaa gctccggaac caccacagaa aaagacacca    6360
ttttctctc aaacatgtct gcgggtttct gcataaacac aaaataaaat aacaaaaaaa    6420
catttaaaca ttagaagcct gtcttacaac aggaaaaaca acccttataa gcataagacg    6480
```

```
gactacggcc atgccggcgt gaccgtaaaa aaactggtca ccgtgattaa aaagcaccac    6540
cgacagctcc tcggtcatgt ccggagtcat aatgtaagac tcggtaaaca catcaggttg    6600
attcatcggt cagtgctaaa aagcgaccga aatagcccgg gggaatacat acccgcaggc    6660
gtagagacaa cattacagcc cccataggag gtataacaaa attaatagga gagaaaaaca    6720
cataaacacc tgaaaaaccc tcctgcctag gcaaaatagc accctcccgc tccagaacaa    6780
catacagcgc ttcacagcgg cagcctaaca gtcagcctta ccagtaaaaa agaaaaccta    6840
ttaaaaaaac accactcgac acggcaccag ctcaatcagt cacagtgtaa aaagggcca    6900
agtgcagagc gagtatatat aggactaaaa aatgacgtaa cggttaaagt ccacaaaaaa    6960
cacccagaaa accgcacgcg aacctacgcc cagaaacgaa agccaaaaaa cccacaactt    7020
cctcaaatcg tcacttccgt tttcccacgt tacgtaactt cccattttaa gaaaactaca    7080
attcccaaca catacaagtt actccgcccct aaaacctacg tcacccgccc cgttcccacg    7140
ccccgcgcca cgtcacaaac tccaccccct cattatcata ttggcttcaa tccaaaataa    7200
ggtatattat tgatgatgtt aattaacatg catggatcca tatgcggtgt gaaataccgc    7260
acagatgcgt aaggagaaaa taccgcatca ggcgctcttc cgcttcctcg ctcactgact    7320
cgctgcgctc ggtcgttcgg ctgcggcgag cggtatcagc tcactcaaag gcggtaatac    7380
ggttatccac agaatcaggg gataacgcag gaaagaacat gtgagcaaaa ggccagcaaa    7440
aggccaggaa ccgtaaaaag gccgcgttgc tggcgttttt ccataggctc cgcccccctg    7500
acgagcatca caaaaatcga cgctcaagtc agaggtggcg aaacccgaca ggactataaa    7560
gataccaggc gtttccccct ggaagctccc tcgtgcgctc tcctgttccg accctgccgc    7620
ttaccggata cctgtccgcc tttctccctt cgggaagcgt ggcgctttct catagctcac    7680
gctgtaggta tctcagttcg gtgtaggtcg ttcgctccaa gctgggctgt gtgcacgaac    7740
cccccgttca gcccgaccgc tgcgccttat ccggtaacta tcgtcttgag tccaacccgg    7800
taagacacga cttatcgcca ctggcagcag ccactggtaa caggattagc agagcgaggt    7860
atgtaggcgg tgctacagag ttcttgaagt ggtggcctaa ctacggctac actagaagga    7920
cagtatttgg tatctgcgct ctgctgaagc cagttacctt cggaaaaaga gttggtagct    7980
cttgatccgg caaacaaacc accgctggta gcggtggttt ttttgtttgc aagcagcaga    8040
ttacgcgcag aaaaaaagga tctcaagaag atcctttgat cttttctacg gggtctgacg    8100
ctcagtggaa cgaaaactca cgttaaggga ttttggtcat gagattatca aaaaggatct    8160
tcacctagat ccttttaaat taaaaatgaa gttttaaatc aatctaaagt atatatgagt    8220
aaacttggtc tgacagttac caatgcttaa tcagtgaggc acctatctca gcgatctgtc    8280
tatttcgttc atccatagtt gcctgactcc ccgtcgtgta gataactacg atacgggagg    8340
gcttaccatc tggccccagt gctgcaatga taccgcgaga cccacgctca ccggctccag    8400
atttatcagc aataaaccag ccagccggaa gggccgagcg cagaagtggt cctgcaactt    8460
tatccgcctc catccagtct attaattgtt gccgggaagc tagagtaagt agttcgccag    8520
ttaatagttt gcgcaacgtt gttgccattg ctgcagccat gagattatca aaaaggatct    8580
tcacctagat cctttttcacg tagaaagcca gtccgcagaa acggtgctga ccccggatga    8640
atgtcagcta ctgggctatc tggacaaggg aaaacgcaag cgcaaagaga aagcaggtag    8700
cttgcagtgg gcttacatgg cgatagctag actgggcggt tttatggaca gcaagcgaac    8760
cggaattgcc agctggggcg ccctctggta aggttgggaa gccctgcaaa gtaaactgga    8820
```

-continued

```
tggctttctc gccgccaagg atctgatggc gcagggatc aagctctgat caagagacag    8880
gatgaggatc gtttcgcatg attgaacaag atggattgca cgcaggttct ccggccgctt    8940
gggtggagag gctattcggc tatgactggg cacaacagac aatcggctgc tctgatgccg    9000
ccgtgttccg gctgtcagcg caggggcgcc cggttctttt tgtcaagacc gacctgtccg    9060
gtgccctgaa tgaactgcaa gacgaggcag cgcggctatc gtggctggcc acgacgggcg    9120
ttccttgcgc agctgtgctc gacgttgtca ctgaagcggg aagggactgg ctgctattgg    9180
gcgaagtgcc ggggcaggat ctcctgtcat ctcaccttgc tcctgccgag aaagtatcca    9240
tcatggctga tgcaatgcgg cggctgcata cgcttgatcc ggctacctgc ccattcgacc    9300
accaagcgaa acatcgcatc gagcgagcac gtactcggat ggaagccggt cttgtcgatc    9360
aggatgatct ggacgaagag catcaggggc tcgcgccagc cgaactgttc gccaggctca    9420
aggcgagcat gcccgacggc gaggatctcg tcgtgaccca tggcgatgcc tgcttgccga    9480
atatcatggt ggaaaatggc cgcttttctg gattcatcga ctgtggccgg ctgggtgtgg    9540
cggaccgcta tcaggacata gcgttggcta cccgtgatat tgctgaagag cttggcggcg    9600
aatgggctga ccgcttcctc gtgctttacg gtatcgccgc tcccgattcg cagcgcatcg    9660
ccttctatcg ccttcttgac gagttcttct gaattttgtt aaaattttg ttaaatcagc    9720 tcattttta accaataggc cgaaatcggc aacatccctt ataaatcaaa agaatagacc    9780
gcgatagggt tgagtgttgt tccagtttgg aacaagagtc cactattaaa gaacgtggac    9840
tccaacgtca aagggcgaaa aaccgtctat cagggcgatg gcccactacg tgaaccatca    9900
cccaaatcaa gttttttgcg gtcgaggtgc cgtaaagctc taaatcggaa ccctaaaggg    9960
agcccccgat ttagagcttg acggggaaag ccggcgaacg tggcgagaaa ggaagggaag    10020
aaagcgaaag gagcgggcgc tagggcgctg gcaagtgtag cggtcacgct gcgcgtaacc    10080
accacacccg cgcgcttaat gcgccgctac agggcgcgtc cattcgccat tcaggatcga    10140
attaattctt aat                                                        10153
```

<210> SEQ ID NO 8
<211> LENGTH: 46
<212> TYPE: DNA
<213> ORGANISM: Artificial Sequence
<220> FEATURE:
<223> OTHER INFORMATION: short hairpin RNA TLR-3 agonist

<400> SEQUENCE: 8

```
gatggtgctt caagctagta cttaagtact agcttgaagc accatc                    46
```

<210> SEQ ID NO 9
<211> LENGTH: 48
<212> TYPE: DNA
<213> ORGANISM: Artificial Sequence
<220> FEATURE:
<223> OTHER INFORMATION: short hairpin RNA TLR-3 agonist (g1)

<400> SEQUENCE: 9

```
gatggtgctt caagctagta cggatccgta ctagcttgaa gcaccatc                  48
```

<210> SEQ ID NO 10
<211> LENGTH: 48
<212> TYPE: DNA
<213> ORGANISM: Artificial Sequence
<220> FEATURE:
<223> OTHER INFORMATION: short hairpin RNA TLR-3 agonist (luc), luc1
    segment of DNA designed to make hairpin of
    double-stranded RNA

```
<400> SEQUENCE: 10
gaaacgatat gggctgaata cggatccgta ttcagcccat atcgtttc                    48

<210> SEQ ID NO 11
<211> LENGTH: 46
<212> TYPE: DNA
<213> ORGANISM: Artificial Sequence
<220> FEATURE:
<223> OTHER INFORMATION: short hairpin RNA TLR-3 agonist (m1), dsRNA
      hairpin

<400> SEQUENCE: 11
cctaataatt atcaaaatgt ggatccacat tttgataatt attagg                      46

<210> SEQ ID NO 12
<211> LENGTH: 44
<212> TYPE: DNA
<213> ORGANISM: Artificial Sequence
<220> FEATURE:
<223> OTHER INFORMATION: short hairpin RNA TLR-3 agonist

<400> SEQUENCE: 12
cctaataatt atcaaaatgt aattacattt tgataattat tagg                        44

<210> SEQ ID NO 13
<211> LENGTH: 9387
<212> TYPE: DNA
<213> ORGANISM: Artificial Sequence
<220> FEATURE:
<223> OTHER INFORMATION: chimeric adenoviral vector DS1c encoding
      hemagglutinin (HA) from influenza A/PR/8/34 in
      pShuttle-CMV vector (Ad-CMV-HA plus TLR-3 agonist)

<400> SEQUENCE: 13
taacatcatc aataatatac cttatttttgg attgaagcca aatgataat gagggggtgg        60 agtttgtgac gtggcgcggg gcgtgggaac ggggcgggtg acgtagtagt gtggcggaag       120
tgtgatgttg caagtgtggc ggaacacatg taagcgacgg atgtggcaaa agtgacgttt       180
ttggtgtgcg ccggtgtaca caggaagtga caattttcgc gcggttttag gcggatgttg      240
tagtaaattt gggcgtaacc gagtaagatt tggccatttt cgcgggaaaa ctgaataaga       300
ggaagtgaaa tctgaataat tttgtgttac tcatagcgcg taatactgta atagtaatca       360
attacggggt cattagttca tagcccatat atggagttcc gcgttacata acttacggta       420
aatggcccgc ctggctgacc gcccaacgac ccccgcccat tgacgtcaat aatgacgtat       480
gttcccatag taacgccaat agggactttc cattgacgtc aatgggtgga gtatttacgg       540
taaactgccc acttggcagt acatcaagtg tatcatatgc caagtacgcc ccctattgac       600
gtcaatgacg gtaaatggcc cgcctggcat tatgcccagt acatgacctt atgggacttt       660
cctacttggc agtacatcta cgtattagtc atcgctatta ccatggtgat gcggttttgg       720
cagtacatca atgggcgtgg atagcggttt gactcacggg gatttccaag tctccacccc       780
attgacgtca atgggagttt gttttggcac caaaatcaac gggactttcc aaaatgtcgt       840
aacaactccg ccccattgac gcaaatgggc ggtaggcgtg tacggtggga ggtctatata      900
agcagagctg gtttagtgaa ccgtcagatc cgctagagat ctggtaccga gctcggatcc       960
gccaccatgg aggcaaacct actggtcctg ttatgtgcac ttgcagctgc agatgcagac      1020
acaatatgta taggctacca tgcgaacaat tcaaccgaca ctggtgacac agtactcgag      1080
aagaatgtga cagtgacaca ctctgttaac ctgctcgaag acagccacaa cggaaaacta      1140
```

-continued

```
tgtagattaa aaggaatagc cccactacaa ttggggaaat gtaacatcgc cggatggctc      1200
ttgggaaacc cagaatgcga cccactgctt ccagtgagat catggtccta cattgtagaa      1260
acaccaaact ctgagaatgg aatatgttat ccaggagatt tcatcgacta tgaggagctg      1320
agggagcaat tgagctcagt gtcatcattc gaaagattcg aaatatttcc caagaaagc       1380
tcatggccca accacaacac aaccaaagga gtaacggcag catgctccca tgcgggaaa        1440
agcagttttt acagaaattt gctatggctg acggagaagg agggctcata cccaaagctg      1500
aaaaattctt atgtgaacaa gaaagggaaa gaagtccttg tactgtgggg tattcatcac      1560
ccgtctaaca gtaaggatca acagaatatc tatcagaatg aaaatgctta tgtctctgta      1620
gtgacttcaa attataacag gagatttacc ccggaaatag cagaaagacc caaagtaaga      1680
gatcaagctg ggaggatgaa ctattactgg accttgctaa acccggaga cacaataata       1740
tttgaggcaa atggaaatct aatagcacca aggtatgctt tcgcactgag tagaggcttt      1800
gggtccggca tcatcacctc aaacgcatca atgcatgagt gtaacacgaa gtgtcaaaca      1860
cccctgggag ctataaacag cagtctccct ttccagaata tacacccagt cacaatagga     1920
gagtgcccaa aatacgtcag gagtgccaaa ttgaggatgg ttacaggact aaggaacatt      1980
ccgtccattc aatccagagg tctatttgga gccattgccg gttttattga agggggatgg      2040
actgaatga tagatggatg gtacggttat catcatcaga tgaacaggg atcaggctat        2100
gcagcggatc aaaaaagcac acaaaatgcc attaacggga ttacaaacaa ggtgaactct      2160
gttatcgaga aaatgaacat tcaattcaca gctgtgggta agaattcaa caaattagaa       2220
aaaggatgg aaaatttaaa taaaaaagtt gatgatggat ttctggacat ttggacatat       2280
aatgcagaat tgttagttct actggaaaat gaaaggactc tggatttcca tgactcaaat      2340
gtgaagaatc tgtatgagaa agtaaaaagc caattaaaga ataatgccaa agaaatcgga     2400
aatgatgtt tgagttcta ccacaagtgt gacaatgaat gcatggaaag tgtaagaaat       2460
gggacttatg attatcccaa atattcagaa gagtcaaagt tgaacaggga aaaggtagat      2520
ggagtgaaat tggaatcaat ggggatctat cagattctgg cgatctactc aactgtcgcc      2580
agttcactgg tgcttttggt ctccctgggg gcaatcagtt tctggatgtg ttctaatgga      2640
tctttgcagt gcagaatatg catctgagat tagaatttca gagatatgag gaaaacacc       2700
cttgttttcta ctcccaagct ttaatgcggt agtttatcac agttaaattg ctaacgcagt     2760
caggcaccgt gtatgaaatc taacaatgcg ctcatcgtca tcctcggcac cgtcaccctg     2820
gatgctgtag gcataggctt ggttatgccg gtactgccgg gcctcttgcg ggatgggcgg      2880
ccgctcgagc ctaagcttct agataagata tccgatccac cggatctaga taactgatca     2940
taatcagcca taccacattt gtagaggttt tacttgcttt aaaaaacctc ccacacctcc      3000
ccctgaacct gaaacataaa atgaatgcaa ttgttgttgt taacttgttt attgcagctt      3060
ataatggtta caaataaagc aatagcatca caaatttcac aaataaagca ttttttcac      3120
tgcattctag ttgtggtttg tccaaactca tcaatgtatc ttaacgcgga tctgggcgtg     3180
gttaagggtg ggaaagaata tataaggtgg gggtcttatg tagttttgta tctgttttgc     3240
agcagccgcc gccgccatga gcaccaactc gtttgatgga agcattgtga gctcatattt     3300
gacaacgcgc atgcccccat gggccggggt gcgtcagaat gtgatgggct ccagcattga     3360
tggtcgcccc gtcctgcccg caaactctac taccttgacc tacgagaccg tgtctggaac     3420
gccgttggag actgcagcct ccgccgccgc ttcagccgct gcagccaccg cccgcgggat     3480
```

```
tgtgactgac tttgctttcc tgagcccgct tgcaagcagt gcagcttccc gttcatccgc    3540
ccgcgatgac aagttgacgg ctcttttggc acaattggat tctttgaccc gggaacttaa    3600
tgtcgtttct cagcagctgt tggatctgcg ccagcaggtt tctgccctga aggcttcctc    3660
ccctcccaat gcggtttaaa acataaataa aaaaccagac tctgtttgga tttggatcaa    3720
gcaagtgtct tgctgtcttt atttaggggt tttgcgcgcg cggtaggccc gggaccagcg    3780
gtctcggtcg ttgagggtcc tgtgtatttt ttccaggacg tggtaaaggt gactctggat    3840
gttcagatac atgggcataa gcccgtctct ggggtggagg tagcaccact gcagagcttc    3900
atgctgcggg gtggtgttgt agatgatcca gtcgtagcag gagcgctggg cgtggtgcct    3960
aaaaatgtct ttcagtagca agctgattgc caggggcagg cccttggtgt aagtgtttac    4020
aaagcggtta agctgggatg ggtgcatacg tggggatatg agatgcatct tggactgtat    4080
ttttaggttg gctatgttcc cagccatatc cctccgggga ttcatgttgt gcagaaccac    4140
cagcacagtg tatccggtgc acttgggaaa tttgtcatgt agcttagaag gaaatgcgtg    4200
gaagaacttg gagacgccct tgtgacctcc aagatttttcc atgcattcgt ccataatgat    4260
ggcaatgggc ccacgggcgg cggcctgggc gaagatattt ctgggatcac taacgtcata    4320
gttgtgttcc aggatgagat cgtcataggc catttttaca aagcgcgggc ggagggtgcc    4380
agactgcggg ataatggttc catccggccc aggggcgtag ttaccctcac agatttgcat    4440
ttcccacgct ttgagttcag atggggggat catgtctacc tgcggggcga tgaagaaaac    4500
ggtttccggg gtaggggaga tcagctggga agaaagcagg ttcctgagca gctgcgactt    4560
accgcagccg gtgggcccgt aaatcacacc tattaccggg tgcaactggt agttaagaga    4620
gctgcagctg ccgtcatccc tgagcagggg ggccacttcg ttaagcatgt ccctgactcg    4680
catgttttcc ctgaccaaat ccgccagaag gcgctcgccg cccagcgata gcagttcttg    4740
caaggaagca aagttttttca acggtttgag accgtccgcc gtaggcatgc ttttgagcgt    4800
ttgaccaagc agttccaggc ggtcccacag ctcggtcacc tgctctacgg catctcgatc    4860
cagcatatct cctcgtttcg cgggttgggg cggcttcgc tgtacggcag tagtcggtgc    4920
tcgtccagac gggccagggt catgtctttc cacgggcgca gggtcctcgt cagcgtagtc    4980
tgggtcacgg tgaaggggtg cgctccgggc tgcgcgctgg ccagggtgcg cttgaggctg    5040
gtcctgctgg tgctgaagcg ctgccggtct tcgccctgcg cgtcggccag gtagcatttg    5100
accatggtgt catagtccag cccctccgcg gcgtggccct tggcgcgcag cttgcccttg    5160
gaggaggcgc cgcacgaggg gcagtgcaga cttttgaggg cgtagagctt gggcgcgaga    5220
aataccgatt ccggggagta ggcatccgcg ccgcaggccc cgcagacggt ctcgcattcc    5280
acgagccagg tgagctctgg ccgttcgggg tcaaaaacca ggtttccccc atgctttttg    5340
atgcgtttct tacctctggt ttccatgagc cggtgtccac gctcggtgac gaaaaggctg    5400
tccgtgtccc cgtatacaga cttgagaggg agtttaaacg aattcaatag cttgttgcat    5460
gggcggcgat ataaaatgca aggtgctgct caaaaaatca ggcaaagcct cgcgcaaaaa    5520
agaaagcaca tcgtagtcat gctcatgcag ataaaggcag gtaagctccg gaaccaccac    5580
agaaaaagac accattttttc tctcaaacat gtctgcgggt ttctgcataa acacaaaata    5640
aaataacaaa aaaacattta acattagaa gcctgtctta caacaggaaa acaacccctt    5700
ataagcataa gacggactac ggccatgccg gcgtgaccgt aaaaaaactg gtcaccgtga    5760
ttaaaaagca ccaccgacag ctcctcggtc atgtccggag tcataatgta agactcggta    5820
aacacatcag gttgattcat cggtcagtgc taaaaagcga ccgaaatagc ccgggggaat    5880
```

```
acatacccgc aggcgtagag acaacattac agcccccata ggaggtataa caaaattaat    5940
aggagagaaa aacacataaa cacctgaaaa accctcctgc ctaggcaaaa tagcacccctc   6000
ccgctccaga acaacataca gcgcttcaca gcggcagcct aacagtcagc cttaccagta    6060
aaaaagaaaa cctattaaaa aaacaccact cgacacggca ccagctcaat cagtcacagt    6120
gtaaaaaagg gccaagtgca gagcgagtat atataggact aaaaaatgac gtaacggtta    6180
aagtccacaa aaaacaccca gaaaaccgca cgcgaaccta cgcccagaaa cgaaagccaa    6240
aaaacccaca acttcctcaa atcgtcactt ccgttttccc acgttacgta acttcccatt    6300
ttaagaaaac tacaattccc aacacataca agttactccg ccctaaaacc tacgtcaccc    6360
gccccgttcc cacgccccgc gccacgtcac aaactccacc ccctcattat catattggct    6420
tcaatccaaa ataaggtata ttattgatga tgttaattaa catgcatgga tccatatgcg    6480
gtgtgaaata ccgcacagat gcgtaaggag aaaataccgc atcaggcgct cttccgcttc    6540
ctcgctcact gactcgctgc gctcggtcgt tcggctgcgg cgagcggtat cagctcactc    6600
aaaggcggta atacggttat ccacagaatc aggggataac gcaggaaaga acatgtgagc    6660
aaaaggccag caaaaggcca ggaaccgtaa aaaggccgcg ttgctggcgt ttttccatag    6720
gctccgcccc cctgacgagc atcacaaaaa tcgacgctca agtcagaggt ggcgaaaccc    6780
gacaggacta taaagatacc aggcgtttcc ccctggaagc tccctcgtgc gctctcctgt    6840
tccgaccctg ccgcttaccg gatacctgtc cgcctttctc ccttcgggaa gcgtggcgct    6900
ttctcatagc tcacgctgta ggtatctcag ttcggtgtag tcgttcgct  ccaagctggg    6960
ctgtgtgcac gaaccccccg ttcagcccga ccgctgcgcc ttatccggta actatcgtct    7020
tgagtccaac ccggtaagac acgacttatc gccactggca gcagccactg gtaacaggat    7080
tagcagagcg aggtatgtag gcggtgctac agagttcttg aagtggtggc ctaactacgg    7140
ctacactaga aggacagtat ttggtatctg cgctctgctg aagccagtta ccttcggaaa    7200
aagagttggt agctcttgat ccggcaaaca aaccaccgct ggtagcggtg gtttttttgt    7260
ttgcaagcag cagattacgc gcagaaaaaa aggatctcaa gaagatcctt tgatcttttc    7320
tacggggtct gacgctcagt ggaacgaaaa ctcacgttaa gggattttgg tcatgagatt    7380
atcaaaaagg atcttcacct agatcctttt aaattaaaaa tgaagtttta atcaatcta    7440
aagtatatat gagtaaactt ggtctgacag ttaccaatgc ttaatcagtg aggcacctat    7500
ctcagcgatc tgtctatttc gttcatccat agttgcctga ctccccgtcg tgtagataac    7560
tacgatacgg gagggcttac catctggccc cagtgctgca atgataccgc gagacccacg    7620
ctcaccggct ccagatttat cagcaataaa ccagccagcc ggaagggccg agcgcagaag    7680
tggtcctgca actttatccg cctccatcca gtctattaat tgttgccggg aagctagagt    7740
aagtagttcg ccagttaata gtttgcgcaa cgttgttgcc attgctgcag ccatgagatt    7800
atcaaaaagg atcttcacct agatcctttt cacgtagaaa gccagtccgc agaaacggtg    7860
ctgaccccgg atgaatgtca gctactgggc tatctggaca agggaaaacg caagcgcaaa    7920
gagaaagcag gtagcttgca gtgggcttac atggcgatag ctagactggg cggttttatg    7980
gacagcaagc gaaccggaat tgccagctgg ggcgccctct ggtaaggttg gaagccctg     8040
caaagtaaac tggatggctt tctcgccgcc aaggatctga tggcgcaggg gatcaagctc    8100
tgatcaagag acaggatgag gatcgtttcg catgattgaa caagatggat tgcacgcagg    8160
ttctccggcc gcttgggtgg agaggctatt cggctatgac tgggcacaac agacaatcgg    8220
```

-continued

```
ctgctctgat gccgccgtgt tccggctgtc agcgcagggg cgcccggttc tttttgtcaa     8280
gaccgacctg tccggtgccc tgaatgaact gcaagacgag gcagcgcggc tatcgtggct     8340
ggccacgacg ggcgttcctt gcgcagctgt gctcgacgtt gtcactgaag cgggaaggga     8400
ctggctgcta ttgggcgaag tgccggggca ggatctcctg tcatctcacc ttgctcctgc     8460
cgagaaagta tccatcatgg ctgatgcaat gcggcggctg catacgcttg atccggctac     8520
ctgcccattc gaccaccaag cgaaacatcg catcgagcga gcacgtactc ggatggaagc     8580
cggtcttgtc gatcaggatg atctggacga gagcatcag gggctcgcgc cagccgaact     8640
gttcgccagg ctcaaggcga gcatgcccga cggcgaggat ctcgtcgtga cccatggcga     8700
tgcctgcttg ccgaatatca tggtggaaaa tggccgcttt tctggattca tcgactgtgg     8760
ccggctgggt gtggcggacc gctatcagga catagcgttg gctacccgtg atattgctga     8820
agagcttggc ggcgaatggg ctgaccgctt cctcgtgctt tacggtatcg ccgctcccga     8880
ttcgcagcgc atcgccttct atcgccttct tgacgagttc ttctgaattt tgttaaaatt     8940
tttgttaaat cagctcattt tttaaccaat aggccgaaat cggcaacatc ccttataaat     9000
caaaagaata accgcgata gggttgagtg ttgttccagt ttggaacaag agtccactat     9060
taaagaacgt ggactccaac gtcaaagggc gaaaaaccgt ctatcagggc gatggcccac     9120
tacgtgaacc atcacccaaa tcaagttttt tgcggtcgag gtgccgtaaa gctctaaatc     9180
ggaaccctaa agggagcccc cgatttagag cttgacgggg aaagccggcg aacgtggcga     9240
gaaaggaagg gaagaaagcg aaaggagcgg gcgctagggc gctggcaagt gtagcggtca     9300
cgctgcgcgt aaccaccaca cccgcgcgct taatgcgccg ctacagggcg cgtccattcg     9360
ccattcagga tcgaattaat tcttaat                                        9387
```

<210> SEQ ID NO 14
<211> LENGTH: 8473
<212> TYPE: DNA
<213> ORGANISM: Artificial Sequence
<220> FEATURE:
<223> OTHER INFORMATION: chimeric adenoviral vector DS2beta-luc encoding
   TLR-3 agonist luc and human beta actin promotor,
   generic shuttle vector, rapid cloning vector

<400> SEQUENCE: 14

```
taacatcatc aataatatac cttattttgg attgaagcca atatgataat gaggggtgg      60 agtttgtgac gtggcgcggg gcgtgggaac ggggcgggtg acgtagtagt gtggcggaag    120
tgtgatgttg caagtgtggc ggaacacatg taagcgacgg atgtggcaaa agtgacgttt    180
ttggtgtgcg ccggtgtaca caggaagtga caattttcgc gcggttttag gcggatgttg    240
tagtaaattt gggcgtaacc gagtaagatt tggccatttt cgcgggaaaa ctgaataaga    300
ggaagtgaaa tctgaataat tttgtgttac tcatagcgcg taatactgct agagatctgg    360 cgaaggggg atgtgctgca aggcgattaa gttgggtaac gccagggttt tcccagtcac    420
gacgttgtaa aacgacggcc agtgaattgt aatacgactc actatagggc gaattgggta    480
ctggccacag agcttggccc attgcatacg ttgtatccat atcataatat gtacatttat    540
attggctcat gtccaacatt accgccatgt tgacattgat tattgactag ttattaatag    600
taatcaatta cggggtcatt agttcatagc ccatatatgg agttccgcgt tacataactt    660
acggtaaatg gcccgcctgg ctgaccgccc aacgaccccc gcccattgac gtcaataatg    720
acgtatgttc ccatagtaac gccaataggg actttccatt gacgtcaatg ggtggagtat    780
ttacggtaaa ctgcccactt ggcagtacat caagtgtatc atatgccaag tacgccccct    840
```

```
attgacgtca atgacggtaa atggcccgcc tggcattatg cccagtacat gaccttatgg    900
gactttccta cttggcagta catctacgta ttagtcatcg ctattaccat ggtgatgcgg    960
ttttggcagt acatcaatgg gcgtggatag cggtttgact cacggggatt tccaagtctc   1020
caccccattg acgtcaatgg gagtttgttt tggcaccaaa atcaacggga ctttccaaaa   1080
tgtcgtaaca actccgcccc attgacgcaa atgggcggta ggcgtgtacg gtgggaggtc   1140
tatataagca gagctcgttt agtgaaccgt cagatcgcct ggagacgcca tccacgctgt   1200
tttgacctcc atagaagaca ccgggaccga tccagcctga ctctagccta gctctgaagt   1260
tggtggtgag gccctgggca ggttggtatc aaggttacaa gacaggttta aggagaccaa   1320
tagaaactgg gcatgtggag acagagaaga ctcttgggtt tctgataggc actgactctc   1380
tctgcctatt ggtctatttt cccacccctta ggctgctggt ctgagcctag agatctctc   1440
gaggtcgacg gtatcgatgg gtaccggcgg ccgccctatt ctatagtgtc acctaaatgc   1500
tagagctcgc tgatcagcct cgactgtgcc ttctagttgc cagccatctg ttgtttgccc   1560
ctcccccgtg ccttccttga ccctggaagg tgccactccc actgtccttt cctaataaaa   1620
tgaggaaatt gcatcgcatt gtctgagtag gtgtcattct attctggggg gtggggtggg   1680
gcaggacagc aaggggggagg attgggaaga caatagcagg catgctgggg atgcggtggg   1740
ctctatggct tctgaggcgg aaagaaccta tggcttctga ggcggaaaga accaaccacc   1800
gcggtggcgg ccgccacaca aaaaccaac acacagatgt aatgaaaata agatatttt   1860
atttctagag aaacgatatg gctgaatac ggatccgtat tcagcccata tcgtttcctg   1920
caggaattcg ccctttagat atcatcgatg tctcggcggt ggtggcgcgt cgcgccgctg   1980
ggttttatag ggcgccgccg cggccgctcg agccataaaa ggcaactttc ggaacggcgc   2040
acgctgattg gccccgcgcc gctcactcac cggcttcgcc gcacagtgca gcattttttt   2100
accccctctc ccctccttt gcgaaaaaaa aaagagcga gagcgagatt gaggaagagg   2160
aggagggaga gttttggcgt tggccgcctt ggggtgctgg gcgtcgacga tatctaaggg   2220
cgaattcgat atcaagctag cttgtcgact cgaagatctg ggcgtggtta agggtgggaa   2280
agaatatata aggtggggt cttatgtagt tttgtatctg ttttgcagca gccgccgccg   2340
ccatgagcac caactcgttt gatggaagca ttgtgagctc atatttgaca acgcgcatgc   2400
ccccatgggc cggggtgcgt cagaatgtga tgggctccag cattgatggt cgccccgtcc   2460
tgcccgcaaa ctctactacc ttgacctacg agaccgtgtc tggaacgccg ttggagactg   2520
cagcctccgc cgccgcttca gccgctgcag ccaccgcccg cgggattgtg actgactttg   2580
ctttcctgag cccgcttgca agcagtgcag cttcccgttc atccgcccgc gatgacaagt   2640
tgacggctct tttggcacaa ttggattctt tgacccggga acttaatgtc gtttctcagc   2700
agctgttgga tctgcgccag caggtttctg ccctgaaggc ttcctcccct cccaatgcgg   2760
tttaaaacat aaataaaaaa ccagactctg tttggatttg gatcaagcaa gtgtcttgct   2820
gtctttattt aggggttttg cgcgcgcggt aggcccggga ccagcggtct cggtcgttga   2880
gggtcctgtg tatttttcc aggacgtggt aaaggtgact ctggatgttc agatacatgg   2940
gcataagccc gtctctgggg tggaggtagc accactgcag agcttcatgc tgcggggtgg   3000
tgttgtagat gatccagtcg tagcaggagc gctgggcgtg gtgcctaaaa atgtctttca   3060
gtagcaagct gattgccagg ggcaggccct tggtgtaagt gtttacaaag cggttaagct   3120
gggatgggtg catacgtggg gatatgagat gcatcttgga ctgtatttt aggttggcta   3180
```

```
tgttcccagc catatccctc cggggattca tgttgtgcag aaccaccagc acagtgtatc    3240
cggtgcactt gggaaatttg tcatgtagct tagaaggaaa tgcgtggaag aacttggaga    3300
cgcccttgtg acctccaaga ttttccatgc attcgtccat aatgatggca atgggcccac    3360
gggcggcggc ctgggcgaag atatttctgg gatcactaac gtcatagttg tgttccagga    3420
tgagatcgtc ataggccatt tttacaaagc gcgggcggag ggtgccagac tgcggtataa    3480
tggttccatc cggcccaggg gcgtagttac cctcacagat ttgcatttcc cacgctttga    3540
gttcagatgg ggggatcatg tctacctgcg gggcgatgaa gaaaacggtt ccggggtag     3600 gggagatcag ctgggaagaa agcaggttcc tgagcagctg cgacttaccg cagccggtgg    3660
gcccgtaaat cacacctatt accgggtgca actggtagtt aagagagctg cagctgccgt    3720
catccctgag caggggggcc acttcgttaa gcatgtccct gactcgcatg ttttccctga    3780
ccaaatccgc cagaaggcgc tcgccgccca gcgatagcag ttcttgcaag gaagcaaagt    3840
ttttcaacgg tttgagaccg tccgccgtag gcatgctttt gagcgtttga ccaagcagtt    3900
ccaggcggtc ccacagctcg gtcacctgct ctacggcatc tcgatccagc atatctcctc    3960
gtttcgcggg ttggggcggc tttcgctgta cggcagtagt cggtgctcgt ccagacgggc    4020
cagggtcatg tctttccacg ggcgcagggt cctcgtcagc gtagtctggg tcacggtgaa    4080
ggggtgcgct ccgggctgcg cgctggccag ggtgcgcttg aggctggtcc tgctggtgct    4140
gaagcgctgc cggtcttcgc cctgcgcgtc ggccaggtag catttgacca tggtgtcata    4200
gtccagcccc tccgcggcgt ggcccttggc gcgcagcttg cccttggagg aggcgccgca    4260
cgaggggcag tgcagacttt tgagggcgta gagcttgggc gcgagaaata ccgattccgg    4320
ggagtaggca tccgcgccgc aggccccgca gacggtctcg cattccacga gccaggtgag    4380
ctctggccgt tcggggtcaa aaaccaggtt tcccccatgc ttttgatgc gtttcttacc     4440 tctggttttcc atgagccggt gtccacgctc ggtgacgaaa aggctgtccg tgtccccgta    4500
tacagacttg agagggagtt taaacgaatt caatagcttg ttgcatgggc ggcgatataa    4560
aatgcaaggt gctgctcaaa aaatcaggca aagcctcgcg caaaaaagaa agcacatcgt    4620
agtcatgctc atgcagataa aggcaggtaa gctccggaac caccacagaa aaagacacca    4680 ttttctctc aaacatgtct gcgggtttct gcataaacac aaaataaaat aacaaaaaaa     4740
catttaaaca ttagaagcct gtcttacaac aggaaaaaca acccttataa gcataagacg    4800
gactacggcc atgccggcgt gaccgtaaaa aaactggtca ccgtgattaa aaagcaccac    4860
cgacagctcc tcggtcatgt ccggagtcat aatgtaagac tcggtaaaca catcaggttg    4920
attcatcggt cagtgctaaa aagcgaccga aatagcccgg gggaatacat acccgcaggc    4980
gtagagacaa cattacagcc cccataggag gtataacaaa attaatagga gagaaaaaca    5040
cataaacacc tgaaaaaccc tcctgcctag gcaaaatagc accctcccgc tccagaacaa    5100
catacagcgc ttcacagcgg cagcctaaca gtcagcctta ccagtaaaaa agaaaaccta    5160
ttaaaaaaac accactcgac acggcaccag ctcaatcagt cacagtgtaa aaaagggcca    5220
agtgcagagc gagtatatat aggactaaaa aatgacgtaa cggttaaagt ccacaaaaaa    5280 caccccagaaa accgcacgcg aacctacgcc cagaaacgaa agccaaaaaa cccacaactt    5340
cctcaaatcg tcacttccgt tttcccacgt tacgtaactt cccattttaa gaaaactaca    5400
attcccaaca catacaagtt actccgccct aaaacctacg tcacccgccc cgttcccacg    5460 cccccgcgcca cgtcacaaac tccaccccct cattatcata ttggcttcaa tccaaaataa    5520
ggtatattat tgatgatgtt aattaacatg catggatcca tatgcggtgt gaaataccgc    5580
```

```
acagatgcgt aaggagaaaa taccgcatca ggcgctcttc cgcttcctcg ctcactgact   5640
cgctgcgctc ggtcgttcgg ctgcggcgag cggtatcagc tcactcaaag gcggtaatac   5700
ggttatccac agaatcaggg gataacgcag gaaagaacat gtgagcaaaa ggccagcaaa   5760
aggccaggaa ccgtaaaaag gccgcgttgc tggcgttttt ccataggctc cgcccccctg   5820
acgagcatca caaaaatcga cgctcaagtc agaggtggcg aaacccgaca ggactataaa   5880
gataccaggc gtttccccct ggaagctccc tcgtgcgctc tcctgttccg accctgccgc   5940
ttaccggata cctgtccgcc tttctccctt cgggaagcgt ggcgctttct catagctcac   6000
gctgtaggta tctcagttcg gtgtaggtcg ttcgctccaa gctgggctgt gtgcacgaac   6060
cccccgttca gcccgaccgc tgcgccttat ccggtaacta tcgtcttgag tccaacccgg   6120
taagacacga cttatcgcca ctggcagcag ccactggtaa caggattagc agagcgaggt   6180
atgtaggcgg tgctacagag ttcttgaagt ggtggcctaa ctacggctac actagaagga   6240
cagtatttgg tatctgcgct ctgctgaagc cagttacctt cggaaaaaga gttggtagct   6300
cttgatccgg caaacaaacc accgctggta gcggtggttt ttttgtttgc aagcagcaga   6360
ttacgcgcag aaaaaaagga tctcaagaag atcctttgat cttttctacg ggtctgacg   6420
ctcagtggaa cgaaaactca cgttaaggga ttttggtcat gagattatca aaaaggatct   6480
tcacctagat ccttttaaat taaaaatgaa gttttaaatc aatctaaagt atatatgagt   6540
aaacttggtc tgacagttac caatgcttaa tcagtgaggc acctatctca gcgatctgtc   6600
tatttcgttc atccatagtt gcctgactcc ccgtcgtgta gataactacg atacgggagg   6660
gcttaccatc tggccccagt gctgcaatga taccgcgaga cccacgctca ccggctccag   6720
atttatcagc aataaaccag ccagccggaa gggccgagcg cagaagtggt cctgcaactt   6780
tatccgcctc catccagtct attaattgtt gccgggaagc tagagtaagt agttcgccag   6840
ttaatagttt gcgcaacgtt gttgccattg ctgcagccat gagattatca aaaaggatct   6900
tcacctagat ccttttcacg tagaaagcca gtccgcagaa acgtgctga ccccggatga   6960
atgtcagcta ctgggctatc tggacaaggg aaaacgcaag cgcaaagaga agcaggtag   7020
cttgcagtgg gcttacatgg cgatagctag actgggcggt tttatggaca gcaagcgaac   7080
cggaattgcc agctggggcg ccctctggta aggttgggaa gccctgcaaa gtaaactgga   7140
tggctttctc gccgccaagg atctgatggc gcagggatc aagctctgat caagagacag   7200
gatgaggatc gtttcgcatg attgaacaag atggattgca cgcaggttct ccggccgctt   7260
gggtggagag gctattcggc tatgactggg cacaacagac aatcggctgc tctgatgccg   7320
ccgtgttccg gctgtcagcg caggggcgcc cggttctttt tgtcaagacc gacctgtccg   7380
gtgccctgaa tgaactgcaa gacgaggcag cgcggctatc gtggctggcc acgacgggcg   7440
ttccttgcgc agctgtgctc gacgttgtca ctgaagcggg aagggactgg ctgctattgg   7500
gcgaagtgcc ggggcaggat ctcctgtcat ctcaccttgc tcctgccgag aaagtatcca   7560
tcatggctga tgcaatgcgg cggctgcata cgcttgatcc ggctacctgc ccattcgacc   7620
accaagcgaa acatcgcatc gagcgagcac gtactcggat ggaagccggt cttgtcgatc   7680
aggatgatct ggacgaagag catcaggggc tcgcgccagc cgaactgttc gccaggctca   7740
aggcgagcat gcccgacggc gaggatctcg tcgtgaccca tggcgatgcc tgcttgccga   7800
atatcatggt ggaaaatggc cgcttttctg gattcatcga ctgtggccgg ctgggtgtgg   7860
cggaccgcta tcaggacata gcgttggcta cccgtgatat tgctgaagag cttggcggcg   7920
```

```
aatgggctga ccgcttcctc gtgctttacg gtatcgccgc tcccgattcg cagcgcatcg    7980
ccttctatcg ccttcttgac gagttcttct gaattttgtt aaaattttg ttaaatcagc     8040 tcattttta accaataggc cgaaatcggc aacatcctt ataaatcaaa agaatagacc      8100 gcgataggg tgagtgttgt tccagtttgg aacaagagtc cactattaaa gaacgtggac    8160
tccaacgtca aagggcgaaa aaccgtctat caggggcgatg gccactacg tgaaccatca   8220 cccaaatcaa gttttttgcg gtcgaggtgc cgtaaagctc taaatcggaa ccctaaaggg   8280 agccccgat ttagagcttg acggggaaag ccggcgaacg tggcgagaaa ggaagggaag    8340
aaagcgaaag gagcgggcgc tagggcgctg gcaagtgtag cggtcacgct gcgcgtaacc   8400
accacacccg cgcgcttaat gcgccgctac agggcgcgtc cattcgccat tcaggatcga   8460
attaattctt aat                                                       8473

<210> SEQ ID NO 15
<211> LENGTH: 9073
<212> TYPE: DNA
<213> ORGANISM: Artificial Sequence
<220> FEATURE:
<223> OTHER INFORMATION: chimeric adenoviral vector DS2C-luc encoding
      TLR-3 agonist luc and cytomegalovirus (CMV) promotor,
      generic shuttle vector, rapid cloning vector

<400> SEQUENCE: 15
taacatcatc aataatatac cttatttggg attgaagcca atatgataat gagggggtgg      60
agtttgtgac gtggcgcggg gcgtgggaac ggggcgggtg acgtagtagt gtggcggaag     120
tgtgatgttg caagtgtggc ggaacacatg taagcgacgg atgtggcaaa agtgacgttt     180
ttggtgtgcg ccggtgtaca caggaagtga caattttcgc gcggttttag gcggatgttg     240
tagtaaattt gggcgtaacc gagtaagatt tggccatttt cgcgggaaaa ctgaataaga     300
ggaagtgaaa tctgaataat tttgtgttac tcatagcgcg taatactgct agagatctgg     360
cgaaaggggg atgtgctgca aggcgattaa gttgggtaac gccagggttt tcccagtcac     420
gacgttgtaa aacgacggcc agtgaattgt aatacgactc actatagggc gaattgggta    480
ctggccacag agcttggccc attgcatacg ttgtatccat atcataatat gtacatttat     540
attggctcat gtccaacatt accgccatgt tgacattgat tattgactag ttattaatag     600
taatcaatta cggggtcatt agttcatagc ccatatatgg agttccgcgt tacataactt     660
acggtaaatg gcccgcctgg ctgaccgccc aacgacccc gcccattgac gtcaataatg      720
acgtatgttc ccatagtaac gccaataggg actttccatt gacgtcaatg ggtggagtat     780
ttacggtaaa ctgcccactt ggcagtacat caagtgtatc atatgccaag tacgccccct     840
attgacgtca atgacggtaa atggcccgcc tggcattatg cccagtacat gaccttatgg     900
gactttccta cttggcagta catctacgta ttagtcatcg ctattaccat ggtgatgcgg     960
ttttggcagt acatcaatgg gcgtggatag cggtttgact cacggggatt ccaagtctc    1020 caccccattg acgtcaatgg gagtttgttt tggcaccaaa atcaacggga ctttccaaaa    1080
tgtcgtaaca actccgcccc attgacgcaa atgggcggta ggcgtgtacg gtgggaggtc    1140
tatataagca gagctcgttt agtgaaccgt cagatcgcct ggagacgcca tccacgctgt    1200
tttgacctcc atagaagaca ccgggaccga tccagcctga ctctagccta gctctgaagt    1260
tggtggtgag gccctgggca ggttggtatc aaggttacaa gacaggttta aggagaccaa    1320
tagaaactgg gcatggtgag acagagaaga ctcttgggtt tctgataggc actgactctc    1380
tctgcctatt ggtctatttt cccaccctta ggctgctggt ctgagcctag gagatctctc    1440
```

```
gaggtcgacg gtatcgatgg gtaccggcgg ccgccctatt ctatagtgtc acctaaatgc    1500
tagagctcgc tgatcagcct cgactgtgcc ttctagttgc cagccatctg ttgtttgccc    1560
ctcccccgtg ccttccttga ccctggaagg tgccactccc actgtccttt cctaataaaa    1620
tgaggaaatt gcatcgcatt gtctgagtag gtgtcattct attctggggg gtggggtggg    1680
gcaggacagc aagggggagg attgggaaga caatagcagg catgctgggg atgcggtggg    1740
ctctatggct tctgaggcgg aaagaaccaa agcttaggct cgagcggccg ccacacaaaa    1800
aaccaacaca cagatgtaat gaaaataaag atattttatt tctagagaaa cgatatgggc    1860
tgaatacgga tccgtattca gcccatatcg tttcccagat ctctagcgga tctgacggtt    1920
cactaaacca gctctgctta tatagacctc ccaccgtaca cgcctaccgc ccatttgcgt    1980
caatggggcg gagttgttac gacattttgg aaagtcccgt tgattttggt gccaaaacaa    2040
actcccattg acgtcaatgg ggtggagact tggaaatccc cgtgagtcaa accgctatcc    2100
acgcccattg atgtactgcc aaaaccgcat caccatggta atagcgatga ctaatacgta    2160
gatgtactgc caagtaggaa agtcccataa ggtcatgtac tgggcataat gccaggcggg    2220
ccatttaccg tcattgacgt caataggggg cgtacttggc atatgataca cttgatgtac    2280
tgccaagtgg gcagtttacc gtaaatactc cacccattga cgtcaatgga aagtccctat    2340
tggcgttact atgggaacat acgtcattat tgacgtcaat gggcgggggt cgttgggcgg    2400
tcagccaggc gggccattta ccgtaagtta tgtaacgcgg aactccatat atgggctatg    2460
aactaatgac cccgtaattg attactatta cagtattacg cgctatgagt aacacaaaat    2520
tattcagatt tcacttcctc ttattcagtt ttcccgcgaa aatggccaaa tcttactcgg    2580
ttacgcccaa atttactaca acatccgcct aaaaccgcgc gaaaattgtc acttcctgtg    2640
tacaccggcg cacaccaaaa acgtcacttt tgccacatcc gtcgcttaca tgtgttccgc    2700
cacacttgca acatcacact tccgccacac tactacgtca cccgcccgt tcccacgccc    2760
cgcgccacgt cacaaactcc acccccctcat tatcatattg gcttcaatcc aaaataaggt    2820
atattattga tgatgttaag cttgtcgact cgaagatctg ggcgtggtta agggtgggaa    2880
agaatatata aggtgggggt cttatgtagt tttgtatctg ttttgcagca gccgccgccg    2940
ccatgagcac caactcgttt gatggaagca ttgtgagctc atatttgaca acgcgcatgc    3000
ccccatgggc cggggtgcgt cagaatgtga tgggctccag cattgatggt cgccccgtcc    3060
tgcccgcaaa ctctactacc ttgacctacg agaccgtgtc tggaacgccg ttggagactg    3120
cagcctccgc cgccgcttca gccgctgcag ccaccgcccg cgggattgtg actgactttg    3180
ctttcctgag cccgcttgca agcagtgcag cttcccgttc atccgcccgc gatgacaagt    3240
tgacggctct tttggcacaa ttggattctt tgacccggga acttaatgtc gtttctcagc    3300
agctgttgga tctgcgccag caggtttctg ccctgaaggc ttcctcccct cccaatgcgg    3360
tttaaaacat aaataaaaaa ccagactctg tttggatttg gatcaagcaa gtgtcttgct    3420
gtctttattt agggggttttg cgcgcgcggt aggcccggga ccagcggtct cggtcgttga    3480
gggtcctgtg tattttttcc aggacgtggt aaaggtgact ctggatgttc agatacatgg    3540
gcataagccc gtctctgggg tggaggtagc accactgcag agcttcatgc tgcgggtgg    3600
tgttgtagat gatccagtcg tagcaggagc gctgggcgtg gtgcctaaaa atgtctttca    3660
gtagcaagct gattgccagg ggcaggccct tggtgtaagt gtttacaaag cggttaagct    3720
gggatgggtg catacgtggg gatatgagat gcatcttgga ctgtattttt aggttggcta    3780
```

```
tgttcccagc catatccctc cggggattca tgttgtgcag aaccaccagc acagtgtatc    3840
cggtgcactt gggaaatttg tcatgtagct tagaaggaaa tgcgtggaag aacttggaga    3900
cgcccttgtg acctccaaga ttttccatgc attcgtccat aatgatggca atgggcccac    3960
gggcggcggc ctgggcgaag atatttctgg gatcactaac gtcatagttg tgttccagga    4020
tgagatcgtc ataggccatt tttacaaagc gcgggcggag ggtgccagac tgcggtataa    4080
tggttccatc cggcccaggg gcgtagttac cctcacagat ttgcatttcc cacgctttga    4140
gttcagatgg ggggatcatg tctacctgcg gggcgatgaa gaaaacggtt tccggggtag    4200
gggagatcag ctgggaagaa agcaggttcc tgagcagctg cgacttaccg cagccggtgg    4260
gcccgtaaat cacacctatt accgggtgca actggtagtt aagagagctg cagctgccgt    4320
catccctgag caggggggcc acttcgttaa gcatgtccct gactcgcatg ttttccctga    4380
ccaaatccgc cagaaggcgc tcgccgccca gcgatagcag ttcttgcaag gaagcaaagt    4440
ttttcaacgg tttgagaccg tccgccgtag gcatgctttt gagcgtttga ccaagcagtt    4500
ccaggcggtc ccacagctcg gtcacctgct ctacggcatc tcgatccagc atatctcctc    4560
gtttcgcggg ttggggcggc tttcgctgta cggcagtagt cggtgctcgt ccagacgggc    4620
cagggtcatg tctttccacg ggcgcagggt cctcgtcagc gtagtctggg tcacggtgaa    4680
ggggtgcgct ccgggctgcg cgctggccag ggtgcgcttg aggctggtcc tgctggtgct    4740
gaagcgctgc cggtcttcgc cctgcgcgtc ggccaggtag catttgacca tggtgtcata    4800
gtccagcccc tccgcggcgt ggcccttggc gcgcagcttg cccttggagg aggcgccgca    4860
cgaggggcag tgcagacttt tgagggcgta gagcttgggc gcgagaaata ccgattccgg    4920
ggagtaggca tccgcgccgc aggccccgca gacggtctcg cattccacga gccaggtgag    4980
ctctggccgt tcggggtcaa aaaccaggtt tccccatgc tttttgatgc gtttcttacc     5040
tctggtttcc atgagccggt gtccacgctc ggtgacgaaa aggctgtccg tgtccccgta    5100
tacagacttg agagggagtt taaacgaatt caatagcttg ttgcatgggc ggcgatataa    5160
aatgcaaggt gctgctcaaa aaatcaggca aagcctcgcg caaaaaagaa agcacatcgt    5220
agtcatgctc atgcagataa aggcaggtaa gctccggaac caccacagaa aaagacacca    5280
tttttctctc aaacatgtct gcgggtttct gcataaacac aaaataaaat aacaaaaaaa    5340
catttaaaca ttagaagcct gtcttacaac aggaaaaaca acccttataa gcataagacg    5400
gactacggcc atgccggcgt gaccgtaaaa aaactggtca ccgtgattaa aaagcaccac    5460
cgacagctcc tcggtcatgt ccggagtcat aatgtaagac tcggtaaaca catcaggttg    5520
attcatcggt cagtgctaaa aagcgaccga aatagcccgg gggaatacat acccgcaggc    5580
gtagagacaa cattacagcc cccataggag gtataacaaa attaatagga gagaaaaaca    5640
cataaacacc tgaaaaaccc tcctgcctag gcaaaatagc accctcccgc tccagaacaa    5700
catacagcgc ttcacagcgg cagcctaaca gtcagcctta ccagtaaaaa agaaaaccta    5760
ttaaaaaaac accactcgac acggcaccag ctcaatcagt cacagtgtaa aaaagggcca    5820
agtgcagagc gagtatatat aggactaaaa aatgacgtaa cggttaaagt ccacaaaaaa    5880
cacccagaaa accgcacgcg aacctacgcc cagaaacgaa agccaaaaaa cccacaactt    5940
cctcaaatcg tcacttccgt tttcccacgt tacgtaactt cccattttaa gaaaactaca    6000
attcccaaca catacaagtt actccgccct aaaacctacg tcacccgccc cgttcccacg    6060
ccccgcgcca cgtcacaaac tccaccccct cattatcata ttggcttcaa tccaaaataa    6120
ggtatattat tgatgatgtt aattaacatg catggatcca tatgcggtgt gaaataccgc    6180
```

```
acagatgcgt aaggagaaaa taccgcatca ggcgctcttc cgcttcctcg ctcactgact    6240
cgctgcgctc ggtcgttcgg ctgcggcgag cggtatcagc tcactcaaag gcggtaatac    6300
ggttatccac agaatcaggg gataacgcag gaaagaacat gtgagcaaaa ggccagcaaa    6360
aggccaggaa ccgtaaaaag gccgcgttgc tggcgttttt ccataggctc cgcccccctg    6420
acgagcatca caaaaatcga cgctcaagtc agaggtggcg aaacccgaca ggactataaa    6480
gataccaggc gtttccccct ggaagctccc tcgtgcgctc tcctgttccg accctgccgc    6540
ttaccggata cctgtccgcc tttctccctt cgggaagcgt ggcgctttct catagctcac    6600
gctgtaggta tctcagttcg gtgtaggtcg ttcgctccaa gctgggctgt gtgcacgaac    6660 ccccgttca gcccgaccgc tgcgccttat ccggtaacta tcgtcttgag tccaacccgg    6720
taagacacga cttatcgcca ctggcagcag ccactggtaa caggattagc agagcgaggt    6780
atgtaggcgg tgctacagag ttcttgaagt ggtggcctaa ctacggctac actagaagga    6840
cagtatttgg tatctgcgct ctgctgaagc cagttacctt cggaaaaaga gttggtagct    6900
cttgatccgg caaacaaacc accgctggta gcggtggttt ttttgtttgc aagcagcaga    6960
ttacgcgcag aaaaaaagga tctcaagaag atcctttgat cttttctacg gggtctgacg    7020
ctcagtggaa cgaaaactca cgttaaggga ttttggtcat gagattatca aaaaggatct    7080
tcacctagat ccttttaaat taaaaatgaa gttttaaatc aatctaaagt atatatgagt    7140
aaacttggtc tgacagttac caatgcttaa tcagtgaggc acctatctca gcgatctgtc    7200
tatttcgttc atccatagtt gcctgactcc ccgtcgtgta gataactacg atacgggagg    7260
gcttaccatc tggccccagt gctgcaatga taccgcgaga cccacgctca ccggctccag    7320
atttatcagc aataaaccag ccagccggaa gggccgagcg cagaagtggt cctgcaactt    7380
tatccgcctc catccagtct attaattgtt gccgggaagc tagagtaagt agttcgccag    7440
ttaatagttt gcgcaacgtt gttgccattg ctgcagccat gagattatca aaaaggatct    7500
tcacctagat ccttttcacg tagaaagcca gtccgcagaa acggtgctga ccccggatga    7560
atgtcagcta ctgggctatc tggacaaggg aaaacgcaag cgcaaagaga aagcaggtag    7620
cttgcagtgg gcttacatgg cgatagctag actgggcggt tttatggaca gcaagcgaac    7680
cggaattgcc agctggggcg ccctctggta aggttgggaa gccctgcaaa gtaaactgga    7740
tggctttctc gccgccaagg atctgatggc gcagggatc aagctctgat caagagacag    7800
gatgaggatc gtttcgcatg attgaacaag atggattgca cgcaggttct ccggccgctt    7860
gggtggagag gctattcggc tatgactggg cacaacagac aatcggctgc tctgatgccg    7920
ccgtgttccg gctgtcagcg caggggcgcc cggttctttt tgtcaagacc gacctgtccg    7980
gtgccctgaa tgaactgcaa gacgaggcag cgcggctatc gtggctggcc acgacgggcg    8040
ttccttgcgc agctgtgctc gacgttgtca ctgaagcggg aagggactgg ctgctattgg    8100
gcgaagtgcc ggggcaggat ctcctgtcat ctcaccttgc tcctgccgag aaagtatcca    8160
tcatggctga tgcaatgcgg cggctgcata cgcttgatcc ggctacctgc ccattcgacc    8220
accaagcgaa acatcgcatc gagcgagcac gtactcggat ggaagccggt cttgtcgatc    8280
aggatgatct ggacgaagag catcaggggc tcgcgccagc cgaactgttc gccaggctca    8340
aggcgagcat gcccgacggc gaggatctcg tcgtgaccca tggcgatgcc tgcttgccga    8400
atatcatggt ggaaaatggc cgcttttctg gattcatcga ctgtggccgg ctgggtgtgg    8460
cggaccgcta tcaggacata gcgttggcta cccgtgatat tgctgaagag cttggcggcg    8520
```

-continued

```
aatgggctga ccgcttcctc gtgctttacg gtatcgccgc tcccgattcg cagcgcatcg   8580
ccttctatcg ccttcttgac gagttcttct gaattttgtt aaaatttttg ttaaatcagc   8640
tcatttttta accaataggc cgaaatcggc aacatccctt ataaatcaaa agaatagacc   8700
gcgatagggt tgagtgttgt tccagtttgg aacaagagtc cactattaaa gaacgtggac   8760
tccaacgtca aagggcgaaa aaccgtctat cagggcgatg gcccactacg tgaaccatca   8820
cccaaatcaa gttttttgcg gtcgaggtgc cgtaaagctc taaatcggaa ccctaaaggg   8880
agcccccgat ttagagcttg acggggaaag ccggcgaacg tggcgagaaa ggaagggaag   8940
aaagcgaaag gagcgggcgc tagggcgctg gcaagtgtag cggtcacgct gcgcgtaacc   9000
accacacccg cgcgcttaat gcgccgctac agggcgcgtc cattcgccat tcaggatcga   9060
attaattctt aat                                                      9073
```

```

<210> SEQ ID NO 16
<211> LENGTH: 50475
<212> TYPE: DNA
<213> ORGANISM: Artificial Sequence
<220> FEATURE:
<223> OTHER INFORMATION: chimeric adenoviral vector DS2bC-HA encoding
      TLR-3 agonist luc1, influenza hemagglutinin (HA)
      (A/Indo/5/2005; avian flu) and cytomegalovirus
      (CMV) promotor, pShuttle vector
<220> FEATURE:
<221> NAME/KEY: modified_base
<222> LOCATION: (1)...(50475)
<223> OTHER INFORMATION: n = g, a, c or t

<400> SEQUENCE: 16
taacatcatc aataatatac cttattttgg attgaagcca atatgataat gaggggggtgg     60 agtttgtgac gtggcgcggg gcgtgggaac ggggcgggtg acgtagtagt gtggcggaag    120
tgtgatgttg caagtgtggc ggaacacatg taagcgacgg atgtggcaaa agtgacgttt    180
ttggtgtgcg ccggtgtaca caggaagtga caattttcgc gcggttttag gcggatgttg    240
tagtaaattt gggcgtaacc gagtaagatt tggccatttt cgcgggaaaa ctgaataaga    300
ggaagtgaaa tctgaataat tttgtgttac tcatagcgcg taatactgct agagatctgg    360
cgaaaggggg atgtgctgca aggcgattaa gttgggtaac gccagggttt tcccagtcac    420
gacgttgtaa aacgacggcc agtgaattgt aatacgactc actatagggc gaattgggta    480
ctggccacag agcttggccc attgcatacg ttgtatccat atcataatat gtacatttat    540
attggctcat gtccaacatt accgccatgt tgacattgat tattgactag ttattaatag    600
taatcaatta cggggtcatt agttcatagc ccatatatgg agttccgcgt tacataactt    660
acggtaaatg gcccgcctgg ctgaccgccc aacgaccccc gcccattgac gtcaataatg    720
acgtatgttc ccatagtaac gccaataggg actttccatt gacgtcaatg ggtggagtat    780
ttacggtaaa ctgcccactt ggcagtacat caagtgtatc atatgccaag tacgccccct    840
attgacgtca atgacggtaa atggcccgcc tggcattatg cccagtacat gaccttatgg    900
gactttccta cttggcagta catctacgta ttagtcatcg ctattaccat ggtgatgcgg    960
ttttggcagt acatcaatgg gcgtggatag cggtttgact cacggggatt tccaagtctc   1020
caccccattg acgtcaatgg gagtttgttt tggcaccaaa atcaacggga ctttccaaaa   1080
tgtcgtaaca actccgcccc attgacgcaa atgggcggta ggcgtgtacg gtgggaggtc   1140
tatataagca gagctcgttt agtgaaccgt cagatcgcct ggagacgcca tccacgctgt   1200
tttgacctcc atagaagaca ccgggaccga tccagcctga ctctagccta gctctgaagt   1260
```

```
tggtggtgag gccctgggca ggttggtatc aaggttacaa gacaggttta aggagaccaa   1320
tagaaactgg gcatgtggag acagagaaga ctcttgggtt tctgataggc actgactctc   1380
tctgcctatt ggtctatttt cccacccTta ggctgctggt ctgagcctag gagatctctc   1440
gaggtcgacg gtatcgatgc caccatggag aaaatcgtcc tgttgctcgc tattgtgtct   1500
ctagtgaaga gcgatcaaat ttgtatcggc taccatgcca ataactcaac agagcaggtc   1560
gatactatca tggagaaaaa cgtaacagtt actcatgccc aagacatctt ggaaaagacc   1620
cacaacggca aactttgcga cctggatgga gtgaagcccc tgatcctccg ggactgttca   1680
gtcgctggtt ggctgctcgg gaaccctatg tgtgatgagt ttatcaacgt gcctgaatgg   1740
tcttacattg tggagaaggc taaccctacc aatgacctct gctatcctgg gtcatttaac   1800
gattacgagg aactgaaaca cctgttgtct agaattaacc actttgaaaa gatacagatt   1860
atacccaagt ctagttggag tgatcacgaa gcctcctcag gcgttagctc agcgtgtccc   1920
tatctgggct ctccatcctt ctttagaaat gtggtctggt taatcaaaaa gaacagtacc   1980
tacccaacca tcaaaaagtc ttataacaat accaatcagg aggacctgct cgtgttgtgg   2040
ggtatccatc acccgaacga cgccgctgaa cagactaggc tgtatcagaa ccccactaca   2100
tacatcagta ttggcacgag tactctgaac cagcgattag tgccaaagat tgcaacacgg   2160
agcaaagtaa atgggcaatc tggcaggatg gagttttTct ggacaatctt aaaacccaac   2220
gatgcgataa atttcgagtc caatggcaat ttcatcgccc ctgaatacgc ctataagatc   2280
gtgaaaaagg gggactctgc aattatgaag tccgaattag agtatggcaa ttgcaacacg   2340
aagtgccaga caccaatggg agccattaat agctcaatgc ccttccataa tattcatcca   2400
ttgaccattg gggagtgccc aaagtacgtg aagtccaacc gcctggtcct cgcaaccggt   2460
ctaagaaata gcccgcagag agaatcgcgg aggaagaaac gtggcctgtt tggcgcgatt   2520
gccggattca tcgagggagg ctggcagggt atggtcgatg gttggtacgg ataccaccat   2580
agcaacgaac agggtccgg ctatgcagca gataaggaga gcactcagaa agctattgac   2640
ggagttacaa acaaggttaa tagtattata gataaaatga acgcaattt cgaggccgtt   2700 gggagggagt ttaacaatct ggaacgccgg atcgaaaatc tgaataagaa aatggaagac   2760
ggcttccttg acgtgtggac ttataatgca gagctgcttg tactcatgga gaacgagagg   2820
accctggatt ccacgatag caacgtgaag aacctttacg acaaggtgag acttcagctc   2880
cgagacaacg ccaaggagct ggggaatgga tgcttcgagt tttaccacaa atgtgacaat   2940
gagtgcatgg aaagtatacg caacgggacc tacaattacc ctcagtatag cgaagaggct   3000
cggctcaaac gcgaagagat aagcggggtg aaattggaat caatcggaac atatcaaatc   3060
ctgtccatct attccaccgt cgcctcttcg ctggccctcg ctatcatgat ggctggtctg   3120
tccctatgga tgtgttccaa tggaagcctt cagtgccgta tttgtatatg agcggccgcc   3180
ctattctata gtgtcaccta aatgctagag ctcgctgatc agcctcgact gtgccttcta   3240
gttgccagcc atctgttgtt tgcccctccc ccgtgccttc cttgaccctg gaaggtgcca   3300
ctcccactgt cctttcctaa taaaatgagg aaattgcatc gcattgtctg agtaggtgtc   3360
attctattct gggggggtggg gtggggcagg acagcaaggg ggaggattgg gaagacaata   3420
gcaggcatgc tggggatgcg gtgggctcta tggcttctga gcggaaaga accaaagctt   3480 aacatcatca ataatatacc ttattttgga ttgaagccaa tatgataatg aggggggtgga   3540 gtttgtgacg tggcgcgggg cgtgggaacg gggcgggtga cgtagtagtg tggcggaagt   3600
gtgatgttgc aagtgtggcg gaacacatgt aagcgacgga tgtggcaaaa gtgacgtttt   3660
```

```
tggtgtgcgc cggtgtacac aggaagtgac aattttcgcg cggttttagg cggatgttgt   3720
agtaaatttg ggcgtaaccg agtaagattt ggccattttc gcgggaaaac tgaataagag   3780
gaagtgaaat ctgaataatt ttgtgttact catagcgcgt aatactgtaa tagtaatcaa   3840
ttacggggtc attagttcat agcccatata tggagttccg cgttacataa cttacggtaa   3900
atggcccgcc tggctgaccg cccaacgacc cccgcccatt gacgtcaata atgacgtatg   3960
ttcccatagt aacgccaata gggactttcc attgacgtca atgggtggag tatttacggt   4020
aaactgccca cttggcagta catcaagtgt atcatatgcc aagtacgccc cctattgacg   4080
tcaatgacgg taaatggccc gcctggcatt atgcccagta catgacctta tgggactttc   4140
ctacttggca gtacatctac gtattagtca tcgctattac catggtgatg cggttttggc   4200
agtacatcaa tgggcgtgga tagcggtttg actcacgggg atttccaagt ctccacccca   4260
ttgacgtcaa tgggagtttg ttttggcacc aaaatcaacg ggactttcca aatgtcgta   4320 acaactccgc cccattgacg caaatgggcg gtaggcgtgt acggtgggag gtctatataa   4380
gcagagctgg tttagtgaac cgtcagatcc gctagagatc tgggaaacga tatgggctga   4440
atacggatcc gtattcagcc catatcgttt ctctagaaat aaaatatctt tattttcatt   4500
acatctgtgt gttggttttt tgtgtggcgg ccgctcgagc ctaagcttct agataagata   4560
tccgatccac cggatctaga taactgatca taatcagcca taccacattt gtagaggttt   4620
tacttgcttt aaaaaacctc ccacacctcc cctgaacct gaaacataaa atgaatgcaa   4680
ttgttgttgt taacttgttt attgcagctt ataatggtta caaataaagc aatagcatca   4740
caaatttcac aaataaagca tttttttcac tgcattctag ttgtggtttg tccaaactca   4800
tcaatgtatc ttaacgcgga tctgggcgtg gttaagggtg ggaaagaata tataaggtgg   4860
gggtcttatg tagttttgta tctgttttgc agcagccgcc gccgccatga gcaccaactc   4920
gtttgatgga agcattgtga gcttgtcgac tcgaagatct gggcgtggtt aagggtggga   4980
aagaatatat aaggtggggg tcttatgtag ttttgtatct gttttgcagc agccgccgcc   5040
gccatgagca ccaactcgtt tgatggaagc attgtgagct catatttgac aacgcgcatg   5100
cccccatggg ccggggtgcg tcagaatgtg atgggctcca gcattgatgg tcgccccgtc   5160
ctgcccgcaa actctactac cttgacctac gagaccgtgt ctggaacgcc gttggagact   5220
gcagcctccg ccgccgcttc agccgctgca gccaccgccc gcgggattgt gactgacttt   5280
gctttcctga gccgcttgc aagcagtgca gcttcccgtt catccgcccg cgatgacaag   5340
ttgacggctc ttttggcaca attggattct ttgacccggg aacttaatgt cgtttctcag   5400
cagctgttgg atctgcgcca gcaggtttct gccctgaagg cttcctcccc tcccaatgcg   5460
gtttaaaaca taaataaaaa accagactct gtttggattt ggatcaagca agtgtcttgc   5520
tgtctttatt tagggttttt gcgcgcgcgg taggcccggg accagcggtc tcggtcgttg   5580
agggtcctgt gtattttttc caggacgtgg taaaggtgac tctggatgtt cagatacatg   5640
ggcataagcc cgtctctggg gtggaggtag caccactgca gagcttcatg ctgcggggtg   5700
gtgttgtaga tgatccagtc gtagcaggag cgctgggcgt ggtgcctaaa aatgtctttc   5760
agtagcaagc tgattgccag gggcaggccc ttggtgtaag tgtttacaaa gcggttaagc   5820
tgggatgggt gcatacgtgg ggatatgaga tgcatcttgg actgtatttt taggttggct   5880
atgttcccag cctatatccct ccggggattc atgttgtgca gaaccaccag cacagtgtat   5940
ccggtgcact tgggaaattt gtcatgtagc ttagaaggaa atgcgtggaa gaacttggag   6000
```

```
acgcccttgt gacctccaag attttccatg cattcgtcca taatgatggc aatgggccca    6060
cgggcggcgg cctgggcgaa gatatttctg ggatcactaa cgtcatagtt gtgttccagg    6120
atgagatcgt cataggccat ttttacaaag cgcgggcgga gggtgccaga ctgcggtata    6180
atggttccat ccggcccagg ggcgtagtta ccctcacaga tttgcatttc ccacgctttg    6240
agttcagatg gggggatcat gtctacctgc ggggcgatga agaaaacggt ttccggggta    6300
ggggagatca gctgggaaga aagcaggttc ctgagcagct gcgacttacc gcagccggtg    6360
ggcccgtaaa tcacacctat taccgggtgc aactggtagt taagagagct gcagctgccg    6420
tcatccctga gcaggggggc cacttcgtta agcatgtccc tgactcgcat gttttccctg    6480
accaaatccg ccagaaggcg ctcgccgccc agcgatagca gttcttgcaa ggaagcaaag    6540
tttttcaacg gtttgagacc gtccgccgta ggcatgcttt tgagcgtttg accaagcagt    6600
tccaggcggt cccacagctc ggtcacctgc tctacggcat ctcgatccag catatctcct    6660
cgtttcgcgg gttggggcgg ctttcgctgt acggcagtag tcggtgctcg tccagacggg    6720
ccagggtcat gtctttccac gggcgcaggg tcctcgtcag cgtagtctgg gtcacggtga    6780
aggggtgcgc tccgggctgc gcgctggcca gggtgcgctt gaggctggtc ctgctggtgc    6840
tgaagcgctg ccggtcttcg ccctgcgcgt cggccaggta gcatttgacc atggtgtcat    6900
agtccagccc ctccgcggcg tggcccttgg cgcgcagctt gcccttggag gaggcgccgc    6960
acgaggggca gtgcagactt tgagggcgt agagcttggg cgcgagaaat accgattccg    7020
gggagtaggc atccgcgccg caggcccgc agacggtctc gcattccacg agccaggtga    7080
gctctggccg ttcggggtca aaaccaggt ttcccccatg cttttgatg cgtttcttac    7140 ctctggtttc catgagccgg tgtccacgct cggtgacgaa aaggctgtcc gtgtccccgt    7200
atacagactt gagagggagt ttaaacgaat tcaatagctt gttgcatggg cggcgatata    7260
aaatgcaagt tgctgctcaa aaaatcaggc aaagcctcgc gcaaaaaaga aagcacatcg    7320
tagtcatgct catgcagata aaggcaggta agctccggaa ccaccacaga aaaagacacc    7380 attttttctct caaacatgtc tgcgggtttc tgcataaaca caaaataaaa taacaaaaaa    7440
acatttaaac attagaagcc tgtcttacaa caggaaaaac aacccttata agcataagac    7500
ggactacggc catgccggcg tgaccgtaaa aaaactggtc accgtgatta aaaagcacca    7560
ccgacagctc ctcggtcatg tccggagtca taatgtaaga ctcggtaaac acatcaggtt    7620
gattcatcgg tcagtgctaa aaagcgaccg aaatagcccg ggggaataca tacccgcagg    7680
cgtagagaca acattacagc ccccatagga ggtataacaa aattaatagg agagaaaaac    7740
acataaacac ctgaaaaacc ctcctgccta ggcaaaatag caccctcccg ctccagaaca    7800
acatacagcg cttcacagcg gcagcctaac agtcagcctt accagtaaaa aagaaaacct    7860
attaaaaaaa caccactcga cacggcacca gctcaatcag tcacagtgta aaaaagggcc    7920
aagtgcagag cgagtatata taggactaaa aaatgacgta acggttaaag tccacaaaaa    7980
acacccagaa aaccgcacgc gaacctacgc ccagaaacga aagccaaaaa acccacaact    8040
tcctcaaatc gtcacttccg ttttcccacg ttacgtaact tcccatttta agaaaactac    8100
aattcccaac acatacaagt tactccgccc taaaacctac gtcacccgcc ccgttcccac    8160
gccccgcgcc acgtcacaaa ctccacccc tcattatcat attggcttca atccaaaata    8220
aggtatatta ttgatgatgt taattaacat gcatggatcc atatgcggtg tgaaataccg    8280
cacagatgcg taaggagaaa ataccgcatc aggcgctctt ccgcttcctc gctcactgac    8340
tcgctgcgct cggtcgttcg gctgcggcga gcggtatcag ctcactcaaa ggcggtaata    8400
```

```
cggttatcca cagaatcagg ggataacgca ggaaagaaca tgtgagcaaa aggccagcaa    8460
aaggccagga accgtaaaaa ggccgcgttg ctggcgtttt tccataggct ccgcccccct    8520
gacgagcatc acaaaaatcg acgctcaagt cagaggtggc gaaacccgac aggactataa    8580
agataccagg cgtttccccc tggaagctcc ctcgtgcgct ctcctgttcc gaccctgccg    8640
cttaccggat acctgtccgc ctttctccct tcgggaagcg tggcgctttc tcatagctca    8700
cgctgtaggt atctcagttc ggtgtaggtc gttcgctcca agctgggctg tgtgcacgaa    8760
ccccccgttc agcccgaccg ctgcgcctta tccggtaact atcgtcttga gtccaacccg    8820
gtaagacacg acttatcgcc actggcagca gccactggta acaggattag cagagcgagg    8880
tatgtaggcg gtgctacaga gttcttgaag tggtggccta actacggcta cactagaagg    8940
acagtatttg gtatctgcgc tctgctgaag ccagttacct tcggaaaaag agttggtagc    9000
tcttgatccg gcaaacaaac caccgctggt agcggtggtt tttttgtttg caagcagcag    9060
attacgcgca gaaaaaaagg atctcaagaa gatcctttga tcttttctac ggggtctgac    9120
gctcagtgga acgaaaactc acgttaaggg attttggtca tgagattatc aaaaaggatc    9180
ttcacctaga tccttttaaa ttaaaaatga agttttaaat caatctaaag tatatatgag    9240
taaacttggt ctgacagtta ccaatgctta atcagtgagg cacctatctc agcgatctgt    9300
ctatttcgtt catccatagt tgcctgactc cccgtcgtgt agataactac gatacgggag    9360
ggcttaccat ctggccccag tgctgcaatg ataccgcgag acccacgctc accggctcca    9420
gatttatcag caataaacca gccagccgga agggccgagc gcagaagtgg tcctgcaact    9480
ttatccgcct ccatccagtc tattaattgt tgccgggaag ctagagtaag tagttcgcca    9540
gttaatagtt tgcgcaacgt tgttgccatt gctgcagcca tgagattatc aaaaaggatc    9600
ttcacctaga tccttttcac gtagaaagcc agtccgcaga aacggtgctg accccggatg    9660
aatgtcagct actgggctat ctggacaagg gaaaacgcaa cgcaaagag aaagcaggta    9720 gcttgcagtg gcttacatg gcgatagcta gactgggcgg ttttatggac agcaagcgaa    9780
ccggaattgc cagctggggc gccctctggt aaggttggga agccctgcaa agtaaactgg    9840
atggctttct cgccgccaag gatctgatgg cgcagggat caagctctga tcaagagaca    9900
ggatgaggat cgtttcgcat gattgaacaa gatggattgc acgcaggttc tccgccgct    9960 tgggtggaga ggctattcgg ctatgactgg gcacaacaga caatcggctg ctctgatgcc    10020
gccgtgttcc ggctgtcagc gcaggggcgc ccggttcttt ttgtcaagac cgacctgtcc    10080
ggtgccctga atgaactgca agacgaggca gcgcggctat cgtggctggc cacgacgggc    10140
gttccttgcg cagctgtgct cgacgttgtc actgaagcgg gaagggactg gctgctattg    10200
ggcgaagtgc cggggcagga tctcctgtca tctcaccttg ctcctgccga gaaagtatcc    10260
atcatggctg atgcaatgcg gcggctgcat acgcttgatc cggctacctg cccattcgac    10320
caccaagcga aacatcgcat cgagcgagca cgtactcgga tggaagccgg tcttgtcgat    10380
caggatgatc tggacgaaga gcatcagggg ctcgcgccag ccgaactgtt cgccaggctc    10440
aaggcgagca tgcccgacgg cgaggatctc gtcgtgaccc atggcgatgc ctgcttgccg    10500
aatatcatgg tggaaaatgg ccgcttttct ggattcatcg actgtggccg ctgggtgtg    10560 gcggaccgct atcaggacat agcgttggct acccgtgata ttgctgaaga gcttggcggc    10620
gaatgggctg accgcttcct cgtgctttac ggtatcgccg ctcccgattc gcagcgcatc    10680
gccttctatc gccttcttga cgagttcttc tgaatttttgt taaattttt gttaaatcag    10740
```

```
ctcattttttt aaccaatagg ccgaaatcgg caacatccct tataaatcaa aagaatagac    10800
cgcgataggg ttgagtgttg ttccagtttg gaacaagagt ccactattaa agaacgtgga    10860
ctccaacgtc aaagggcgaa aaaccgtcta tcagggcgat ggcccactac gtgaaccatc    10920
acccaaatca agttttttgc ggtcgaggtg ccgtaaagct ctaaatcgga accctaaagg    10980
gagcccccga tttagagctt gacggggaaa gccggcgaac gtggcgagaa aggaagggaa    11040
gaaagcgaaa ggagcgggcg ctagggcgct ggcaagtgta gcggtcacgc tgcgcgtaac    11100
caccacaccc gcgcgcttaa tgcgccgcta cagggcgcgt ccattcgcca ttcaggatcg    11160
aattaattct taattaagga tccnnnncctg tcctcgaccg atgcccttga gagccttcaa    11220
cccagtcagc tccttccggt gggcgcgggg catgactatc gtcgccgcac ttatgactgt    11280
cttctttatc atgcaactcg taggacaggt gccggcagcg ctctgggtca ttttcggcga    11340
ggaccgcttt cgctggagcg cgacgatgat cggcctgtcg cttgcggtat tcggaatctt    11400
gcacgccctc gctcaagcct tcgtcactgg tcccgccacc aaacgtttcg gcgagaagca    11460
ggccattatc gccggcatgg cggccgacgc gctgggctac gtcttgctgg cgttcgcgac    11520
gcgaggctgg atggccttcc ccattatgat tcttctcgct tccggcggca tcgggatgcc    11580
cgcgttgcag gccatgctgt ccaggcaggt agatgacgac catcagggac agcttcaagg    11640
atcgctcgcg gctcttacca gcctaacttc gatcactgga ccgctgatcg tcacggcgat    11700
ttatgccgcc tcggcgagca catggaacgg gttggcatgg attgtaggcg ccgccctata    11760
ccttgtctgc ctccccgcgt tgcgtcgcgg tgcatggagc cgggccacct cgacctgaat    11820
ggaagccggc ggcacctcgc taacggattc accactccaa gaattggagc caatcaattc    11880
ttgcggagaa ctgtgaatgc gcaaaccaac ccttggcaga acatatccat cgcgtccgcc    11940
atctccagca gccgcacgcg gcgcatctcg gcagcgttg  ggtcctggcc acgggtgcgc    12000
atgatcgtgc tcctgtcgtt gaggacccgg ctaggctggc ggggttgcct tactggttag    12060
cagaatgaat caccgatacg cgagcgaacg tgaagcgact gctgctgcaa aacgtctgcg    12120
acctgagcaa caacatgaat ggtcttcggt ttccgtgttt cgtaaagtct ggaaacgcgg    12180
aagtcagcgc cctgcaccat tatgttccgg atctgcatcg caggatgctg ctggctaccc    12240
tgtggaacac ctacatctgt attaacgaag cgctggcatt gaccctgagt gattttctc     12300
tggtcccgcc gcatccatac cgccagttgt ttaccctcac aacgttccag taaccgggca    12360
tgttcatcat cagtaacccg tatcgtgagc atcctctctc gtttcatcgg tatcattacc    12420
cccatgaaca gaaattcccc cttacacgga ggcatcaagt gaccaaacag gaaaaaaccg    12480
cccttaacat ggcccgcttt atcagaagcc agacattaac gcttctggag aaactcaacg    12540
agctggacgc ggatgaacag gcagacatct gtgaatcgct tcacgaccac gctgatgagc    12600
tttaccgcag ctgcctcgcg cgtttcggtg atgacggtga aaacctctga cacatgcagc    12660
tcccggagac ggtcacagct tgtctgtaag cggatgccgg gagcagacaa gcccgtcagg    12720
gcgcgtcagc gggtgttggc gggtgtcggg gcgcagccat gacccagtca cgtagcgata    12780
gcggagtgta tactggctta actatgcggc atcagagcag attgtactga gagtgcacca    12840
tatgcggtgt gaaataccgc acagatgcgt aaggagaaaa taccgcatca ggcgctcttc    12900
cgcttcctcg ctcactgact cgctgcgctc ggtcgttcgg ctgcggcgag cggtatcagc    12960
tcactcaaag gcggtaatac ggttatccac agaatcaggg gataacgcag gaaagaacat    13020
gtgagcaaaa ggccagcaaa aggccaggaa ccgtaaaaag gccgcgttgc tggcgttttt    13080
ccataggctc cgcccccctg acgagcatca caaaaatcga cgctcaagtc agaggtggcg    13140
```

```
aaacccgaca ggactataaa gataccaggc gtttcccect ggaagctccc tcgtgcgctc   13200
tcctgttccg accctgccgc ttaccggata cctgtccgcc tttctcccett cgggaagcgt   13260 ggcgctttct caatgctcac gctgtaggta tctcagttcg gtgtaggtcg ttcgctccaa   13320
gctgggctgt gtgcacgaac ccccegttca gcccgaccgc tgcgccttat ccggtaacta   13380
tcgtcttgag tccaacccgg taagacacga cttatcgcca ctggcagcag ccactggtaa   13440
caggattagc agagcgaggt atgtaggcgg tgctacagag ttcttgaagt ggtggcctaa   13500
ctacggctac actagaagga cagtatttgg tatctgcgct ctgctgaagc cagttacctt   13560
cggaaaaaga gttggtagct cttgatccgg caaacaaacc accgctggta gcggtggttt   13620
ttttgtttgc aagcagcaga ttacgcgcag aaaaaaagga tctcaagaag atcctttgat   13680
cttttctacg gggtctgacg ctcagtggaa cgaaaactca cgttaaggga ttttggtcat   13740
gagattatca aaaggatctt caccctagat ccttttaaat taaaaatgaa gttttaaatc   13800
aatctaaagt atatatgagt aaacttggtc tgacagttac caatgcttaa tcagtgaggc   13860
acctatctca gcgatctgtc tatttcgttc atccatagtt gcctgactcc ccgtcgtgta   13920
gataactacg atacgggagg gcttaccatc tggccccagt gctgcaatga taccgcgaga   13980
cccacgctca ccggctccag atttatcagc aataaaccag ccagccggaa gggccgagcg   14040
cagaagtggt cctgcaactt tatccgcctc catccagtct attaattgtt gccgggaagc   14100
tagagtaagt agttcgccag ttaatagttt gcgcaacgtt gttgccattg ctgcagccat   14160
gagattatca aaaggatctt caccctagat ccttttcacg tagaaagcca gtccgcagaa   14220
acggtgctga ccccggatga atgtcagcta ctgggctatc tggacaaggg aaaacgcaag   14280
cgcaaagaga agcaggtag cttgcagtgg gcttacatgg cgatagctag actgggcggt   14340
tttatggaca gcaagcgaac cggaattgcc agctggggcg ccctctggta aggttgggaa   14400
gccctgcaaa gtaaactgga tggctttctc gccgccaagg atctgatggc caggggatc   14460 aagctctgat caagagacag gatgaggatc gtttcgcatg attgaacaag atggattgca   14520
cgcaggttct ccgccgcctt gggtggagag gctattcggc tatgactggg cacaacagac   14580
aatcggctgc tctgatgccg ccgtgttccg gctgtcagcg caggggcgcc cggttctttt   14640
tgtcaagacc gacctgtccg gtgccctgaa tgaactgcaa gacgaggcag cgcggctatc   14700
gtggctggcc acgacgggcg ttccttgcgc agctgtgctc gacgttgtca ctgaagcggg   14760
aagggactgg ctgctattgg gcgaagtgcc ggggcaggat ctcctgtcat ctcaccttgc   14820
tcctgccgag aaagtatcca tcatggctga tgcaatgcgg cggctgcata cgcttgatcc   14880
ggctacctgc ccattcgacc accaagcgaa acatcgcatc gagcgagcac gtactcggat   14940
ggaagccggt cttgtcgatc aggatgatct ggacgaagag catcaggggc tcgcgccagc   15000
cgaactgttc gccaggctca aggcgagcat gcccgacggc gaggatctcg tcgtgaccca   15060
tggcgatgcc tgcttgccga atatcatggt ggaaaatggc cgcttttctg gattcatcga   15120
ctgtggccgg ctgggtgtgg cggaccgcta tcaggacata gcgttggcta cccgtgatat   15180
tgctgaagag cttggcggcg aatgggctga ccgcttcctc gtgctttacg gtatcgccgc   15240
tcccgattcg cagcgcatcg ccttctatcg ccttcttgac gagttcttct gaattttgtt   15300
aaaatttttg ttaaatcagc tcattttta accaataggc cgaaatcggc aacatccctt   15360
ataaatcaaa agaatagacc gcgatagggt tgagtgttgt tccagtttgg aacaagagtc   15420
cactattaaa gaacgtggac tccaacgtca agggcgaaa aaccgtctat cagggcgatg   15480
```

```
gcccactacg tgaaccatca cccaaatcaa gttttttgcg gtcgaggtgc cgtaaagctc    15540
taaatcggaa ccctaaaggg agcccccgat ttagagcttg acggggaaag ccggcgaacg    15600
tggcgagaaa ggaagggaag aaagcgaaag gagcgggcgc tagggcgctg gcaagtgtag    15660
cggtcacgct gcgcgtaacc accacacccg cgcgcttaat gcgccgctac agggcgcgtc    15720
cattcgccat tcaggatcga attaattctt aattaacatc atcaataata taccttattt    15780
tggattgaag ccaatatgat aatgaggggg tggagtttgt gacgtggcgc ggggcgtggg    15840
aacggggcgg gtgacgtagt agtgtggcgg aagtgtgatg ttgcaagtgt ggcggaacac    15900
atgtaagcga cggatgtggc aaaagtgacg ttttggtgt gcgccggtgt acacaggaag    15960
tgacaatttt cgcgcggttt taggcggatg ttgtagtaaa tttgggcgta accgagtaag    16020
atttggccat tttcgcggga aaactgaata agaggaagtg aaatctgaat aattttgtgt    16080
tactcatagc gcgtaatact gctagagatc tggcgaaagg gggatgtgct gcaaggcgat    16140
taagttgggt aacgccaggg ttttcccagt cacgacgttg taaaacgacg gccagtgaat    16200
tgtaatacga ctcactatag ggcgaattgg gtactggcca cagagcttgg cccattgcat    16260
acgttgtatc catatcataa tatgtacatt tatattggct catgtccaac attaccgcca    16320
tgttgacatt gattattgac tagttattaa tagtaatcaa ttacggggtc attagttcat    16380
agcccatata tggagttccg cgttacataa cttacggtaa atggcccgcc tggctgaccg    16440
cccaacgacc cccgcccatt gacgtcaata atgacgtatg ttcccatagt aacgccaata    16500
gggactttcc attgacgtca atgggtggag tatttacggt aaactgccca cttggcagta    16560
catcaagtgt atcatatgcc aagtacgccc cctattgacg tcaatgacgg taaatggccc    16620
gcctggcatt atgcccagta catgacctta tgggactttc ctacttggca gtacatctac    16680
gtattagtca tcgctattac catggtgatg cggttttggc agtacatcaa tgggcgtgga    16740
tagcggtttg actcacgggg atttccaagt ctccacccca ttgacgtcaa tgggagtttg    16800
ttttggcacc aaaatcaacg ggactttcca aaatgtcgta caactccgc cccattgacg    16860
caaatgggcg gtaggcgtgt acggtgggag gtctatataa gcagagctcg tttagtgaac    16920
cgtcagatcg cctggagacg ccatccacgc tgttttgacc tccatagaag acaccgggac    16980
cgatccagcc tgactctagc ctagctctga agttggtggt gaggccctgg gcaggttggt    17040
atcaaggtta caagacaggt ttaaggagac caatagaaac tgggcatgtg agacagaga    17100
agactcttgg gtttctgata ggcactgact ctctctgcct attggtctat tttcccaccc    17160
ttaggctgct ggtctgagcc taggagatct ctcgaggtcg acggtatcga tgccaccatg    17220
gagaaaatcg tcctgttgct cgctattgtg tctctagtga agagcgatca aatttgtatc    17280
ggctaccatg ccaataactc aacagagcag gtcgatacta tcatggagaa aaacgtaaca    17340
gttactcatg cccaagacat cttggaaaag acccacaacg gcaaactttg cgacctggat    17400
ggagtgaagc cctgatcct ccgggactgt tcagtcgctg gttggctgct cgggaacct    17460
atgtgtgatg agtttatcaa cgtgcctgaa tggtcttaca ttgtggagaa ggctaaccct    17520
accaatgacc tctgctatcc tgggtcattt aacgattacg aggaactgaa acacctgttg    17580
tctagaatta accactttga aaagatacag attataccca agtctagttg gagtgatcac    17640
gaagcctcct caggcgttag ctcagcgtgt ccctatctgg gctctccatc cttctttaga    17700
aatgtggtct ggttaatcaa aaagaacagt acctacccaa ccatcaaaaa gtcttataac    17760
aataccaatc aggaggacct gctcgtgttg tggggtatcc atcacccgaa cgacgccgct    17820
gaacagacta ggctgtatca gaaccccact acatacatca gtattggcac gagtactctg    17880
```

```
aaccagcgat tagtgccaaa gattgcaaca cggagcaaag taaatgggca atctggcagg   17940
atggagtttt tctggacaat cttaaaaccc aacgatgcga taaatttcga gtccaatggc   18000
aatttcatcg cccctgaata cgcctataag atcgtgaaaa aggggactc tgcaattatg    18060 aagtccgaat tagagtatgg caattgcaac acgaagtgcc agacaccaat gggagccatt   18120
aatagctcaa tgcccttcca taatattcat ccattgacca ttggggagtg cccaaagtac   18180
gtgaagtcca accgcctggt cctcgcaacc ggtctaagaa atagcccgca gagagaatcg   18240
cggaggaaga aacgtggcct gtttggcgcg attgccggat tcatcgaggg aggctggcag   18300
ggtatggtcg atggttggta cggataccac catagcaacg aacaggggtc cggctatgca   18360
gcagataagg agagcactca gaaagctatt gacggagtta caaacaaggt taatagtatt   18420
atagataaaa tgaacacgca attcgaggcc gttgggaggg agtttaacaa tctggaacgc   18480
cggatcgaaa atctgaataa gaaaatggaa gacggcttcc ttgacgtgtg gacttataat   18540
gcagagctgc ttgtactcat ggagaacgag aggaccctgg atttccacga tagcaacgtg   18600
aagaaccttt acgacaaggt gagacttcag ctccgagaca acgccaagga gctggggaat   18660
ggatgcttcg agttttacca caaatgtgac aatgagtgca tggaaagtat acgcaacggg   18720
acctacaatt accctcagta tagcgaagag gctcggctca aacgcgaaga gataagcggg   18780
gtgaaattgg aatcaatcgg aacatatcaa atcctgtcca tctattccac cgtcgcctct   18840
tcgctggccc tcgctatcat gatggctggt ctgtccctat ggatgtgttc caatggaagc   18900
cttcagtgcc gtatttgtat atgagcggcc gccctattct atagtgtcac ctaaatgcta   18960
gagctcgctg atcagcctcg actgtgcctt ctagttgcca gccatctgtt gtttgccct    19020 cccccgtgcc ttccttgacc ctggaaggtg ccactcccac tgtcctttcc taataaaatg   19080
aggaaattgc atcgcattgt ctgagtaggt gtcattctat tctgggggt ggggtggggc    19140 aggacagcaa gggggaggat tgggaagaca atagcaggca tgctgggat gcggtgggct    19200 ctatggcttc tgaggcggaa agaaccaaag cttaacatca tcaataatat accttatttt   19260
ggattgaagc caatatgata atgagggggt ggagtttgtg acgtggcgcg gggcgtggga   19320
acggggcggg tgacgtagta gtgtggcgga agtgtgatgt tgcaagtgtg gcggaacaca   19380
tgtaagcgac ggatgtggca aaagtgacgt ttttggtgtg cgccggtgta cacaggaagt   19440
gacaattttc gcgcggtttt aggcggatgt tgtagtaaat ttgggcgtaa ccgagtaaga   19500
tttggccatt ttcgcgggaa aactgaataa gaggaagtga atctgaata attttgtgtt    19560 actcatagcg cgtaatactg taatagtaat caattacggg gtcattagtt catagcccat   19620
atatggagtt ccgcgttaca taacttacgg taaatggccc gcctggctga ccgcccaacg   19680 accccgccc attgacgtca ataatgacgt atgttccat agtaacgcca atagggactt     19740
tccattgacg tcaatgggtg gagtatttac ggtaaactgc ccacttggca gtacatcaag   19800
tgtatcatat gccaagtacg ccccctattg acgtcaatga cggtaaatgg cccgcctggc   19860
attatgccca gtacatgacc ttatgggact ttcctacttg gcagtacatc tacgtattag   19920
tcatcgctat taccatggtg atgcggtttt ggcagtacat caatgggcgt ggatagcggt   19980
ttgactcacg gggatttcca agtctccacc ccattgacgt caatgggagt ttgttttggc   20040
accaaaatca acgggacttt ccaaaatgtc gtaacaactc cgccccattg acgcaaatgg   20100
gcggtaggcg tgtacggtgg gaggtctata taagcagagc tggtttagtg aaccgtcaga   20160
tccgctagag atctgggaaa cgatatgggc tgaatacgga tccgtattca gcccatatcg   20220
```

-continued

```
tttctctaga aataaaatat ctttattttc attacatctg tgtgttggtt ttttgtgtgg    20280
cggccgctcg agcctaagct tctagataag atatccgatc caccggatct agataactga    20340
tcataatcag ccataccaca tttgtagagg ttttacttgc tttaaaaaac ctcccacacc    20400
tccccctgaa cctgaaacat aaaatgaatg caattgttgt tgttaacttg tttattgcag    20460
cttataatgg ttacaaataa agcaatagca tcacaaattt cacaaataaa gcattttttt    20520
cactgcattc tagttgtggt ttgtccaaac tcatcaatgt atcttaacgc ggatctgggc    20580
gtggttaagg gtgggaaaga atatataagg tgggggtctt atgtagtttt gtatctgttt    20640
tgcagcagcc gccgccgcca tgagcaccaa ctcgtttgat ggaagcattg tgagcttgtc    20700
gactcgaaga tctgggcgtg gttaagggtg ggaagaata tataaggtgg gggtcttatg    20760
tagttttgta tctgttttgc agcagccgcc gccgccatga gcaccaactc gtttgatgga    20820
agcattgtga gctcatattt gacaacgcgc atgcccccat gggccggggt gcgtcagaat    20880
gtgatgggct ccagcattga tggtcgcccc gtcctgcccg caaactctac taccttgacc    20940
tacgagaccg tgtctggaac gccgttggag actgcagcct ccgccgccgc ttcagccgct    21000
gcagccaccg cccgcgggat tgtgactgac tttgctttcc tgagcccgct tgcaagcagt    21060
gcagcttccc gttcatccgc ccgcgatgac aagttgacgg ctcttttggc acaattggat    21120
tctttgaccc gggaacttaa tgtcgtttct cagcagctgt tggatctgcg ccagcaggtt    21180
tctgccctga aggcttcctc ccctcccaat gcggtttaaa acataaataa aaaaccagac    21240
tctgttggat tttggatcaa gcaagtgtct tgctgtcttt atttaggggt tttgcgcgcg    21300
cggtaggccc gggaccagcg gtctcggtcg ttgagggtcc tgtgtatttt ttccaggacg    21360
tggtaaaggt gactctggat gttcagatac atgggcataa gcccgtctct ggggtggagg    21420
tagcaccact gcagagcttc atgctgcggg gtggtgttgt agatgatcca gtcgtagcag    21480
gagcgctggg cgtggtgcct aaaaatgtct ttcagtagca agctgattgc caggggcagg    21540
cccttggtgt aagtgtttac aaagcggtta agctgggatg ggtgcatacg tggggatatg    21600
agatgcatct tggactgtat ttttaggttg gctatgttcc cagccatatc cctccgggga    21660
ttcatgttgt gcagaaccac cagcacagtg tatccggtgc acttgggaaa tttgtcatgt    21720
agcttagaag gaaatgcgtg gaagaacttg gagacgccct tgtgacctcc aagattttcc    21780
atgcattcgt ccataatgat ggcaatgggc ccacgggcgg cggcctgggc gaagatattt    21840
ctgggatcac taacgtcata gttgtgttcc aggatgagat cgtcataggc catttttaca    21900
aagcgcgggc ggagggtgcc agactgcggt ataatggttc catccggccc aggggcgtag    21960
ttaccctcac agatttgcat ttcccacgct ttgagttcag atgggggggat catgtctacc    22020
tgcggggcga tgaagaaaac ggtttccggg gtaggggaga tcagctggga agaaagcagg    22080
ttcctgagca gctgcgactt accgcagccg gtgggcccgt aaatcacacc tattaccggg    22140
tgcaactggt agttaagaga gctgcagctg ccgtcatccc tgagcagggg ggccacttcg    22200
ttaagcatgt ccctgactcg catgtttttcc ctgaccaaat ccgccagaag gcgctcgccg    22260
cccagcgata gcagttcttg caaggaagca aagttttttca acggtttgag accgtccgcc    22320
gtaggcatgc ttttgagcgt ttgaccaagc agttccaggc ggtcccacag ctcggtcacc    22380
tgctctacgg catctcgatc cagcatatct cctcgtttcg cggttgggg cggctttcgc    22440
tgtacggcag tagtcggtgc tcgtccagac gggccagggt catgtctttc cacggcgca    22500
gggtcctcgt cagcgtagtc tgggtcacgg tgaaggggtg cgctccgggc tgcgcgctgg    22560
ccagggtgcg cttgaggctg gtcctgctgg tgctgaagcg ctgccggtct tcgccctgcg    22620
```

```
cgtcggccag gtagcatttg accatggtgt catagtccag cccctccgcg gcgtggccct   22680
tggcgcgcag cttgcccttg gaggaggcgc cgcacgaggg gcagtgcaga cttttgaggg   22740
cgtagagctt gggcgcgaga ataccgatt  ccggggagta ggcatccgcg ccgcaggccc   22800
cgcagacggt ctcgcattcc acgagccagg tgagctctgg ccgttcgggg tcaaaaacca   22860
ggtttccccc atgctttttg atgcgtttct tacctctggt ttccatgagc cggtgtccac   22920
gctcggtgac gaaaaggctg tccgtgtccc cgtatacaga cttgagaggc ctgtcctcga   22980
gcggtgttcc gcggtcctcc tcgtatagaa actcggacca ctctgagaca aaggctcgcg   23040
tccaggccag cacgaaggag gctaagtggg aggggtagcg gtcgttgtcc actaggggt   23100
ccactcgctc cagggtgtga agacacatgt cgccctcttc ggcatcaagg aaggtgattg   23160
gtttgtaggt gtaggccacg tgaccgggtg ttcctgaagg ggggctataa aaggggggtgg  23220
gggcgcgttc gtcctcactc tcttccgcat cgctgtctgc gagggccagc tgttggggtg   23280
agtactccct ctgaaaagcg ggcatgactt ctgcgctaag attgtcagtt tccaaaaacg   23340
aggaggattt gatattcacc tggcccgcgg tgatgccttt gagggtggcc gcatccatct   23400
ggtcagaaaa gacaatcttt ttgttgtcaa gcttggtggc aaacgacccg tagagggcgt   23460
tggacagcaa cttggcgatg gagcgcaggg tttggttttt gtcgcgatcg gcgcgctcct   23520
tggccgcgat gtttagctgc acgtattcgc gcgcaacgca ccgccattcg ggaaagacgt   23580
tggtgcgctc gtcgggcacc aggtgcacgc gccaaccgcg gttgtgcagg gtgacaaggt   23640
caacgctggt ggctacctct ccgcgtaggc gctcgttggt ccagcagagg cggccgccct   23700
tgcgcgagca gaatggcggt aggggggtcta gctgcgtctc gtccggggggg tctgcgtcca   23760
cggtaaagac cccgggcagc aggcgcgcgt cgaagtagtc tatcttgcat ccttgcaagt   23820
ctagcgcctg ctgccatgcg cgggcggcaa gcgcgcgctc gtatgggttg agtgggggac   23880
cccatggcat ggggtgggtg agcgcggagg cgtacatgcc gcaaatgtcg taaacgtaga   23940
ggggctctct gagtattcca agatatgtag ggtagcatct tccaccgcgg atgctggcgc   24000
gcacgtaatc gtatagttcg tgcgagggag cgaggaggtc gggaccgagg ttgctacggg   24060
cgggctgctc tgctcggaag actatctgcc tgaagatggc atgtgagttg gatgatatgg   24120
ttggacgctg gaagacgttg aagctggcgt ctgtgagacc taccgcgtca cgcacgaagg   24180
aggcgtagga gtcgcgcagc ttgttgacca gctcggcggt gacctgcacg tctagggcgc   24240
agtagtccag ggtttccttg atgatgtcat acttatcctg tccctttttt ttccacagct   24300
cgcggttgag gacaaactct cgcggtctt  tccagtactc ttggatcgga aacccgtcgg   24360
cctccgaacg gtaagagcct agcatgtaga actggttgac ggcctggtag gcgcagcatc   24420
cctttttctac gggtagcgcg tatgcctgcg cggccttccg gagcgaggtg tgggtgagcg   24480
caaaggtgtc cctgaccatg actttgaggt actggtattt gaagtcagtg tcgtcgcatc   24540
cgccctgctc ccagagcaaa aagtccgtgc gcttttttgga acgcggattt ggcagggcga   24600
aggtgacatc gttgaagagt atcttttccg cgcgaggcat aaagttgcgt gtgatgcgga   24660
agggtcccgg cacctcggaa cggttgttaa ttacctgggc ggcgagcacg atctcgtcaa   24720
agccgttgat gttgtggccc acaatgtaaa gttccaagaa gcgcgggatg cccttgatgg   24780
aaggcaattt tttaagttcc tcgtaggtga gctcttcagg ggagctgagc ccgtgctctg   24840
aaagggccca gtctgcaaga tgagggtgg  aagcgacgaa tgagctccac aggtcacggg   24900
ccattagcat ttgcaggtgg tcgcgaaagg tcctaaactg gcgacctatg gccattttt   24960
```

```
ctggggtgat gcagtagaag gtaagcgggt cttgttccca gcggtcccat ccaaggttcg    25020
cggctaggtc tcgcgcggca gtcactagag gctcatctcc gccgaacttc atgaccagca    25080
tgaagggcac gagctgcttc ccaaaggccc ccatccaagt ataggtctct acatcgtagg    25140
tgacaaagag acgctcggtg cgaggatgcg agccgatcgg gaagaactgg atctcccgcc    25200
accaattgga ggagtggcta ttgatgtggt gaaagtagaa gtccctgcga cgggccgaac    25260
actcgtgctg gcttttgtaa aaacgtgcgc agtactggca gcggtgcacg ggctgtacat    25320
cctgcacgag gttgacctga cgaccgcgca caaggaagca gagtgggaat ttgagcccct    25380
cgcctggcgg gtttggctgg tggtcttcta cttcggctgc ttgtccttga ccgtctggct    25440
gctcgagggg agttacggtg gatcggacca ccacgccgcg cgagcccaaa gtccagatgt    25500
ccgcgcgcgg cggtcggagc ttgatgacaa catcgcgcag atgggagctg tccatggtct    25560
ggagctcccg cggcgtcagg tcaggcggga gctcctgcag gtttacctcg catagacggg    25620
tcagggcgcg ggctagatcc aggtgatacc taatttccag gggctggttg gtggcggcgt    25680
cgatggcttg caagaggccg catccccgcg gcgcgactac ggtaccgcgc ggcgggcggt    25740
gggccgcggg ggtgtccttg gatgatgcat ctaaaagcgg tgacgcgggc gagccccgg    25800 aggtaggggg ggctccggac ccgccgggag aggggggcagg ggcacgtcgg cgccgcgcgc    25860
gggcaggagc tggtgctgcg cgcgtaggtt gctggcgaac gcgacgacgc ggcggttgat    25920
ctcctgaatc tggcgcctct gcgtgaagac gacgggcccg gtgagcttga gcctgaaaga    25980
gagttcgaca gaatcaattt cggtgtcgtt gacggcggcc tggcgcaaaa tctcctgcac    26040
gtctcctgag ttgtcttgat aggcgatctc ggccatgaac tgctcgatct cttcctcctg    26100
gagatctccg cgtccggctc gctccacggt ggcggcgagg tcgttggaaa tgcgggccat    26160
gagctgcgag aaggcgttga ggcctccctc gttccagacg cggctgtaga ccacgccccc    26220
ttcggcatcg cgggcgcgca tgaccacctg cgcgagattg agctccacgt gccgggcgaa    26280
gacggcgtag tttcgcaggc gctgaaagag gtagttgagg gtggtggcgg tgtgttctgc    26340
cacgaagaag tacataaccc agcgtcgcaa cgtggattcg ttgatatccc ccaaggcctc    26400
aaggcgctcc atggcctcgt agaagtccac ggcgaagttg aaaaactggg agttgcgcgc    26460
cgacacggtt aactcctcct ccagaagacg gatgagctcg gcgacagtgt cgcgcacctc    26520
gcgctcaaag gctacagggg cctcttcttc ttcttcaatc tcctcttcca taagggcctc    26580
cccttcttct tcttctggcg gcggtggggg aggggggaca cggcggcgac gacggcgcac    26640
cgggaggcgg tcgacaaagc gctcgatcat ctccccgcgg cgacgcgca tggtctcggt    26700 gacggcgcgg ccgttctcgc gggggcgcag ttggaagacg ccgcccgtca tgtcccggtt    26760
atgggttggc ggggggctgc catgcggcag ggatacggcg ctaacgatgc atctcaacaa    26820
ttgttgtgta ggtactccgc cgccgaggga cctgagcgag tccgcatcga ccggatcgga    26880
aaacctctcg agaaaggcgt ctaaccagtc acagtcgcaa ggtaggctga gcaccgtggc    26940
gggcggcagc gggcggcggt cggggttgtt tctggcggag gtgctgctga tgatgtaatt    27000
aaagtaggcg gtcttgagac ggcggatggt cgacagaagc accatgtcct tgggtccggc    27060
ctgctgaatg cgcaggcggt cggccatgcc ccaggcttcg ttttgacatc ggcgcaggtc    27120
tttgtagtag tcttgcatga gcctttctac cggcacttct tcttctcctt cctcttgtcc    27180
tgcatctctt gcatctatcg ctgcggcggc ggcggagttt ggccgtaggt ggcgccctct    27240
tcctcccatg cgtgtgaccc cgaagcccct catcggctga agcagggcta ggtcggcgac    27300
aacgcgctcg gctaatatgg cctgctgcac ctgcgtgagg gtagactgga agtcatccat    27360
```

-continued

```
gtccacaaag cggtggtatg cgcccgtgtt gatggtgtaa gtgcagttgg ccataacgga    27420
ccagttaacg gtctggtgac ccggctgcga gagctcggtg tacctgagac gcgagtaagc    27480
cctcgagtca aatacgtagt cgttgcaagt ccgcaccagg tactggtatc ccaccaaaaa    27540
gtgcggcggc ggctggcggt agaggggcca gcgtagggtg gccggggctc cgggggcgag    27600
atcttccaac ataaggcgat gatatccgta gatgtacctg gacatccagg tgatgccggc    27660
ggcggtggtg gaggcgcgcg gaaagtcgcg gacgcggttc cagatgttgc gcagcggcaa    27720
aaagtgctcc atggtcggga cgctctggcc ggtcaggcgc gcgcaatcgt tgacgctcta    27780
ccgtgcaaaa ggagagcctg taagcgggca ctcttccgtg gtctggtgga taaattcgca    27840
agggtatcat ggcggacgac cggggttcga gccccgtatc cggccgtccg ccgtgatcca    27900
tgcggttacc gcccgcgtgt cgaacccagg tgtgcgacgt cagacaacgg gggagtgctc    27960
cttttggctt ccttccaggc gcggcggctg ctgcgctagc ttttttggcc actggccgcg    28020
cgcagcgtaa gcggttaggc tggaaagcga aagcattaag tggctcgctc cctgtagccg    28080
gagggttatt ttccaagggt tgagtcgcgg gaccccggt tcgagtctcg gaccggccgg     28140
actgcggcga acgggggttt gcctccccgt catgcaagac cccgcttgca aattcctccg    28200
gaaacaggga cgagccccctt ttttgctttt cccagatgca tccggtgctg cggcagatgc    28260 gccccccctcc tcagcagcgg caagagcaag agcagcggca gacatgcagg gcaccctccc    28320
ctcctcctac cgcgtcagga ggggcgacat ccgcggttga cgcggcagca gatggtgatt    28380
acgaaccccc gcgcgccgg gcccggcact acctggactt ggaggagggc gagggcctgg     28440
cgcggctagg agcgccctct cctgagcggt acccaagggt gcagctgaag cgtgatacgc    28500
gtgaggcgta cgtgccgcgg cagaacctgt ttcgcgaccg cgaggagag gagcccgagg     28560 agatgcggga tcgaaagttc cacgcagggc gcgagctgcg gcatggcctg aatcgcgagc    28620
ggttgctgcg cgaggaggac tttgagcccg acgcgcgaac cgggattagt cccgcgcgcg    28680
cacacgtggc ggccgccgac ctggtaaccg catacgagca gacggtgaac caggagatta    28740
actttcaaaa aagctttaac aaccacgtgc gtacgcttgt ggcgcgcgag gaggtggcta    28800
taggactgat gcatctgtgg gactttgtaa gcgcgctgga gcaaaaccca aatagcaagc    28860
cgctcatggc gcagctgttc cttatagtgc agcacagcag ggacaacgag gcattcaggg    28920
atgcgctgct aaacatagta gagcccgagg gccgctggct gctcgatttg ataaacatcc    28980
tgcagagcat agtggtgcag gagcgcagct tgagcctggc tgacaaggtg gccgccatca    29040
actattccat gcttagcctg ggcaagtttt acgcccgcaa gatataccat accccttacg    29100
ttcccataga caaggaggta aagatcgagg ggttctacat gcgcatggcg ctgaaggtgc    29160
ttaccttgag cgacgacctg ggcgtttatc gcaacgagcg catccacaag gccgtgagcg    29220
tgagccggcg cgcgagctc agcgaccgcg agctgatgca cagcctgcaa agggccctgg    29280
ctggcacggg cagcggcgat agagaggccg agtcctactt tgacgcgggc gctgacctgc    29340
gctgggcccc aagccgacgc gccctggagg cagctgggc cggacctggg ctggcggtgg     29400
cacccgcgcg cgctggcaac gtcggcggcg tgaggaata tgacgaggac gatgagtacg    29460
agccagagga cggcgagtac taagcggtga tgtttctgat cagatgatgc aagacgcaac    29520
ggacccggcg gtgcgggcgg cgctgcagag ccagccgtcc ggccttaact ccacggacga    29580
ctggcgccag gtcatggacc gcatcatgtc gctgactgcg cgcaatcctg acgcgttccg    29640
gcagcagccg caggccaacc ggctctccgc aattctggaa gcggtggtcc cggcgcgcgc    29700
```

```
aaaccccacg cacgagaagg tgctggcgat cgtaaacgcg ctggccgaaa acagggccat    29760
ccggcccgac gaggccggcc tggtctacga cgcgctgctt cagcgcgtgg ctcgttacaa    29820
cagcggcaac gtgcagacca acctggaccg gctggtgggg gatgtgcgcg aggccgtggc    29880
gcagcgtgag cgcgcgcagc agcagggcaa cctgggctcc atggttgcac taaacgcctt    29940
cctgagtaca cagcccgcca acgtgccgcg gggacaggag gactacacca actttgtgag    30000
cgcactgcgg ctaatggtga ctgagacacc gcaaagtgag gtgtaccagt ctgggccaga    30060
ctattttttc cagaccagta gacaaggcct gcagaccgta aacctgagcc aggctttcaa    30120
aaacttgcag gggctgtggg gggtgcgggc tcccacaggc gaccgcgcga ccgtgtctag    30180
cttgctgacg cccaactcgc gcctgttgct gctgctaata gcgcccttca cggacagtgg    30240
cagcgtgtcc cggacacat acctaggtca cttgctgaca ctgtaccgcg aggccatagg    30300
tcaggcgcat gtggacgagc atactttcca ggagattaca agtgtcagcc gcgcgctggg    30360
gcaggaggac acgggcagcc tggaggcaac cctaaactac ctgctgacca accggcggca    30420
gaagatcccc tcgttgcaca gtttaaacag cgaggaggag cgcatttgc gctacgtgca    30480 gcagagcgtg agccttaacc tgatgcgcga cggggtaacg cccagcgtgg cgctggacat    30540
gaccgcgcgc aacatggaac cgggcatgta tgcctcaaac cggccgtta tcaaccgcct    30600 aatggactac ttgcatcgcg cggccgccgt gaaccccgag tatttcacca atgccatctt    30660
gaacccgcac tggctaccgc ccctggtttt ctacaccggg ggattcgagg tgcccgaggg    30720
taacgatgga ttcctctggg acgacataga cgacagcgtg ttttccccgc aaccgcagac    30780
cctgctagag ttgcaacagc gcgagcaggc agaggcggcg ctgcgaaagg aaagcttccg    30840
caggccaagc agcttgtccg atctaggcgc tgcggcccg cggtcagatg ctagtagccc    30900
atttccaagc ttgatagggt ctcttaccag cactcgcacc acccgcccgc gcctgctggg    30960
cgaggaggag tacctaaaca actcgctgct gcagccgcag cgcgaaaaaa acctgcctcc    31020
ggcatttccc aacaacggga tagagagcct agtggacaag atgagtagat ggaagacgta    31080
cgcgcaggag cacagggacg tgccaggccc gcgcccgccc acccgtcgtc aaaggcacga    31140
ccgtcagcgg ggtctggtgt gggaggacga tgactcggca gacgacagca gcgtcctgga    31200
tttgggaggg agtggcaacc cgtttgcgca ccttcgcccc aggctgggga gaatgtttta    31260
aaaaaaaaaa agcatgatgc aaaataaaaa actcaccaag gccatggcac cgagcgttgg    31320
ttttcttgta ttcccccttag tatgcggcgc gcggcgatgt atgaggaagg tcctcctccc    31380
tcctacgaga gtgtggtgag cgcggcgcca gtggcggcg cgctggggttc tcccttcgat    31440 gctcccctgg acccgccgtt tgtgcctccg cggtacctgc ggcctaccgg ggggagaaac    31500
agcatccgtt actctgagtt ggcaccccta ttcgacacca cccgtgtgta cctggtggac    31560
aacaagtcaa cggatgtggc atccctgaac taccagaacg accacagcaa ctttctgacc    31620
acggtcattc aaaacaatga ctacagcccg ggggaggcaa gcacacagac catcaatctt    31680
gacgaccggt cgcactgggg cggcgacctg aaaaccatcc tgcataccaa catgccaaat    31740
gtgaacgagt tcatgtttac caataagttt aaggcgcggg tgatggtgtc gcgcttgcct    31800
actaaggaca atcaggtgga gctgaaatac gagtgggtgg agttcacgct gcccgagggc    31860
aactactccg agaccatgac catagacctt atgaacaacg cgatcgtgga gcactacttg    31920
aaagtgggca gacagaacgg ggttctggaa agcgacatcg gggtaaagtt tgacacccgc    31980
aacttccagc tgggggttga ccccgtcact ggtcttgtca tgcctggggt atatacaaac    32040
gaagccttcc atccagacat cattttgctg ccaggatgcg gggtggactt cacccacagc    32100
```

```
cgcctgagca acttgttggg catccgcaag cggcaaccct tccaggaggg ctttaggatc    32160
acctacgatg atctggaggg tggtaacatt cccgcactgt tggatgtgga cgcctaccag    32220
gcgagcttga aagatgacac cgaacagggc ggggtggcg caggcggcag caacagcagt    32280
ggcagcggcg cggaagagaa ctccaacgcg gcagccgcgg caatgcagcc ggtggaggac    32340
atgaacgatc atgccattcg cggcgacacc tttgccacac gggctgagga gaagcgcgct    32400
gaggccgaag cagcggccga agctgccgcc cccgctgcgc aacccgaggt cgagaagcct    32460
cagaagaaac cggtgatcaa acccctgaca gaggacagca agaaacgcag ttacaaccta    32520
ataagcaatg acagcacctt cacccagtac cgcagctggt accttgcata caactacggc    32580
gaccctcaga ccggaatccg ctcatggacc ctgctttgca ctcctgacgt aacctgcggc    32640
tcggagcagg tctactggtc gttgccagac atgatgcaag accccgtgac cttccgctcc    32700
acgcgccaga tcagcaactt ccggtggtg ggcgccgagc tgttgcccgt gcactccaag    32760
agcttctaca acgaccaggc cgtctactcc caactcatcc gccagtttac ctctctgacc    32820
cacgtgttca atcgctttcc cgagaaccag attttggcgc gcccgccagc ccccaccatc    32880
accaccgtca gtgaaaacgt tcctgctctc acagatcacg ggacgctacc gctgcgcaac    32940
agcatcggag gagtccagcg agtgaccatt actgacgcca gacgccgcac ctgcccctac    33000
gtttacaagg ccctgggcat agtctcgccg cgcgtcctat cgagccgcac tttttgagca    33060
agcatgtcca tccttatatc gcccagcaat aacacaggct ggggcctgcg cttcccaagc    33120
aagatgtttg gcggggccaa gaagcgctcc gaccaacacc cagtgcgcgt gcgcgggcac    33180
taccgcgcgc cctggggcgc gcacaaacgc ggccgcactg ggcgcaccac cgtcgatgac    33240
gccatcgacg cggtggtgga ggaggcgcgc aactacacgc ccacgccgcc accagtgtcc    33300
acagtggacg cggccattca gaccgtggtg cgcggagccc ggcgctatgc taaaatgaag    33360
agacggcgga ggcgcgtagc acgtcgccac cgccgccgac ccggcactgc cgcccaacgc    33420
gcggcggcgg ccctgcttaa ccgcgcacgt cgcaccggcc gacgggcggc catgcgggcc    33480
gctcgaaggc tggccgcggg tattgtcact gtgcccccca ggtccaggcg acgagcggcc    33540
gccgcagcag ccgcggccat tagtgctatg actcagggtc gcaggggcaa cgtgtattgg    33600
gtgcgcgact cggttagcgg cctgcgcgtg cccgtgcgca cccgcccccc gcgcaactag    33660
attgcaagaa aaaactactt agactcgtac tgttgtatgt atccagcggc ggcggcgcgc    33720
aacgaagcta tgtccaagcg caaaatcaaa gaagagatgc tccaggtcat cgcgccgag    33780 atctatggcc ccccgaagaa ggaagagcag gattacaagc cccgaaagct aaagcgggtc    33840
aaaaagaaaa agaagatga tgatgatgaa cttgacgacg aggtggaact gctgcacgct    33900
accgcgccca ggcgacgggt acagtggaaa ggtcgacgcg taaaacgtgt tttgcgaccc    33960
ggcaccaccg tagtctttac gccggtgag cgctccaccc gcacctacaa gcgcgtgtat    34020
gatgaggtgt acgcgacga ggacctgctt gagcaggcca acgagcgcct cggggagttt    34080
gcctacggaa agcggcataa ggacatgctg gcgttgccgc tggacgaggg caacccaaca    34140
cctagcctaa agcccgtaac actgcagcag gtgctgcccg cgcttgcacc gtccgaagaa    34200
aagcgcggcc taaagcgcga gtctggtgac ttggcaccca ccgtgcagct gatggtaccc    34260
aagcgccagc gactggaaga tgtcttggaa aaaatgaccg tggaacctgg gctggagccc    34320
gaggtccgcg tgcggccaat caagcaggtg gcgccgggac tgggcgtgca gaccgtggac    34380
gttcagatac ccactaccag tagcaccagt attgccaccg ccacagaggg catggagaca    34440
```

```
caaacgtccc cggttgcctc agcggtggcg gatgccgcgg tgcaggcggt cgctgcggcc    34500
gcgtccaaga cctctacgga ggtgcaaacg gacccgtgga tgtttcgcgt ttcagccccc    34560
cggcgcccgc gcggttcgag gaagtacggc gccgccagcg cgctactgcc cgaatatgcc    34620
ctacatcctt ccattgcgcc tacccccggc tatcgtggct acacctaccg ccccagaaga    34680
cgagcaacta cccgacgccg aaccaccact ggaacccgcc gccgccgtcg ccgtcgccag    34740
cccgtgctgg ccccgatttc cgtgcgcagg gtggctcgcg aaggaggcag gaccctggtg    34800
ctgccaacag cgcgctacca ccccagcatc gtttaaaagc cggtctttgt ggttcttgca    34860
gatatggccc tcacctgccg cctccgtttc ccggtgccgg gattccgagg aagaatgcac    34920
cgtaggaggg gcatggccgg ccacggcctg acgggcggca tgcgtcgtgc gcaccaccgg    34980
cggcggcgcg cgtcgcaccg tcgcatgcgc ggcggtatcc tgcccctcct tattccactg    35040
atcgccgcgg cgattggcgc cgtgcccgga attgcatccg tggccttgca ggcgcagaga    35100
cactgattaa aaacaagttg catgtggaaa atcaaaata aaaagtctgg actctcacgc    35160
tcgcttggtc ctgtaactat tttgtagaat ggaagacatc aactttgcgt ctctggcccc    35220
gcgacacggc tcgcgcccgt tcatgggaaa ctggcaagat atcggcacca gcaatatgag    35280
cggtggcgcc ttcagctggg gctcgctgtg gagcggcatt aaaaatttcg gttccaccgt    35340
taagaactat ggcagcaagg cctggaacag cagcacaggc cagatgctga gggataagtt    35400
gaaagagcaa aatttccaac aaaaggtggt agatggcctg gcctctggca ttagcggggt    35460
ggtggacctg gccaaccagg cagtgcaaaa taagattaac agtaagcttg atccccgccc    35520
tcccgtagag gagcctccac cggccgtgga gacagtgtct ccagagggc gtggcgaaaa    35580
gcgtccgcgc cccgacaggg aagaaactct ggtgacgcaa atagacgagc ctccctcgta    35640
cgaggaggca ctaaagcaag gcctgcccac cacccgtccc atcgcgccca tggctaccgg    35700
agtgctgggc cagcacacac ccgtaacgct ggacctgcct ccccccgccg acacccagca    35760
gaaacctgtg ctgccaggcc cgaccgccgt tgttgtaacc cgtcctagcc gcgcgtccct    35820
gcgccgcgcc gccagcggtc cgcgatcgtt gcggcccgta gccagtggca actggcaaag    35880
cacactgaac agcatcgtgg gtctggggt gcaatccctg aagcgccgac gatgcttctg    35940
aatagctaac gtgtcgtatg tgtgtcatgt atgcgtccat gtcgccgcca gaggagctgc    36000
tgagccgccg cgcgcccgct ttccaagatg gctacccctt cgatgatgcc gcagtggtct    36060
tacatgcaca tctcgggcca ggacgcctcg gagtacctga gccccgggct ggtgcagttt    36120
gcccgcgcca ccgagacgta cttcagcctg aataacaagt ttagaaaccc cacggtggcg    36180
cctacgcacg acgtgaccac agaccggtcc cagcgtttga cgctgcggtt catccctgtg    36240
gaccgtgagg atactgcgta ctcgtacaag gcgcggttca ccctagctgt gggtgataac    36300
cgtgtgctgg acatggcttc cacgtacttt gacatccgcg gcgtgctgga caggggccct    36360
actttaagc cctactctgg cactgcctac aacgccctgg ctcccaaggg tgccccaaat    36420
ccttgcgaat gggatgaagc tgctactgct cttgaaataa acctagaaga agaggacgat    36480
gacaacgaag acgaagtaga cgagcaagct gagcagcaaa aaactcacgt atttgggcag    36540
gcgccttatt ctggtatata tattacaaag gagggtattc aaataggtgt cgaaggtcaa    36600
acacctaaat atgccgataa acatttcaa cctgaacctc aaataggaga atctcagtgg    36660
tacgaaactg aaattaatca tgcagctggg agagtcctta aaagactac cccaatgaaa    36720
ccatgttacg gttcatatgc aaaacccaca atgaaaatg gagggcaagg cattcttgta    36780
aagcaacaaa atggaaagct agaaagtcaa gtggaaatgc aatttttctc aactactgag    36840
```

```
gcgaccgcag gcaatggtga taacttgact cctaaagtgg tattgtacag tgaagatgta   36900
gatatagaaa ccccagacac tcatatttct tacatgccca ctattaagga aggtaactca   36960
cgagaactaa tgggccaaca atctatgccc aacaggccta attacattgc ttttagggac   37020
aattttattg gtctaatgta ttacaacagc acgggtaata tgggtgttct ggcgggccaa   37080
gcatcgcagt tgaatgctgt tgtagatttg caagacagaa acacagagct ttcataccag   37140
cttttgcttg attccattgg tgatagaacc aggtactttt ctatgtggaa tcaggctgtt   37200
gacagctatg atccagatgt tagaattatt gaaaatcatg gaactgaaga tgaacttcca   37260
aattactgct ttccactggg aggtgtgatt aatacagaga ctcttaccaa ggtaaaacct   37320
aaaacaggtc aggaaaatgg atgggaaaaa gatgctacag aattttcaga taaaaatgaa   37380
ataagagttg gaaataattt tgccatggaa atcaatctaa atgccaacct gtggagaaat   37440
ttcctgtact ccaacatagc gctgtatttg cccgacaagc taaagtacag tccttccaac   37500
gtaaaatttc ctgataaccc aaacacctac gactacatga acaagcgagt ggtggctccc   37560
gggttagtgg actgctacat taaccttgga gcacgctggt cccttgacta tatgacaac   37620
gtcaacccat ttaaccacca ccgcaatgct ggcctgcgct accgctcaat gttgctgggc   37680
aatggtcgct atgtgccctt ccacatccag gtgcctcaga agttctttgc cattaaaaac   37740
ctccttctcc tgccgggctc atacacctac gagtggaact tcaggaagga tgttaacatg   37800
gttctgcaga gctccctagg aaatgaccta agggttgacg gagccagcat taagtttgat   37860
agcatttgcc tttacgccac cttcttcccc atggcccaca acaccgcctc cacgcttgag   37920
gccatgctta gaaacgacac caacgaccag tcctttaacg actatctctc cgccgccaac   37980
atgctctacc ctatacccgc caacgctacc aacgtgccca tatccatccc ctcccgcaac   38040
tgggcggctt tccgcggctg gccttcacg cgccttaaga ctaaggaaac cccatcactg   38100
ggctcgggct acgacccta ttacacctac tctggctcta taccctacct agatggaacc   38160
ttttaccctca accacacctt taagaaggtg ccattacct ttgactcttc tgtcagctgg   38220
cctggcaatg accgcctgct tacccccaac gagtttgaaa ttaagcgctc agttgacggg   38280
gagggttaca acgttgccca gtgtaacatg accaaagact ggttcctggt acaaatgcta   38340
gctaactaca cattggcta ccagggcttc tatatcccag agagctacaa ggaccgcatg   38400
tactccttct ttagaaactt ccagcccatg agccgtcagg tggtggatga tactaaatac   38460
aaggactacc aacaggtggg catcctacac caacacaaca actctggatt tgttggctac   38520
cttgccccca ccatgcgcga aggacaggcc taccctgcta acttccccta tccgcttata   38580
ggcaagaccg cagttgacag cattacccag aaaaagtttc tttgcgatcg caccctttgg   38640
cgcatcccat tctccagtaa ctttatgtcc atgggcgcac tcacagacct gggccaaaac   38700
cttctctacg ccaactccgc ccacgcgcta gacatgactt tgaggtgga tcccatggac   38760
gagcccaccc ttctttatgt tttgtttgaa gtctttgacg tggtccgtgt gcaccggccg   38820
caccgcggcg tcatcgaaac cgtgtacctg cgcacgccct tctcggccgg caacgccaca   38880
acataaagaa gcaagcaaca tcaacaacag ctgccgccat gggctccagt gagcaggaac   38940
tgaaagccat tgtcaaagat cttggttgtg ggccatattt ttgggcacc tatgacaagc   39000
gctttccagg cttgtttct ccacacaagc tcgcctgcgc catagtcaat acggccggtc   39060
gcgagactgg gggcgtacac tggatggcct ttgcctggaa cccgcactca aaaacatgct   39120
acctctttga gccctttggc ttttctgacc agcgactcaa gcaggtttac cagtttgagt   39180
```

```
acgagtcact cctgcgccgt agcgccattg cttcttcccc cgaccgctgt ataacgctgg  39240
aaaagtccac ccaaagcgta caggggccca actcggccgc ctgtggacta ttctgctgca  39300
tgtttctcca cgcctttgcc aactggcccc aaactcccat ggatcacaac cccaccatga  39360
accttattac cggggtaccc aactccatgc tcaacagtcc ccaggtacag cccaccctgc  39420
gtcgcaacca ggaacagctc tacagcttcc tggagcgcca ctcgccctac ttccgcagcc  39480
acagtgcgca gattaggagc gccacttctt tttgtcactt gaaaaacatg taaaataat  39540
gtactagaga cactttcaat aaaggcaaat gcttttattt gtacactctc gggtgattat  39600
ttaccccac ccttgccgtc tgcgccgttt aaaaatcaaa ggggttctgc cgcgcatcgc  39660
tatgcgccac tggcagggac acgttgcgat actggtgttt agtgctccac ttaaactcag  39720
gcacaaccat ccgcggcagc tcggtgaagt tttcactcca caggctgcgc accatcacca  39780
acgcgtttag caggtcgggc gccgatatct tgaagtcgca gttggggcct ccgccctgcg  39840
cgcgcgagtt gcgatacaca gggttgcagc actggaacac tatcagcgcc gggtggtgca  39900
cgctggccag cacgctcttg tcggagatca gatccgcgtc caggtcctcc gcgttgctca  39960
gggcgaacgg agtcaacttt ggtagctgcc ttcccaaaaa gggcgcgtgc ccaggctttg  40020
agttgcactc gcaccgtagt ggcatcaaaa ggtgaccgtg cccggtctgg cgttaggat  40080
acagcgcctg cataaaagcc ttgatctgct aaaagccac ctgagccttt gcgccttcag  40140
agaagaacat gccgcaagac ttgccggaaa actgattggc cggacaggcc gcgtcgtgca  40200
cgcagccct tgcgtcggtg ttggagatct gcaccacatt tcggcccac cggttcttca  40260
cgatcttggc cttgctagac tgctccttca gcgcgcgctg cccgttttcg ctcgtcacat  40320
ccatttcaat cacgtgctcc ttatttatca taatgcttcc gtgtagacac ttaagctcgc  40380
cttcgatctc agcgcagcgg tgcagccaca acgcgcagcc cgtgggctcg tgatgcttgt  40440
aggtcacctc tgcaaacgac tgcaggtacg cctgcaggaa tcgccccatc atcgtcacaa  40500
aggtcttgtt gctggtgaag gtcagctgca acccgcggtg ctcctcgttc agccaggtct  40560
tgcatacggc cgccagagct tccacttggt caggcagtag tttgaagttc gcctttagat  40620
cgttatccac gtggtacttg tccatcagcg cgcgcgcagc ctccatgccc ttctcccacg  40680
cagacacgat cggcacactc agcgggttca tcaccgtaat ttcactttcc gcttcgctgg  40740
gctcttcctc ttcctcttgc gtccgcatac cacgcgccac tgggtcgtct tcattcagcc  40800
gccgcactgt gcgcttacct cctttgccat gcttgattag caccggtggg ttgctgaaac  40860
ccaccatttg tagcgccaca tcttctcttt cttcctcgct gtccacgatt acctctggtg  40920
atggcgggcg ctcgggcttg ggagaagggc gcttcttttt cttcttgggc gcaatggcca  40980
aatccgccgc cgaggtcgat ggccgcgggc tgggtgtgcg cggcaccagc gcgtcttgtg  41040
atgagtcttc ctcgtcctcg gactcgatac gccgcctcat ccgcttttttt ggggcgccc  41100
ggggaggcgg cggcgacggg gacggggacg acacgtcctc catggttggg ggacgtcgcg  41160
ccgcaccgcg tccgcgctcg ggggtggttt cgcgctgctc ctcttcccga ctggccattt  41220
ccttctccta taggcagaaa aagatcatgg agtcagtcga gaagaaggac agcctaaccg  41280
cccctctga gttcgccacc accgcctcca ccgatgccgc caacgcgcct accaccttcc  41340
ccgtcgaggc accccgcttg aggaggagg aagtgattat cgagcaggac ccaggttttg  41400
taagcgaaga cgacgaggac cgctcagtac caacagagga taaaaagcaa gaccaggaca  41460
acgcagaggc aaacgaggaa caagtcgggc gggggacga aaggcatggc gactacctag  41520
atgtgggaga cgacgtgctg ttgaagcatc tgcagcgcca gtgcgccatt atctgcgacg  41580
```

```
cgttgcaaga gcgcagcgat gtgccctcg ccatagcgga tgtcagcctt gcctacgaac    41640
gccacctatt ctcaccgcgc gtacccccca aacgccaaga aaacggcaca tgcgagccca    41700
acccgcgcct caacttctac cccgtatttg ccgtgccaga ggtgcttgcc acctatcaca    41760 tcttttttcca aaactgcaag ataccctat cctgccgtgc caaccgcagc cgagcggaca    41820
agcagctggc cttgcggcag ggcgctgtca tacctgatat cgcctcgctc aacgaagtgc    41880
caaaaatctt tgagggtctt ggacgcgacg agaagcgcgc ggcaaacgct ctgcaacagg    41940
aaaacagcga aaatgaaagt cactctggag tgttggtgga actcgagggt gacaacgcgc    42000
gcctagccgt actaaaacgc agcatcgagg tcacccactt tgcctacccg gcacttaacc    42060 tacccccccaa ggtcatgagc acagtcatga gtgagctgat cgtgcgccgt gcgcagcccc    42120
tggagaggga tgcaaatttg caagaacaaa cagaggaggg cctacccgca gttggcgacg    42180
agcagctagc gcgctggctt caaacgcgcg agcctgccga cttggaggag cgacgcaaac    42240
taatgatggc cgcagtgctc gttaccgtgg agcttgagtg catgcagcgg ttctttgctg    42300
acccggagat gcagcgcaag ctagaggaaa cattgcacta cacctttcga cagggctacg    42360
tacgccaggc ctgcaagatc tccaacgtgg agctctgcaa cctggtctcc taccttggaa    42420
ttttgcacga aaaccgcctt gggcaaaacg tgcttcattc cacgctcaag ggcgaggcgc    42480
gccgcgacta cgtccgcgac tgcgtttact tatttctatg ctacacctgg cagacggcca    42540
tgggcgtttg gcagcagtgc ttggaggagt gcaacctcaa ggagctgcag aaactgctaa    42600
agcaaaactt gaaggaccta tggacggcct tcaacgagcg ctccgtggcc gcgcacctgg    42660
cggacatcat tttccccgaa cgcctgctta aaaccctgca acagggtctg ccagacttca    42720
ccagtcaaag catgttgcag aactttagga actttatcct agagcgctca ggaatcttgc    42780
ccgccacctg ctgtgcactt cctagcgact ttgtgcccat taagtaccgc gaatgccctc    42840
cgccgctttg gggccactgc taccttctgc agctagccaa ctaccttgcc taccactctg    42900
acataatgga agacgtgagc ggtgacggtc tactggagtg tcactgtcgc tgcaacctat    42960
gcaccccgca ccgctccctg gtttgcaatt cgcagctgct taacgaaagt caaattatcg    43020
gtacctttga gctgcagggt ccctcgcctg acgaaaagtc cgcggctccg gggttgaaac    43080
tcactccggg gctgtggacg tcggcttacc ttcgcaaatt tgtacctgag gactaccacg    43140
cccacgagat taggttctac gaagaccaat cccgcccgcc aaatgcggag cttaccgcct    43200
gcgtcattac ccagggccac attcttggcc aattgcaagc catcaacaaa gcccgccaag    43260
agtttctgct acgaaaggga cgggggtttt acttggaccc ccagtccggc gaggagctca    43320
acccaatccc cccgccgccg cagccctatc agcagcagcc gcgggcccct gcttcccagg    43380
atggcaccca aaaagaagct gcagctgccg ccgccaccca cggacgagga ggaatactgg    43440
gacagtcagg cagaggaggt tttggacgag gaggaggagg acatgatgga agactgggag    43500
agcctagacg aggaagcttc cgaggtcgaa gaggtgtcag acgaaacacc gtcaccctcg    43560
gtcgcattcc cctcgccggc gccccagaaa tcggcaaccg gttccagcat ggctacaacc    43620
tccgctcctc aggcgccgcc ggcactgccc gttcgccgac ccaaccgtag atgggacacc    43680
actggaacca gggccggtaa gtccaagcag ccgccgccgt tagcccaaga gcaacaacag    43740
cgccaaggct accgctcatg gcgcgggcac aagaacgcca tagttgcttg cttgcaagac    43800
tgtgggggca acatctcctt cgcccgccgc tttcttctct accatcacgg cgtggccttc    43860
ccccgtaaca tcctgcatta ctaccgtcat ctctacagcc catactgcac cggcggcagc    43920
```

```
ggcagcggca gcaacagcag cggccacaca gaagcaaagg cgaccggata gcaagactct   43980
gacaaagccc aagaaatcca cagcggcggc agcagcagga ggaggagcgc tgcgtctggc   44040
gcccaacgaa cccgtatcga cccgcgagct tagaaacagg attttttccca ctctgtatgc   44100 tatatttcaa cagagcaggg gccaagaaca agagctgaaa ataaaaaaca ggtctctgcg   44160
atccctcacc cgcagctgcc tgtatcacaa aagcgaagat cagcttcggc gcacgctgga   44220
agacgcggag gctctcttca gtaaatactg cgcgctgact cttaaggact agtttcgcgc   44280
cctttctcaa atttaagcgc gaaaactacg tcatctccag cggccacacc cggcgccagc   44340
acctgtcgtc agcgccatta tgagcaagga aattcccacg ccctacatgt ggagttacca   44400
gccacaaatg ggacttgcgg ctggagctgc ccaagactac tcaacccgaa taaactacat   44460
gagcgcggga ccccacatga tatcccgggt caacggaatc cgcgcccacc gaaaccgaat   44520
tctcttggaa caggcggcta ttaccaccac acctcgtaat aaccttaatc cccgtagttg   44580
gcccgctgcc ctggtgtacc aggaaagtcc cgctcccacc actgtggtac ttcccagaga   44640
cgcccaggcc gaagttcaga tgactaactc aggggcgcag cttgcgggcg gctttcgtca   44700
cagggtgcgt tcgcccgggc agggtataac tcacctgaca atcagagggc gaggtattca   44760
gctcaacgac gagtcggtga gctcctcgct tggtctccgt ccggacggga catttcagat   44820
cggcggcgcg ggccgtcctt cattcacgcc tcgtcaggca atcctaactc tgcagacctc   44880
gtcctctgag ccgcgctctg gaggcattgg aactctgcaa tttattgagg agtttgtgcc   44940
atcggtctac tttaaccccct tctcgggacc tcccggccac tatccggatc aatttattcc   45000
taactttgac gcggtaaagg actcggcgga cggctacgac tgaatgttaa gtggagaggc   45060
agagcaactg cgcctgaaac acctggtcca ctgtcgccgc cacaagtgct ttgcccgcga   45120
ctccggtgag ttttgctact ttgaattgcc cgaggatcat atcgagggcc cggcgcacgg   45180
cgtccggctt accgcccagg gagagcttgc ccgtagcctg attcgggagt ttacccagcg   45240
ccccctgcta gttgagcggg acaggggacc ctgtgttctc actgtgattt gcaactgtcc   45300
taaccttgga ttcatcaag atcctctagt tataactaga gtaccgggg atcttattcc   45360 ctttaactaa taaaaaaaaa taataaagca tcacttactt aaaatcagtt agcaaatttc   45420
tgtccagttt attcagcagc acctccttgc cctcctccca gctctggtat tgcagcttcc   45480
tcctggctgc aaactttctc cacaatctaa atggaatgtc agtttcctcc tgttcctgtc   45540
catccgcacc cactatcttc atgttgttgc agatgaagcg cgcaagaccg tctgaagata   45600
ccttcaaccc cgtgtatcca tatgacacgg aaaccggtcc tccaactgtg ccttttctta   45660
ctcctccctt tgtatccccc aatgggtttc aagagagtcc ccctggggta ctctctttgc   45720
gcctatccga acctctagtt acctccaatg gcatgcttgc gctcaaaatg ggcaacggcc   45780
tctctctgga cgaggccggc aaccttacct cccaaaatgt aaccactgtg agcccacctc   45840
tcaaaaaaac caagtcaaac ataaacctgg aaatatctgc accctcaca gttacctcag   45900 aagccctaac tgtggctgcc gccgcacctc taatggtcgc gggcaacaca ctcaccatgc   45960
aatcacaggc cccgctaacc gtgcacgact ccaaacttag cattgccacc caaggacccc   46020
tcacagtgtc agaaggaaag ctagccctgc aaacatcagg cccctcacc accaccgata   46080 gcagtaccct tactatcact gcctcacccc tctaactac tgccactggt agcttgggca   46140
ttgacttgaa agagcccatt tatacacaaa atggaaaact aggactaaag tacggggctc   46200
ctttgcatgt aacagacgac ctaaacactt tgaccgtagc aactggtcca ggtgtgacta   46260
ttaataatac ttccttgcaa actaaagtta ctggagcctt gggttttgat tcacaaggca   46320
```

```
atatgcaact taatgtagca ggaggactaa ggattgattc tcaaaacaga cgccttatac   46380
ttgatgttag ttatccgttt gatgctcaaa accaactaaa tctaagacta ggacagggcc   46440 ctcttttat aaactcagcc cacaacttgg atattaacta caacaaaggc ctttacttgt    46500
ttacagcttc aaacaattcc aaaaagcttg aggttaacct aagcactgcc aagggggttga  46560 tgtttgacgc tacagccata gccattaatg caggagatgg gcttgaattt ggttcaccta   46620
atgcaccaaa cacaaatccc ctcaaaacaa aaattggcca tggcctagaa tttgattcaa   46680
acaaggctat ggttcctaaa ctaggaactg gccttagttt tgacagcaca ggtgccatta   46740
cagtaggaaa caaaaataat gataagctaa ctttgtggac cacaccagct ccatctccta   46800
actgtagact aaatgcagag aaagatgcta aactcacttt ggtcttaaca aaatgtggca   46860
gtcaaatact tgctacagtt tcagttttgg ctgttaaagg cagtttggct ccaatatctg   46920
gaacagttca aagtgctcat cttattataa gatttgacga aaatggagtg ctactaaaca   46980
attccttcct ggacccagaa tattggaact ttagaaatgg agatcttact gaaggcacag   47040
cctatacaaa cgctgttgga tttatgccta acctatcagc ttatccaaaa tctcacggta   47100
aaactgccaa aagtaacatt gtcagtcaag tttacttaaa cggagacaaa actaaacctg   47160
taacactaac cattacacta aacggtacac aggaaacagg agacacaact ccaagtgcat   47220
actctatgtc atttcatgg gactggtctg gccacaacta cattaatgaa atatttgcca    47280
catcctctta cacttttca tacattgccc aagaataaag aatcgtttgt gttatgtttc    47340
aacgtgttta ttttcaatt gcagaaaatt tcaagtcatt tttcattcag tagtatagcc    47400
ccaccaccac atagcttata cagatcaccg taccttaatc aaactcacag aaccctagta   47460
ttcaacctgc cacctccctc ccaacacaca gagtacacag tcctttctcc ccggctggcc   47520
ttaaaaagca tcatatcatg ggtaacagac atattcttag gtgttatatt ccacacggtt   47580
tcctgtcgag ccaaacgctc atcagtgata ttaataaact ccccgggcag ctcacttaag   47640
ttcatgtcgc tgtccagctg ctgagccaca ggctgctgtc caacttgcgg ttgcttaacg   47700
ggcggcgaag gagaagtcca cgcctacatg ggggtagagt cataatcgtg catcaggata   47760
gggcggtggt gctgcagcag cgcgcgaata aactgctgcc gccgccgctc cgtcctgcag   47820
gaatacaaca tggcagtggt ctcctcagcg atgattcgca ccgcccgcag cataaggcgc   47880
cttgtcctcc gggcacagca gcgcaccctg atctcactta aatcagcaca gtaactgcag   47940
cacagcacca caatattgtt caaaatccca cagtgcaagg cgctgtatcc aaagctcatg   48000
gcggggacca cagaacccac gtggccatca taccacaagc gcaggtagat taagtggcga   48060
cccctcataa acacgctgga cataaacatt acctcttttg gcatgttgta attcaccacc   48120
tcccggtacc atataaacct ctgattaaac atggcgccat ccaccaccat cctaaaccag   48180
ctggccaaaa cctgcccgcc ggctatacac tgcaggaac cgggactgga acaatgacag    48240
tggagagccc aggactcgta accatggatc atcatgctcg tcatgatatc aatgttggca   48300
caacacaggc acacgtgcat acacttcctc aggattacaa gctcctcccg cgttagaacc   48360
atatcccagg gaacaaccca ttcctgaatc agcgtaaatc ccacactgca gggaagacct   48420
cgcacgtaac tcacgttgtg cattgtcaaa gtgttacatt cgggcagcag cggatgatcc   48480
tccagtatgg tagcgcgggt ttctgtctca aaaggaggta gacgatccct actgtacgga   48540
gtgcgccgag acaaccgaga tcgtgttggt cgtagtgtca tgccaaatgg aacgccggac   48600
gtagtcatat ttcctgaagc aaaaccaggt gcgggcgtga caaacagatc tgcgtctccg   48660
```

```
gtctcgccgc ttagatcgct ctgtgtagta gttgtagtat atccactctc tcaaagcatc    48720
caggcgcccc ctggcttcgg gttctatgta aactccttca tgcgccgctg ccctgataac    48780
atccaccacc gcagaataag ccacacccag ccaacctaca cattcgttct gcgagtcaca    48840
cacgggagga gcgggaagag ctggaagaac catgttttt ttttattcc aaaagattat      48900 ccaaaacctc aaaatgaaga tctattaagt gaacgcgctc ccctccggtg gcgtggtcaa    48960
actctacagc caaagaacag ataatggcat ttgtaagatg ttgcacaatg gcttccaaaa    49020
ggcaaacggc cctcacgtcc aagtggacgt aaaggctaaa cccttcaggg tgaatctcct    49080
ctataaacat tccagcacct tcaaccatgc caaataatt ctcatctcgc caccttctca     49140
atatatctct aagcaaatcc cgaatattaa gtccggccat tgtaaaaatc tgctccagag    49200
cgccctccac cttcagcctc aagcagcgaa tcatgattgc aaaaattcag gttcctcaca    49260
gacctgtata agattcaaaa gcggaacatt aacaaaaata ccgcgatccc gtaggtccct    49320
tcgcagggcc agctgaacat aatcgtgcag gtctgcacgg accagcgcgg ccacttcccc    49380
gccaggaacc ttgacaaaag aacccacact gattatgaca cgcatactcg gagctatgct    49440
aaccagcgta gccccgatgt aagctttgtt gcatgggcgg cgatataaaa tgcaaggtgc    49500
tgctcaaaaa atcaggcaaa gcctcgcgca aaaagaaag cacatcgtag tcatgctcat      49560
gcagataaag gcaggtaagc tccggaacca ccacagaaaa agacaccatt tttctctcaa    49620
acatgtctgc gggtttctgc ataaacacaa aataaaataa caaaaaaaca tttaaacatt    49680
agaagcctgt cttacaacag gaaaacaac cctataagc ataagacgga ctacggccat      49740
gccggcgtga ccgtaaaaaa actggtcacc gtgattaaaa agcaccaccg acagctcctc    49800
ggtcatgtcc ggagtcataa tgtaagactc ggtaaacaca tcaggttgat tcatcggtca    49860
gtgctaaaaa gcgaccgaaa tagcccgggg gaatacatac ccgcaggcgt agagacaaca    49920
ttacagcccc cataggaggt ataacaaaat taataggaga gaaaaacaca taaacacctg    49980
aaaaaccctc ctgcctaggc aaaatagcac cctcccgctc cagaacaaca tacagcgctt    50040
cacagcggca gcctaacagt cagccttacc agtaaaaag aaaacctatt aaaaaaacac     50100
cactcgacac ggcaccagct caatcagtca cagtgtaaaa aagggccaag tgcagagcga    50160
gtatatatag gactaaaaaa tgacgtaacg gttaaagtcc acaaaaaaca cccagaaaac    50220
cgcacgcgaa cctacgccca gaaacgaaag ccaaaaaacc cacaacttcc tcaaatcgtc    50280
acttccgttt tcccacgtta cgtaacttcc cattttaaga aaactacaat tcccaacaca    50340
tacaagttac tccgccctaa aacctacgtc acccgccccg ttcccacgcc ccgcgccacg    50400
tcacaaactc cacccctca ttatcatatt ggcttcaatc caaaataagg tatattattg       50460
atgatnnnnn ttaat                                                      50475
```

<210> SEQ ID NO 17
<211> LENGTH: 39301
<212> TYPE: DNA
<213> ORGANISM: Artificial Sequence
<220> FEATURE:
<223> OTHER INFORMATION: chimeric adenoviral vector ND1.1 214, pAd vector containing DS2C-luc
<220> FEATURE:
<221> NAME/KEY: modified_base
<222> LOCATION: (1)...(39301)
<223> OTHER INFORMATION: n = g, a, c or t

<400> SEQUENCE: 17

```
taaggatccn nncctgtcct cgaccgatgc ccttgagagc cttcaaccca gtcagctcct          60
```

```
tccggtgggc gcggggcatg actatcgtcg ccgcacttat gactgtcttc tttatcatgc    120
aactcgtagg acaggtgccg gcagcgctct gggtcatttt cggcgaggac cgctttcgct    180
ggagcgcgac gatgatcggc ctgtcgcttg cggtattcgg aatcttgcac gccctcgctc    240
aagccttcgt cactggtccc gccaccaaac gtttcggcga aagcaggcc attatcgccg      300 gcatggcggc cgacgcgctg ggctacgtct tgctggcgtt cgcgacgcga ggctggatgg    360 ccttcccat tatgattctt ctcgcttccg gcggcatcgg gatgcccgcg ttgcaggcca      420
tgctgtccag gcaggtagat gacgaccatc agggacagct tcaaggatcg ctcgcggctc    480
ttaccagcct aacttcgatc actggaccgc tgatcgtcac ggcgatttat gccgcctcgg    540
cgagcacatg gaacgggttg gcatggattg taggcgccgc cctataccct gtctgcctcc    600
ccgcgttgcg tcgcggtgca tggagccggg ccacctcgac ctgaatggaa gccggcggca    660
cctcgctaac ggattcacca ctccaagaat tggagccaat caattcttgc ggagaactgt    720
gaatgcgcaa accaaccctt ggcagaacat atccatcgcg tccgccatct ccagcagccg    780
cacgcggcgc atctcgggca gcgttgggtc ctggccacgg gtgcgcatga tcgtgctcct    840
gtcgttgagg acccggctag gctggcgggg ttgccttact ggttagcaga atgaatcacc    900
gatacgcgag cgaacgtgaa gcgactgctg ctgcaaaacg tctgcgacct gagcaacaac    960
atgaatggtc ttcggtttcc gtgtttcgta aagtctggaa acgcggaagt cagcgccctg    1020
caccattatg ttccggatct gcatcgcagg atgctgctgg ctaccctgtg aacacctac    1080 atctgtatta acgaagcgct ggcattgacc ctgagtgatt tttctctggt cccgccgcat   1140
ccataccgcc agttgtttac cctcacaacg ttccagtaac cgggcatgtt catcatcagt    1200
aacccgtatc gtgagcatcc tctctcgttt catcggtatc attaccccca tgaacagaaa    1260 ttcccccta cacggaggca tcaagtgacc aaacaggaaa aaaccgccct taacatggcc     1320
cgctttatca gaagccagac attaacgctt ctggagaaac tcaacgagct ggacgcggat    1380
gaacaggcag acatctgtga atcgcttcac gaccacgctg atgagcttta ccgcagctgc    1440
ctcgcgcgtt tcggtgatga cggtgaaaac ctctgacaca tgcagctccc ggagacggtc    1500
acagcttgtc tgtaagcgga tgccgggagc agacaagccc gtcagggcgc gtcagcgggt    1560
gttggcgggt gtcggggcgc agccatgacc cagtcacgta gcgatagcgg agtgtatact    1620
ggcttaacta tgcggcatca gagcagattg tactgagagt gcaccatatg cggtgtgaaa    1680
taccgcacag atgcgtaagg agaaaatacc gcatcaggcg ctcttccgct tcctcgctca    1740
ctgactcgct gcgctcggtc gttcggctgc ggcgagcggt atcagctcac tcaaaggcgg    1800
taatacggtt atccacagaa tcaggggata acgcaggaaa gaacatgtga gcaaaaggcc    1860
agcaaaaggc caggaaccgt aaaaaggccg cgttgctggc gtttttccat aggctccgcc    1920
cccctgacga gcatcacaaa aatcgacgct caagtcagag gtggcgaaac ccgacaggac    1980
tataaagata ccaggcgttt ccccctggaa gctccctcgt gcgctctcct gttccgaccc    2040
tgccgcttac cggatacctg tccgcctttc tcccttcggg aagcgtggcg ctttctcaat    2100
gctcacgctg taggtatctc agttcggtgt aggtcgttcg ctccaagctg ggctgtgtgc    2160
acgaaccccc cgttcagccc gaccgctgcg ccttatccgg taactatcgt cttgagtcca    2220
acccggtaag acacgactta tcgccactgg cagcagccac tggtaacagg attagcagag    2280
cgaggtatgt aggcggtgct acagagttct tgaagtggtg gcctaactac ggctacacta    2340
gaaggacagt atttggtatc tgcgctctgc tgaagccagt taccttcgga aaagagttg    2400 gtagctcttg atccggcaaa caaaccaccg ctggtagcgg tggtttttt gtttgcaagc    2460
```

```
agcagattac gcgcagaaaa aaaggatctc aagaagatcc tttgatcttt tctacggggt    2520
ctgacgctca gtggaacgaa aactcacgtt aagggatttt ggtcatgaga ttatcaaaaa    2580
ggatcttcac ctagatcctt ttaaattaaa aatgaagttt aaatcaatc taaagtatat    2640 atgagtaaac ttggtctgac agttaccaat gcttaatcag tgaggcacct atctcagcga    2700
tctgtctatt tcgttcatcc atagttgcct gactcccgt cgtgtagata actacgatac     2760
gggagggctt accatctggc cccagtgctg caatgatacc gcgagaccca cgctcaccgg    2820
ctccagattt atcagcaata aaccagccag ccggaagggc cgagcgcaga gtggtcctg     2880 caactttatc cgcctccatc cagtctatta attgttgccg ggaagctaga gtaagtagtt    2940
cgccagttaa tagtttgcgc aacgttgttg ccattgctgc agccatgaga ttatcaaaaa    3000
ggatcttcac ctagatcctt ttcacgtaga aagccagtcc gcagaaacgg tgctgacccc    3060
ggatgaatgt cagctactgg gctatctgga caagggaaaa cgcaagcgca agagaaagc     3120 aggtagcttg cagtgggctt acatggcgat agctagactg ggcggtttta tggacagcaa    3180
gcgaaccgga attgccagct ggggcgccct ctggtaaggt tgggaagccc tgcaaagtaa    3240 actgatggc tttctcgccg ccaaggatct gatgcgcag gggatcaagc tctgatcaag      3300
agacaggatg aggatcgttt cgcatgattg aacaagatgg attgcacgca ggttctccgg    3360
ccgcttgggt ggagaggcta ttcggctatg actgggcaca acagacaatc ggctgctctg    3420
atgccgccgt gttccggctg tcagcgcagg ggcgcccggt tcttttttgtc aagaccgacc   3480 tgtccggtgc cctgaatgaa ctgcaagacg aggcagcgcg gctatcgtgg ctggccacga    3540
cgggcgttcc ttgcgcagct gtgctcgacg ttgtcactga agcgggaagg gactggctgc    3600
tattgggcga agtgccgggg caggatctcc tgtcatctca ccttgctcct gccgagaaag    3660
tatccatcat ggctgatgca atgcggcggc tgcatacgct tgatccggct acctgcccat    3720
tcgaccacca agcgaaacat cgcatcgagc gagcacgtac tcggatggaa gccggtcttg    3780
tcgatcagga tgatctggac gaagagcatc aggggctcgc gccagccgaa ctgttcgcca    3840
ggctcaaggc gagcatgccc gacggcgagg atctcgtcgt gacccatggc gatgcctgct    3900
tgccgaatat catggtggaa aatggccgct tttctggatt catcgactgt ggccggctgg    3960
gtgtggcgga ccgctatcag gacatagcgt tggctacccg tgatattgct gaagagcttg    4020
gcggcgaatg ggctgaccgc ttcctcgtgc tttacggtat cgccgctccc gattcgcagc    4080
gcatcgcctt ctatcgcctt cttgacgagt tcttctgaat tttgttaaaa tttttgttaa    4140
atcagctcat tttttaacca ataggccgaa atcggcaaca tcccttataa atcaaaagaa    4200
tagaccgcga tagggttgag tgttgttcca gtttggaaca agagtccact attaaagaac    4260
gtggactcca acgtcaaagg gcgaaaaacc gtctatcagg gcgatggccc actacgtgaa    4320
ccatcaccca atcaagtttt ttgcggtcg aggtgccgta aagctctaaa tcggaaccct     4380
aaagggagcc cccgatttag agcttgacgg ggaaagccgg cgaacgtggc gagaaaggaa    4440
gggaagaaag cgaaaggagc gggcgctagg gcgctggcaa gtgtagcggt cacgctgcgc    4500
gtaaccacca caccgcgcg cttaatgcgc cgctacaggg cgcgtccatt cgccattcag     4560
gatcgaatta attcttaatt aacatcatca ataatatacc ttattttgga ttgaagccaa    4620
tatgataatg agggggtgga gtttgtgacg tggcgcgggg cgtgggaacg gggcgggtga    4680
cgtagtagtg tggcggaagt gtgatgttgc aagtgtggcg gaacacatgt aagcgacgga    4740
tgtggcaaaa gtgacgtttt tggtgtgcgc cggtgtacac aggaagtgac aattttcgcg    4800
```

```
cggttttagg cggatgttgt agtaaatttg ggcgtaaccg agtaagattt ggccattttc    4860
gcgggaaaac tgaataagag gaagtgaaat ctgaataatt ttgtgttact catagcgcgt    4920
aatactgcta gagatctggc gaaagggga tgtgctgcaa ggcgattaag ttgggtaacg    4980
ccagggtttt cccagtcacg acgttgtaaa acgacggcca gtgaattgta atacgactca    5040
ctatagggcg aattgggtac tggccacaga gcttggccca ttgcatacgt tgtatccata    5100
tcataatatg tacatttata ttggctcatg tccaacatta ccgccatgtt gacattgatt    5160
attgactagt tattaatagt aatcaattac ggggtcatta gttcatagcc catatatgga    5220
gttccgcgtt acataactta cggtaaatgg cccgcctggc tgaccgccca cgacccccg    5280 cccattgacg tcaataatga cgtatgttcc catagtaacg ccaataggga ctttccattg    5340
acgtcaatgg gtggagtatt tacgtaaac tgcccacttg gcagtacatc aagtgtatca    5400
tatgccaagt acgccccta ttgacgtcaa tgacggtaaa tggcccgcct ggcattatgc    5460
ccagtacatg accttatggg actttcctac ttggcagtac atctacgtat tagtcatcgc    5520
tattaccatg gtgatgcggt tttggcagta catcaatggg cgtggatagc ggtttgactc    5580
acggggattt ccaagtctcc accccattga cgtcaatggg agtttgtttt ggcaccaaaa    5640
tcaacgggac tttccaaaat gtcgtaacaa ctccgcccca ttgacgcaaa tgggcggtag    5700
gcgtgtacgg tgggaggtct atataagcag agctcgttta gtgaaccgtc agatcgcctg    5760
gagacgccat ccacgctgtt ttgacctcca tagaagacac cgggaccgat ccagcctgac    5820
tctagcctag ctctgaagtt ggtggtgagg ccctgggcag gttggtatca aggttacaag    5880
acaggtttaa ggagaccaat agaaactggg catgtggaga cagagaagac tcttgggttt    5940
ctgataggca ctgactctct ctgcctattg gtctattttc ccacccttag gctgctggtc    6000
tgagcctagg agatctctcg aggtcgacgg tatcgatgcc accatggaga aaatcgtcct    6060
gttgctcgct attgtgtctc tagtgaagag cgatcaaatt tgtatcggct accatgccaa    6120
taactcaaca gagcaggtcg atactatcat ggagaaaaac gtaacagtta ctcatgccca    6180
agacatcttg gaaagaccc acaacggcaa actttgcgac ctggatggag tgaagcccct    6240
gatcctccgg gactgttcag tcgctggttg gctgctcggg aaccctatgt gtgatgagtt    6300
tatcaacgtg cctgaatggt cttacattgt ggagaaggct aaccctacca atgacctctg    6360
ctatcctggg tcatttaacg attacgagga actgaaacac ctgttgtcta gaattaacca    6420 cttttgaaaag atacagatta tacccaagtc tagttggagt gatcacgaag cctcctcagg    6480
cgttagctca gcgtgtccct atctgggctc tccatccttc tttagaaatg tggtctggtt    6540
aatcaaaaag aacagtacct acccaaccat caaaaagtct tataacaata ccaatcagga    6600
ggacctgctc gtgttgtggg gtatccatca cccgaacgac gccgctgaac agactaggct    6660
gtatcagaac cccactacat acatcagtat tggcacgagt actctgaacc agcgattagt    6720
gccaaagatt gcaacacgga gcaaagtaaa tgggcaatct ggcaggatgg agtttttctg    6780
gacaatctta aaacccaacg atgcgataaa tttcgagtcc aatggcaatt tcatcgcccc    6840
tgaatacgcc tataagatcg tgaaaaaggg ggactctgca attatgaagt ccgaattaga    6900
gtatggcaat tgcaacacga agtgccagac accaatggga gccattaata gctcaatgcc    6960
cttccataat attcatccat tgaccattgg ggagtgccca agtacgtga agtccaaccg    7020 cctggtcctc gcaaccggtc taagaaatag cccgcagaga gaatcgcgga ggaagaaacg    7080
tggcctgttt ggcgcgattg ccggattcat cgagggaggc tggcagggta tggtcgatgg    7140
ttggtacgga taccaccata gcaacgaaca ggggtccggc tatgcagcag ataaggagag    7200
```

```
cactcagaaa gctattgacg gagttacaaa caaggttaat agtattatag ataaaatgaa    7260
cacgcaattc gaggccgttg ggagggagtt taacaatctg gaacgccgga tcgaaaatct    7320
gaataagaaa atggaagacg gcttccttga cgtgtggact tataatgcag agctgcttgt    7380
actcatggag aacgagagga ccctggattt ccacgatagc aacgtgaaga acctttacga    7440
caaggtgaga cttcagctcc gagacaacgc caaggagctg gggaatggat gcttcgagtt    7500
ttaccacaaa tgtgacaatg agtgcatgga aagtatacgc aacgggacct acaattaccc    7560
tcagtatagc gaagaggctc ggctcaaacg cgaagagata agcggggtga aattggaatc    7620
aatcggaaca tatcaaatcc tgtccatcta ttccaccgtc gcctcttcgc tggccctcgc    7680
tatcatgatg gctggtctgt ccctatggat gtgttccaat ggaagccttc agtgccgtat    7740
ttgtatatga gcggccgccc tattctatag tgtcacctaa atgctagagc tcgctgatca    7800
gcctcgactg tgccttctag ttgccagcca tctgttgttt gccctcccc cgtgccttcc     7860 ttgaccctgg aaggtgccac tcccactgtc ctttcctaat aaaatgagga aattgcatcg    7920
cattgtctga gtaggtgtca ttctattctg ggggtgggg tggggcagga cagcaagggg     7980
gaggattggg aagacaatag caggcatgct ggggatgcgg tgggctctat ggcttctgag    8040
gcggaaagaa ccaaagctta acatcatcaa taatatacct tattttggat tgaagccaat    8100
atgataatga gggggtggag tttgtgacgt ggcgcggggc gtgggaacgg ggcgggtgac    8160
gtagtagtgt ggcggaagtg tgatgttgca agtgtggcgg aacacatgta agcgacggat    8220
gtggcaaaag tgacgttttt ggtgtgcgcc ggtgtacaca ggaagtgaca attttcgcgc    8280
ggttttaggc ggatgttgta gtaaatttgg gcgtaaccga gtaagatttg gccattttcg    8340
cgggaaaact gaataagagg aagtgaaatc tgaataattt tgtgttactc atagcgcgta    8400
atactgtaat agtaatcaat tacggggtca ttagttcata gcccatatat ggagttccgc    8460
gttacataac ttacggtaaa tggcccgcct ggctgaccgc ccaacgaccc ccgcccattg    8520
acgtcaataa tgacgtatgt tcccatagta acgccaatag ggactttcca ttgacgtcaa    8580
tgggtggagt atttacggta aactgcccac ttggcagtac atcaagtgta tcatatgcca    8640
agtacgcccc ctattgacgt caatgacggt aaatggcccg cctggcatta tgcccagtac    8700
atgaccttat gggactttcc tacttggcag tacatctacg tattagtcat cgctattacc    8760
atggtgatgc ggttttggca gtacatcaat gggcgtggat agcggtttga ctcacgggga    8820
tttccaagtc tccaccccat tgacgtcaat gggagtttgt tttggcacca aaatcaacgg    8880
gactttccaa aatgtcgtaa caactccgcc ccattgacgc aaatgggcgg taggcgtgta    8940
cggtgggagg tctatataag cagagctggt ttagtgaacc gtcagatccg ctagagatct    9000
gggaaacgat atgggctgaa tacggatccg tattcagccc atatcgtttc tctagaaata    9060
aaatatcttt attttcatta catctgtgtg ttggttttt gtgtggcggc cgctcgagcc    9120
taagcttcta gataagatat ccgatccacc ggatctagat aactgatcat aatcagccat    9180
accacatttg tagaggtttt acttgcttta aaaaacctcc cacacctccc cctgaacctg    9240
aaacataaaa tgaatgcaat tgttgttgtt aacttgttta ttgcagctta taatggttac    9300
aaataaagca atagcatcac aaatttcaca aataaagcat ttttttcact gcattctagt    9360
tgtggtttgt ccaaactcat caatgtatct taacgcggat ctgggcgtgg ttaagggtgg    9420
gaaagaatat ataaggtggg ggtcttatgt agttttgtat ctgttttgca gcagccgccg    9480
ccgccatgag caccaactcg tttgatggaa gcattgtgag cttgtcgact cgaagatctg    9540
```

```
ggcgtggtta agggtgggaa agaatatata aggtggggt cttatgtagt tttgtatctg    9600
ttttgcagca gccgccgccg ccatgagcac caactcgttt gatggaagca ttgtgagctc    9660
atatttgaca acgcgcatgc ccccatgggc cggggtgcgt cagaatgtga tgggctccag    9720
cattgatggt cgccccgtcc tgcccgcaaa ctctactacc ttgacctacg agaccgtgtc    9780
tggaacgccg ttggagactg cagcctccgc cgccgcttca gccgctgcag ccaccgcccg    9840
cgggattgtg actgactttg cttcctgag cccgcttgca agcagtgcag cttcccgttc    9900
atccgcccgc gatgacaagt tgacggctct tttggcacaa ttggattctt tgacccggga    9960
acttaatgtc gtttctcagc agctgttgga tctgcgccag caggtttctg ccctgaaggc   10020
ttcctcccct cccaatgcgg tttaaaacat aaataaaaaa ccagactctg tttggatttg   10080
gatcaagcaa gtgtcttgct gtctttattt aggggttttg cgcgcgcggt aggcccggga   10140
ccagcggtct cggtcgttga gggtcctgtg tattttttcc aggacgtggt aaaggtgact   10200
ctggatgttc agatacatgg gcataagccc gtctctgggg tggaggtagc accactgcag   10260
agcttcatgc tgcggggtgg tgttgtagat gatccagtcg tagcaggagc gctgggcgtg   10320
gtgcctaaaa atgtctttca gtagcaagct gattgccagg ggcaggccct tggtgtaagt   10380
gtttacaaag cggttaagct gggatggtg catacgtggg gatatgagat gcatcttgga   10440
ctgtattttt aggttggcta tgttcccagc catatccctc cggggattca tgttgtgcag   10500
aaccaccagc acagtgtatc cggtgcactt gggaaatttg tcatgtagct tagaaggaaa   10560
tgcgtggaag aacttggaga cgcccttgtg acctccaaga ttttccatgc attcgtccat   10620
aatgatggca atgggcccac gggcggcggc ctgggcgaag atatttctgg gatcactaac   10680
gtcatagttg tgttccagga tgagatcgtc ataggccatt tttacaaagc gcgggcggag   10740
ggtgccagac tgcggtataa tggttccatc cggcccaggg gcgtagttac cctcacagat   10800
ttgcatttcc cacgctttga gttcagatgg ggggatcatg tctacctgcg gggcgatgaa   10860
gaaaacggtt tccggggtag gggagatcag ctgggaagaa agcaggttcc tgagcagctg   10920
cgacttaccg cagccggtgg gcccgtaaat cacacctatt accgggtgca actggtagtt   10980
aagagagctg cagctgccgt catccctgag cagggggggcc acttcgttaa gcatgtccct   11040
gactcgcatg ttttccctga ccaaatccgc cagaaggcgc tcgccgccca gcgatagcag   11100
ttcttgcaag gaagcaaagt ttttcaacgg tttgagaccg tccgccgtag gcatgctttt   11160
gagcgtttga ccaagcagtt ccaggcggtc ccacagctcg gtcacctgct ctacggcatc   11220
tcgatccagc atatctcctc gtttcgcggg ttggggcggc tttcgctgta cggcagtagt   11280
cggtgctcgt ccagacgggc cagggtcatg tctttccacg ggcgcagggt cctcgtcagc   11340
gtagtctggg tcacggtgaa ggggtgcgct ccgggctgcg cgctggccag ggtgcgcttg   11400
aggctggtcc tgctggtgct gaagcgctgc cggtcttcgc cctgcgcgtc ggccaggtag   11460
catttgacca tggtgtcata gtccagcccc tccgcgcgt ggcccttggc gcgcagcttg   11520
cccttggagg aggcgccgca cgaggggcag tgcagacttt tgagggcgta gagcttgggc   11580
gcgagaaata ccgattccgg ggagtaggca tccgcgccgc aggcccccgca gacggtctcg   11640 cattccacga gccaggtgag ctctggccgt tcggggtcaa aaaccaggtt tccccccatgc   11700 tttttgatgc gtttcttacc tctggtttcc atgagccggt gtccacgctc ggtgacgaaa   11760
aggctgtccg tgtccccgta tacagacttg agaggcctgt cctcgagcgg tgttccgcgg   11820
tcctcctcgt atagaaactc ggaccactct gagacaaagg ctcgcgtcca ggccagcacg   11880
aaggaggcta agtgggaggg gtagcggtcg ttgtccacta gggggtccac tcgctccagg   11940
```

```
gtgtgaagac acatgtcgcc ctcttcggca tcaaggaagg tgattggttt gtaggtgtag    12000
gccacgtgac cgggtgttcc tgaagggggg ctataaaagg gggtggggc gcgttcgtcc     12060 tcactctctt ccgcatcgct gtctgcgagg gccagctgtt ggggtgagta ctccctctga    12120
aaagcgggca tgacttctgc gctaagattg tcagtttcca aaaacgagga ggatttgata    12180
ttcacctggc ccgcggtgat gcctttgagg gtggccgcat ccatctggtc agaaaagaca    12240 atcttttgt tgtcaagctt ggtggcaaac gacccgtaga gggcgttgga cagcaacttg     12300
gcgatggagc gcagggtttg gttttgtcg cgatcggcgc gctccttggc cgcgatgttt      12360
agctgcacgt attcgcgcgc aacgcaccgc cattcgggaa agacggtggt gcgctcgtcg    12420
ggcaccaggt gcacgcgcca accgcggttg tgcagggtga caaggtcaac gctggtggct    12480
acctctccgc gtaggcgctc gttggtccag cagaggcggc cgcccttgcg cgagcagaat    12540
ggcggtaggg ggtctagctg cgtctcgtcc gggggtctg cgtccacggt aaagaccccg     12600
ggcagcaggc gcgcgtcgaa gtagtctatc ttgcatcctt gcaagtctag cgcctgctgc    12660
catgcgcggg cggcaagcgc gcgctcgtat gggttgagtg ggggacccca tggcatgggg    12720
tgggtgagcg cggaggcgta catgccgcaa atgtcgtaaa cgtagagggg ctctctgagt    12780
attccaagat atgtagggta gcatcttcca ccgcggatgc tggcgcgcac gtaatcgtat    12840
agttcgtgcg agggagcgag gaggtcggga ccgaggttgc tacgggcggg ctgctctgct    12900
cggaagacta tctgcctgaa gatggcatgt gagttggatg atatggttgg acgctggaag    12960
acgttgaagc tggcgtctgt gagacctacc gcgtcacgca cgaaggaggc gtaggagtcg    13020
cgcagcttgt tgaccagctc ggcggtgacc tgcacgtcta gggcgcagta gtccagggtt    13080
tccttgatga tgtcatactt atcctgtccc ttttttttcc acagctcgcg gttgaggaca    13140
aactcttcgc ggtctttcca gtactcttgg atcggaaacc cgtcggcctc cgaacggtaa    13200
gagcctagca tgtagaactg gttgacggcc tggtaggcgc agcatccctt ttctacgggt    13260
agcgcgtatg cctgcgcggc cttccggagc gaggtgtggg tgagcgcaaa ggtgtccctg    13320
accatgactt tgaggtactg gtatttgaag tcagtgtcgt cgcatccgcc ctgctcccag    13380
agcaaaaagt ccgtgcgctt tttggaacgc ggatttggca gggcgaaggt gacatcgttg    13440
aagagtatct ttcccgcgcg aggcataaag ttgcgtgtga tgcggaaggg tcccggcacc    13500
tcggaacggt tgttaattac ctgggcggcg agcacgatct cgtcaaagcc gttgatgttg    13560
tggcccacaa tgtaaagttc caagaagcgc gggatgccct tgatgaagg caattttta     13620 agttcctcgt aggtgagctc ttcaggggag ctgagcccgt gctctgaaag gcccagtct     13680 gcaagatgag ggttggaagc gacgaatgag ctccacaggt cacgggccat tagcatttgc    13740
aggtggtcgc gaaaggtcct aaactggcga cctatggcca ttttttctgg ggtgatgcag    13800
tagaaggtaa gcgggtcttg ttcccagcgg tcccatccaa ggttcgcggc taggtctcgc    13860
gcggcagtca ctagaggctc atctccgccg aacttcatga ccagcatgaa gggcacgagc    13920
tgcttcccaa aggcccccat ccaagtatag gtctctacat cgtaggtgac aaagagacgc    13980
tcggtgcgag gatgcgagcc gatcgggaag aactggatct cccgccacca attggaggag    14040
tggctattga tgtggtgaaa gtagaagtcc ctgcgacggg ccgaacactc gtgctggctt    14100
ttgtaaaaac gtgcgcagta ctggcagcgg tgcacgggct gtacatcctg cacgaggttg    14160
acctgacgac cgcgcacaag gaagcagagt gggaatttga gccctcgcc tggcgggttt     14220 ggctggtggt cttctacttc ggctgcttgt ccttgaccgt ctggctgctc gagggagtt    14280
```

```
acggtggatc ggaccaccac gccgcgcgag cccaaagtcc agatgtccgc gcgcggcggt   14340
cggagcttga tgacaacatc gcgcagatgg gagctgtcca tggtctggag ctcccgcggc   14400
gtcaggtcag gcgggagctc ctgcaggttt acctcgcata gacgggtcag ggcgcgggct   14460
agatccaggt gatacctaat ttccagggc tggttggtgg cggcgtcgat ggcttgcaag    14520
aggccgcatc cccgcggcgc gactacggta ccgcgcggcg ggcggtgggc cgcggggtg    14580
tccttggatg atgcatctaa aagcggtgac gcgggcgagc ccccggaggt aggggggggct  14640
ccggacccgc cggagagggg ggcagggggca cgtcggcgcc gcgcgcgggc aggagctggt   14700
gctgcgcgcg taggttgctg gcgaacgcga cgacgcggcg gttgatctcc tgaatctggc   14760
gcctctgcgt gaagacgacg ggcccggtga gcttgagcct gaaagagagt tcgacagaat   14820
caatttcggt gtcgttgacg gcggcctggc gcaaaatctc ctgcacgtct cctgagttgt   14880
cttgataggc gatctcggcc atgaactgct cgatctcttc ctcctggaga tctccgcgtc   14940
cggctcgctc cacggtggcg gcgaggtcgt tggaaatgcg ggccatgagc tgcgagaagg   15000
cgttgaggcc tccctcgttc cagacgcggc tgtagaccac gccccctccg gcatcgcggg   15060
cgcgcatgac cacctgcgcg agattgagct ccacgtgccg ggcgaagacg gcgtagtttc   15120
gcaggcgctg aaagaggtag ttgagggtgg tggcggtgtg ttctgccacg aagaagtaca   15180
taacccagcg tcgcaacgtg gattcgttga tatcccccaa ggcctcaagg cgctccatgg   15240
cctcgtagaa gtccacggcg aagttgaaaa actgggagtt gcgcgccgac acggttaact   15300
cctcctccag aagacggatg agctcggcga cagtgtcgcg cacctcgcgc tcaaaggcta   15360
caggggcctc ttcttcttct tcaatctcct cttccataag ggcctcccct tcttcttctt   15420
ctggcggcgg tgggggaggg gggacacggc ggcgacgacg gcgcaccggg aggcggtcga   15480
caaagcgctc gatcatctcc ccgcggcgac ggcgcatggt ctcggtgacg gcgcggccgt   15540
tctcgcgggg gcgcagttgg aagacgccgc ccgtcatgtc ccggttatgg gttggcgggg   15600
ggctgccatg cggcagggat acggcgctaa cgatgcatct caacaattgt tgtgtaggta   15660
ctccgccgcc gagggacctg agcgagtccg catcgaccgg atcggaaaac ctctcgagaa   15720
aggcgtctaa ccagtcacag tcgcaaggta ggctgagcac cgtggcgggc ggcagcgggc   15780
ggcggtcggg gttgtttctg gcggaggtgc tgctgatgat gtaattaaag taggcggtct   15840
tgagacggcg gatggtcgac agaagcacca tgtccttggg tccggcctgc tgaatgcgca   15900
ggcggtcggc catgccccag gcttcgtttt gacatcggcg caggtctttg tagtagtctt   15960
gcatgagcct ttctaccggc acttcttctt ctccttcctc ttgtcctgca tctcttgcat   16020
ctatcgctgc ggcggcggcg gagtttggcc gtaggtggcg ccctcttcct cccatgcgtg   16080
tgaccccgaa gcccctcatc ggctgaagca gggctaggtc ggcgacaacg cgctcggcta   16140
atatggcctg ctgcacctgc gtgagggtag actggaagtc atccatgtcc acaaagcggt   16200
ggtatgcgcc cgtgttgatg gtgtaagtgc agttggccat aacggaccag ttaacggtct   16260
ggtgacccgg ctgcgagagc tcggtgtacc tgagacgcga gtaagccctc gagtcaaata   16320
cgtagtcgtt gcaagtccgc accaggtact ggtatcccac caaaaagtgc ggcggcgct    16380
ggcggtagag gggccagcgt agggtggccg gggctccggg ggcgagatct tccaacataa   16440
ggcgatgata tccgtagatg tacctggaca tccaggtgat gccggcggcg gtggtggagg   16500
cgcgcggaaa gtcgcggacg cggttccaga tgttgcgcag cggcaaaaag tgctccatgg   16560
tcgggacgct ctgccggtc aggcgcgcgc aatcgttgac gctctaccgt gcaaaaggag    16620
agcctgtaag cgggcactct tccgtggtct ggtggataaa ttcgcaaggg tatcatggcg   16680
```

```
gacgaccggg gttcgagccc cgtatccggc cgtccgccgt gatccatgcg gttaccgccc   16740
gcgtgtcgaa cccaggtgtg cgacgtcaga caacggggga gtgctccttt tggcttcctt   16800
ccaggcgcgg cggctgctgc gctagctttt ttggccactg gccgcgcgca gcgtaagcgg   16860
ttaggctgga aagcgaaagc attaagtggc tcgctccctg tagccggagg gttatttcc    16920 aagggttgag tcgcgggacc cccggttcga gtctcggacc ggccggactg cggcgaacgg   16980
gggtttgcct ccccgtcatg caagaccccg cttgcaaatt cctccggaaa cagggacgag   17040
cccctttttt gcttttccca gatgcatccg gtgctgcggc agatgcgccc cctcctcag    17100 cagcggcaag agcaagagca gcggcagaca tgcagggcac cctcccctcc tcctaccgcg   17160
tcaggagggg cgacatccgc ggttgacgcg gcagcagatg gtgattacga accccgcgg    17220 cgccgggccc ggcactacct ggacttggag gagggcgagg gcctggcgcg gctaggagcg   17280
ccctctcctg agcggtaccc aagggtgcag ctgaagcgtg atacgcgtga ggcgtacgtg   17340
ccgcggcaga acctgtttcg cgaccgcgag ggagaggagc ccgaggagat gcgggatcga   17400
aagttccacg cagggcgcga gctgcggcat ggcctgaatc gcgagcggtt gctgcgcgag   17460
gaggactttg agcccgacgc gcgaaccggg attagtcccg cgcgcgcaca cgtggcggcc   17520
gccgacctgg taaccgcata cgagcagacg gtgaaccagg agattaactt tcaaaaaagc   17580
tttaacaacc acgtgcgtac gcttgtggcg cgcgaggagg tggctatagg actgatgcat   17640
ctgtgggact ttgtaagcgc gctggagcaa aacccaaata gcaagccgct catggcgcag   17700
ctgttcctta tagtgcagca cagcagggac aacgaggcat tcagggatgc gctgctaaac   17760
atagtagagc ccgagggccg ctggctgctc gatttgataa acatcctgca gagcatagtg   17820
gtgcaggagc gcagcttgag cctggctgac aaggtggccg ccatcaacta ttccatgctt   17880
agcctgggca gttttacgc ccgcaagata taccataccc cttacgttcc catagacaag   17940
gaggtaaaga tcgaggggtt ctacatgcgc atggcgctga aggtgcttac cttgagcgac   18000
gacctgggcg tttatcgcaa cgagcgcatc cacaaggccg tgagcgtgag ccggcggcgc   18060
gagctcagcg accgcgagct gatgcacagc ctgcaaaggg ccctggctgg cacgggcagc   18120
ggcgatagag aggccgagtc ctactttgac gcgggcgctg acctgcgctg gccccaagc    18180 cgacgcgccc tggaggcagc tggggccgga cctgggctgg cggtggcacc cgcgcgcgct   18240
ggcaacgtcg gcggcgtgga ggaatatgac gaggacgatg agtacgagcc agaggacggc   18300
gagtactaag cggtgatgtt tctgatcaga tgatgcaaga cgcaacggac ccggcggtgc   18360
gggcggcgct gcagagccag ccgtccggcc ttaactccac ggacgactgg cgccaggtca   18420
tggaccgcat catgtcgctg actgcgcgca atcctgacgc gttccggcag cagccgcagg   18480
ccaaccggct ctccgcaatt ctggaagcgg tggtcccggc gcgcgcaaac cccacgcacg   18540
agaaggtgct ggcgatcgta aacgcgctgg ccgaaaacag ggccatccgg cccgacgagg   18600
ccggcctggt ctacgacgcg ctgcttcagc gcgtggctcg ttacaacagc ggcaacgtgc   18660
agaccaacct ggaccggctg gtgggggatg tgcgcgaggc cgtggcgcag cgtgagcgcg   18720
cgcagcagca gggcaacctg ggctccatgg ttgcactaaa cgccttcctg agtacacagc   18780
ccgccaacgt gccgcgggga caggaggact acaccaactt tgtgagcgca ctgcggctaa   18840
tggtgactga gacaccgcaa agtgaggtgt accagtctgg gccagactat ttttccaga    18900 ccagtagaca aggcctgcag accgtaaacc tgagccaggc tttcaaaaac ttgcaggggc   18960 tgtgggggt gcgggctccc acaggcgacc gcgcgaccgt gtctagcttg ctgacgccca   19020
```

```
actcgcgcct gttgctgctg ctaatagcgc ccttcacgga cagtggcagc gtgtcccggg   19080
acacatacct aggtcacttg ctgacactgt accgcgaggc cataggtcag gcgcatgtgg   19140
acgagcatac tttccaggag attacaagtg tcagccgcgc gctggggcag gaggacacgg   19200
gcagcctgga ggcaacccta aactacctgc tgaccaaccg gcggcagaag atccccctcgt  19260 tgcacagttt aaacagcgag gaggagcgca ttttgcgcta cgtgcagcag agcgtgagcc   19320
ttaacctgat gcgcgacggg gtaacgccca gcgtggcgct ggacatgacc gcgcgcaaca   19380
tggaaccggg catgtatgcc tcaaaccggc cgtttatcaa ccgcctaatg gactacttgc   19440
atcgcgcggc cgccgtgaac cccgagtatt tcaccaatgc catcttgaac ccgcactggc   19500
taccgccccc tggtttctac accgggggat tcgaggtgcc cgagggtaac gatggattcc   19560
tctgggacga catagacgac agcgtgtttt ccccgcaacc gcagaccctg ctagagttgc   19620
aacagcgcga gcaggcagag gcggcgctgc gaaaggaaag cttccgcagg ccaagcagct   19680
tgtccgatct aggcgctgcg gccccgcggt cagatgctag tagcccattt ccaagcttga   19740
tagggtctct taccagcact cgcaccaccc gcccgcgcct gctgggcgag gaggagtacc   19800
taaacaactc gctgctgcag ccgcagcgcg aaaaaaacct gcctccggca tttcccaaca   19860
acgggataga gagcctagtg gacaagatga gtagatggaa gacgtacgcg caggagcaca   19920
gggacgtgcc aggcccgcgc ccgcccaccc gtcgtcaaag gcacgaccgt cagcggggtc   19980
tggtgtggga ggacgatgac tcggcagacg acagcagcgt cctggatttg ggagggagtg   20040
gcaacccgtt tgcgcacctt cgccccaggc tggggagaat gttttaaaaa aaaaaaagca   20100
tgatgcaaaa taaaaaactc accaaggcca tggcaccgag cgttggtttt cttgtattcc   20160
ccttagtatg cggcgcgcgg cgatgtatga ggaaggtcct cctccctcct acgagagtgt   20220
ggtgagcgcg gcgccagtgg cggcggcgct gggttctccc ttcgatgctc ccctggaccc   20280
gccgtttgtg cctccgcggt acctgcggcc taccgggggg agaaacagca tccgttactc   20340
tgagttggca cccctattcg acaccacccg tgtgtacctg gtggacaaca agtcaacgga   20400
tgtggcatcc ctgaactacc agaacgacca cagcaacttt ctgaccacgg tcattcaaaa   20460
caatgactac agcccggggg aggcaagcac acagaccatc aatcttgacg accggtcgca   20520
ctggggcggc gacctgaaaa ccatcctgca taccaacatg ccaaatgtga acgagttcat   20580
gtttaccaat aagtttaagg cgcgggtgat ggtgtcgcgc ttgcctacta aggacaatca   20640
ggtggagctg aaatacgagt gggtggagtt cacgctgccc gagggcaact actccgagac   20700
catgaccata gaccttatga acaacgcgat cgtggagcac tacttgaaag tgggcagaca   20760 gaacgggggtt ctggaaagcg acatcgggggt aaagtttgac acccgcaact tcagactggg   20820 gtttgaccccc gtcactggtc ttgtcatgcc tgggggtatat acaaacgaag ccttccatcc   20880
agacatcatt ttgctgccag gatgcggggt ggacttcacc cacagccgcc tgagcaactt   20940
gttgggcatc cgcaagcggc aacccttcca ggagggcttt aggatcacct acgatgatct   21000
ggagggtggt aacattcccg cactgttgga tgtggacgcc taccaggcga gcttgaaaga   21060
tgacaccgaa cagggcgggg gtggcgcagg cggcagcaac agcagtggca gcggcgcgga   21120
agagaactcc aacgcggcag ccgcggcaat gcagccggtg gaggacatga acgatcatgc   21180
cattcgcggc gacacctttg ccacacgggc tgaggagaag cgcgctgagg ccgaagcagc   21240
ggccgaagct gccgcccccg ctgcgcaacc cgaggtcgag aagcctcaga gaaaccggt    21300 gatcaaaccc ctgacagagg acagcaagaa acgcagttac aacctaataa gcaatgacag   21360
caccttcacc cagtaccgca gctggtacct tgcatacaac tacggcgacc ctcagaccgg   21420
```

```
aatccgctca tggaccctgc tttgcactcc tgacgtaacc tgcggctcgg agcaggtcta  21480
ctggtcgttg ccagacatga tgcaagaccc cgtgaccttc cgctccacgc gccagatcag  21540
caactttccg gtggtgggcg ccgagctgtt gcccgtgcac tccaagagct tctacaacga  21600
ccaggccgtc tactcccaac tcatccgcca gtttacctct ctgacccacg tgttcaatcg  21660
ctttcccgag aaccagattt tggcgcgccc gccagccccc accatcacca ccgtcagtga  21720
aaacgttcct gctctcacag atcacgggac gctaccgctg cgcaacagca tcggaggagt  21780
ccagcgagtg accattactg acgccagacg ccgcacctgc ccctacgttt acaaggccct  21840
gggcatagtc tcgccgcgcg tcctatcgag ccgcactttt tgagcaagca tgtccatcct  21900
tatatcgccc agcaataaca caggctgggg cctgcgcttc ccaagcaaga tgtttggcgg  21960
ggccaagaag cgctccgacc aacacccagt gcgcgtgcgc gggcactacc gcgcgccctg  22020
gggcgcgcac aaacgcggcc gcactgggcg caccaccgtc gatgacgcca tcgacgcggt  22080
ggtggaggag gcgcgcaact acacgcccac gccgccacca gtgtccacag tggacgcggc  22140
cattcagacc gtggtgcgcg agcccggcg ctatgctaaa atgaagagac ggcggaggcg  22200
cgtagcacgt cgccaccgcc gccgaccgg cactgccgcc caacgcgcgg cggcggccct  22260
gcttaaccgc gcacgtcgca ccggccgacg ggcggccatg cgggccgctc gaaggctggc  22320
cgcgggtatt gtcactgtgc cccccaggtc caggcgacga gcggccgccg cagcagccgc  22380
ggccattagt gctatgactc agggtcgcag gggcaacgtg tattgggtgc gcgactcggt  22440
tagcggcctg cgcgtgcccg tgcgcacccg cccccgcgc aactagattg caagaaaaaa  22500
ctacttagac tcgtactgtt gtatgtatcc agcggcggcg gcgcgcaacg aagctatgtc  22560
caagcgcaaa atcaaagaag agatgctcca ggtcatcgcg ccggagatct atggccccc   22620
gaagaaggaa gagcaggatt acaagccccg aaagctaaag cgggtcaaaa agaaaaagaa  22680
agatgatgat gatgaacttg acgacgaggt ggaactgctg cacgctaccg cgcccaggcg  22740
acgggtacag tggaaaggtc gacgcgtaaa acgtgttttg cgacccggca ccaccgtagt  22800
ctttacgccc ggtgagcgct ccacccgcac ctacaagcgc gtgtatgatg aggtgtacgg  22860
cgacgaggac ctgcttgagc aggccaacga gcgcctcggg gagtttgcct acggaaagcg  22920
gcataaggac atgctggcgt tgccgctgga cgagggcaac ccaacaccta gcctaaagcc  22980
cgtaacactg cagcaggtgc tgcccgcgct tgcaccgtcc gaagaaaagc gcggcctaaa  23040
gcgcgagtct ggtgacttgg cacccaccgt gcagctgatg gtacccaagc gccagcgact  23100
ggaagatgtc ttggaaaaaa tgaccgtgga acctgggctg gagcccgagg tccgcgtgcg  23160
gccaatcaag caggtggcgc cgggactggg cgtgcagacc gtggacgttc agatacccac  23220
taccagtagc accagtattg ccaccgccac agagggcatg gagacacaaa cgtccccggt  23280
tgcctcagcg gtggcggatg ccgcggtgca ggcggtcgct gcggccgcgt ccaagacctc  23340
tacggaggtg caaacggacc cgtggatgtt tcgcgtttca gcccccggc gcccgcgcgg  23400
ttcgaggaag tacggcgccg ccagcgcgct actgccgaa tatgccctac atccttccat  23460
tgcgcctacc cccggctatc gtggctacac ctaccgcccc agaagacgag caactacccg  23520
acgccgaacc accactggaa cccgccgccg ccgtcgccgt cgccagcccg tgctggcccc  23580
gatttccgtg cgcagggtgg ctcgcgaagg aggcaggacc ctggtgctgc aacagcgcg   23640
ctaccacccc agcatcgttt aaagccggt ctttgtggtt cttgcagata tggccctcac   23700
ctgccgcctc cgtttcccgg tgccgggatt ccgaggaaga atgcaccgta ggaggggcat   23760
```

```
ggccggccac ggcctgacgg gcggcatgcg tcgtgcgcac caccggcggc ggcgcgcgtc    23820
gcaccgtcgc atgcgcggcg gtatcctgcc cctccttatt ccactgatcg ccgcggcgat    23880
tggcgccgtg cccggaattg catccgtggc cttgcaggcg cagagacact gattaaaaac    23940
aagttgcatg tggaaaaatc aaaataaaaa gtctggactc tcacgctcgc ttggtcctgt    24000
aactattttg tagaatggaa gacatcaact ttgcgtctct ggccccgcga cacggctcgc    24060
gcccgttcat gggaaactgg caagatatcg gcaccagcaa tatgagcggt ggcgccttca    24120 gctgggctc gctgtggagc ggcattaaaa atttcggttc caccgttaag aactatggca    24180
gcaaggcctg aacagcagc acaggccaga tgctgaggga taagttgaaa gagcaaaatt    24240
tccaacaaaa ggtggtagat ggcctggcct ctggcattag cggggtggtg gacctggcca    24300
accaggcagt gcaaaataag attaacagta agcttgatcc ccgccctccc gtagaggagc    24360
ctccaccggc cgtggagaca gtgtctccag aggggcgtgg cgaaaagcgt ccgcgccccg    24420
acagggaaga aactctggtg acgcaaatag acgagcctcc ctcgtacgag gaggcactaa    24480
agcaaggcct gcccaccacc cgtcccatcg cgcccatggc taccggagtg ctgggccagc    24540 acacaccgt aacgctggac ctgcctcccc ccgccgacac ccagcagaaa cctgtgctgc    24600
caggcccgac cgccgttgtt gtaacccgtc ctagccgcgc gtccctgcgc cgcgccgcca    24660
gcggtccgcg atcgttgcgg cccgtagcca gtggcaactg gcaaagcaca ctgaacagca    24720
tcgtgggtct gggggtgcaa tccctgaagc gccgacgatg cttctgaata gctaacgtgt    24780
cgtatgtgtg tcatgtatgc gtccatgtcg ccgccagagg agctgctgag ccgccgcgcg    24840
cccgctttcc aagatggcta ccccttcgat gatgccgcag tggtcttaca tgcacatctc    24900
gggccaggac gcctcggagt acctgagccc cgggctggtg cagtttgccc gcgccaccga    24960
gacgtacttc agcctgaata caagtttag aaaccccacg gtggcgccta cgcacgacgt    25020
gaccacagac cggtcccagc gttttgacgct gcggttcatc cctgtggacc gtgaggatac    25080
tgcgtactcg tacaaggcgc ggttcaccct agctgtgggt gataaccgtg tgctggacat    25140
ggcttccacg tactttgaca tccgcggcgt gctggacagg ggccctactt ttaagcccta    25200
ctctggcact gcctacaacg ccctggctcc caagggtgcc ccaaatcctt gcgaatggga    25260
tgaagctgct actgctcttg aaataaacct agaagaagag gacgatgaca acgaagacga    25320
agtagacgag caagctgagc agcaaaaaac tcacgtattt gggcaggcgc cttattctgg    25380
tataaatatt acaaggagg gtattcaaat aggtgtcgaa ggtcaaacac ctaaatatgc    25440
cgataaaaca tttcaacctg aacctcaaat aggagaatct cagtggtacg aaactgaaat    25500
taatcatgca gctgggagag tccttaaaaa gactaccca atgaaaccat gttacggttc    25560
atatgcaaaa cccacaaatg aaaatggagg gcaaggcatt cttgtaaagc aacaaaatgg    25620
aaagctagaa agtcaagtgg aaatgcaatt tttctcaact actgaggcga ccgcaggcaa    25680
tggtgataac ttgactccta agtggtatt gtacagtgaa gatgtagata tagaaacccc    25740
agacactcat atttcttaca tgcccactat taaggaaggt aactcacgag aactaatggg    25800
ccaacaatct atgcccaaca ggcctaatta cattgctttt agggacaatt ttattggtct    25860
aatgtattac aacagcacgg gtaatatggg tgttctggcg ggccaagcat cgcagttgaa    25920
tgctgttgta gatttgcaag acagaaacac agagctttca taccagcttt tgcttgattc    25980
cattggtgat agaaccaggt acttttctat gtggaatcag gctgttgaca gctatgatcc    26040
agatgttaga attattgaaa atcatggaac tgaagatgaa cttccaaatt actgctttcc    26100
actgggaggt gtgattaata cagagactct taccaaggta aaacctaaaa caggtcagga    26160
```

```
aaatggatgg gaaaaagatg ctacagaatt ttcagataaa aatgaaataa gagttggaaa   26220
taattttgcc atggaaatca atctaaatgc caacctgtgg agaaatttcc tgtactccaa   26280
catagcgctg tatttgcccg acaagctaaa gtacagtcct tccaacgtaa aaatttctga   26340
taacccaaac acctacgact acatgaacaa gcgagtggtg gctcccgggt tagtggactg   26400
ctacattaac cttggagcac gctggtccct tgactatatg gacaacgtca acccatttaa   26460
ccaccaccgc aatgctggcc tgcgctaccg ctcaatgttg ctgggcaatg gtcgctatgt   26520
gcccttccac atccaggtgc ctcagaagtt ctttgccatt aaaaacctcc ttctcctgcc   26580
gggctcatac acctacgagt ggaacttcag gaaggatgtt aacatggttc tgcagagctc   26640
cctaggaaat gacctaaggg ttgacggagc cagcattaag tttgatagca tttgcctta    26700 cgccaccttc ttccccatgg cccacaacac cgcctccacg cttgaggcca tgcttagaaa   26760
cgacaccaac gaccagtcct ttaacgacta tctctccgcc gccaacatgc tctaccctat   26820
acccgccaac gctaccaacg tgcccatatc catcccctcc cgcaactggg cggctttccg   26880
cggctgggcc ttcacgcgcc ttaagactaa ggaaacccca tcactgggct cgggctacga   26940
cccttattac acctactctg gctctatacc ctacctagat ggaaccttt acctcaacca    27000 cacctttaag aaggtggcca ttacctttga ctcttctgtc agctggcctg gcaatgaccg   27060
cctgcttacc cccaacgagt ttgaaattaa gcgctcagtt gacggggagg gttacaacgt   27120
tgcccagtgt aacatgacca aagactggtt cctggtacaa atgctagcta actacaaacat  27180 tggctaccag ggcttctata tcccagagag ctacaaggac cgcatgtact ccttctttag   27240
aaacttccag cccatgagcc gtcaggtggt ggatgatact aaatacaagg actaccaaca   27300
ggtgggcatc ctacaccaac acaacaactc tggatttgtt ggctaccttg cccccaccat   27360
gcgcgaagga caggcctacc ctgctaactt cccctatccg cttataggca agaccgcagt   27420
tgacagcatt acccagaaaa agtttctttg cgatcgcacc ctttggcgca tcccattctc   27480
cagtaacttt atgtccatgg gcgcactcac agacctgggc caaaaccttc tctacgccaa   27540
ctccgcccac gcgctagaca tgactttga ggtggatccc atggacgagc ccacccttct    27600
ttatgttttg tttgaagtct ttgacgtggt ccgtgtgcac cggccgcacc gcggcgtcat   27660
cgaaaccgtg tacctgcgca cgccttctc ggccggcaac gccacaacat aaagaagcaa    27720
gcaacatcaa caacagctgc cgccatgggc tccagtgagc aggaactgaa agccattgtc   27780
aaagatcttg gttgtgggcc atatttttg ggcacctatg acaagcgctt tccaggcttt    27840
gtttctccac acaagctcgc ctgcgccata gtcaatacgg ccggtcgcga gactgggggc   27900
gtacactgga tggcctttgc ctggaacccg cactcaaaaa catgctacct ctttgagccc   27960
tttggctttt ctgaccagcg actcaagcag gtttaccagt ttgagtacga gtcactcctg   28020
cgccgtagcg ccattgcttc ttcccccgac cgctgtataa cgctggaaaa gtccaccaa    28080 agcgtacagg ggcccaactc ggccgcctgt ggactattct gctgcatgtt tctccacgcc   28140
tttgccaact ggccccaaac tcccatggat cacaacccca ccatgaacct tattaccggg   28200
gtacccaact ccatgctcaa cagtcccag gtacagccca cctgcgtcg caaccaggaa     28260 cagctctaca gcttcctgga gcgccactcg ccctacttcc gcagccacag tgcgcagatt   28320
aggagcgcca cttcttttg tcacttgaaa aacatgtaaa aataatgtac tagagacact    28380
ttcaataaag gcaaatgctt ttatttgtac actctcgggt gattatttac ccccacccctt  28440 gccgtctgcg ccgtttaaaa atcaaagggg ttctgccgcg catcgctatg cgccactggc   28500
```

```
agggacacgt tgcgatactg gtgtttagtg ctccacttaa actcaggcac aaccatccgc   28560
ggcagctcgg tgaagttttc actccacagg ctgcgcacca tcaccaacgc gtttagcagg   28620 tcggcgccg atatcttgaa gtcgcagttg gggcctccgc cctgcgcgcg cgagttgcga    28680
tacacagggt tgcagcactg gaacactatc agcgccgggt ggtgcacgct ggccagcacg   28740
ctcttgtcgg agatcagatc cgcgtccagg tcctccgcgt tgctcagggc gaacggagtc   28800
aactttggta gctgccttcc caaaaagggc gcgtgcccag gctttgagtt gcactcgcac   28860
cgtagtggca tcaaaaggtg accgtgcccg gtctgggcgt taggatacag cgcctgcata   28920
aaagccttga tctgcttaaa agccacctga gcctttgcgc cttcagagaa gaacatgccg   28980
caagacttgc cggaaaactg attggccgga caggccgcgt cgtgcacgca gcaccttgcg   29040
tcggtgttgg agatctgcac cacatttcgg ccccaccggt tcttcacgat cttggccttg   29100
ctagactgct ccttcagcgc gcgctgcccg ttttcgctcg tcacatccat ttcaatcacg   29160
tgctccttat ttatcataat gcttccgtgt agacacttaa gctcgccttc gatctcagcg   29220
cagcggtgca gccacaacgc gcagcccgtg ggctcgtgat gcttgtaggt cacctctgca   29280
aacgactgca ggtacgcctg caggaatcgc cccatcatcg tcacaaaggt cttgttgctg   29340
gtgaaggtca gctgcaaccc gcggtgctcc tcgttcagcc aggtcttgca tacggccgcc   29400
agagcttcca cttggtcagg cagtagtttg aagttcgcct ttagatcgtt atccacgtgg   29460
tacttgtcca tcagcgcgcg cgcagcctcc atgcccttct cccacgcaga cacgatcggc   29520
acactcagcg ggttcatcac cgtaatttca ctttccgctt cgctgggctc ttcctcttcc   29580
tcttgcgtcc gcataccacg cgccactggg tcgtcttcat tcagccgccg cactgtgcgc   29640
ttacctcctt tgccatgctt gattagcacc ggtgggttgc tgaaacccac catttgtagc   29700
gccacatctt ctctttcttc ctcgctgtcc acgattacct ctggtgatgg cgggcgctcg   29760
ggcttgggag aagggcgctt cttttcttc ttgggcgcaa tggccaaatc cgccgccgag    29820
gtcgatggcc gcgggctggg tgtgcgcggc accagcgcgt cttgtgatga gtcttcctcg   29880
tcctcggact cgatacgccg cctcatccgc ttttttgggg gcgcccgggg aggcggcggc   29940 gacgggacg gggacgacac gtcctccatg gttggggac gtcgcgccgc accgcgtccg     30000
cgctcggggg tggtttcgcg ctgctcctct tcccgactgg ccatttcctt ctcctatagg   30060
cagaaaaaga tcatggagtc agtcgagaag aaggacagcc taaccgcccc ctctgagttc   30120
gccaccaccg cctccaccga tgccgccaac gcgcctacca ccttccccgt cgaggcaccc   30180
ccgcttgagg aggaggaagt gattatcgag caggacccag gttttgtaag cgaagacgac   30240
gaggaccgct cagtaccaac agaggataaa aagcaagacc aggacaacgc agaggcaaac   30300
gaggaacaag tcgggcgggg ggacgaaagg catggcgact acctagatgt gggagacgac   30360
gtgctgttga agcatctgca gcgccagtgc gccattatct gcgacgcgtt gcaagagcgc   30420
agcgatgtgc ccctcgccat agcggatgtc agccttgcct acgaacgcca ctattctca    30480 ccgcgcgtac cccccaaacg ccaagaaaac ggcacatgcg agcccaaccc gcgcctcaac   30540
ttctaccccg tatttgccgt gccagaggtg cttgccacct atcacatctt tttccaaaac   30600
tgcaagatac ccctatcctg ccgtgccaac cgcagccgag cggacaagca gctggccttg   30660
cggcagggcg ctgtcatacc tgatatcgcc tcgctcaacg aagtgccaaa aatctttgag   30720
ggtcttggac gcgacgagaa gcgcgcggca aacgctctgc aacaggaaaa cagcgaaaat   30780
gaaagtcact ctggagtgtt ggtggaactc gagggtgaca acgcgcgcct agccgtacta   30840
aaacgcagca tcgaggtcac ccactttgcc tacccggcac ttaacctacc ccccaaggtc   30900
```

```
atgagcacag tcatgagtga gctgatcgtg cgccgtgcgc agcccctgga gagggatgca   30960
aatttgcaag aacaaacaga ggagggccta cccgcagttg gcgacgagca gctagcgcgc   31020
tggcttcaaa cgcgcgagcc tgccgacttg gaggagcgac gcaaactaat gatggccgca   31080
gtgctcgtta ccgtggagct tgagtgcatg cagcggttct ttgctgaccc ggagatgcag   31140
cgcaagctag aggaaacatt gcactacacc tttcgacagg gctacgtacg ccaggcctgc   31200
aagatctcca acgtggagct ctgcaacctg gtctcctacc ttggaatttt gcacgaaaac   31260
cgccttgggc aaaacgtgct tcattccacg ctcaagggcg aggcgcgccg cgactacgtc   31320
cgcgactgcg tttacttatt tctatgctac acctggcaga cggccatggg cgtttggcag   31380
cagtgcttgg aggagtgcaa cctcaaggag ctgcagaaac tgctaaagca aaacttgaag   31440
gacctatgga cggccttcaa cgagcgctcc gtggccgcgc acctggcgga catcattttc   31500
cccgaacgcc tgcttaaaac cctgcaacag ggtctgccag acttcaccag tcaaagcatg   31560
ttgcagaact ttaggaactt tatcctagag cgctcaggaa tcttgcccgc cacctgctgt   31620
gcacttccta cgactttgt gcccattaag taccgcgaat gccctccgcc gctttgggc    31680
cactgctacc ttctgcagct agccaactac cttgcctacc actctgacat aatggaagac   31740
gtgagcggtg acggtctact ggagtgtcac tgtcgctgca acctatgcac cccgcaccgc   31800
tccctggttt gcaattcgca gctgcttaac gaaagtcaaa ttatcggtac ctttgagctg   31860
cagggtccct cgcctgacga aaagtccgcg gctccggggt tgaaactcac tccggggctg   31920
tggacgtcgg cttaccttcg caaatttgta cctgaggact accacgccca cgagattagg   31980
ttctacgaag accaatcccg cccgccaaat gcggagctta ccgcctgcgt cattacccag   32040
ggccacattt ttggccaatt gcaagccatc aacaaagccc gccaagagtt tctgctacga   32100
aagggacggg gggtttactt ggaccccag tccggcgagg agctcaaccc aatccccccg    32160
ccgccgcagc cctatcagca gcagccgcgg gcccttgctt cccaggatgg cacccaaaaa   32220
gaagctgcag ctgccgccgc cacccacgga cgaggaggaa tactgggaca gtcaggcaga   32280
ggaggttttg gacgaggagg aggaggacat gatggaagac tgggagagcc tagacgagga   32340
agcttccgag gtcgaagagg tgtcagacga acaccgtca ccctcggtcg cattcccctc     32400
gccgcgccc cagaaatcgg caaccggttc cagcatggct acaacctccg ctcctcaggc    32460
gccgccggca ctgccgttc gccgacccaa ccgtagatgg acaccactg gaaccagggc    32520
cggtaagtcc aagcagccgc cgccgttagc ccaagagcaa caacagcgcc aaggctaccg   32580
ctcatggcgc gggcacaaga acgccatagt tgcttgcttg caagactgtg ggggcaacat   32640
ctccttcgcc cgccgctttc ttctctacca tcacggcgtg gccttccccc gtaacatcct   32700
gcattactac cgtcatctct acagcccata ctgcaccggc ggcagcggca gcggcagcaa   32760
cagcagcggc cacacagaag caaaggcgac cggatagcaa gactctgaca aagcccaaga   32820
aatccacagc ggcggcagca gcaggaggag gagcgctgcg tctggcgccc aacgaacccg   32880
tatcgacccg cgagcttaga aacaggattt ttcccactct gtatgctata tttcaacaga   32940
gcaggggcca agaacaagag ctgaaaataa aaaacaggtc tctgcgatcc ctcacccgca   33000
gctgcctgta tcacaaaagc gaagatcagc ttcggcgcac gctggaagac gcggaggctc   33060
tcttcagtaa atactgcgcg ctgactctta aggactagtt tcgcgccctt tctcaaattt   33120
aagcgcgaaa actacgtcat ctccagcggc cacaccccgc gccagcacct gtcgtcagcg   33180
ccattatgag caaggaaatt cccacgccct acatgtggag ttaccagcca caaatgggac   33240
```

```
ttgcggctgg agctgcccaa gactactcaa cccgaataaa ctacatgagc gcgggacccc   33300
acatgatatc ccgggtcaac ggaatccgcg cccaccgaaa ccgaattctc ttggaacagg   33360
cggctattac caccacacct cgtaataacc ttaatccccg tagttggccc gctgccctgg   33420
tgtaccagga aagtcccgct cccaccactg tggtacttcc cagagacgcc caggccgaag   33480
ttcagatgac taactcaggg gcgcagcttg cgggcggctt tcgtcacagg gtgcggtcgc   33540
ccgggcaggg tataactcac ctgacaatca gagggcgagg tattcagctc aacgacgagt   33600
cggtgagctc ctcgcttggt ctccgtccgg acgggacatt tcagatcggc ggcgccggcc   33660
gtccttcatt cacgcctcgt caggcaatcc taactctgca gacctcgtcc tctgagccgc   33720
gctctggagg cattggaact ctgcaattta ttgaggagtt tgtgccatcg gtctacttta   33780
accccttctc gggacctccc ggccactatc cggatcaatt tattcctaac tttgacgcgg   33840
taaaggactc ggcggacggc tacgactgaa tgttaagtgg agaggcagag caactgcgcc   33900
tgaaacacct ggtccactgt cgccgccaca agtgctttgc ccgcgactcc ggtgagtttt   33960
gctactttga attgcccgag gatcatatcg agggcccggc gcacggcgtc cggcttaccg   34020
cccagggaga gcttgcccgt agcctgattc gggagtttac ccagcgcccc ctgctagttg   34080
agcgggacag gggaccctgt gttctcactg tgatttgcaa ctgtcctaac cttggattac   34140
atcaagatcc tctagttata actagagtac ccggggatct tattccctt  aactaataaa   34200 aaaaaataat aaagcatcac ttacttaaaa tcagttagca aatttctgtc cagtttattc   34260
agcagcacct ccttgccctc ctcccagctc tggtattgca gcttcctcct ggctgcaaac   34320
tttctccaca atctaaatgg aatgtcagtt tcctcctgtt cctgtccatc cgcacccact   34380
atcttcatgt tgttgcagat gaagcgcgca agaccgtctg aagatacctt caaccccgtg   34440
tatccatatg acacggaaac cggtcctcca actgtgcctt ttcttactcc tcccttt gta   34500 tccccccaatg ggtttcaaga gagtcccct gggtactct cttttgcgcct atccgaacct   34560 ctagttacct ccaatggcat gcttgcgctc aaaatgggca acggcctctc tctgacgag   34620 gccggcaacc ttacctccca aaatgtaacc actgtgagcc cacctctcaa aaaaccaag   34680 tcaaacataa acctggaaat atctgcaccc ctcacagtta cctcagaagc cctaactgtg   34740
gctgccgccg cacctctaat ggtcgcgggc aacacactca ccatgcaatc acaggccccg   34800
ctaaccgtgc acgactccaa acttagcatt gccacccaag gacccctcac agtgtcagaa   34860
ggaaagctag ccctgcaaac atcaggcccc ctcaccacca ccgatagcag tacccttact   34920
atcactgcct cacccctct  aactactgcc actggtagct tgggcattga cttgaaagag   34980
cccatttata cacaaaatgg aaaactagga ctaaagtacg gggctccttt gcatgtaaca   35040
gacgacctaa acactttgac cgtagcaact ggtccaggtg tgactattaa taatacttcc   35100
ttgcaaacta aagttactgg agccttgggt tttgattcac aaggcaatat gcaacttaat   35160
gtagcaggag gactaaggat tgattctcaa aacagacgcc ttatacttga tgttagttat   35220
ccgtttgatg ctcaaaacca actaaatcta agactaggac agggccctct ttttataaac   35280
tcagcccaca cttggatat  taactacaac aaaggccttt acttgtttac agcttcaaac   35340
aattccaaaa agcttgaggt taacctaagc actgccaagg ggttgatgtt tgacgctaca   35400
gccatagcca ttaatgcagg agatgggctt gaatttggtt cacctaatgc accaaacaca   35460
aatcccctca aaacaaaaat tggccatggc ctagaatttg attcaaacaa ggctatggtt   35520
cctaaactag gaactggcct tagtttttgac agcacaggtg ccattacagt aggaaacaaa   35580
aataatgata agctaacttt gtggaccaca ccagctccat ctcctaactg tagactaaat   35640
```

```
gcagagaaag atgctaaact cactttggtc ttaacaaaat gtggcagtca aatacttgct    35700
acagtttcag ttttggctgt taaaggcagt ttggctccaa tatctggaac agttcaaagt    35760
gctcatctta ttataagatt tgacgaaaat ggagtgctac taaacaattc cttcctggac    35820
ccagaatatt ggaactttag aaatggagat cttactgaag gcacagccta tacaaacgct    35880
gttggattta tgcctaacct atcagcttat ccaaaatctc acggtaaaac tgccaaaagt    35940
aacattgtca gtcaagttta cttaaacgga gacaaaacta aacctgtaac actaaccatt    36000
acactaaacg gtacacagga aacaggagac acaactccaa gtgcatactc tatgtcattt    36060
tcatgggact ggtctggcca caactacatt aatgaaatat ttgccacatc ctcttacact    36120
ttttcataca ttgcccaaga ataaagaatc gtttgtgtta tgtttcaacg tgtttatttt    36180
tcaattgcag aaaatttcaa gtcatttttc attcagtagt atagccccac caccacatag    36240
cttatacaga tcaccgtacc ttaatcaaac tcacagaacc ctagtattca acctgccacc    36300
tccctcccaa cacacagagt acacagtcct ttctccccgg ctggccttaa aaagcatcat    36360
atcatgggta acagacatat tcttaggtgt tatattccac acggtttcct gtcgagccaa    36420
acgctcatca gtgatattaa taaactcccc gggcagctca cttaagttca tgtcgctgtc    36480
cagctgctga gccacaggct gctgtccaac ttgcggttgc ttaacgggcg gcgaaggaga    36540
agtccacgcc tacatggggg tagagtcata atcgtgcatc aggatagggc ggtggtgctg    36600
cagcagcgcg cgaataaaact gctgccgccg ccgctccgtc ctgcaggaat acaacatggc    36660
agtggtctcc tcagcgatga ttcgcaccgc ccgcagcata aggcgccttg tcctccgggc    36720
acagcagcgc accctgatct cacttaaatc agcacagtaa ctgcagcaca gcaccacaat    36780
attgttcaaa atcccacagt gcaaggcgct gtatccaaag ctcatggcgg ggaccacaga    36840
acccacgtgg ccatcatacc acaagcgcag gtagattaag tggcgacccc tcataaacac    36900
gctggacata aacattacct ctttggcat gttgtaattc accacctccc ggtaccatat    36960
aaacctctga ttaaacatgg cgccatccac caccatccta aaccagctgg ccaaaacctg    37020
cccgccggct atacactgca gggaaccggg actggaacaa tgacagtgga gagcccagga    37080
ctcgtaacca tggatcatca tgctcgtcat gatatcaatg ttggcacaac acaggcacac    37140
gtgcatacac ttcctcagga ttacaagctc ctcccgcgtt agaaccatat cccagggaac    37200
aacccattcc tgaatcagcg taaatcccac actgcaggga agacctcgca cgtaactcac    37260
gttgtgcatt gtcaaagtgt tacattcggg cagcagcgga tgatcctcca gtatggtagc    37320
gcgggtttct gtctcaaaag gaggtagacg atccctactg tacggagtgc gccgagacaa    37380 ccagatcgt gttggtcgta gtgtcatgcc aaatggaacg ccggacgtag tcatatttcc    37440
tgaagcaaaa ccaggtgcgg gcgtgacaaa cagatctgcg tctccggtct cgccgcttag    37500
atcgctctgt gtagtagttg tagtatatcc actctctcaa agcatccagg cgccccctgg    37560
cttcgggttc tatgtaaact ccttcatgcg ccgctgccct gataacatcc accaccgcag    37620
aataagccac acccagccaa cctacacatt cgttctgcga gtcacacacg ggaggagcgg    37680
gaagagctgg aagaaccatg tttttttttt tattccaaaa gattatccaa aacctcaaaa    37740
tgaagatcta ttaagtgaac gcgctcccct ccggtggcgt ggtcaaactc tacagccaaa    37800
gaacagataa tggcatttgt aagatgttgc acaatggctt ccaaaaggca acggccctc    37860 acgtccaagt ggacgtaaag gctaaaccct tcagggtgaa tctcctctat aaacattcca    37920
gcaccttcaa ccatgcccaa ataattctca tctcgccacc ttctcaatat atctctaagc    37980
```

```
aaatcccgaa tattaagtcc ggccattgta aaaatctgct ccagagcgcc ctccaccttc  38040
agcctcaagc agcgaatcat gattgcaaaa attcaggttc ctcacagacc tgtataagat  38100
tcaaaagcgg aacattaaca aaaataccgc gatcccgtag gtccccttcgc agggccagct  38160 gaacataatc gtgcaggtct gcacggacca gcgcggccac ttccccgcca ggaaccttga  38220
caaaagaacc cacactgatt atgacacgca tactcggagc tatgctaacc agcgtagccc  38280
cgatgtaagc tttgttgcat gggcggcgat ataaaatgca aggtgctgct caaaaaatca  38340
ggcaaagcct cgcgcaaaaa agaaagcaca tcgtagtcat gctcatgcag ataaaggcag  38400
gtaagctccg gaaccaccac agaaaaagac accattttc tctcaaacat gtctgcgggt  38460
ttctgcataa acacaaaata aaataacaaa aaaacattta aacattagaa gcctgtctta  38520
caacaggaaa aacaaccctt ataagcataa gacggactac ggccatgccg gcgtgaccgt  38580
aaaaaaactg gtcaccgtga ttaaaaagca ccaccgacag ctcctcggtc atgtccggag  38640
tcataatgta agactcggta aacacatcag gttgattcat cggtcagtgc taaaaagcga  38700
ccgaaatagc ccgggggaat acatacccgc aggcgtagag acaacattac agccccata  38760 ggaggtataa caaattaat aggagagaaa acacataaa cacctgaaaa accctcctgc  38820
ctaggcaaaa tagcaccctc ccgctccaga acaacataca gcgcttcaca gcggcagcct  38880
aacagtcagc cttaccagta aaaagaaaa cctattaaaa aaacaccact cgacacggca  38940
ccagctcaat cagtcacagt gtaaaaaagg gccaagtgca gagcgagtat atataggact  39000
aaaaaatgac gtaacggtta aagtccacaa aaaacaccca gaaaaccgca cgcgaaccta  39060
cgcccagaaa cgaaagccaa aaaacccaca acttcctcaa atcgtcactt ccgttttccc  39120
acgttacgta acttcccatt ttaagaaaac tacaattccc aacacataca agttactccg  39180
ccctaaaacc tacgtcaccc gccccgttcc cacgcccgc gccacgtcac aaactccacc  39240
ccctcattat catattggct tcaatccaaa ataaggtata ttattgatga tnnnnnttaa  39300
t                                                                  39301
```

US 7,879,602 B2

CHIMERIC ADENOVIRAL VECTORS

CROSS-REFERENCES TO RELATED APPLICATIONS

The present application claims priority to U.S. Provisional Patent Application No. 60/778,026, filed Feb. 28, 2006, U.S. Provisional Patent Application No. 60/801,645, filed May 19, 2006, U.S. Provisional Patent Application No. 60/802,992, filed May 22, 2006, U.S. Provisional Patent Application No. 60/821,492, filed Aug. 4, 2006, U.S. Provisional Patent Application No. 60/846,658, filed Sep. 22, 2006, and U.S. Provisional Patent Application No. 60/848,195, filed Sep. 28, 2006), the disclosures of which are hereby incorporated by reference in their entirety for all purposes.

STATEMENT AS TO RIGHTS TO INVENTIONS MADE UNDER FEDERALLY SPONSORED RESEARCH OR DEVELOPMENT

Not applicable.

BACKGROUND OF THE INVENTION

Vaccines are an important means for preventing and/or treating a number of diseases and disorders (e.g., viral infection, bacterial infection, and cancer). Nucleic acid-based vaccines have several advantages over protein or attenuated-live vaccines. Introduction of a nucleic acid that expresses an antigen into a target cell allows for rapid development of vaccine that generates and immune response against an antigen of interest. For protein vaccines, an effective and efficient method of protein purification needs to be developed each time a new vaccine is created. For live vaccines, a method of attenuation needs to be identified that doesn't completely stop the growth of the pathogen, yet proven to be completely safe in humans. Development of protein purification and attenuation methodologies are extremely time-consuming processes. In contrast, most nucleic acid-based vaccines can be manufactured very quickly using the same manufacturing techniques each time with just a quick change in the nucleic acid encoding the antigen of interest. Replication incompetent adenovirus is one nucleic acid-based vaccine system which is rapidly, predictably, and inexpensively made at high titer [Polo, J. M. and Dubensky, T. W., Jr., *Drug Discov Today,* 7(13), 719-727 (2002)]. However, the efficiency of the antigen-specific response following administration of adenoviral vectors known in the art is low. Thus, there is a need in the art for new adenoviral vectors that can be used to efficientlyt elicit an immune response against an antigen of interest. The present invention satisfies these and other needs.

SUMMARY OF THE INVENTION

The present invention provides chimeric adenoviral vectors comprising nucleic acids encoding a heterologous polypeptide and methods for eliciting an immune response against the heterologous polypeptide.

One embodiment of the invention provideschimeric adenoviral expression vectors comprising an expression cassette comprising: (a) first promoter operably linked to a nucleic acid encoding a toll-like receptor (TLR)-3 agonist; and (b) a second promoter operably linked to a nucleic acid encoding a heterologous polypeptide. In some embodiments, the TLR-3 agonist is dsRNA. In some embodiments, the nucleic acid encoding the TLR agonist comprises a sequence selected from SEQ ID NOS: 3, 7, 8, 9, 10, 11, and 12. In some embodiments, the heterologous polypeptide is selected from an HIV envelope polypeptide (e.g., gp41, gp120 or gp160) and influenza HA polypeptide. In some embodiments, the first and second promoters are the same. In some embodiments, the first and second embodiments are different. In some embodiments, the promoters are selected from the beta actin promoter and the CMV promoter. The invention also provides immunogenic compositions comprising the expression vector.

A further embodiment of the invention provides methods of eliciting an immune response against the heterologous polypeptide by administering an immunogenically effective amount of the compositions to a mammalian subject (e.g., a rodent such as a mouse, a rat, or a guinea pig or a primate such as a chimpanzee, a rhesus macaque, or a human). In some embodiments, the vector is administered via any non-parenteral route (e.g., orally, intranasally, or mucosally). In some embodiments, the heterologous polypeptide is expressed in a cell selected from a dendritic cell, a microfold cell, and an intestinal epithelial cell.

A further embodiment of the invention provides immunogenic compositions comprising: (a) a chimeric adenoviral expression vector comprising a promoter operably linked to a nucleic acid encoding a heterologous polypeptide; and (b) a TLR-3 agonist (e.g., a dsRNA). In some embodiments, the TLR-3 agonist is encoded by a nucleic acid. The invention also provides methods of eliciting an immune response by administering the compositions to a mammalian subject (e.g., a rodent such as a mouse, a rat, or a guinea pig or a primate such as a chimpanzee, a rhesus macaque, or a human) via any non-parenteral route (e.g., oral, intranasal, or mucosal).

Another embodiment of the invention provides an isolated nucleic acid comprising the sequence set forth in SEQ ID NOS:1, 2, 6, 7, 13, 14, 15, 16, or 17.

BRIEF DESCRIPTION OF THE DRAWINGS

FIG. 1 illustrates data demonstrating that a chimeric adnenoviral vector of the invention (i.e., DS1) in combination with a TLR-3 agonist is more effective than a standard adenoviral vector (i.e., rAd5) at inducing an antigen specific immune response following oral vector delivery.

FIG. 2 illustrates data demonstrating that a chimeric adenoviral vector of the invention (i.e., DS1b or DS1c) in combination with a TLR-3 agonist is more effective at inducing an antigen specific immune response than a standard adenoviral vector (i.e., rAd5).

FIG. 3 illustrates data demonstrating that the chimeric adenoviral vectors of the invention are superior for eliciting immune responses when administered non-parenterally.

FIG. 4 illustrates data demonstrating that the expressed TLR-3 ligand agonists can induce activation of antigen presenting cells.

FIG. 6 illustrates data depicting anti-gp120 antibody titer 3 weeks following oral administration of a chimeric adenoviral comprising a nucleic acid sequence encoding the dsRNA TLR-3 agonist luc1.

FIG. 8 illustrates data demonstrating that chimeric adenoviral vectors of the invention are effective at inducing an antigen-specific immune response following oral delivery.

BRIEF DESCRIPTION OF THE SEQUENCES

Figure 1A:
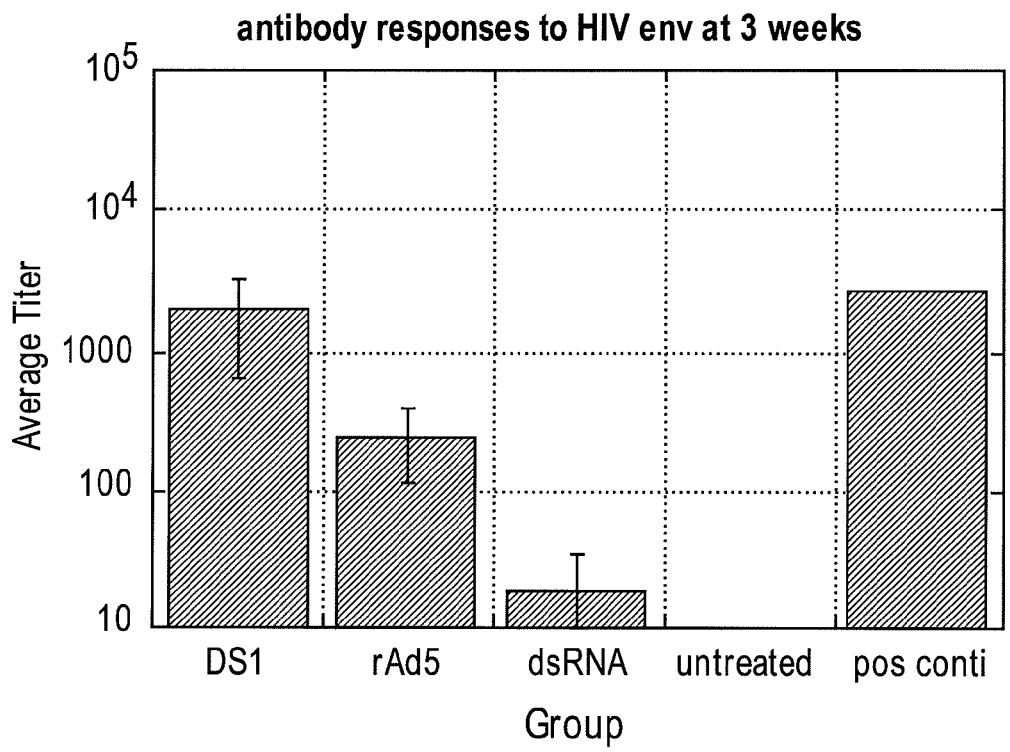
FIG. 1A illustrates data depicting the antibody titer to HIV envelope protein (i.e., gp120) at 3 weeks following oral delivery of the adenoviral vectors.

SEQ ID NO:1 sets forth the nucleotide sequence for the chimeric adenoviral vector DS1.

SEQ ID NO:2 sets forth the nucleotide sequence for the chimeric adenoviral vector DS2.

SEQ ID NO:3 sets forth a nucleotide sequence encoding a TLR-3 agonist.

SEQ ID NO:4 sets forth a nucleotide sequence encoding a TLR-3 agonist.

SEQ ID NO:5 sets forth a nucleotide sequence encoding a TLR-3 agonist.

SEQ ID NO:6 sets forth a nucleotide sequence for a chimeric adenoviral vector comprising a nucleic acid encoding influenza HA and a nucleic acid encoding a TLR-3 agonist (luc), wherein the influenza HA and the TLR-3 agonist are in the same orientation.

SEQ ID NO: 7 sets forth a nucleotide sequence for a chimeric adenoviral vector comprising a nucleic acid encoding influenza HA and a nucleic acid encoding a TLR-3 agonist (luc), wherein the influenza HA and the TLR-3 agonist are in the opposite orientation.

SEQ ID NO:8 sets forth a nucleotide sequence encoding a short hairpin RNA TLR-3 agonist. Complementary portions of the sequence are shown in capital letters and the linker sequence is shown in lower case letters.

SEQ ID NO: 9 sets forth a nucleotide sequence encoding a short hairpin RNA TLR-3 agonist (g1). Complementary portions of the sequence are shown in capital letters and the linker sequence is shown in lower case letters.

SEQ ID NO: 10 sets forth a nucleotide sequence encoding a short hairpin RNA TLR-3 agonist (luc). Complementary portions of the sequence are shown in capital letters and the linker sequence is shown in lower case letters.

SEQ ID NO: 11 sets forth a nucleotide sequence encoding a short hairpin RNA TLR-3 agonist (m1). Complementary portions of the sequence are shown in capital letters and the linker sequence is shown in lower case letters.

SEQ ID NO: 12 sets forth a nucleotide sequence encoding a short hairpin RNA TLR-3 agonist. Complementary portions of the sequence are shown in capital letters and the linker sequence is shown in lower case letters.

SEQ ID NO: 13 sets forth the nucleotide sequence for the chimeric adenoviral vector DS1c. The sequence comprises a nucleotide encoding HA(PR8/34).

SEQ ID NO: 14 sets forth the nucleotide sequence for the chimeric adenoviral vector DS2beta-luc. The vector comprises a sequence encoding the TLR-3 agonist luc under the control of the beta actin promoter. The vector also comprises open cloning sites for insertion of nucleic acid sequence(s) encoding an antigen of interest.

SEQ ID NO: 15 sets forth the nucleotide sequence for the chimeric adenoviral vector DS2C-luc The vector comprises a sequence encoding the TLR-3 agonist luc under the control of the CMV promoter. The vector also comprises open cloning sites for insertion of nucleic acid sequence(s) encoding an antigen of interest.

SEQ ID NO: 16 sets forth the nucleotide sequence for the pShuttle vector comprising a nucleic acid sequence encoding the TLR-3 agonist luc under the control of the CMV promoter and a nucleic acid sequence encoding HA (avian flu) under the control of a separate CMV promoter.

SEQ ID NO: 17 sets forth the nucleotide sequence for the chimeric adenoviral vector ND1.1 214. The nucleic acid encoding the heterologous antigen is in bold text and is flanked by a Cla I recognition site on the 5' end and a Not 1 recognition site on the 3'end. The nucleic acid sequence encoding the TLR-3 agonists is in italic, with the linker sequence in bold.

DETAILED DESCRIPTION OF THE INVENTION

I. Introduction

The present invention provides novel chimeric adenoviral vectors that can be administered non-parenterally to elicit an immune response against an antigen of interest. The chimeric adenoviral vectors of the invention comprise a nucleic acid encoding a heterologous polypeptide and a nucleic acid encoding a TLR-3 agonist. The chimeric adenoviral vectors elicit strong and effective immune responses specific for the heterologous polypeptide, particularly when administered via a non-parenteral route (e.g., orally, intranasally, or mucosally).

The invention is based on the suprising discovery that administration of dsRNA TLR-3 agonists are effective adjuvants when administered in conjunction with viral vectors. In fact, the use of dsRNA as an adjuvant for viral vectors would be counterintuitive considering that the major proposed utility of the dsRNA mimetic poly I:C was as an antiviral agent [Nemes, et al., *Proc Soc Exp Biol Med*. (1969) 132:776; Schafer, et al, *Nature*. (1970) 226:449; Fenje, et al, *Nature* (1970) 226:171.].

II. Definitions

The term "chimeric" or "recombinant" as used herein with reference, e.g., to a nucleic acid, protein, or vector, indicates that the nucleic acid, protein or vector, has been modified by the introduction of a heterologous nucleic acid or protein or the alteration of a native nucleic acid or protein. Thus, for example, chimeric and and recombinant vectors include nucleic acid sequences that are not found within the native (non-chimeric or non-recombinant) form of the vector. A chimeric adenoviral expression vector refers to an adenoviral expression vector comprising a nucleic acid sequence encoding a heterologous polypeptide.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "promoter" and "expression control sequence" are used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Promoters include constitutive and inducible promoters. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The terms "TLR agonist" or "Toll-like receptor agonist" as used herein refers to a compound that binds and stimulates a Toll-like receptor including, e.g., TLR-2, TLR-3, TLR-6, TLR-7, or TLR-8. TLR agonists are reviewed in MacKichan, *IAVI Report*. 9:1-5 (2005) and Abreu et al., *J Immunol*, 174 (8), 4453-4460 (2005). Agonists induce signa transduction following binding to their receptor.

The terms "TLR-3 agonist" or "Toll-like receptor 3 agonist" as used herein refers to a compound that binds and stimulates the TLR-3. TLR-3 agonists have been identified including double-stranded RNA, virally derived dsRNA, several chemically synthesized analogs to double-stranded RNA including polyinosine-polycytidylic acid (poly I:C)—polyadenylic-polyuridylic acid (poly A:U) and poly I:poly C, and antibodies (or cross-linking of antibodies) to TLR-3 that lead to IFN-beta production [Matsumoto, M, et al, *Biochem Biophys Res Commun* 24:1364 (2002), de Bouteiller, et al, *J Biol Chem* 18:38133-45 (2005)]. TLR-3 agonists also include expressed dsRNA (e.g., dsRNA encoded by a nucleic acid comprising a sequence set forth in SEQ ID NOS: 3, 7, 8, 9, 10, 11, or 12).

The terms "TLR-7/8 agonist" or "Toll-like receptor 7/8 agonist" as used herein refers to a compound that binds and stimulates either the TLR-7 or TLR-8 receptors; these receptors recognize several of same ligands. Several TLR-7/8 agonists have been identified such as viral single-stranded RNA, imiquimod, loxoribine, polyuridylic acid, or resiquimod.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

Antigen—refers to a protein or part of a polypeptide chain that can be recognized by T cell receptors and/or antibodies. Typically, antigens are derived from bacterial, viral, or fungal proteins.

An "immunogenically effective dose or amount" of the of the compositions of the present invention is an amount that elicits or modulates an immune response specific for the heterologous polypeptide. Immune responses include humoral immune responses and cell-mediated immune responses. An immunogenic composition can be used therapeutically or prophylactically to treat or prevent disease at any stage.

"Humoral immune responses" are mediated by cell free components of the blood, i.e., plasma or serum; transfer of the serum or plasma from one individual to another transfers immunity.

"Cell mediated immune responses" are mediated by antigen specific lymphocytes; transfer of the antigen specific lymphocytes from one individual to another transfers immunity.

A "therapeutic dose" or "therapeutically effective amount" or "effective amount" of a chimeric adenoviral vector or a composition comprising a chimeric adenoviral vector is an amount of the vector or composition comprising the vector which prevents, alleviates, abates, or reduces the severity of symptoms of diseases and disorders associated with the source of the heterologous polypeptide (e.g., a virus, bacteria, a parasite, or a cancer).

Antibody—refers to a polypeptide encoded by an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

T cells—refer to a particular class of lymphocytes that express a specific receptor (T cell receptor) encoded by a family of genes. The recognized T cell receptor genes include alpha, beta, delta, and gamma loci, and the T cell receptors typically (but not universally) recognize a combination of MHC plus a short peptide.

Adaptive immune response—refers to T cell and/or antibody recognition of antigen.

Antigen presenting cells (APCs)—as used herein refers to cells that are able to present immunogenic peptides or fragments thereof to T cells to activate or enhance an immune response. APCs include dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may be isolated from any of a variety of biological fluids and organs including bone marrow, peripheral blood, tumor and peritumoral tissues, and may be autologous, allogeneic, syngeneic or xenogeneic cells. APCs typically utilize a receptor from the major histocompatability (MHC) locus to present short polypeptides to T cells.

Adjuvant—is a non-specific immune response enhancer. Suitable adjuvants include, for example, cholera toxin, monophosphoryl lipid A (MPL), Freund's Complete Adjuvant, Freund's Incomplete Adjuvant, Quil A, and Al(OH). Adjuvants can also be those substances that cause APC activation and enhanced presentation of T cells through secondary signaling molecules like Toll-like receptors. Examples of Toll-like receptors include the receptors that recognize double-stranded RNA, bacterial flagella, LPS, CpG DNA, and bacterial lipopeptide (Reviewed recently in [Abreu et al., *J Immunol*, 174(8), 4453-4460 (2005)]).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an γ carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine I, Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point I for the specific sequence at a defined ionic strength Ph. The $T_m$ is the temperature (under defined ionic strength, Ph, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at Ph 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to fusion proteins can be selected to obtain only those polyclonal antibodies that are specifically immunoreactive with fusion protein and not with individual components of the fusion proteins. This selection may be achieved by subtracting out antibodies that cross-react with the individual antigens. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

Polynucleotides may comprise a native sequence (i.e., an endogenous sequence that encodes an individual polypeptide or dsRNA or a portion thereof) or may comprise a variant of such a sequence. Polynucleotide variants may contain one or more substitutions, additions, deletions and/or insertions such that the biological activity of the encoded polypeptide is not diminished, relative to a polypeptide comprising native antigens. Polynucleotide variants may contain one or more substitutions, additions, deletions and/or insertions such that the TLR-3 agonist activity of the encoded dsRNA is not diminished, relative to a dsRNA that does not contain the substitutions, additions, deletions and/or insertions. Variants preferably exhibit at least about 50%, 55%, 60%, 65%, 70%, 75%, 80%, 85%, 90%, 91%, 92%, 93%, 94%, 95%, 96%, 97%, 98%, 99%, to a polynucleotide sequence that encodes a native polypeptide or a portion thereof or to a polynucleotide sequence that encodes a dsRNA with TLR-3 agonist activity.

The terms "identical" or percent "identity," in the context of two or more nucleic acids (e.g., a dsRNA that is a TLR-3 agonist) or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 91%, 92%, 93%, 94%, 95%, 96%, 97%, 98%, 99%, or more identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 10 to about 100, about 20 to about 75, about 30 to about 50 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions from about 10 to about 500, about 25 to about 200, 50 to about 150, in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

III. Compositions of the Present Invention

The invention provides compositions comprising chimerical adenoviral vectors. In some embodiments, the chimeric adenoviral vectors of the invention comprise a first promoter operably linked to a nucleic acid encoding a heterologous polypeptide and a second promoter operably linked to a nucleic acid encoding a TLR3 agonist. The first and second promoters may be the same or different. In some embodiments, the first and second promoters are independently selected from: the beta actin promoter and the CMV promoter.

In some embodiments, the chimeric adenoviral vector comprises the adenoviral genome (minus the E1 and E3 genes) and a nucleic acid encoding a a gene that activates IRF-3 and other signaling molecules downstream of TLR-3. The chimeric vector can be administered to a cell that expresses Ad's E1 gene such that recombinant adenovirus (rAd) is produced by the cell. This rAd can be harvested and is capable of a single round of infection that will deliver the transgenic compostion to another cell within a mammal in order to elicit immune responses to the heterologous polypeptide.

A. Suitable Adenoviral Vectors

In some embodiments, the adenoviral vector is adenovirus 5, including, for example, Ad5 with deletions of the E1/E3 regions and Ad5 with a deletion of the E4 region. Other suitable adenoviral vectors include strains 2, orally tested strains 4 and 7, enteric adenoviruses 40 and 41, and other strains (e.g. Ad34) that are sufficient for delivering an antigen and eliciting an adaptive immune response to the transgene antigen [Lubeck et al., *Proc Natl Acad Sci USA,* 86(17), 6763-6767 (1989); Shen et al., *J Virol,* 75(9), 4297-4307 (2001); Bailey et al., *Virology,* 202(2), 695-706 (1994)]. In some embodiments, the adenoviral vector is a live, replication incompetent adenoviral vector (such as E1 and E3 deleted rAd5), live and attenuated adenoviral vector (such as the E1B55K deletion viruses), or a live adenoviral vector with wild-type replication.

The transcriptional and translational control sequences in expression vectors to be used in transforming vertebrate cells in vivo may be provided by viral sources. For example, commonly used promoters and enhancers are derived, e.g., from beta actin, adenovirus, simian virus (SV40), and human cytomegalovirus (CMV). For example, vectors allowing expression of proteins under the direction of the CMV promoter, SV40 early promoter, SV40 later promoter, metallothionein promoter, murine mammary tumor virus promoter, Rous sarcoma virus promoter, transducer promoter, or other promoters shown effective for expression in mammalian cells are suitable. Further viral genomic promoter, control and/or signal sequences may be used, provided such control sequences are compatible with the host cell chosen.

B. Heterologous Polypeptides

Nucleic acids encoding suitable heterologous polypeptides may be derived from antigens, such as, for example, viral antigens, bacterial antigens, cancer antigens, fungal antigens, or parasite antigens.

Viral antigens may be derived from, for example, human immunodeficiency virus (e.g., gag (p55 and p160), pol, env (gp120 and gp41) as set forth in Shiver et al. *Nature* 415 (6869):331 (2002); the HIV genomic sequences set forth in Genbank Accession Nos. EF363127; EF363126; EF363125; EF363124; EF363123; EF363122; EF192592; and EF192591; the HIV gag sequences set forth in Genbank Accession Nos. EF396891; EF396890; EF396889; EF396888; EF396887; EF396886; EF396885; EF396884; EF396883; EF396882; EF396881; EF396880; EF396879; EF396878; EF396877; EF396876; EF39687; EF396874; EF396873; and EF396872; the HIV pol sequences set forth in Genbank Accession Nos. EF396810; EF396809; EF396808; EF396807; EF396806; EF396805; EF396804; EF396803; EF396802; EF396801; EF396800; EF396799; EF396798; EF396797; EF396796; EF396795; EF396794; EF396793; EF396792; and EF396791; and the HIV env sequences set forth in Genbank Accession Nos. 9: EF367234; EF367233; EF367232; EF367231; EF367230; EF367229; EF367228; EF367227; EF367226; EF367225; EF367224; and EF367223, human papilloma virus (e.g., capsid protein L1 as described in, e.g., Donnelly et al. J Infect Dis. 173:314 (1996) and the sequences set forth in Genbank Accession Nos. EF362755; EF362754; NC_001694; NC_001693; NC_001691; NC_001690; NC_005134; NC_001458; NC_001457; NC_001354; NC_001352; NC_001526; and X94164), Epstein Barr virus, herpes simplex virus, human herpes virus, rhinoviruses, cocksackieviruses, enteroviruses, hepatitis A, B, C, and E (e.g., hepatitis B surface antigen as described in e.g., Lubeck et al, *PNAS USA* 86:6763 (1989) and the sequences set forth in GenBank Accession Nos. AB236481; AB236471; AB206501; AB206489; AB206487; AB221788; AB221777; AB221773; AR933671;AR933670; AB236514; AB236513; AB236512; AB236511; AB236510; AB236509; AB236508; AB236507); hepatitis C NS5 (see, e.g., Genbank Accession Nos. X59609; DQ911563; S71627; S70787; S70786; S70341; S62220; S70790; S70789; S70788; and AB204642)), mumps virus, rubella virus, measles virus, poliovirus, smallpox virus, rabies virus, and Variella-zoster virus. Influenza antigens include, e.g., hemagluttinin (HA), matrix protein 1 (M1), and nucleoprotein (NP) (see, e.g., Donnelly, et al, *Vaccine* 15:865 (1997) and the influenza HA sequences set forth in Genbank Accession Nos. AB294219; AB294217; AB294215; AB294213; EF102944; EF102943; EF102942; EF102941; EF102940; EF102939; EF102938; EF102937; EF102936; EF102935; EF102934; EF102933; DQ643982; DQ464354; CY019432; CY019424; CY019416; CY019408; CY019400; CY019392; CY019384; CY019376; CY019368; CY019360; CY019352; EF124794; EF110519; EF110518; EF165066; EF165065; EF165064; and EF165063; the influenza M1 sequences set forth in Genbank Accession Nos. AB292791; CY019980; CY019972; CY019964; CY019956; CY019948; CY019940; CY019628; CY019652; CY019644; CY019632; CY019924; CY019916; CY019908; CY019900; CY019892; CY019884; CY019876; CY019868; CY019860; and the influenza NP sequences set forth in Genbank Accession Nos. AB292790; CY019461; CY019974; CY019966; CY019958; CY019950; CY019942; CY019630; CY019654; CY019646; CY019934; CY019926; CY019918 CY019910; CY019902; CY019894; CY019886; CY019878; CY019870; and CY019862.

Suitable viral antigens also include, e.g., viral nonstructural proteins. The term "Viral nonstructural protein" as used herein refers to proteins encoded by viral nucleic acid that do not encode for structural polypeptides, such as those that make capsid or the protein surrounding a virus. Non-structural proteins include those proteins that promote viral nucleic acid replication and viral gene expression such as, for example, Nonstructural proteins 1, 2, 3, and 4 (NS1, NS2, NS3, and NS4, respectively) from Venezuelan Equine encephalitis (VEE), EEE, or Semliki Forest virus [Dubensky et al., *J Virol,* 70(1), 508-519 (1996); Petrakova et al *J Virol* 2005 79(12): 7597-608; U.S. Pat. Nos. 5,185,440; 5,739,026; 6,566,093; and 5,814,482. Several representative examples of suitable alphaviruses include Aura (ATCC VR-368), Bebaru virus (ATCC VR-600, ATCC VR-1240), Cabassou (Genbank Accession Nos. AF398387, ATCC VR-922), Chikungunya virus (ATCC VR-64, ATCC VR-1241), Eastern equine encephalomyelitis virus (Genbank Accession Nos. AY705241, AY705240, ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (Genbank Accession Nos. AJ251359, ATCC VR-67, ATCC VR-1247), Sindbis virus (Genbank Accession Nos. J02363, ATCC VR-68, ATCC VR-1248), Tonate (ATCC VR-925), Triniti (ATCC VR-469), Una (ATCC VR-374), Venezuelan equine encephalomyelitis (ATCC VR-69), Venezuelan equine encephalomyelitis virus (Genbank Accession Nos. AY986475, AY973944, NC 001449, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

Bacterial antigens may be derived from, for example, *Staphylococcus aureus, Staphylococcus epidermis, Helicobacter pylori, Streptococcus bovis, Streptococcus pyogenes, Streptococcus pneumoniae, Listeria monocytogenes, Mycobacterium tuberculosis, Mycobacterium leprae, Corynebacterium diphtheriae, Borrelia burgdorferi, Bacillus anthracis, Bacillus cereus, Clostridium botulinum, Clostridium difficile, Salmonella typhi, Vibrio chloerae, Haemophilus influenzae, Bordetella pertussis, Yersinia pestis, Neisseria gonorrhoeae, Treponema pallidum, Mycoplasm* sp., *Neisseria* □ransducer□s, *Legionella pneumophila, Rickettsia typhi, Chlamydia trachomatis,* and *Shigella dysenteriae, Vibrio cholera*(e.g., Cholera toxin subunit B as set forth in Genbank Accession Nos. U25679; A09803; EF158842; X76391; AF390572; cholera toxin-coregulated pilus (TCP) as described in Wu et al., *Infection and Immunity Vol.* 69(12): 7695 (2001) and as set forth in Genbank Accession Nos. NC_002505 and AE004169); *Helicobacter pylorii* (VacA as set forth in Genbank Accession Nos. AY848858; AF042737; AF042736; AF042735; AF042734; NC_000921; CagA as set forth in Genbank Accession Nos. AF043490; AF043489; AF043488; AF043487; NAP as set forth in Genbank Accession Nos. AF284121; AF284120; AF284119; AF284118; AF284117; AF284116; AB045143; AB045142; AF227081; AF227080; AF227079; AF227078; AF227077; AF227076; AF227075; AF227074; Hsp or catalase as set forth in Genbank Accession No. NC_000921; urease as set forth in Genbank Accession Nos. AM417610; AM417609; AM417608;

AM417607; AM417606; AM417605; AM417604; AM417603; AM417602; AM417601; and AM417600; *E. coli* antigens as set forth in Genbank Accession Nos. NC_000913; U00096; NC_002655; BA000007; AE014075; including *E. coli* fimbrial antigens as set forth in Genbank Accession Nos. AB214865; AB214864; AB214863; AB214862; *E. coli* heat-labile enterotoxin as set forth in Genbank Accession Nos. X83966; V00275; X83966; J01646; V00275; M35581; M17873; M17874; K01995; M61015; M17894; M17101; K00433.

Parasite antigens may be derived from, for example, *Giardia lamblia, Leishmania* sp., *Trypanosoma* sp., *Trichomonas* sp., *Plasmodium* sp. (e.g., *P. faciparum* surface protein antigens such as pfs25 sequences as set forth in Genbank Accession Nos. XM_001347551; X07802; AF193769; AF179423; AF154117; and AF030628, pfs28 sequences as set forth in Genbank Accession No. L25843, pfs45 sequences as set forth in Genbank Accession Nos. EF158081; EF158079; EF158078; EF158076; EF158075; and EF158085, pfs84, pfs 48/45 sequences as set forth in Genbank Accession Nos. AF356146; AF356145; AF356144; AF356143; AF356142; AF356141; AF356140; AF356139; AF356138; AF356137; AF356136; AF356135; AF356134; AF356133; AF356132; AF356131; AF356130; AF356129; AF356128; AF356127, pfs 230 sequences as set forth in Genbank Accession Nos. NC_000910; XM_001349564; AE001393; L22219; L08135; and AF269242, *P. vivax* antigens such as Pvs25 sequences as set forth in Genbank Accession Nos. DQ641509; DQ641508; DQ641507; AY639972; AY639971; AY639970; AY639969; AY639968; AY639967; AY639966; and AY639965; and Pvs28 sequences as set forth in Genbank Accession Nos. AB033364; AB033363; AB033362; AB033361; AB033360; AB033359; AB033358; AB033357; AB033356; B033355; AB033354; AB033353; AB033352; AB033351; AB033350; AB033349; AB033348; AB033347; AB033346; and AB033345), *Schistosoma* sp., *Mycobacterium tuberculosis* (e.g., Ag85 sequences as set forth in Genbank Accession Nos. AX253506; AX253504; AX253502; and AX211309; MPT64, ESAT-6, CFP10, R8307, MTB-32 MTB-39, CSP, LSA-1, LSA-3, EXP1, SSP-2, SALSA, STARP, GLURP, MSP-1, MSP-2, MSP-3, MSP-4, MSP-5, MSP-8, MSP-9, AMA-1, Type 1 integral membrane protein, RESA, EBA-175, and DBA sequences as set forth in Genbank Accession Nos. BX842572; BX842573; BX842574; BX842575; BX842576; BX842577; BX842578; BX842579; BX842580; BX842581; BX842582; BX842583; BX842584 and NC_000962, HSP65 sequences as set forth in Genbank Accession Nos. AY299175; AY299174; AY299144; AF547886; and AF547885).

Cancer antigens include, for example, antigens expressed, for example, in colon cancer, stomach cancer, pancreatic cancer, lung cancer, ovarian cancer, prostate cancer, breast cancer, skin cancer (e.g., melanoma), leukemia, lymphoma, or myeloma, exemplary cancer antigens include, for example, HPV L1, HPV L2, HPV E1, HPV E2, placental alkaline phosphatase, AFP, BRCA1, Her2/neu, CA 15-3, CA 19-9, CA-125, CEA, Hcg, urokinase-type plasminogen activator (Upa), plasminogen activator inhibitor.

Fungal antigens may be derived from, for example, *Tinea pedis, Tinea corporus, Tinea cruris, Tinea unguium, Cladosporium carionii, Coccidioides immitis, Candida* sp., *Aspergillus fumigatus*, and *Pneumocystis carinii*.

The nucleic acids encoding immunogenic polypeptides, are typically produced by recombinant DNA methods (see, e.g., Ausubel, et al. ed. (2001) *Current Protocols in Molecular Biology*). For example, the DNA sequences encoding the immunogenic polypeptide can be assembled from cDNA fragments and short oligonucleotide linkers, or from a series of oligonucleotides, or amplified from cDNA using appropriate primers to provide a synthetic gene which is capable of being inserted in a recombinant expression vector (i.e., a plasmid vector or a viral vector) and expressed in a recombinant transcriptional unit. Once the nucleic acid encoding an immunogenic polypeptide is produced, it may be inserted into a recombinant expression vector that is suitable for in vivo or ex-vivo expression.

Recombinant expression vectors contain a DNA sequence encoding an immunogenic polypeptide operably linked to suitable transcriptional or translational regulatory elements derived from mammalian or viral genes. Such regulatory elements include a transcriptional promoter, an optional operator sequence to control transcription, a sequence encoding suitable mRNA ribosomal binding sites, and sequences which control the termination of transcription and translation. An origin of replication and a selectable marker to facilitate recognition of transformants may additionally be incorporated. The genes utilized in the recombinant expression vectors may be divided between more than one virus such that the gene products are on two different vectors, and the vectors are used for co-transduction to provide all the gene products in trans. There may be reasons to divide up the gene products such as size limitations for insertions, or toxicity of the combined gene products to the virus produce cell-lines.

C. TLR Agonists

According to the methods of the invention, TLR agonists are used to enhance the immune response to the heterologous polypeptide. In some embodiments, TLR-3 agonists are used. In other embodiments, TLR 7/8 agonists are used. The TLR agonists described herein can be delivered simultaneously with the expression vector encoding an antigen of interest or delivered separately (i.e., temporally or spatially) from the expression vector encoding an antigen of interest. For example, the expression vector may be administered via a non-parenteral route (e.g., orally, intranasally, or mucosally), while the TLR-agonist is delivered by a parenteral route (e.g., intramuscularly, intraperitoneally, or subcutaneously).

1. TLR-3 Agonists

In a preferred embodiment of the present invention, a TLR-3 agonist is used to stimulate immune recognition of an antigen of interest. TLR-3 agonists include, for example, short hairpin RNA, virally derived RNA, short segments of RNA that can form double-strands or short hairpin RNA, and short interfering RNA (siRNA). In one embodiment of the invention, the TLR-3 agonist is virally derived dsRNA, such as for example, a dsRNA derived from a Sindbis virus or dsRNA viral intermediates [Alexopoulou et al, *Nature* 413: 732-8 (2001)]. In some embodiments, the TLR-3 agonists is a short hairpin RNA. Short hairpin RNA sequences typically comprise two complementary sequences joined by a linker sequence. The particular linker sequence is not a critical aspect of the invention. Any appropriate linker sequence can be used so long as it does not interfere with the binding of the two complementary sequences to form a dsRNA.

In some embodiments, the short hairpin RNA comprises a sequence set forth in SEQ ID NOS: 3, 4, 5, 8, 9, 10, 11, or 12, a sequence with substantial identity to a sequence set forth in SEQ ID NOS: 3, 4, 5, 8, 9, 10, 11, or 12, or a variant of a sequence set forth in SEQ ID NOS: 3, 4, 5, 8, 9, 10, 11, or 12. In certain embodiments, dsRNA that is a TLR-3 agonist does not encode a particular polypeptide, but produces a pro-inflammatory cytokine (e.g. IL-6, IL-8, TNF-alpha, IFN-alpha, IFN-beta) when contacted with a responder cell (e.g., a dendritic cell, a peripheral blood mononuclear cell, or a macrophage) in vitro or in-vivo. In some cases, the nucleic acid encoding the TLR-3 agonist (e.g., an expressed dsRNA) and the chimeric adenoviral vector comprising a nucleic acid encoding a heterologous antigen are administered in the same formulation. In other cases the nucleic acid encoding the TLR-3 agonist and the chimeric adenoviral vector comprising a nucleic acid encoding a heterologous polypeptide are administered in different formulations. When the nucleic acid encoding the TLR-3 agonist and the adenoviral vector comprising a nucleic acid encoding a heterologous antigen are administered in different formulations, their administration may be simultaneous or sequential. For example, the nucleic acid encoding the TLR-3 agonist may be administered first, followed by the chimeric adenoviral vector (e.g., 1, 2, 4, 8, 12, 16, 20, or 24 hours, 2, 4, 6, 8, or 10 days later). Alternatively, the adenoviral vector may be administered first, followed by the nucleic acid encoding the TLR-3 agonist (e.g., 1, 2, 4, 8, 12, 16, 20, or 24 hours, 2, 4, 6, 8, or 10 days later). In some embodiment, the nucleic acid encoding the TLR-3 agonist and the nucleic acid encoding the heterologous antigen are under the control of the same promoter. In other embodiments, the nucleic acid encoding the TLR-3 agonist and the nucleic acid encoding the heterologous antigen are under the control of different promoters.

Several chemically synthesized analogs to double-stranded RNA are commercially available. These include polyinosine-polycytidylic acid (poly I:C), polyadenylic:polyuridylic acid (poly A:U), and poly I:poly C. Antibodies (or cross-linking of antibodies) to TLR-3 can also lead to IFN- beta or pro-inflammatory cytokine production [Matsumoto et al, *Biochem. Biophys. Res. Commun.* 24:1364 (2002), de Bouteiller et al, *J Biol. Chem.* 18:38133-45 (2005)]. Commercially available siRNA segments of any sequence can also be obtained through sources such as Invitrogen.

2. TLR7/8 Agonists

In some embodiments, the TLR agonists are TLR7/8 agonists. TLR7/8 ligands are typically single-stranded, virally derived RNA. Because the receptors are expressed in intracellular compartments such as the endosome, not all short segments of RNA will trigger the TLR7/8 signaling cascade because they need to reach the correct compartment. Some ligands that have been shown to trigger this through exogenous addition are polyuridylic acid, resiquimod, and imiquimod [Westwood, et al, *Vaccine* 24:1736-1745(2006)].

IV. Pharmaceutical Compositions

Pharmaceutical compositions comprising the vectors described herein may also contain other compounds, which may be biologically active or inactive. Polypeptides may, but need not, be conjugated to other macromolecules as described, for example, in U.S. Pat. Nos. 4,372,945 and 4,474,757. Pharmaceutical compositions may generally be used for prophylactic and therapeutic purposes. Pharmaceutical compositions may be composed of methods to protect against stomach degradation such that the administered chimeric adenoviral vector may reach the desired locations. For the oral environment, several of these are available including the Eudragit and the TimeClock release systems as well as other methods specifically designed for adenovirus [Lubeck et al., *Proc Natl Acad Sci USA,* 86(17), 6763-6767 (1989); Chourasia and Jain, *J Pharm Pharm Sci,* 6(1), 33-66 (2003)]. There are also several methods already described for microencapsulation of DNA and drugs for oral delivery (see, e.g., U.S. Patent Publication No. 2004043952). In some embodiments, the Eudragit system will be used to to deliver the chimeric adenoviral vecto to the lower small intestine. However, delivery to other locations of the small intestine should also work.

As noted above, the chimeric adenoviral vectors on the invention may be delivered using any delivery systems known to those of ordinary skill in the art. Numerous gene delivery techniques are well known in the art, such as those described by Rolland (1998) *Crit. Rev. Therap. Drug Carrier Systems* 15:143-198, and references cited therein.

It will be apparent that an immunogenic compostions may contain pharmaceutically acceptable salts of the polynucleotides encoding the heterologous polypeptides (e.g., immunogenic polypeptides). Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts). Some particular examples of salts include phosphate buffered saline and saline for injection.

Any suitable carrier known to those of ordinary skill in the art may be employed in the pharmaceutical compositions of this invention. Suitable carriers include, for example, water, saline, alcohol, a fat, a wax, a buffer, a solid carrier, such as mannitol, lactose, starch, magnesium stearate, sodium saccharine, talcum, cellulose, glucose, sucrose, and magnesium carbonate, or biodegradable microspheres (e.g., polylactate polyglycolate). Suitable biodegradable microspheres are disclosed, for example, in U.S. Pat. Nos. 4,897,268; 5,075,109; 5,928,647; 5,811,128; 5,820,883. The immunogenic polypeptide and/or carrier virus may be encapsulated within the biodegradable microsphere or associated with the surface of the microsphere.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

In some embodiments of the present invention, the compositions further comprise an adjuvant. Suitable adjuvants include, for example, the lipids and non-lipid compounds, cholera toxin (CT), CT subunit B, CT derivative CTK63, *E. coli* heat labile enterotoxin (LT), LT derivative LTK63, Al(OH)$_3$, and polyionic organic acids as described in e.g., WO 04/020592, Anderson and Crowle, *Infect. Immun.* 31(1): 413-418 (1981), Roterman et al., *J. Physiol. Pharmacol.,* 44(3):213-32 (1993), Arora and Crowle, *J. Reticuloendothel.* 24(3):271-86 (1978), and Crowle and May, *Infect. Immun.* 38(3):932-7 (1982)). Suitable polyionic organic acids include for example, 6,6'-[3,3'-demithyl[1,1'-biphenyl]-4,4'-diyl]bis(azo)bis[4-amino-5-hydroxy-1,3-naphthalene-disulfonic acid] (Evans Blue) and 3,3'-[1,1'biphenyl]-4,4'-diylbis(azo)bis[4-amino-1-naphthalenesulfonic acid] (Congo Red). It will be appreciated by those of skill in the art that the polyionic organic acids may be used for any genetic vaccination method in conjunction with any type of administration.

Other suitable adjuvants include topical immunomodulators such as, members of the imidazoquinoline family such as, for example, imiquimod and resiquimod (see, e.g., Hengge et al., *Lancet Infect. Dis.* 1(3):189-98 (2001). Expressed TLR-3 agonists (e.g., dsRNA) and TLR-7 agonists (e.g., ssRNA) could also be used with the invention Additional suitable adjuvants are commercially available as, for example, additional alum-based adjuvants (e.g., Alhydrogel, Rehydragel, aluminum phosphate, Algammulin); oil based adjuvants (Freund's Incomplete Adjuvant and Complete Adjuvant (Difco Laboratories, Detroit, Mich.), Specol, RIBI, TiterMax, Montanide ISA50 or Seppic MONTANIDE ISA 720); nonionic block copolymer-based adjuvants, cytokines (e.g., GM-CSF or Flat3-ligand); Merck Adjuvant 65 (Merck and Company, Inc., Rahway, N.J.); AS-2 (SmithKline Beecham, Philadelphia, Pa.); salts of calcium, iron or zinc; an insoluble suspension of acylated tyrosine; acylated sugars; cationically or anionically derivatized polysaccharides; polyphosphazenes; biodegradable microspheres; monophosphoryl lipid A and Quil A. Cytokines, such as GM-CSF or interleukin-2, -7, or -12, are also suitable adjuvants. Hemocyanins (e.g., keyhole limpet hemocyanin) and hemoerythrins may also be used in the invention. Polysaccharide adjuvants such as, for example, chitin, chitosan, and deacetylated chitin are also suitable as adjuvants. Other suitable adjuvants include muramyl dipeptide (MDP, N acetylmuramyl L alanyl D isoglutamine) bacterial peptidoglycans and their derivatives (e.g., threonyl-MDP, and MTPPE). BCG and BCG cell wall skeleton (CWS) may also be used as adjuvants in the invention, with or without trehalose dimycolate. Trehalose dimycolate may be used itself (see, e.g., U.S. Pat. No. 4,579,945). Detoxified endotoxins are also useful as adjuvants alone or in combination with other adjuvants (see, e.g., U.S. Pat. Nos. 4,866,034; 4,435,386; 4,505,899; 4,436,727; 4,436,728; 4,505,900; and 4,520,019. The saponins QS21, QS17, QS7 are also useful as adjuvants (see, e.g., U.S. Pat. No. 5,057,540; EP 0362 279; WO 96/33739; and WO 96/11711). Other suitable adjuvants include Montanide ISA 720 (Seppic, France), SAF (Chiron, Calif., United States), ISCOMS (CSL), MF-59 (Chiron), the SBAS series of adjuvants (e.g., SBAS-2, SBAS-4 or SBAS-6 or variants thereof, available from SmithKline Beecham, Rixensart, Belgium), Detox (Corixa, Hamilton, Mont.), and RC-529 (Corixa, Hamilton, Mont.).

Superantigens are also contemplated for use as adjuvants in the present invention. Superantigens include *Staphylococcus* exoproteins, such as the α, β, γ and Δ enterotoxins from *S. aureus* and *S. epidermidis*, and the α, β, γ and Δ *E. coli* exotoxins. Common *Staphylococcus* enterotoxins are known as *staphylococcal* enterotoxin A (SEA) and *staphylococcal* enterotoxin B (SEB), with enterotoxins through E (SEE) being described (Rott et al., 1992). *Streptococcus pyogenes* B (SEB), *Clostridium perfringens* enterotoxin (Bowness et al., 1992), cytoplasmic membrane-associated protein (CAP) from *S. pyogenes* (Sato et al., 1994) and toxic shock syndrome toxin 1 (TSST 1) from *S. aureus* (Schwab et al., 1993) are further useful superantigens.

Within the pharmaceutical compositions provided herein, the adjuvant composition can be designed to induce, e.g., an immune response predominantly of the Th1 or Th2 type. High levels of Th1-type cytokines (e.g., IFN-gamma, TNF-alpha, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following oral delivery of a composition comprising an immunogenic polypeptide as provided herein, an immune response that includes Th1- and Th2-type responses will typically be elicited.

The compositions described herein may be administered as part of a sustained release formulation (i.e., a formulation such as a capsule or sponge that effects a slow release of compound following administration). Such formulations may generally be prepared using well known technology (see, e.g., Coombes et al. (1996) *Vaccine* 14:1429-1438). Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), as well as polyacrylate, latex, starch, cellulose and dextran. Other delayed-release carriers include supramolecular biovectors, which comprise a non-liquid hydrophilic core (e.g., a cross-linked polysaccharide or oligosaccharide) and, optionally, an external layer comprising an amphiphilic compound (see, e.g., WO 94/20078; WO 94/23701; and WO 96/06638). The amount of active compound contained within a sustained release formulation depends upon the site of implantation, the rate and expected duration of release and the nature of the condition to be treated or prevented.

The pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

V. Therapeutic Uses of the Invention

One aspect of the present invention involves using the immunogenic compositions described herein to elicit an antigen specific immune response from a subject or patient with a disease such as, for example, a viral infection, bacterial infection, a parasitic infection, a fungal infection, or cancer. As used herein, a "subject" or a "patient" refers to any warm-blooded animal, such as, for example, a rodent, a feline, a canine, or a primate, preferably a human. The immunogenic compositions may be used to treat at any stage of the disease, i.e., at the pre-cancer, cancer, or metastatic stages, or to prevent disease. For example, the compositions described herein may be used to treat a viral disease such as HIV or hepatitis or for prevention or treatment of cancer. Within such methods, pharmaceutical compositions are typically administered to a patient. The patient may or may not be afflicted with the disease or disorder (e.g., a viral infection, a bacterial infection, or cancer). Accordingly, the above pharmaceutical compositions may be used to prevent the development of a disease or disorder (e.g., a viral infection, a bacterial infection, or cancer)or to treat a patient afflicted with the disease or disorder (e.g., a viral infection, a bacterial infection, or cancer). The disease or disorder may be diagnosed using criteria generally accepted in the art. For example, viral infection may be diagnosed by the measurement of viral titer in a sample from the patient, bacterial infection may be diagnosed by detecting the bacteria in a sample from the patient, and cancer may be diagnosed by detecting the presence of a malignant tumor. Pharmaceutical compositions may be adminiastered either prior to or following surgical removal of primary tumors and/or treatment such as administration of radiotherapy or conventional chemotherapeutic drugs.

Immunotherapy is typically active immunotherapy, in which treatment relies on the in vivo stimulation of the endogenous host immune system to react against, e.g., tumors or bacterially or virally infected cells, with the administration of immune response-modifying agents (compositions comprising nucleic acids encoding immunogenic polypeptides as provided herein).

Frequency of administration of the prophylactic or therapeutic compositions described herein, as well as dosage, will vary from individual to individual, and may be readily established using standard techniques. Often between 1 and 10 doses may be administered over a 52 week period. Typically 3 doses are administered, at intervals of 1 month, more typically, 2-3 doses are administered every 2-3 months. It is possible that the intervals will be more like once a year for certain therapies. Booster vaccinations may be given periodically thereafter. Alternate protocols may be appropriate for individual patients and particular diseases and disorders. A suitable dose is an amount of a compound that, when administered as described above, is capable of promoting, e.g., an anti-tumor, an anti-viral, or an antibacterial, immune response, and is at least 10-50% above the basal (i.e., untreated) level. Such response can be monitored by measuring the anti-tumor antibodies in a patient or by vaccine-dependent generation of cytolytic T cells capable of killing, e.g., the patient's tumor cells, the patient's virally infected cells, or the patient's bacterially infected cells in vitro. Such vaccines should also be capable of causing an immune response that leads to an improved clinical outcome (e.g., more frequent remissions, complete or partial or longer disease-free survival) in vaccinated patients as compared to non-vaccinated patients. Typically, the amount of the viral titers will be between $1.0 \times 10^4$ pfu/animal and $1.0 \times 10^{15}$ pfu/animal. Suitable dose sizes will vary with the size of the patient, but will typically range from about 0.01 ml to about 10 ml, more typically from about 0.025 to about 7.5 ml, most typically from about 0.05 to about 5 ml. Those of skill in the art will appreciate that the dose size may be adjusted based on the particular patient or the particular disease or disorder being treated. For oral administration, the chimeric adenoviral vector can conveniently be formulated in a pill.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Such immune responses may generally be evaluated using standard proliferation, cytotoxicity or cytokine assays described above, which may be performed using samples obtained from a patient before and after treatment.

For example, detection of immunocomplexes formed between immunogenic polypeptides and antibodies in body fluid which are specific for immunogenic polypeptides may be used to monitor the effectiveness of therapy, which involves a particular immunogenic polypeptide, for a disease or disorder in which the immunogenic polypeptide is associated. Samples of body fluid taken from an individual prior to and subsequent to initiation of therapy may be analyzed for the immunocomplexes by the methodologies described above. Briefly, the number of immunocomplexes detected in both samples are compared. A substantial change in the number of immunocomplexes in the second sample (post-therapy initiation) relative to the first sample (pre-therapy) reflects successful therapy.

A. Administration of the Compositions of the Present Invention

According to the methods of the present invention, a composition comprising the chimeric adenoviral vector is administered by any non-parenteral route (e.g., orally, intranasally, or mucosally via, for example, the vagina, lungs, salivary glands, nasal cavities, small intestine, colon, rectum, tonsils, or Peyer's patches). The composition may be administered alone or with an adjuvant as described above. In some embodiments, the adjuvants are encoded by a nucleic acid sequence (e.g., a nucleic acid encoding IL-2, GM-CSF, IL-12, or bacterial flagellin). In some embodiments of the present invention, the adjuvant is administered at the same time as the composition. In other embodiments of the present invention, the adjuvant is administered after the composition, e.g., 6, 12, 18, 24, 36, 48, 60, or 72 hours after administration of the composition.

B. Detection of an Immune Response to Atigens of Interest

An immune response to the heterologous polypeptide can be detected using any means know in the art including, for example detecting specific activation of $CD4^+$ or $CD8^+$ T cells or by detecting the presence of antibodies that specifically bind to the polypeptide.

Specific activation of $CD4^+$ or $CD8^+$ T cells associated with a mucosal, humoral, or cell-mediated immune response may be detected in a variety of ways. Methods for detecting specific T cell activation include, but are not limited to, detecting the proliferation of T cells, the production of cytokines (e.g., lymphokines), or the generation of cytolytic activity (i.e., generation of cytotoxic T cells specific for the immunogenic polypeptide). For $CD4^+$ T cells, a preferred method for detecting specific T cell activation is the detection of the proliferation of T cells. For $CD8^+$ T cells, a preferred method for detecting specific T cell activation is the detection of the generation of cytolytic activity using $^{51}Cr$ release assays (see,. e.g., Brossart and Bevan, *Blood* 90(4): 1594-1599 (1997) and Lenz et al., *J. Exp. Med.* 192(8):1135-1142 (2000)).

Detection of the proliferation of T cells may be accomplished by a variety of known techniques. For example, T cell proliferation can be detected by measuring the rate of DNA synthesis. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, Ca2+ flux, or dye uptake, such as 3-(4,5-dimethylthiazol-2-yl)-2,5-diphenyltetrazolium. Alternatively, synthesis of lymphokines (e.g., interferon-gamma) can be measured or the relative number of T cells that can respond to the immunogenic polypeptide may be quantified.

Antibody immune responses (aka Humoral immune responses or B cell responses), including mucosal antibody responses can be detected using immunoassays known in the art [Tucker et al., *Mol Therapy,* 8, 392-399 (2003); Tucker et al., *Vaccine,* 22, 2500-2504 (2004)]. Suitable immunoassays include the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods, E. and S. Livingstone, Edinburgh (*1970)); the "western blot" method of Gordon et al. (U.S. Pat. No. 4,452,901); immunoprecipitation of labeled ligand (Brown et al. (1980) *J. Biol. Chem.* 255:4980-4983); enzyme-linked immunosorbent assays (ELISA) as described, for example, by Raines et al. (1982) *J. Biol. Chem.* 257:5154-5160; immunocytochemical techniques, including the use of fluorochromes (Brooks et al. (1980) *Clin. Exp. Immunol.* 39:477); and neutralization of activity (Bowen-Pope et al. (1984) *Proc. Natl. Acad Sci. USA* 81:2396-2400). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876.

EXAMPLES

The following examples are intended to illustrate, but not to limit the present invention.

Example 1

Construction of a Chimeric Adenoviral Vector (DS1)

To demonstrate that TLR-3 agonists can improve adaptive immune responses to expressed antigens of interest, several different chimeric adenoviral vectors were constructed that comprise nucleic acid sequences encoding several different antigens of interest. In this example, the nucleic acid encoding gp120 (from the NIH AIDS Reagent and Reference Reagent Program) was placed under control of a CMV promoter with a small intron just upstream of the start codon in the shuttle vector (pShuttle, Qbiogene). A poly A tail from bGH was placed downstream of the nucleic acid encoding gp120. The vector sequence is set forth in SEQ ID NO: 1. Homologous recombination with the vector pAd (Qbiogene) was performed to generate a vector capable of producing recombinant Ad (E1/E3 deleted) that contained the nucleic acid encoding gp 120. DS1 was generated by transfecting the new pAd-CMV-gp120 expression construct into 293 cells. Titers were measured by standard methods.

Example 2

Figure 1B:
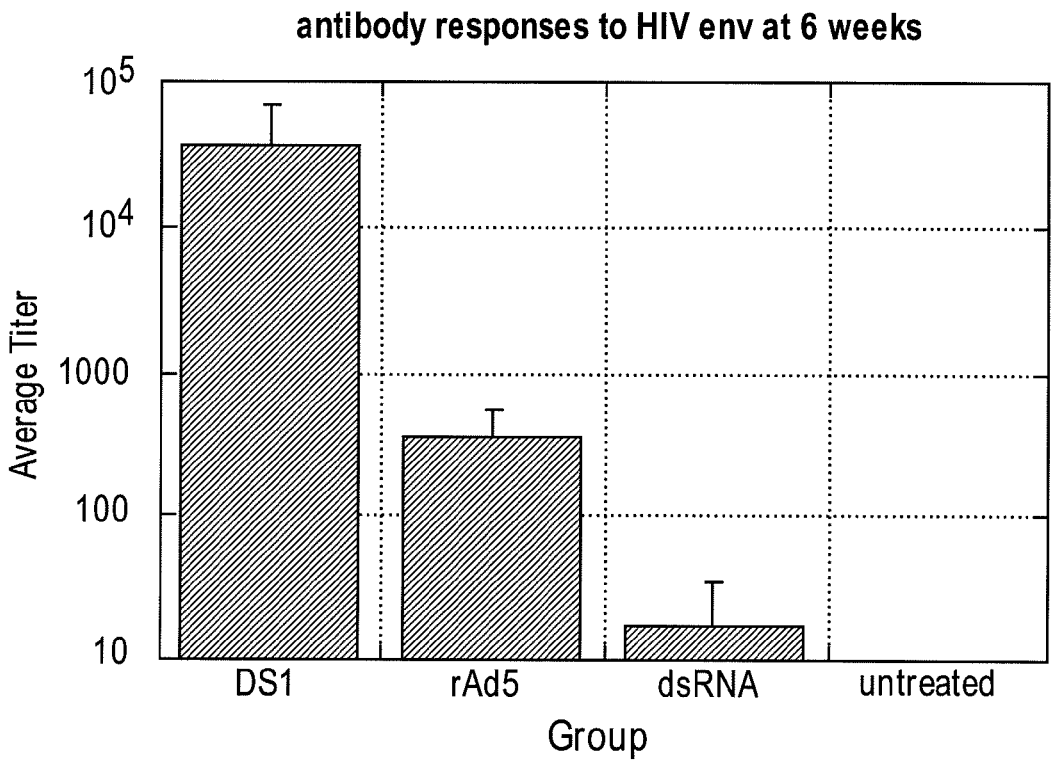
FIG. 1B illustrates data depicting the antibody titer to HIV envelope protein (i.e., gp120) at 6 weeks following oral delivery of the adenoviral vectors.

DS1 (vector plus TLR-3 agonist) is superior to standard rAd5 for inducing an antigen specific immune response To determine whether the addition of TLR-3 agonist could improve adaptive immune responses, $10 \times 10^7$ PFU of either rAd-CMV-gp120 plus 5 ug/ml poly I:C (DS1) or rAd-CMV-gp120 alone (rAd5) were administered to animals by oral gavage on weeks 0 and 3. Both vectors express HIV gp120 under control of the CMV promoter and use recombinant E1/E3 deleted adenovirus type 5. Antibody titers to gp120 were measured in the plasma 3 and 6 weeks after the initial administration by anti-gp120 IgG ELISA as described in Tucker, et al., *Mol Ther* 8:392 (2004)). As shown in FIG. 1, DS1 performed significantly better than rAd5 in eliciting antibody responses to the protein gp120 both at 3 and 6 weeks post initial oral administration. In particular, the average antibody titer to gp120 was 100 fold better with the DS1 group than with the rAd5 group at week 6. It also appears that the DS1 group was boosted by readministration at week 4 in that the average titer increased greater than 20 fold between weeks 3 and 6 whereas the rAd5 group showed only a slight increase in mean antibody titer. The results demonstrate that the addition of a TLR-3 agonist can greatly improve Ad5 mediated antibody responses to antigens of interest following oral administration of a chimeric adenoviral vector comprising a nucleic acid encoding the antigen of interest. As a positive control for the assay, sera from an animal injected subcutaneously with gp120 plus Complete Freund's Adjuvant was also measured in the anti-gp120 ELISA at week 3. Untreated animals and animals administered the dsRNA analog alone (dsRNA) served as negative and background controls respectively for the ELISA. Each group contained 6 animals.

Example 3

Construction of a Second Chimeric Adenoviral Vector (DS1b ) and a Third Chimeric Adenoviral Vector (DS1c)

A nucleic acid encoding green fluorescent protein (GFP) was inserted into pShuttle-CMV (Qbiogene) using standard restriction enzyme digests. The plasmid pShuttleCMV-GFP was combined by homologous recombination with the vector pAd (Qbiogene) as described before in order to generate a vector capable of producing recombinant Ad (E1/E3 eleted) comprising a nucleic acid sequence encoding GFP. A nucleic acid encoding hemagluttinin (HA) from influenza A/PR/8/34 was cloned and placed in the pShuttle-CMV vector (Qbiogene) (SEQ ID NO: 13). The plasmid pShuttleCMV-HA (PR/8) was combined by homologous recombination with the vector pAd (Qbiogene) as described before in order to generate a vector capable of producing recombinant Ad (E1/E3 deleted) comprising a nucleic acid sequence encoding HA. Recombinant Ad was generated by transfecting the new pAd-CMV-GFP and pAd-CMV-HA expression construct into 293 cells. Titers were measured by standard methods.

Example 4

Figure 2A:
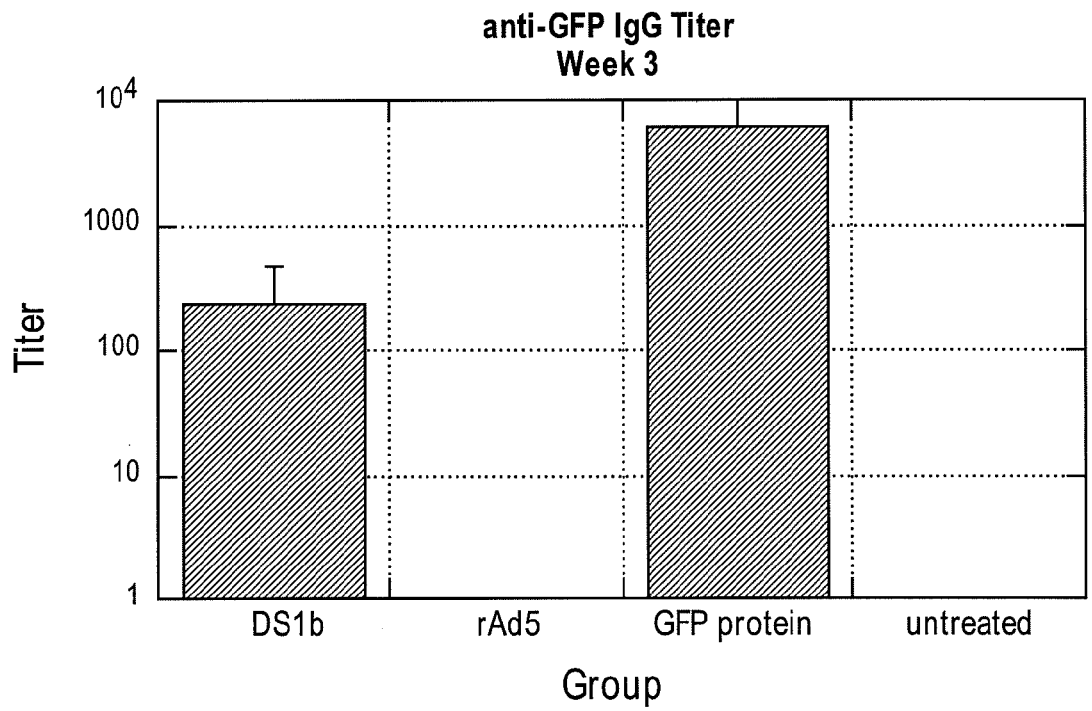
FIG. 2A illustrates data depicting the anti-GFP IgG titer at 3 weeks following oral administration of the vectors.

DS1b (Ad-CMV-GFP plus TLR-3 agonist) and DS1c (Ad-CMV-HA plus TLR-3 agonist) is superior to standard rAd5 for inducing an antigen specific immune response $1.0 \times 10^7$ PFU of either Ad-CMV-GFP plus 5 ug/ml poly I:C (DS1b) or Ad-CMV-GFP (rAd5) were administered to animals by oral gavage on week 0. Both viruses express the GFP under control of the CMV promoter and use recombinant E1/E3 deleted adenovirus type 5. Antibody titers to GFP were measured in the plasma 3 weeks after the initial virus administration by anti-GFP IgG ELISA. As shown in in FIG. 2, the DS1b group performed significantly better than rAd5 in eliciting antibody responses to the protein GFP at 3 weeks post initial oral administration.

Figure 2B:
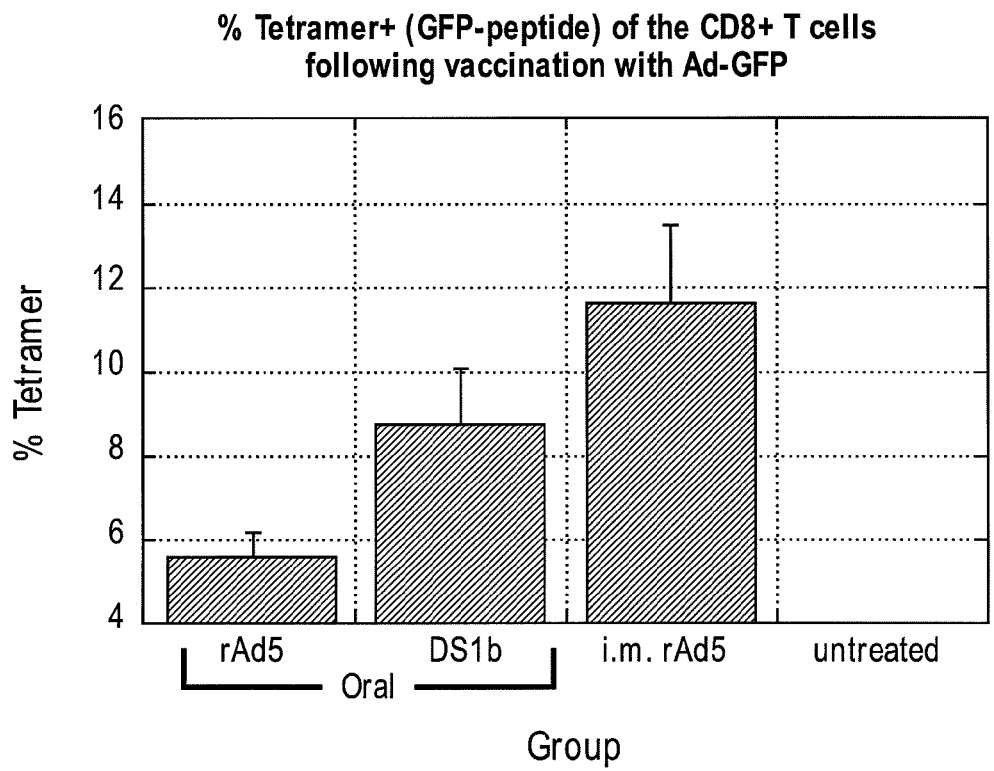
FIG. 2B illustrates data depicting the CD8+ T cell response to GFP at 10 weeks following administration of the vector at 0, 4, and 8 weeks.

The CD8$^+$T cell responses to GFP were measured by tetramer staining of splenocytes. Animals were vaccinated on weeks 0, 4, 8 and spleens were harvested on week 10. The splenocytes were stained with CD8-FITC and the tetramer which recognizes the immunodominant epitope to GFP in Balb/c mice. Results show that oral administration of the DS1b vector was statistically better than rAd alone in inducing tetramer positive CD8 cells (FIG. 2*b*).

Figure 2C:
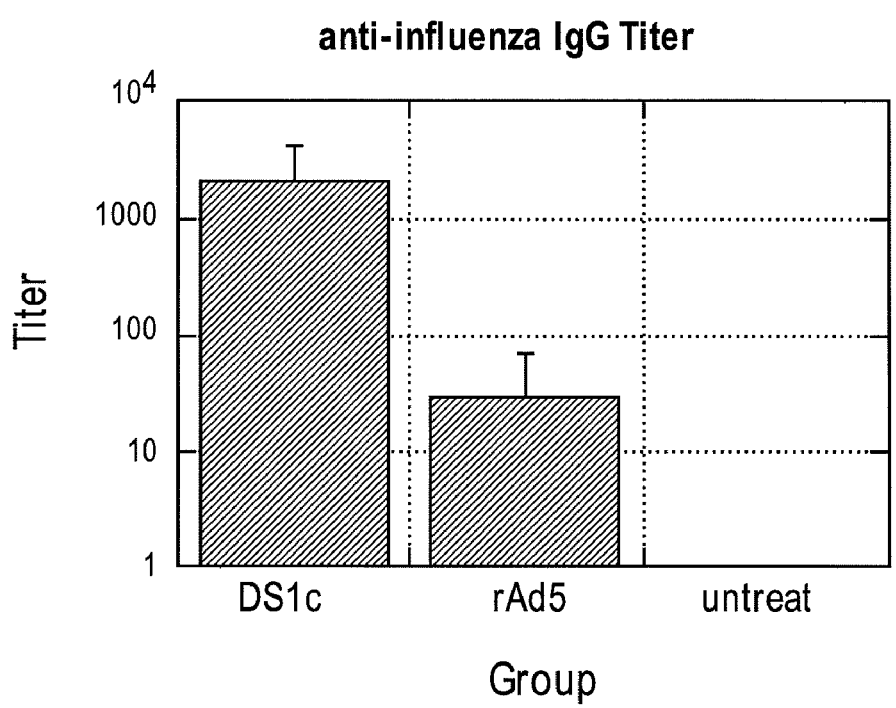
FIG. 2C illustrates data depicting the anti-HA antibody titer at 3 weeks following oral administration of the vectors.

$1.0 \times 10^7$ PFU of either Ad-CMV-HA plus 5 ug/ml poly I:C (DS1c) or Ad-CMV-HA (rAd5) were administered to animals by oral gavage on week 0. Both viruses express HA under control of the CMV promoter and use recombinant E1/E3 deleted adenovirus type 5. Antibody titers to HA were measured in the plasma 3 weeks after the initial virus administration by anti-PR8/34 IgG ELISA. The procedure for measuring antibody responses is similar to that described before with the exception that the ELISA plates were coated with 5 ug/ml of whole A/PR8/34 lysate (Advanced Biotechnology Incorporated, Gaithersburg, Md.). As shown in FIG. 2C, the DS1c group performed significantly better (approximate 100 fold better) than rAd5 in eliciting antibody responses to influenza at 3 weeks post initial oral administration. The results of these studies also demonstrate that the approach of using TLR-3 agonist along with a chimeric recombinant adnoviral vector can be generally applied to multiple different heterologous antigens, with a 100 fold improvement in antibody titer.

Example 5

Non-Parenteral Routes of Delivery Are Superior to Parenteral Routes

Figure 3A:
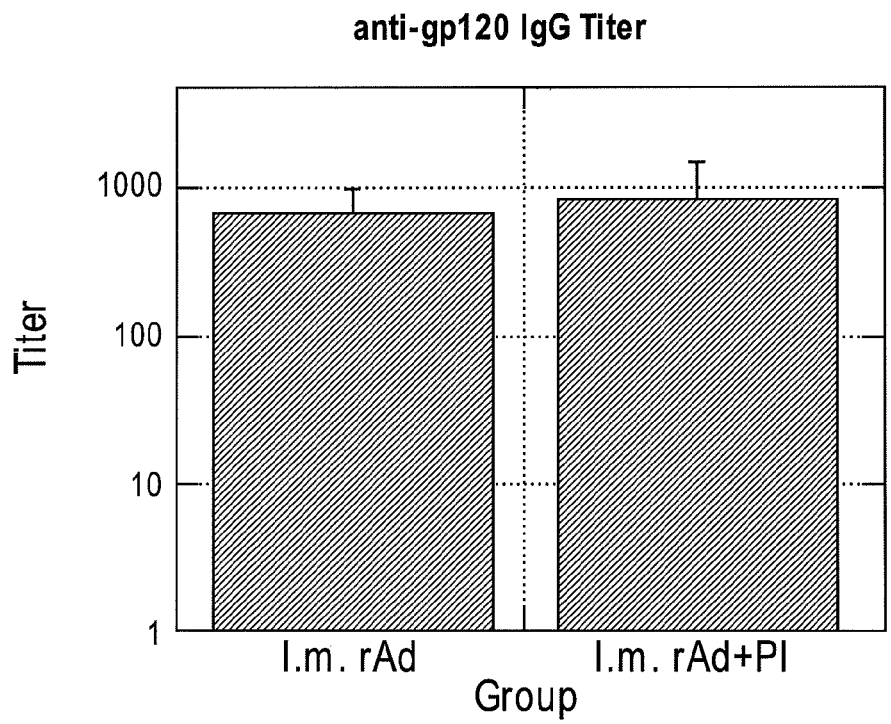
FIG. 3A illustrates data depicting the anti-gp120 antibody titer 3 weeks following intramuscular administration of DS1.
Figure 3B:
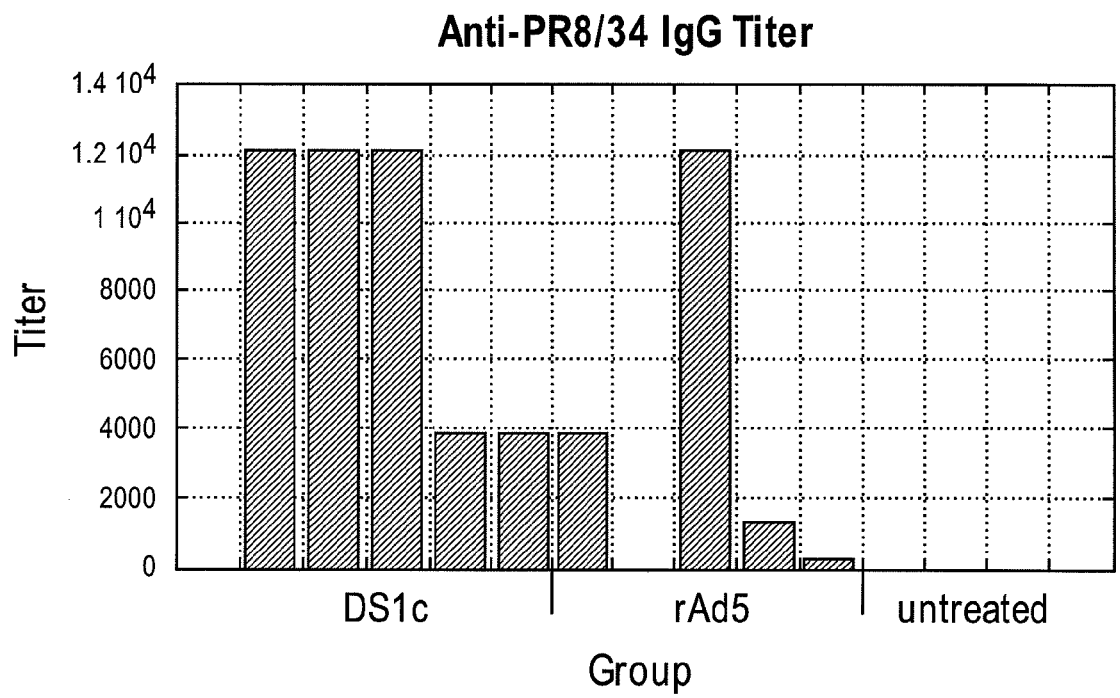
FIG. 3B illustrates data depicting the anti-HA antibody titer three weeks following intransal administration of DS1c.

Intramuscular delivery was tested by directly injecting 1.0×107 pfu of pAd-CMV-gp120 (DS10+/ −poly I:C at 5 ug/ml into the quadriceps of animals. Plasma serum IgG titers to GFP were measured as described before. Each group contained 6 animals. As shown in FIG. 3A, significant antibody titers to gp120 were observed at 3 weeks post administration in the group with TLR-3 agonist (i.m. rAd+PI). (FIG. 3a).

Intranasal administration was tested by administering 20 ul of $1.1×10^6$ pfu of DS1c +/ −5 ug/ml of poly I:C into the nasal cavity of mice. The mice were lightly anesthetized with isoflurane before administering the virus formulated in sterile saline. The results show that the rAd-CMV-HA plus poly I:C (DS1c) had slightly higher antibody titers compared to animals given the standard rAd-CMV-HA. Results are plotted as individual animals for the DS1c (N=6) and the rAd (N=5) groups. Untreated animals (N=4) are used for negative controls.

Example 6

Construction of an Expressed TLR3 Agonist

A short 45 bp segment of DNA was synthesized by ordering of DNA oligos that when annealed together formed a 45 bp seqment designed to make a hairpin of double-stranded RNA (GAAACGATATGGGCTGAATACGGATCCG-TATTCAGCCCATATCGTTTC) (SEQ ID NO:10). This short segment (called luc1) was cloned into the plasmid pSK-containing the human beta actin promoter and a BGH poly A tail. This plasmid is called pSk-luc1.

Example 7

Figure 4A:
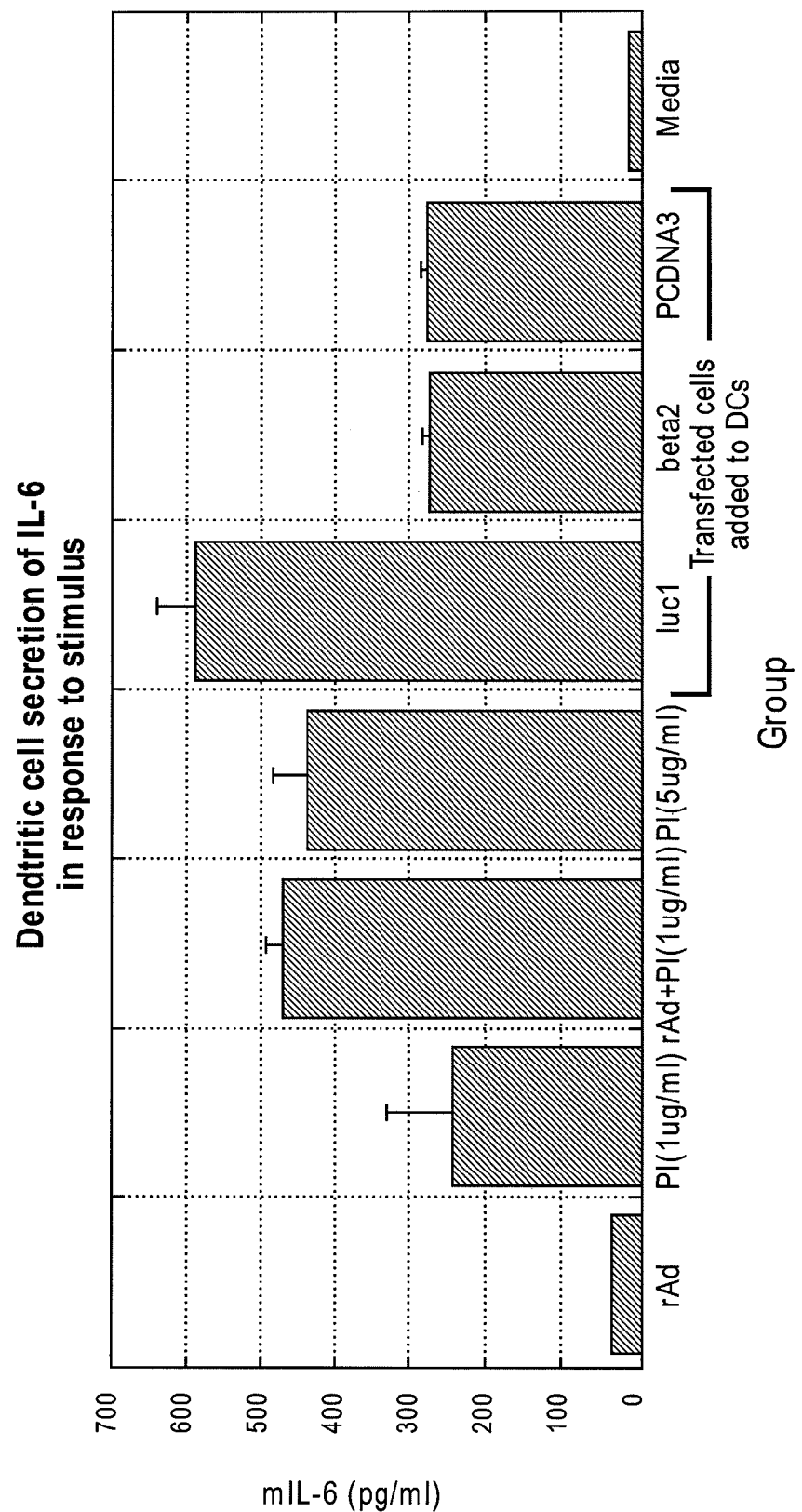
FIG. 4A illustrates data depicting dendritic cell activation by the expressed dsRNA TLR-3 agonist luc1.

The pSK-luc 1 Functions in Dendritic Cell Cultures Like Poly I:C, the Effects of Poly I:C and rAd are Additive To determine whether the expressed TLR-3 agonist of Example 6 above could function as an inducer of pro-inflammatory cytokines and dendritic cell maturation like the TLR-3 ligand poly I:C, an expressed dsRNA TLR-3 agonist was tested in dendritic cell cultures. Bone marrow from the femurs of Balb/c mice were cultured with flt-3 ligand (200 ng/ml), 5% serum, in DMEM media in order to make primary dendritic cell cultures. Five days after primary bone marrow cultures were set-up, 293 cells were transfected with either pSk-luc1, pSK-beta2 (a long seqment of beta galactosidase that forms a 200 bp hairpin), or pcDNA3 (empty expression vector). On day 6, the transfected cells were treated by UV irradiation (20 seconds at 40 kJ/cm2) to cause apoptosis and these cells were given to the dendritic cells. Either poly I:C (1 ug/ml), rAd (1 pfu/cell), rAd+poly I:C, pSK-luc1 transfected cells, pSK-beta2 transfected cells, or pcDNA3 transfected cells were given to the dendritic cells and cultured overnight. As shown in FIG. 4A, pSK-luc1 transfected cells can significantly improve dendritic cell activation as measured by the mouse IL-6 ELISA. The results of this experiment also show that the combination of rAd plus TLR3 ligand (poly I:C) together can greatly improve dendritic cell activity.

Figure 4B:
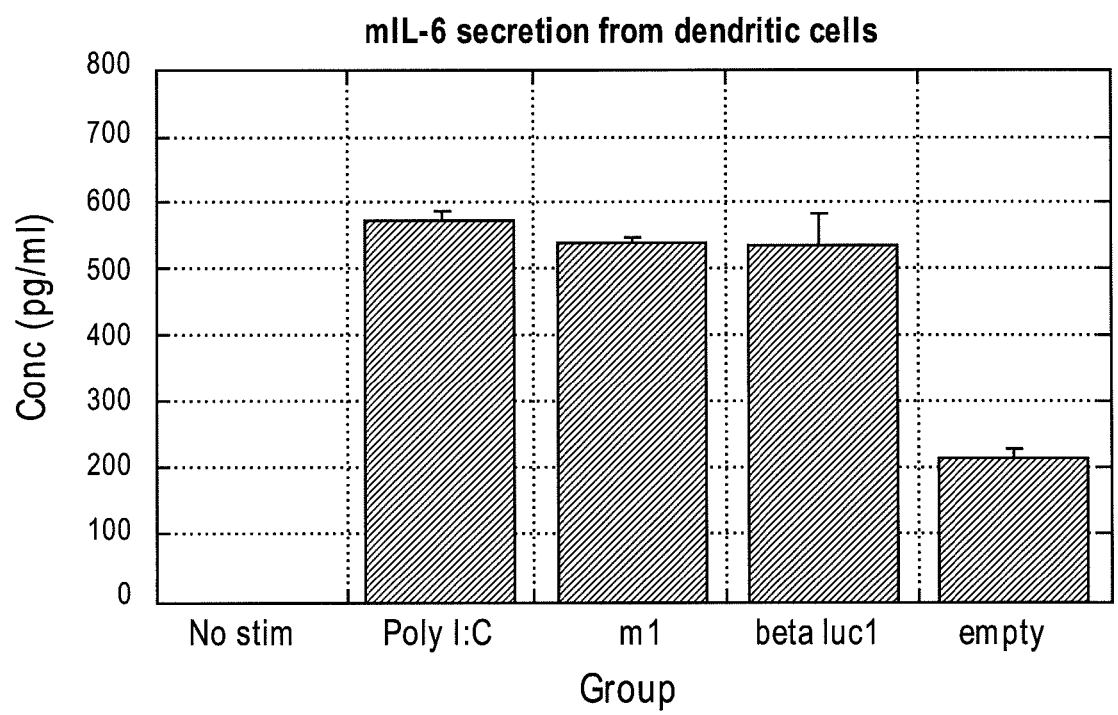
FIG. 4B illustrates data depicting dendritic cell activation by the expressed dsRNA TLR-3 agonists luc1 and m1.

Additional ligands were also tested. The TLR-3 agonist set forth in SEQ ID NO: 11 (m1) also forms a dsRNA hairpin of approximately the same size as luc1. These were made by overlapping oligonucleotides and annealing them together before cloning into the pSK-vector under control of the human beta actin promoter. The vectors were transfected into 293 cells and given to primary dendritic cells as described before. As shown in FIG. 4B, these additional ligands can activate dendritic cells similar to that of the ligand luc1 (FIG. 4B).

Example 8

Construction of a Fourth Chimeric Adenoviral Vector (DS2) and Rapid Cloning Vectors (DS2beta-luc and DS2C-luc)

Figure 5:
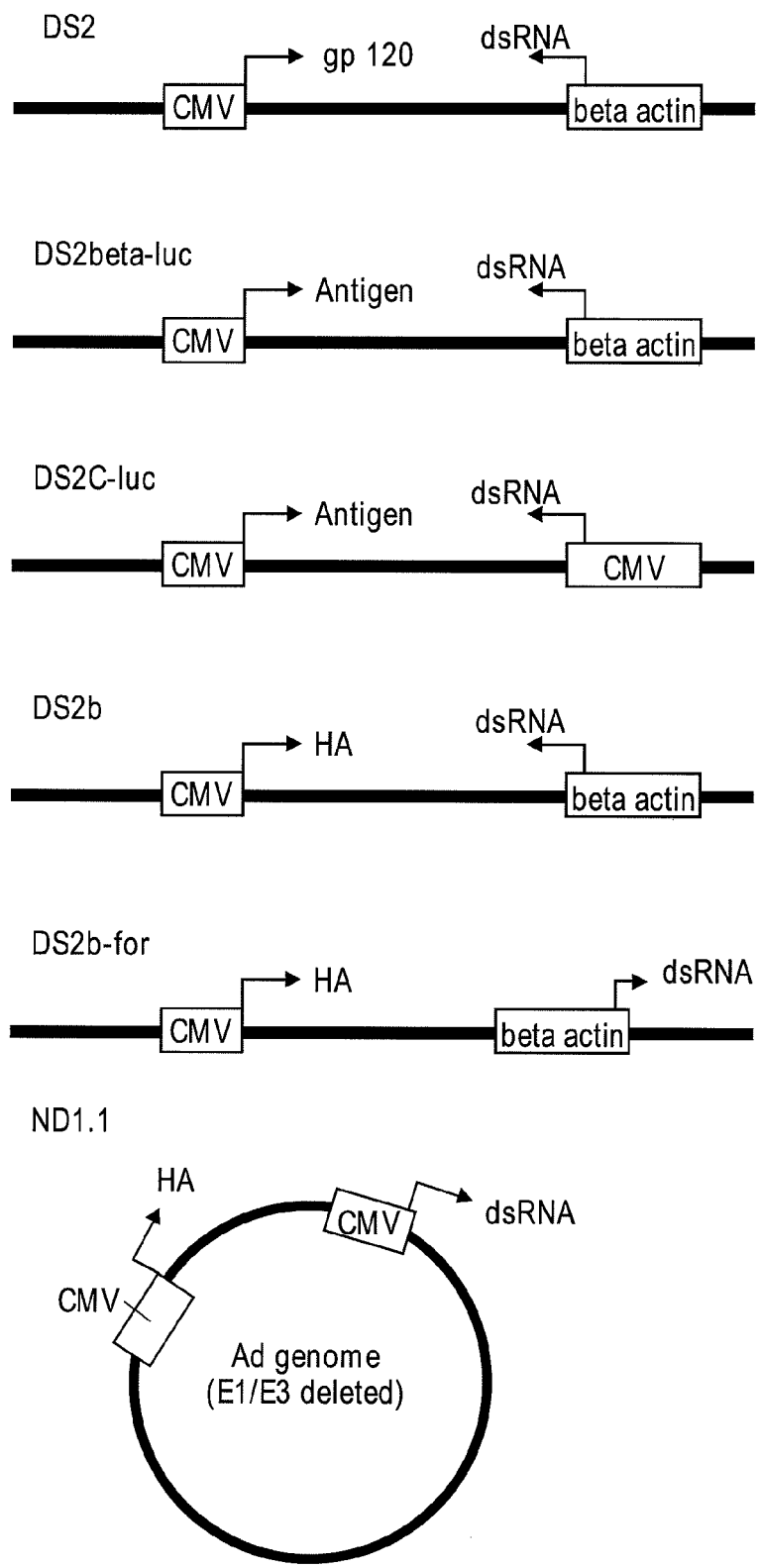
FIG. 5 is a graphic illustration of the chimeric adenoviral vectors of the invention, i.e., chimeric adenoviral vectors comprising nucleic acids encoding expressed ds RNA TLR-3 agonists.

A nucleic acid encoding gp120 (from the NIH AIDS Research and Reference Reagent Program)) was placed under control of a CMV promoter with a small intron just upstream of the start codon in the shuttle vector (pShuttleCMV, Qbiogene). A poly A tail from bGH was placed downstream of the nucleic acid encoding gp120. The dsRNA TLR-3 agonist luc1 under the control of the human beta actin promoter and poly A (described in example 5 above) was inserted into the gp120 pShuttle vector such that both the nucleic acid encoding gp120 and the nucleic acid encoding TLR-3 agonist were contained in a single vector under the control of two separate promoters. The orientation of the expression of the nucleic acid encoding the antigen of interest and the expression of the TLR-3 agonist is illustrated in FIG. 5.

Two generic shuttle vectors called DS2beta-luc (SEQ ID NO: 14) and DS2C-luc (SEQ ID NO: 15) were also constructed such that a nucleic acid encoding any antigen of interest could be inserted under the CMV promoter and either the human beta actin promoter or the CMV promoter is used to drive expression of a dsRNA TLR-3 agonist. In particular, the vector DS2C-luc has a unique Kpn 1 site that a nucleic acid encoding an antigen of interest can easily be cloned into. The purpose of these vectors is to make subsequent vector construction much easier because a nucleic acid encoding any antigen of interest could be inserted into the cloning site to rapidly manufacture a vector capable of eliciting antibody and T cells responses against the antigen of interest. Homologous recombination of DS2 with the vector pAd (Qbiogene) was performed as before in order to generate a vector capable of producing recombinant Ad(E1/E3 deleted) that contained a nucleic acid encoding GFP and a nucleic acid encoding the dsRNA TLR-3 agonist luc 1. Recombinant Ad was generated by transfecting the new pAd-betaactin -luc1-CMV-gp120 expression construct into 293 cells. Titers were measured by standard methods.

Example 9

Induction of an Antigen Specific Immune Response Following Oral Delivery of DS2

Figure 6:
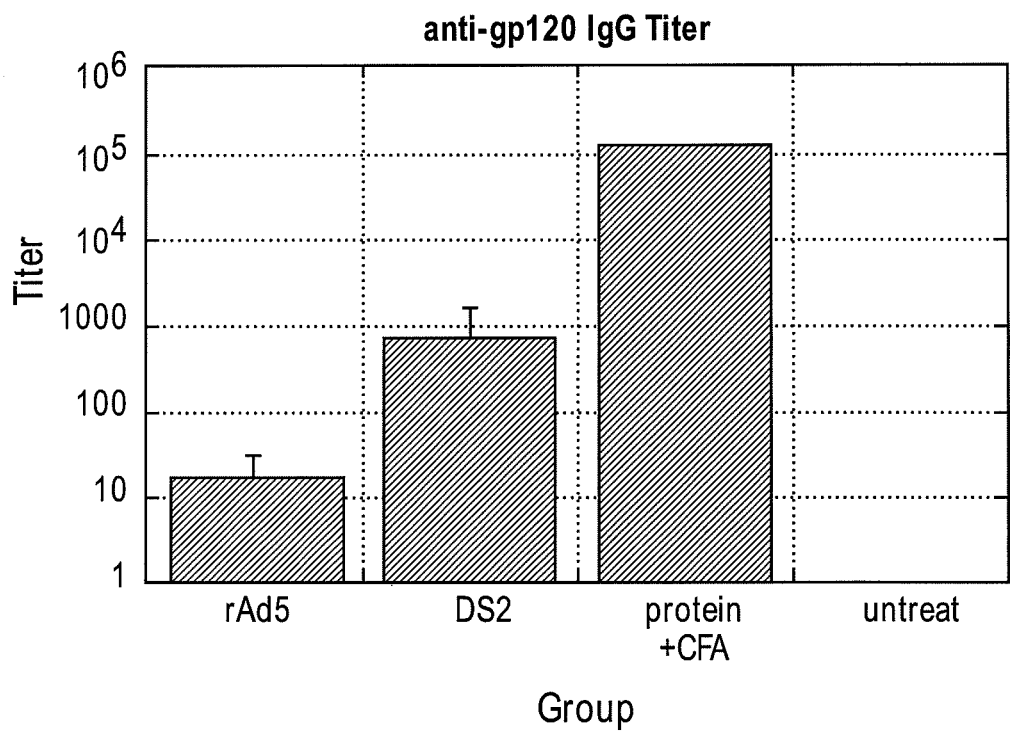
FIG. 6 illustrates data demonstrating that the chimeric adenoviral vectors of the invention are effective at inducing an antigen-specific immune response following oral delivery.

$1.0×10^7$ PFU of either pAd-CMV-gp120 plus the TLR-3 agonist luc1 (DS2) or pAd-CMV-gp120 (rAd5) were administered to animals by oral gavage on week. Both viruses express the gp120 under control of the CMV promoter and use recombinant E1/E3 deleted adenovirus type 5. Antibody titers to gp120 were measured in the plasma 3 weeks after virus administration by anti-gp120 IgG ELISA. The ELISA protcol has been described before (Tucker, et al, Mol Therapy 8:392 (2004)). Results demonstrate that DS2 can induce approximately a 2 log improvement in antibody titer to gp120, the heterologous antigen used in the experiment. The DS2 vector comprises a nucleic acid sequence encoding expressing gp120 and a nucleic acid sequence expressing a dsRNA TLR-3 agonist. As a positive control for the assay, sera from two animals injected subcutaneously with 10 micrograms gp120 protein plus Complete Freund's Adjuvant was also measured in the anti-gp120 ELISA. Untreated animals served as negative controls for the ELISA. Each group contained 6 animals. The results are illustrated in FIG. 6.

Example 10

Induction of an Antigen Specific Immune Response Following Oral Delivery of DS3

Figure 7:
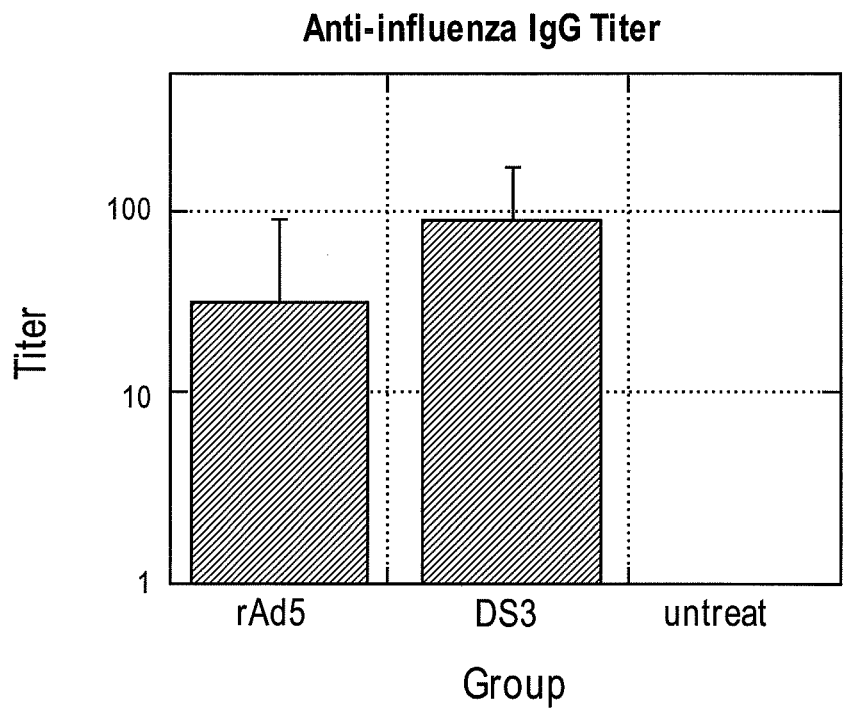
FIG. 7 illustrates data demonstrating that TLR-7/8 agonists have poor effectiveness in inducing an antigen-specific immune response.

$1.0 \times 10^7$ PFU of either pAd-CMV-influenza HA (from A/PR/8/34) plus the TLR7/8 ligand polyuridylic acid (DS3) or pAd-CMV-HA (rAd5) were administered to animals by oral gavage on week 0. Both viruses express influenza HA under control of the CMV promoter and use recombinant E1/E3 deleted adenovirus type 5. Antibody titers to HA were measured in the plasma 3 weeks after virus administration by anti-influenza HA IgG ELISA. Each group contained 6 animals. The results are illustrated in FIG. 7.

Example 11

Construction of a Fifth, Sixth, and Seventh Chimeric Adenoviral Vector (DS2b, DS2b-for and ND1.1 214)

The gene influenza HA (A/Indo/5/2005) was synthesized by CelTek (Nashville, Tenn.) and placed into the vector pShuttleCMV (Qbiogene) which has a CMV promoter with a small intron just upstream of the start codon in the shuttle vector. The luc1 DNA with human beta actin promoter and poly A (described in example 5) were placed into the vector downstream of the antigen, in the orientation shown in FIG. 5 for DS2b. The sequence of luc1 is (GAAACGATATGGGCT-GAATACGGATCCGTATTCAGCCCATATCGTTTC) (SEQ ID NO:10) and the completed pShuttle vector is set forth in SEQ ID NO: 6. An alternative orientation of luc1 with promoter in a shuttle vector is described as SEQ ID NO: 7 and is designated DS2b-for. We have also constructed another pShuttle vector (called DS2bC-HA) (SEQ ID NO: 16) that comprises two separate CMV promoters driving expression of the TLR-3 agonist luc1 and influenza HA described above. Homologous recombination with the vector pAd (Qbiogene) was performed as before in order to generate vectors capable of producing recombinant Ad (E1/E3 deleted) that contained the nucleic acid encoding HA and the TLR-3 agonist luc1 under separate promoters. Recombinant Ad was generated by transfecting the new pAd-constructs into 293 cells. Titers were measured by standard methods. The completed pAd vector containing DS2C-luc was named ND1.1 214 and deposited in the ATCC patent depository on Feb. 22, 2007 (Manassus, Va.). The nucleic acid sequence of this chimeric adenoviral vector is set forth in in SEQ ID NO: 17. The nucleic acid encoding the heterologous antigen is in bold text and is flanked by a Cla I recognition site on the 5' end and a Not I recognition site on the 3'end. The nucleic acid sequence encoding the TLR-3 agonists is in italic, with the linker sequence in bold. A nucleic acid sequence encoding any antigen of interest and a nucleic acid sequence encoding any suitable expressed TLR-3 agonist can be inserted into the chimeric adenoviral vector.

Example 12

Induction of an Antigen Specific Immune Response Following Oral Delivery of DS2b.

Figure 8A:
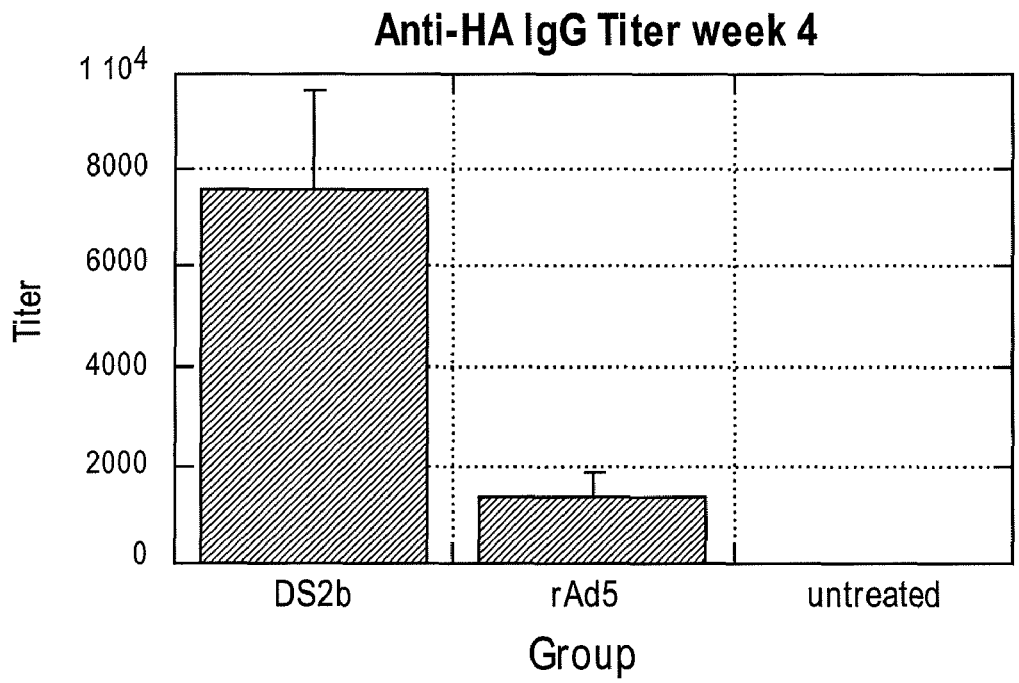
FIG. 8A illustrates data depicting the anti-HA antibody titer 4 weeks following oral administration of a chimeric adenoviral comprising a nucleic acid sequence encoding the dsRNA TLR-3 agonist luc1.

$1.0 \times 10^7$ PFU of either pAd-CMV-HA plus the TLR-3 agonists luc1 in the reverse orientation (DS2b) or forward orientation (DS2b-for), or pAd-CMV-HA (rAd5) were administered to animals by oral gavage on week 0. These viruses express the antigen influenza HA under control of the CMV promoter and use recombinant E1/E3 deleted adenovirus type 5. Antibody titers to HA were measured in the plasma 3 weeks after virus administration by anti-HA IgG ELISA. Results demonstrate that the DS2b vector elicits an antibody responses to the protein HA greater than the standard rAd vector (rAd5). The DS2b vector contains rAd5 expressing HA as well as expresses a toll-like receptor 3 (TLR3) agonist, a hairpin of double-stranded RNA, demonstrating that the use of the encoded dsRNA ligand can improve adaptive immune responses to antigens of interest. As shown in FIG. 8A and FIG. 6, expressed dsRNA can improve adaptive immune responses to multiple different heterologous antigens. Untreated animals served as negative control for the ELISA. Each group contained 6 animals.

Figure 8B:
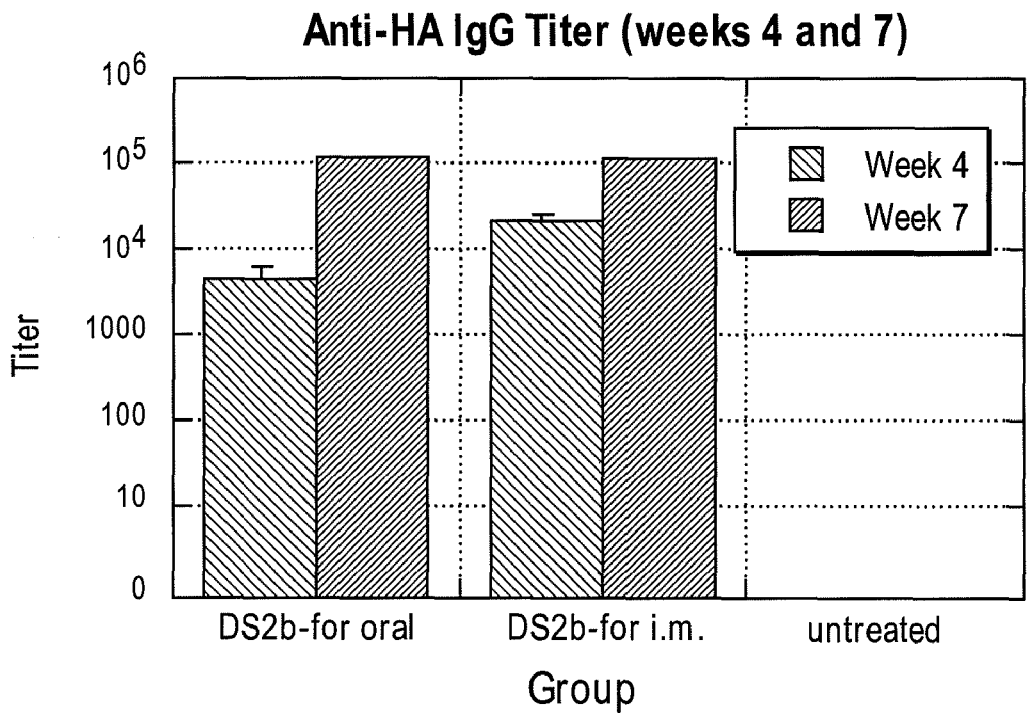
FIG. 8B illustrates data depicting the anti-HA antibody titer 4 weeks or 7 weeks following administration of a chimeric adenoviral comprising a nucleic acid sequence encoding the dsRNA TLR-3 agonist luc1.

Vectors in the opposite orientation (DS2for) were examined for antibody responses following either oral or intramuscular administration of $1.0 \times 10^7$ pfu virus per animal at 0 and 5 weeks. Antibody responses to HA were measured at 4 and 7 weeks post initial administration. As shown in FIG. 8B, the opposite orientation vector can also induce substantial antibody responses to heterologous antigens. The DS1b and DS1bfor vectors induced similar responses to HA at the 4 week time point. Significantly, the effect of boosting of the antibody response was demonstrated with the DS1bfor vector and showed that multiple doses could be used to increase antibody responses to the heterologous antigen.

Figure 8C:
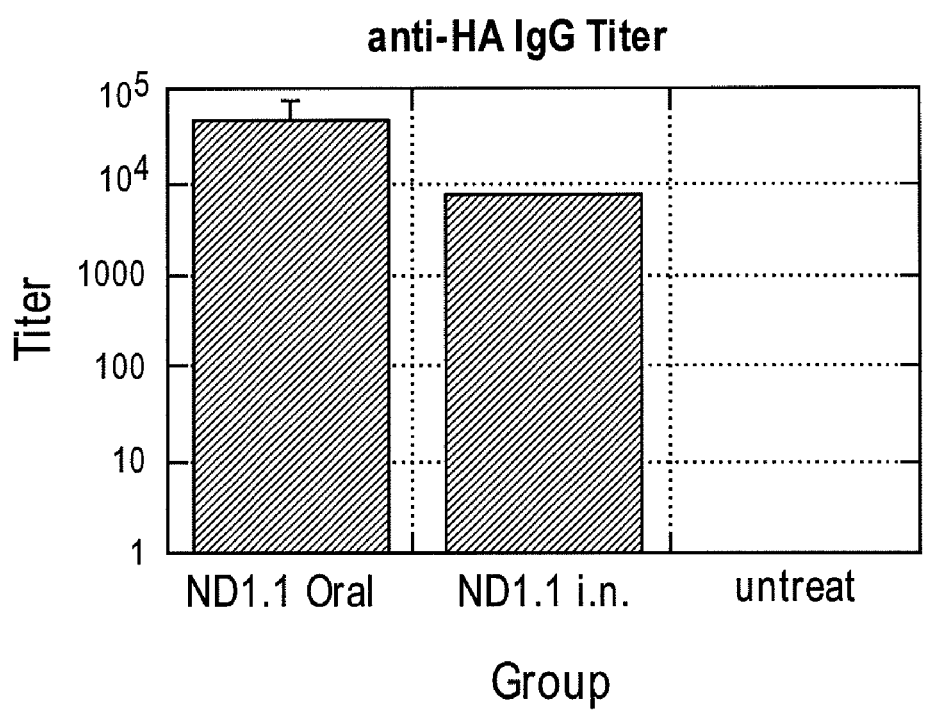
FIG. 8C illustrates data depicting the anti-HA antibody titer 3 weeks following oral or intranasal administration of a chimeric adenoviral comprising a nucleic acid sequence encoding the dsRNA TLR-3 agonist luc1.

Another example of potential of the chimeric adenoviral vector approach was demonstrated as well. The vector ND1.1 214 was given to animals by oral ($1.0 \times 10^7$ pfu) or intranasal administration ($3 \times 10^6$ pfu) and the antibody responses to the heterologous antigen were measured at week 3. As shown in FIG. 8C, substantial antibody responses to HA were measured following oral administration, well beyond the typical values from a single oral administration of rAd vector.

All publications, patent publications, patents, and Genback Accession Nos. applications cited in this specification are herein incorporated by reference in their entirety for all purposes as if each individual publication, patent publication, or patent were specifically and individually indicated to be incorporated by reference.

What is claimed is:

1. A chimeric adenoviral expression vector, said vector comprising an expression cassette comprising the following elements:
    (a) a first promoter operably linked to a nucleic acid encoding a toll-like receptor-3 (TLR-3) agonist, wherein the TLR-3 agonist is a double stranded RNA (dsRNA); and
    (b) a second promoter operably linked to a nucleic acid encoding a heterologous polypeptide, wherein said heterologous polypeptide is selected from the group consisting of:
    influenza virus HA, influenza virus M1, influenza virus NP, HIV gag, and HIV env.

2. The chimeric adenoviral expression vector of claim 1, wherein the heterologous polypeptide is an HIV env polypeptide.

3. The chimeric adenoviral expression vector of claim 2, wherein the HIV env polypeptide is selected from the group consisting of: gp41, gp120, and gp160.

4. The chimeric adenoviral expression vector of claim 1, wherein the heterologous polypeptide is an influenza HA polypeptide.

5. The chimeric adenoviral expression vector of claim 1, wherein the first promoter and the second promoter are the same.

6. The chimeric adenoviral expression vector of claim 5, wherein the first promoter and the second promoter are each a CMV promoter.

7. An immunogenic composition comprising the expression vector of claim 1 and a pharmaceutically acceptable carrier.

8. A chimeric adenoviral expression vector, said vector comprising an expression cassette comprising the following elements:
    (a) a first promoter operably linked to a nucleic acid encoding a toll-like receptor-3 (TLR-3) agonist, wherein the TLR-3 agonist is a double stranded RNA (dsRNA) and wherein the nucleic acid encoding the TLR-3 agonist comprises a sequence selected from the group consisting of: SEQ ID NOS: 8, 9, 10, 11, and 12; and
    (b) a second promoter operably linked to a nucleic acid encoding a heterologous polypeptide.

9. The chimeric adenoviral expression vector of claim 8, wherein the nucleic acid encoding the TLR-3 agonist is a sequence selected from the group consisting of: SEQ ID NOs: 8, 9, 10, 11, and 12.

10. A method for eliciting an immune response, said method comprising administering to a mammalian subject an immunogenically effective amount of a chimeric adenoviral expression vector, said vector comprising an expression cassette comprising the following elements:

(a) a first promoter operably linked to a nucleic acid encoding a toll-like receptor-3 (TLR-3) agonist, wherein the TLR-3 agonist is a double stranded RNA (dsRNA); and (b) a second promoter operably linked to a nucleic acid encoding a heterologous polypeptide, wherein the immune response is directed against the heterologous polypeptide, and wherein the route of administration is selected from the group consisting of: oral, intranasal, and mucosal.

11. The method of claim 10, wherein the heterologous polypeptide is expressed in a cell selected from the group consisting of: a dendritic cell, a microfold cell, and an intestinal epithelial cell.

12. The method of claim 10, wherein said mammal is a human.

13. The method of claim 10, wherein nucleic acid encoding the TLR-3 agonist comprises a sequence selected from the group consisting of: SEQ ID NOS: 8, 9, 10, 11, and 12.

14. The method of claim 10, wherein said heterologous polypeptide is an influenza HA polypeptide.

* * * * *